(12) United States Patent
Komori et al.

(10) Patent No.: US 6,191,070 B1
(45) Date of Patent: Feb. 20, 2001

(54) PYRIMIDINONE DERIVATIVES AND HERBICIDES CONTAINING THEM

(75) Inventors: Takashi Komori; Hisayuki Hoshi, both of Toyonaka (JP)

(73) Assignee: Sumitomo Chemical Company, Limited, Osaka-fu (JP)

( * ) Notice: Under 35 U.S.C. 154(b), the term of this patent shall be extended for 0 days.

(21) Appl. No.: 09/148,074

(22) Filed: Sep. 4, 1998

(30) Foreign Application Priority Data

Sep. 5, 1997 (JP) .................................................... 9-241573
Nov. 28, 1997 (JP) .................................................... 9-370043

(51) Int. Cl.$^7$ ................. C07D 239/553; C07D 239/547; A01N 43/54
(52) U.S. Cl. .................. 504/243; 504/203; 544/311; 544/312; 544/313; 544/314
(58) Field of Search .................... 504/203, 243; 544/311, 312, 313, 314

(56) References Cited

U.S. PATENT DOCUMENTS

| | | | |
|---|---|---|---|
| 3,816,422 | 6/1974 | Stable et al. | 260/256.4 |
| 5,602,077 | 2/1997 | Amuti et al. | 504/203 |

FOREIGN PATENT DOCUMENTS

| | | |
|---|---|---|
| 04 76697A1 | 3/1992 | (EP) . |
| 98 14452A1 | 4/1998 | (WO) . |

OTHER PUBLICATIONS

Liebigs Ann. Chem. 1973, 1275–1281—Ringschlussreaktionen mit 2–Aminoimidazolinen—Helmut Stähle and Herbert Köppe; Wissenschaftliche Abteilung der Fa. Böhringer Sohn, Ingelheim/Germany.

Helvetica Chimica Acta—vol. 59, Fasc 4 (1976)—Nr. 122—Vergleich der Produkte Aus der Reaktion Von Phenylguanidin–Derivaten mit β–Ketoestern bzw. Propiolsäureestern—Hans P. Härter et al.

*Primary Examiner*—Mukund J. Shah
*Assistant Examiner*—Pavanaram K Sripada
(74) *Attorney, Agent, or Firm*—Birch, Stewart, Kolasch & Birch, LLP

(57) ABSTRACT

Pyrimidinone derivatives of the general formula:

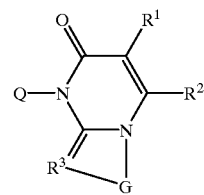

wherein $R^1$ is hydrogen or alkyl; $R^2$ is haloalkyl; $R^3$ is nitrogen or CH; G is optionally substituted ethylene, trimethylene, or vinylene; and Q is selected from several optionally substituted or heterocyclic-condensed phenyl groups, are useful as the active ingredients of herbicides because of their excellent herbicidal activity.

13 Claims, No Drawings

PYRIMIDINONE DERIVATIVES AND HERBICIDES CONTAINING THEM

FILED OF INVENTION

The present invention relates to pyrimidinone derivatives and their use.

OBJECT OF THE INVENTION

It is an object of the present invention to provide compounds with excellent herbicidal activity.

SUMMARY OF THE INVENTION

The present inventors have intensively studied to seek out various compounds with excellent herbicidal activity. As a result, they have found that pyrimidinone derivatives of the general formula as depicted below have excellent herbicidal activity, thereby completing the present invention.

Thus the present invention provides pyrimidinone derivatives of the general formula:

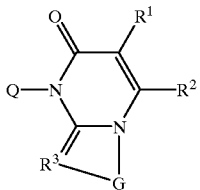

(hereinafter referred to as the present compound(s))
wherein:
$R^1$ is hydrogen or $C_1$–$C_3$ alkyl;
$R^2$ is $C_1$–$C_3$ haloalkyl;
$R^3$ is nitrogen or CH;
G is any group of the general formula:

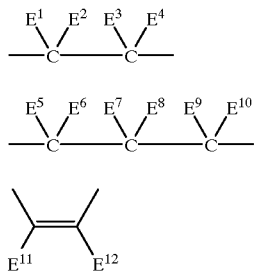

wherein:
$E^1$, $E^2$, $E^3$, $E^4$, $E^5$, $E^6$, $E^7$, $E^8$, $E^9$, $E^{10}$, $E^{11}$, and $E^{12}$ are independently hydrogen or $C_1$–$C_3$ alkyl; and
Q is any group of the general formula:

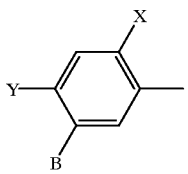

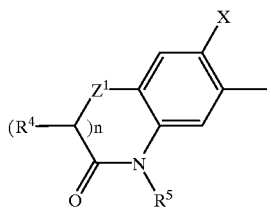

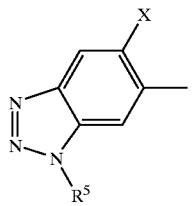

wherein:
X is hydrogen or halogen;
Y is halogen, nitro, cyano, or trifluoromethyl;
$Z^1$ is oxygen, sulfur, NH, or $CH_2$;
n is 0 or 1;
$R^4$ is hydrogen or $C_1$–$C_3$ alkyl;
$R^5$ is hydrogen, $C_1$–$C_6$ alkyl, $C_1$–$C_6$ haloalkyl, ($C_3$–$C_8$ cycloalkyl) $C_1$–$C_6$ alkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_3$ alkoxy $C_1$–$C_3$ alkoxy $C_1$–$C_3$ alkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, $C_1$–$C_4$ alkylthio $C_1$–$C_4$ alkyl, hydroxy $C_1$–$C_6$ alkyl, —$CH_2CON(R^{12})R^{13}$, —$CH_2COON(R^{12})R^{13}$, —$CH(C_1$–$C_4$ alkyl)CON$(R^{12})R^{13}$, or —$CH(C_1$–$C_4$ alkyl)COON$(R^{12})R^{13}$,
wherein:
$R^{12}$ and $R^{13}$ are independently hydrogen, $C_1$–$C_6$ alkyl, $C_3$–$C_8$ cycloalkyl, $C_1$–$C_6$ haloalkyl, $C_3$–$C_6$ alkenyl, $C_3$–$C_6$ alkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_6$ alkoxy)carbonyl $C_1$–$C_6$ alkyl, ($C_3$–$C_8$ cycloalkoxy)carbonyl $C_1$–$C_6$ alkyl, ($C_1$–$C_6$ alkyl)carbonyloxy $C_2$–$C_6$ alkyl, ($C_1$–$C_6$ alkyl)carbonylamino $C_2$–$C_6$ alkyl, hydroxy $C_2$–$C_6$ alkyl, optionally substituted benzyl, optionally substituted phenyl, or {($C_1$–$C_4$ alkoxy) $C_1$–$C_4$ alkyl}carbonyl $C_1$–$C_6$ alkyl, or $R^{12}$ and $R^{13}$ are taken together to form trimethylene, tetramethylene, pentamethylene, ethyleneoxyethylene, or ethylenethioethylene;
and
B is hydrogen, halogen, nitro, cyano, chlorosulfonyl, $OR^{10}$, $SR^{10}$, $SO_2OR^{21}$, $N(R^{12})R^{13}$, $SO_2N(R^{12})R^{13}$, $NR^{12}(COR^9)$, $NR^{12}(SO_2R^{28})$, $N(SO_2R^{28})(SO_2R^{29})$, $N(SO_2R^{28})(COR^9)$, $NHCOOR^{11}$, $CONR^{12}R^{13}$, $CSNR^{12}R^{13}$, $COR^{30}$, $CR^{23}$=$CR^{24}COR^{30}$, $CR^{23}$=$CR^{24}CON(R^{12})R^{13}$, $CH_2CHWCON(R^{12})R^{13}$, $CR^{30}$=$NOR^{31}$, $CR^{30}$=$NN(R^{12})R^{13}$, $CR^{30}(Z^2R^{32})_2$, $OCO_2R^{32}$, $OCOR^{32}$, $COOR^{22}$, $CH_2OR^{10}$, $CR^{23}$=$CR^{24}COOR^{25}$, or $CH_2CHWCOOR^{25}$,
wherein:
$R^{12}$ and $R^{13}$ are as defined above;
W is hydrogen, chlorine, or bromine;
$Z^2$ is oxygen or sulfur;

R⁹ is hydrogen, $C_1$–$C_6$ alkyl, $C_1$–$C_6$ haloalkyl, $C_3$–$C_8$ cycloalkyl, or $C_3$–$C_6$ alkenyl;

R¹¹ is hydrogen, $C_1$–$C_6$ alkyl, $C_3$–$C_8$ cycloalkyl, or $C_3$–$C_6$ alkenyl;

R²⁸ and R²⁹ are independently $C_1$–$C_6$ alkyl, $C_1$–$C_6$ haloalkyl, or phenyl;

R³⁰ is hydrogen, $C_1$–$C_6$ alkyl, $C_3$–$C_6$ alkenyl, or $C_3$–$C_6$ alkynyl;

R³¹ is hydrogen, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_6$ alkoxy)carbonyl $C_1$–$C_6$ alkyl, ($C_3$–$C_8$ cycloalkoxy)-carbonyl $C_1$–$C_6$ alkyl, or {($C_1$–$C_4$ alkoxy) $C_1$–$C_4$ alkoxy}carbonyl $C_1$–$C_6$ alkyl;

R³² is hydrogen, $C_1$–$C_6$ alkyl, $C_3$–$C_8$ cycloalkyl, or $C_3$–$C_6$ alkenyl;

R¹⁰ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_8$ alkoxy)carbonyl $C_1$–$C_6$ alkyl, ($C_1$–$C_6$ haloalkoxy)-carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, ($C_3$–$C_8$ cycloalkyl) $C_1$–$C_6$ alkoxycarbonyl $C_1$–$C_6$ alkyl, —CH₂COON—(R¹²)R¹³,—CH($C_1$–$C_4$ alkyl)COON (R¹²)R¹³,—CH₂CON(R¹²)R¹³, —CH($C_1$–$C_4$ alkyl)CON(R¹²)R¹³ (wherein R¹² and R¹³ are as defined above), $C_2$–$C_6$ alkenyloxycarbonyl $C_1$–$C_6$ alkyl, $C_3$–$C_6$ haloalkenyloxycarbonyl $C_1$–$C_6$ alkyl, $C_3$–$C_6$ alkynyloxycarbonyl $C_1$–$C_6$ alkyl, $C_3$–$C_6$ haloalkynyloxycarbonyl $C_1$–$C_6$ alkyl, ($C_1$–$C_6$ alkylthio)carbonyl $C_1$–$C_6$ alkyl, ($C_1$–$C_6$ haloalkylthio)-carbonyl $C_1$–$C_6$ alkyl, ($C_3$–$C_6$ alkenylthio)carbonyl $C_1$–$C_6$ alkyl, ($C_3$–$C_6$ haloalkenylthio)carbonyl $C_1$–$C_6$ alkyl, ($C_3$–$C_6$ alkynylthio)carbonyl $C_1$–$C_6$ alkyl, ($C_3$–$C_6$ haloalkynylthio)carbonyl $C_1$–$C_6$ alkyl, ($C_3$–$C_8$ cycloalkylthio)carbonyl $C_1$–$C_6$ alkyl, ($C_3$–$C_8$ cyclohaloalkylthio)carbonyl $C_1$–$C_6$ alkyl, (($C_3$–$C_8$ cycloalkyl) $C_1$–$C_6$ alkylthio)carbonyl $C_1$–$C_6$ alkyl, di($C_1$–$C_6$ alkyl)C=NO carbonyl $C_1$–$C_6$ alkyl, (optionally substituted benzylthio)-carbonyl $C_1$–$C_6$ alkyl, (optionally substituted phenylthio)-carbonyl $C_1$–$C_6$ alkyl, hydroxy $C_2$–$C_6$ alkoxycarbonyl $C_1$–$C_6$ alkyl, ($C_1$–$C_6$ alkyl)carbonyloxy $C_2$–$C_6$ alkoxycarbonyl $C_1$–$C_6$ alkyl, ($C_1$–$C_6$ alkyl)carbonylamino $C_2$–$C_6$ alkoxycarbonyl $C_1$–$C_6$ alkyl, {($C_1$–$C_6$ alkoxy)carbonyl $C_1$–$C_6$ alkyloxycarbonyl $C_1$–$C_6$ alkyl, hydroxy $C_1$–$C_6$ alkyl, $C_1$–$C_6$ alkoxycarbonyl, $C_1$–$C_6$ haloalkoxycarbonyl, $C_3$–$C_8$ cycloalkoxycarbonyl, $C_3$–$C_6$ alkenyloxycarbonyl, optionally substituted benzyloxycarbonyl, $C_1$–$C_6$ alkylcarbonyl, optionally substituted benzyloxycarbonyl $C_1$–$C_6$ alkyl, optionally substituted phenoxycarbonyl $C_1$–$C_6$ alkyl, optionally substituted furyloxycarbonyl $C_1$–$C_6$ alkyl, optionally substituted furyl $C_1$–$C_6$ alkyloxycarbonyl $C_1$–$C_6$ alkyl, optionally substituted thienyloxycarbonyl $C_1$–$C_6$ alkyl, optionally substituted thienyl $C_1$–$C_6$ alkyloxycarbonyl $C_1$–$C_6$ alkyl, optionally substituted pyrrolyloxycarbonyl $C_1$–$C_6$ alkyl, optionally substituted pyrrolyloxy $C_1$–$C_6$ alkyloxycarbonyl $C_1$–$C_6$ alkyl, optionally substituted imidazoloxycarbonyl $C_1$–$C_6$ alkyl, optionally substituted imidazoyl $C_1$–$C_6$ alkyloxycarbonyl $C_1$–$C_6$ alkyl, optionally substituted pyrazoyloxycarbonyl $C_1$–$C_6$ alkyl, optionally substituted pyrazoyl $C_1$–$C_6$ alkyloxycarbonyl $C_1$–$C_6$ alkyl, optionally substituted thiazoyloxycarbonyl $C_1$–$C_6$ alkyl, optionally substituted thiazoyl $C_1$–$C_6$ alkyloxycarbonyl $C_1$–$C_6$ alkyl, optionally substituted oxazoyloxycarbonyl $C_1$–$C_6$ alkyl, optionally substituted oxazoyl $C_1$–$C_6$ alkyloxycarbonyl $C_1$–$C_6$ alkyl, optionally substituted isothiazoyloxycarbonyl $C_1$–$C_6$ alkyl, optionally substituted isothiazoyl $C_1$–$C_6$ alkyloxycarbonyl $C_1$–$C_6$ alkyl, optionally substituted isoxazoyloxycarbonyl C—CC alkyl, optionally substituted isoxazoyl $C_1$–$C_6$ alkyloxycarbonyl $C_1$–$C_6$ alkyl, optionally substituted pyridyloxycarbonyl $C_1$–$C_6$ alkyl, optionally substituted pyridyl $C_1$–$C_6$ alkyloxycarbonyl $C_1$–$C_6$ alkyl, optionally substituted pyradinyloxycarbonyl $C_1$–$C_6$ alkyl, optionally substituted pyradinyl $C_1$–$C_6$ alkyloxycarbonyl $C_1$–$C_6$ alkyl, optionally substituted pyriaidinyloxycarbonyl $C_1$–$C_6$ alkyl, optionally substituted pyrimidinyl $C_1$–$C_6$ alkyloxycarbonyl $C_1$–$C_6$ alkyl, optionally substituted yridazinyloxycarbonyl $C_1$–$C_6$ alkyl, optionally substituted pyridazinyl $C_1$–$C_6$ alkyloxycarbonyl $C_1$–$C_6$ alkyl, optionally substituted indolidinyloxycarbonyl $C_1$–$C_6$ alkyl, optionally substituted indolidinyl $C_1$–$C_6$ alkyloxycarbonyl $C_1$–$C_6$ alkyl, optionally substituted indolyloxycarbonyl $C_1$–$C_6$ alkyl, optionally substituted indolyl $C_1$–$C_6$ alkyloxycarbonyl $C_1$–$C_6$ alkyl, optionally substituted indazolyloxycarbonyl $C_1$–$C_6$ alkyl, optionally substituted indazolyl $C_1$–$C_6$ alkyloxycarbonyl $C_1$–$C_6$ alkyl, optionally substituted quinolyloxycarbonyl $C_1$–$C_6$ alkyl, optionally substituted quinolyl $C_1$–$C_6$ alkyloxycarbonyl $C_1$–$C_6$ alkyl, optionally substituted isoquinolyloxycarbonyl $C_1$–$C_6$ alkyl, or optionally substituted isoquinolyl $C_1$–$C_6$ alkyloxycarbonyl $C_1$–$C_6$ alkyl, or a group of the general formula:

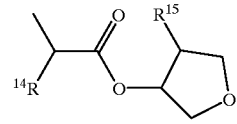

wherein:
R¹⁴ is hydrogen or $C_1$–$C_5$ alkyl; and
R¹⁵ is hydrogen, hydroxyl, or a group of —O—COR¹⁶, wherein:
R¹⁶ is $C_1$–$C_6$ alkyl, $C_1$–$C_6$ haloalkyl, $C_3$–$C_6$ alkenyl, $C_3$–$C_8$ cycloalkyl, optionally substituted phenyl, optionally substituted benzyl, or $C_1$–$C_6$ alkoxy;

or a group of the general formula:

wherein:
R¹⁷ is hydrogen, halogen, or $C_1$–$C_6$ alkyl; and
R¹⁸ is $C_3$–$C_8$ cycloalkyl, benzyl, $C_2$–$C_{10}$ alkyl with an epoxy group, $C_3$–$C_8$ cycloalkyl $C_1$–$C_6$ alkyl, $C_3$–$C_8$ cycloalkyl $C_2$–$C_6$ alkenyl, carboxy $C_2$–$C_6$ alkenyl, ($C_1$–$C_s$ alkoxy)carbonyl $C_2$–$C_6$ alkenyl, ($C_1$–$C_8$ haloalkoxy)carbonyl $C_2$–$C_6$ alkenyl, {($C_1$–$C_4$ alkoxy) $C_1$–$C_4$ alkoxy}carbonyl $C_2$–$C_6$ alkenyl, ($C_3$–$C_8$ cycloalkoxy)-carbonyl $C_2$–$C_6$ alkenyl, $C_1$–$C_6$ alkyl substituted with OR¹⁹ and OR²⁰ on the same carbon atom, $C_2$–$C_6$ alkenyl substituted with OR¹⁹ and OR²⁰ on the same carbon atom, $C_1$–$C_6$ alkyl substituted with $SR^{19}$ and $SR^{20}$ on the same carbon atom, or $C_2$–$C_6$ alkenyl substituted with $SR^{19}$ and $SR^{20}$ on the same carbon atom,
wherein:
$R^{19}$ and $R^{20}$ are independently $C_1$–$C_6$ alkyl, $C_1$–$Cr$ haloalkyl, or $R^{19}$ and $R^{20}$ are taken together to form ethylene optionally substituted with halogen, trimethylene optionally substituted with halogen, tetramethylene optionally substituted with halogen, pentamethylene optionally substituted with halogen, or ethyleneoxyethylene optionally substituted with halogen;

$R^{21}$ is $C_1$–$C_6$ alkyl, $C_1$–$C_6$ haloalkyl, $C_3$–$Cs$ cycloalkyl, $C_3$–$C_6$ alkenyl, $C_3$–$C_6$ haloalkenyl, $C_3$–$C_6$ alkynyl, $C_3$–$C_6$ haloalkynyl, or benzyl;

$R^{22}$ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_8$ alkoxy)carbonyl $C_1$–$C_6$ alkyl, ($C_1$–$C_6$ haloalkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, ($C_1$–$C_6$ alkyl)-carbonyl $C_1$–$C_6$ alkyl, ($C_1$–$C_6$ haloalkyl)carbonyl $C_1$–$C_6$ alkyl, {($C_1$–$C_4$ alkoxy) $C_1$–$C_4$ alkyl}carbonyl $C_1$–$C_6$ alkyl, ($C_3$–$C_8$ cycloalkyl)carbonyl $C_1$–$C_6$ alkyl, {($C_1$–$C_6$ alkoxy)carbonyl $C_1$–$C_6$ alkyl}oxycarbonyl $C_1$–$C_6$ alkyl, hydroxy $C_1$–$C_6$ alkyl, —$CH_2$—$COON(R^{26})R^{27}$, —$CH(C_1$–$C_4$ alkyl) COON $(R^{26})R^{27}$, —$CH_2CON$—$(R^{26})R^{27}$, or —$CH(C_1$–$C_4$ alkyl)$CON(R^{26})R^{27}$,
wherein:
$R^{26}$ and $R^{27}$ are independently hydrogen, $C_1$–$C_6$ alkyl, $C_1$–$C_6$ haloalkyl, $C_3$–$C_6$ alkenyl, $C_3$–$C_6$ alkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_6$ alkoxy)carbonyl $C_1$–$C_6$ alkyl, ($C_3$–$C_8$ cycloalkoxy)-carbonyl $C_1$–$C_6$ alkyl, or {($C_1$–$C_4$ alkoxy) $C_1$–$C_4$ alkyl}-carbonyl $C_1$–$C_6$ alkyl, or $R^{26}$ and $R^{27}$ are taken together to form tetramethylene, pentamethylene, or ethyleneoxyethylene; $R^{23}$ and $R^{24}$ are independently hydrogen or $C_1$–$C_6$ alkyl; and $R^{25}$ is hydrogen, $C_1$–$C_6$ alkyl, $C_1$–$C_6$ haloalkyl, $C_3$–$C_8$ cycloalkyl, or $C_3$–$C_6$ alkenyl; and herbicides containing them as active ingredients.

DETAILED DESCRIPTION OF THE INVENTION

The $C_1$–$C_3$ alkyl represented by $R^1$ may include methyl and ethyl.

The $C_1$–$C_3$ haloalkyl represented by $R^2$ may include trichloromethyl, trifluoromethyl, chlorodifluoromethyl, pentafluoroethyl, and 1,1-difluoroethyl.

The $C_1$–$C_3$ alkyl represented by $E^1$, $E^2$, $E^3$, $E^4$, $E^5$, $E^6$, $E^7$, $E^8$, $E^9$, $E^{10}E^{11}$, or $E^{12}$ may include methyl, ethyl, propyl, and isopropyl.

The halogen represented by B may include fluorine, chlorine, bromine, and iodine.

The halogen, represented by X or Y may include fluorine, chlorine, bromine, and iodine.

The $C_1$–$C_3$ alkyl represented by $R^4$ may include methyl and ethyl.

The $C_1$–$C_6$ alkyl represented by $R^5$ may include methyl, ethyl, propyl, isopropyl, isobutyl, butyl, t-butyl (wherein "t-" means "tertiary-" and this is hereinafter used in the same meaning), and isoamyl.

The $C_1$–$C_6$ haloalkyl represented by $R^5$ may include 2-fluoroethyl, 2-chloroethyl, 2-bromoethyl, 3-chlorobutyl, 3-bromobutyl, and difluoromethyl.

The ($C_3$–$C_8$ cycloalkyl) $C_1$–$C_6$ alkyl represented by $R^5$ may include cyclopentylmethyl.

The $C_3$–$C_6$ alkenyl represented by $R^5$ may include allyl, 1-methyl-2-propenyl, 3-butenyl, 2-butenyl, 3-methyl-2-butenyl, and 2-methyl-3-butenyl.

The $C_3$–$C_6$ haloalkenyl represented by $R^5$ may include 2-chloro-2-propenyl and 3,3-dichloro-2-propenyl.

The $C_3$–$C_6$ alkynyl represented by $R^5$ may include propargyl, 1-methyl-2-propynyl, 2-butynyl, 3-butynyl, and 1,1-dimethyl-2-propynyl.

The $C_3$–$C_6$ haloalkynyl represented by $R^5$ may include 3-iodo-2-propynyl and 3-bromo-2-propynyl.

The cyano $C_1$–$C_6$ alkyl represented by $R^5$ may include cyanomethyl and cyanoethyl.

The $C_1$–$C_4$ alkoxy $C_1$–$C_4$ alkyl represented by $R^5$ may include methoxymethyl, 1-methoxyethyl, and ethoxyethyl.

The $C_1$–$C_3$ alkoxy $C_1$–$C_3$ alkoxy $C_1$–$C_3$ alkyl represented by $R^5$ may include methoxymethoxymethyl, methoxyethoxymethyl, and ethoxymethoxymethyl.

The carboxy $C_1$–$C_6$ alkyl represented by $R^5$ may include carboxymethyl, 1-carboxyethyl, and 2-carboxyethyl.

The ($C_1$–$C_6$ alkoxy)carbonyl $C_1$–$C_6$ alkyl represented by $R^5$ may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, and 1-isoamyloxycarbonylethyl.

The {($C_1$–$C_4$ alkoxy) $C_1$–$C_4$ alkoxy}carbonyl $C_1$–$C_6$ alkyl represented by $R^5$ may include methoxyethoxycarbonylmethyl and 1-methoxymethoxycarbonylethyl.

The ($C_3$–$C_8$ cycloalkoxy)carbonyl $C_1$–$C_6$ alkyl represented by $R^5$ may include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, and 1-cyclohexyloxycarbonylethyl.

The hydroxy $C_1$–$C_6$ alkyl represented by $R^5$ may include hydroxymethyl, hydroxyethyl, and hydroxypropyl.

The $C_1$–$C_4$ alkylthio $C_1$–$C_4$ alkyl represented by $R^5$ may include methylthiomethyl, 1-methylthioethyl, and ethylthiomethyl. s The $C_1$–$C_6$ alkyl represented by $R^9$ may include methyl, ethyl, and isopropyl.

The $C_1$–$C_6$ haloalkyl represented by $R^9$ may include chloromethyl, trichloromethyl, and trifluoromethyl.

The $C_3$–$C_8$ cycloalkyl represented by $R^9$ may include cyclopropyl, cyclobutyl, cyclopentyl, and cyclohexyl.

The $C_3$–$C_6$ alkenyl represented by $R^9$ may include allyl, 1-methyl-2 -propenyl, 3-butenyl, 2-butenyl, 3-methyl-2-butenyl, and 2-methyl-3-butenyl.

The $C_1$–$C_6$ alkyl represented by $R^{10}$ may include methyl, ethyl, propyl, isopropyl, isobutyl, butyl, t-butyl, amyl, isoamyl, and t-amyl.

The $C_1$–$C_6$ haloalkyl represented by $R^{10}$ may include 2-fluoroethyl, 2-chloroethyl, 2-bromoethyl, and 2,2,2-trifluoroethyl.

The $C_3$–$C_8$ cycloalkyl represented by $R^{10}$ may include cyclopropyl, cyclobutyl, cyclopentyl, and cyclohexyl.

The $C_3$–$C_6$ alkenyl represented by $R^{10}$ may include allyl, 1-methyl-2-propenyl, 3-butenyl, 2-butenyl, 3-methyl-2-butenyl, and 2-methyl-3-butenyl.

The $C_3$–$C_6$ haloalkenyl represented by $R^{10}$ may include 2-chloro-2-propenyl and 3,3-dichloro-2-propenyl.

The $C_3$–$C_6$ alkynyl represented by $R^{10}$ may include propargyl, 1-methyl-2-propynyl, 2-butynyl, and 1,1-dimethyl-2-propynyl.

The $C_3$–$C_6$ haloalkynyl represented by $R^{10}$ may include 3-bromopropargyl.

The cyano $C_1$–$C_6$ alkyl represented by $R^{10}$ may include cyanomethyl.

The $C_1$–$C_4$ alkoxy $C_1$–$C_4$ alkyl represented by $R^{10}$ may include methoxymethyl, methoxyethyl, ethoxymethyl, and ethoxyethyl.

The $C_1$–$C_4$ alkylthio $C_1$–$C_4$ alkyl represented by $R^{10}$ may include methylthiomethyl and methylthioethyl.

The carboxy $C_1$–$C_6$ alkyl represented by $R^{10}$ may include carboxymethyl, 1-carboxyethyl, and 2-carboxyethyl.

The ($C_1$–$C_8$ alkoxy)carbonyl $C_1$–$C_6$ alkyl represented by $R^{10}$ may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

The {($C_1$–$C_4$ alkoxy) $C_1$–$C_4$ alkoxy}carbonyl $C_1$–$C_6$ alkyl represented by $R^{10}$ may include methoxymethoxycarbonylmethyl, methoxyethoxycarbonylmethyl, and 1-methoxyethoxycarbonylethyl.

The ($C_3$–$C_8$ cycloalkoxy)carbonyl $C_1$–$C_6$ alkyl represented by $R^{10}$ may include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, and 1-cyclohexyloxycarbonylethyl.

The $C_1$–$C_6$ alkoxycarbonyl represented by $R^{10}$ may include methoxycarbonyl, ethoxycarbonyl, propoxycarbonyl, butoxycarbonyl, isopropoxycarbonyl, isobutoxycarbonyl, and t-butoxycarbonyl.

The $C_1$–$C_6$ haloalkoxycarbonyl represented by $R^{10}$ may include 2,2,2-trichloroethoxycarbonyl.

The $C_3$–$C_8$ cycloalkoxycarbonyl represented by $RI^0$ may include cyclopropyloxycarbonyl and cyclobutyloxycarbonyl.

The $C_3$–$C_6$ alkenyloxycarbonyl represented by $R^{10}$ may include allyloxycarbonyl.

The {($C_1$–$C_6$ alkoxy)carbonyl $C_1$–$C_6$ alkyl}oxycarbonyl $C_1$–$C_6$ alkyl represented by $R^{10}$ may include (methoxycarbonyl)methoxycarbonylmethyl and (ethoxycarbonyl)methoxycarbonylmethyl.

The $C_1$–$C_6$ alkyl represented by $R^{11}$ may include methyl, ethyl, and isopropyl.

The $C_3$–$C_8$ cycloalkyl represented by $R^{11}$ may include cyclopropyl, cyclobutyl, cyclopentyl, and cyclohexyl.

The $C_3$–$C_6$ alkenyl represented by $R^{11}$ may include allyl, 1-methyl-2-propenyl, 3-butenyl, 2-butenyl, 3-methyl-2-butenyl, and 2-methyl-3-butenyl.

The $C_1$–$C_6$ alkyl represented by $R^{12}$ or $R^{13}$ may include methyl, ethyl, propyl, isopropyl, butyl, and isobutyl.

The $C_3$–$C_8$ cycloalkyl represented by $R^{12}$ or $R^{13}$ may include cyclopropyl, cyclobutyl, cyclopentyl, and cyclohexyl.

The $C_1$–$C_6$ haloalkyl represented by $R^{12}$ or $R^{13}$ may include fluoroethyl, chloroethyl, and bromoethyl.

The $C_3$–$C_6$ alkenyl represented by $R^{12}$ or $R^{13}$ may include allyl, 1-methyl-2-propenyl, 3-butenyl, 2-butenyl, 3-methyl-2-butenyl, and 2-methyl-3-butenyl.

The $C_3$–$C_6$ alkynyl represented by $R^{12}$ or $R^{13}$ may include propargyl, 1-methyl-2-propynyl, 2-butynyl, and 1,1-dimethyl-2-propynyl.

The cyano $C_1$–$C_6$ alkyl represented by $R^{12}$ or $R^{13}$ may include cyanomethyl and cyanoethyl.

The $C_1$–$C_4$ alkoxy $C_1$–$C_4$ alkyl represented by $R^{12}$ or $R^{13}$ may include methoxymethyl, methoxyethyl, ethoxymethyl, and ethoxyethyl.

The $C_1$–$C_4$ alkylthio $C_1$–$C_4$ alkyl represented by $R^{12}$ or $R^{13}$ may include methylthiomethyl and methylthioethyl.

The carboxy $C_1$–$C_6$ alkyl represented by $R^{12}$ or $R^{13}$ may include carboxymethyl, 1-carboxyethyl, and 2-carboxyethyl.

The ($C_1$–$C_6$ alkoxy)carbonyl $C_1$–$C_6$ alkyl represented by $R^{12}$ or $R^{13}$ may include methoxycarbonylmethyl, ethoxycarbonylmethyl, propoxycarbonylmethyl, isoporpoxycarbonylmethyl, butoxycarbonylmethyl, isobutoxycarbonylmethyl, t-butoxycarbonylmethyl, amyloxycabronylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

The ($C_3$–$C_8$ cycloalkoxy)carbonyl $C_1$–$C_6$ alkyl represented by $R^{12}$ or $R^{13}$ may include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, and 1-cyclohexyloxycarbonylethyl.

The ($C_1$–$C_6$ alkyl)carbonyloxy $C_2$–$C_6$ alkyl represented by $R^{12}$ or $R^{13}$ may include methylcarbonyloxyethyl and ethylcarbonyloxyethyl.

The ($C_1$–$C_6$ alkyl)carbonylamino $C_2$–$C_6$ alkyl represented by $R^{12}$ or $R^{13}$ may include methylcarbonylaminoethyl and ethylcarbonylaminoethyl.

The hydroxy $C_2$–$C_6$ alkyl represented by $R^{12}$ or $R^{13}$ may include hydroxyethyl and hydroxypropyl.

The optionally substituted benzyl represented by $R^{12}$ or $R^{13}$ may include benzyl.

The optionally substituted phenyl represented by $R^{12}$ or $R^{13}$ may include phenyl.

The {($C_1$–$C_4$ alkoxy) $C_1$–$C_4$ alkyl}carbonyl $C_1$–$C_6$ alkyl represented by $R^{12}$ or $R^{13}$ may include methoxymethylcarbonylmethyl and 1-methoxymethoxycarbonylethyl.

The $C_1$–$C_5$ alkyl represented by $R^{14}$ may include methyl and ethyl.

The $C_1$–$C_6$ alkyl represented by $R^{16}$ may include methyl, ethyl, and isopropyl.

The $C_1-C_6$ haloalkyl represented by $R^{16}$ may include trichloromethyl and trifluoromethyl.

The $C_3-C_6$ alkenyl represented by $R^{16}$ may include allyl, 1-methyl-2-propenyl, 3-butenyl, 2-butenyl, 3-methyl-2-butenyl, and 2-methyl-3-butenyl.

The $C_3-C_8$ cycloalkyl represented by $R^{16}$ may include cyclopropyl, cyclobutyl, cyclopentyl, and cyclohexyl.

The optionally substituted phenyl represented by $R^{16}$ may include phenyl.

The optionally substituted benzyl represented by $R^{16}$ may include benzyl.

The $C_1-C_6$ alkoxy represented by $R^{16}$ may include methoxy and ethoxy.

The halogen represented by $R^{17}$ may include fluorine, chlorine, bromine, and iodine.

The $C_1-C_6$ alkyl represented by $R^{17}$ may include methyl, ethyl, and isopropyl.

The $C_3-C_8$ cycloalkyl represented by $R^{18}$ may include cyclopropyl, cyclobutyl, cyclopentyl, and cyclohexyl.

The $C_2-C_{10}$ alkyl with an epoxy group represented by $R^{18}$ may include 2-oxyranyl and 2-oxyranylmethyl.

The $C_3-C_8$ cycloalkyl $C_1-C_6$ alkyl represented by $R^{18}$ may include cyclopentylmethyl, cyclohexylmethyl, and cyclopropylethyl.

The $C_3-C_8$ cycloalkyl $C_2-C_6$ alkenyl represented by $R^{18}$ may include 3-cyclopentylallyl.

The $C_1-C_6$ alkyl substituted with $OR^{19}$ and $OR^{20}$ on the same carbon atom, which is represented by $R^{18}$, may include —CH($OR^{19}$)($OR^{20}$) and —CH$_2$—CH($OR^{19}$)($OR^{20}$).

The $C_1-C_6$ alkyl substituted with $SR^{19}$ and $SR^{20}$ on the same carbon atom, which is represented by $R^{18}$, may include —CH($SR^{19}$)($SR^{20}$) and —CH$_2$—CH($SR^{19}$)($SR^{20}$).

The carboxy $C_2-C_6$ alkenyl represented by $R^{18}$ may include 3-carboxyallyl.

The ($C_1-C_8$ alkoxy)carbonyl $C_2-C_6$ alkenyl represented by $R^{18}$ may include 3-methoxycarbonylallyl and 3-ethoxycarbonylallyl.

The ($C_1-C_8$ haloalkoxy)carbonyl $C_2-C_6$ alkenyl represented by $R^{18}$ may include 3-(2-fluoroethoxy)carbonylallyl.

The {($C_1-C_4$ alkoxy) $C_1-C_4$ alkoxy}carbonyl $C_2-C_6$ alkenyl represented by $R^{18}$ may include 3-(2-methoxyethoxy)carbonylallyl.

The $C_1-C_6$ alkyl represented by $R^{19}$ or $R^{20}$ may include methyl, ethyl, propyl, isopropyl, butyl, and isobutyl.

The $C_1-C_6$ haloalkyl represented by $R^{19}$ or $R^{20}$ may include 2-chloroethyl and 2-fluoroethyl.

The $C_1-C_6$ alkyl represented by $R^{21}$ may include methyl and ethyl.

The $C_1-C_6$ haloalkyl represented by $R^{21}$ may include fluoroethyl, chloroethyl, and bromoethyl.

The $C_3-C_8$ cycloalkyl represented by $R^{21}$ may include cyclopropyl, cyclobutyl, cyclopentyl, and cyclohexyl.

The $C_3-C_6$ alkenyl represented by $R^{21}$ may include allyl, 1-methyl-2-propenyl, 3-butenyl, 2-butenyl, 3-methyl-2-butenyl, and 2-methyl-3-butenyl.

The $C_3-C_6$ haloalkenyl represented by $R^{21}$ may include 2-chloro-2-propenyl and 3,3-dichloro-2-propenyl.

The $C_3-C_6$ alkynyl represented by $R^{21}$ may include propargyl, 1-methyl-2-propynyl, 2-butynyl, and 1,1-dimethyl-2-propynyl.

The $C_3-C_6$ haloalkynyl represented by $R^{21}$ may include 3-bromopropargyl.

The $C_1-C_6$ alkyl represented by $R^{22}$ may include methyl, ethyl, propyl, isopropyl, isobutyl, butyl, t-butyl, amyl, isoamyl, and t-amyl.

The $C_1-C_6$ haloalkyl represented by $R^{22}$ may include 2-chloroethyl, 2-bromoethyl, and 2,2,2-trifluoroethyl.

The $C_3-C_8$ cycloalkyl represented by $R^{22}$ may include cyclopropyl, cyclobutyl, cyclopentyl, and cyclohexyl.

The $C_3-C_6$ alkenyl represented by $R^{22}$ may include allyl, 1-methyl-2-propenyl, 3-butenyl, 2-butenyl, 3-methyl-2-butenyl, and 2-methyl-3-butenyl.

The $C_3-C_6$ haloalkenyl represented by $R^{22}$ may include 2-chloro-2-propenyl, and 3,3-dichloro-2-propenyl.

The $C_3-C_6$ alkynyl represented by $R^{22}$ may include propargyl, 1-methyl-2-propynyl, and 2-butynyl.

The $C_3-C_6$ haloalkynyl represented by $R^{22}$ may include 3-bromopropargyl.

The cyano $C_1-C_6$ alkyl represented by $R^{22}$ may include cyanoethyl.

The $C_1-C_4$ alkoxy $C_1-C_4$ alkyl represented by $R^{22}$ may include methoxymethyl, methoxyethyl, ethoxymethyl, and ethoxyethyl.

The $C_1-C_4$ alkylthio $C_1-C_4$ alkyl represented by $R^{22}$ may include methylthioethyl.

The carboxy $C_1-C_6$ alkyl represented by $R^{22}$ may include carboxymethyl, 1-carboxyethyl, and 2-carboxyethyl.

The ($C_1-C_8$ alkoxy)carbonyl $C_1-C_6$ alkyl represented by $R^{22}$ may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

The ($C_1-C_6$ haloalkoxy)carbonyl $C_1-C_6$ alkyl represented by $R^{22}$ may include chloroethoxycarbonylmethyl.

The {($C_1-C_4$ alkoxy) $C_1-C_4$ alkoxy}carbonyl $C_1-C_6$ alkyl represented by $R^{22}$ may include methoxymethoxycarbonylmethyl, methoxyethoxycarbonylmethyl, and 1-methoxyethoxycarbonylethyl.

The ($C_3-C_8$ cycloalkoxy)carbonyl $C_1-C_6$ alkyl represented by $R^{22}$ may include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, and 1-cyclohexyloxycarbonylethyl.

The $C_1-C_6$ alkyl represented by $R^{23}$ or $R^{24}$ may include methyl and ethyl.

The $C_1-C_6$ alkyl represented by $R^{25}$ may include methyl, ethyl, propyl, isopropyl, isobutyl, butyl, t-butyl, amyl, isoamyl, and t-amyl.

The $C_1-C_6$ haloalkyl represented by $R^{25}$ may include 2-chloroethyl, 2-bromoethyl, and 2,2,2-trifluoroethyl.

The $C_3-C_8$ cycloalkyl represented by $R^{25}$ may include cyclopropyl, cyclobutyl, cyclopentyl, and cyclohexyl.

The $C_3-C_6$ alkenyl represented by $R^{25}$ may include allyl, 1-methyl-2-propenyl, 3-butenyl, 2-butenyl, 3-methyl-2-butenyl, and 2-methyl-3-butenyl.

The $C_1-C_6$ alkyl represented by $R^{26}$ or $R^{27}$ may include methyl, ethyl, propyl, and isopropyl.

The $C_1$–$C_6$ haloalkyl represented by $R^{26}$ or $R^{27}$ may include chloroethyl and bromoethyl.

The $C_3$–$C_6$ alkenyl represented by $R^{26}$ or $R^{27}$ may include allyl, 1-methyl-2-propenyl, 3-butenyl, 2-butenyl, 3-methyl-2-butenyl, and 2-methyl-3-butenyl.

The $C_3$–$C_6$ alkynyl represented by $R^{26}$ or $R^{27}$ may include propargyl, 1-methyl-2-propynyl, 2-butynyl, and 1,1-dimethyl-2-propynyl.

The cyano $C_1$–$C_6$ alkyl represented by $R^{26}$ or $R^{27}$ may include cyanomethyl and cyanoethyl.

The $C_1$–$C_4$ alkoxy $C_1$–$C_4$ alkyl represented by $R^{26}$ or $R^{27}$ may include methoxymethyl, methoxyethyl, ethoxymethyl, and ethoxyethyl.

The $C_1$–$C_4$ alkylthio $C_1$–$C_4$ alkyl represented by $R^{26}$ or $R^{27}$ may include methylthiomethyl and methylthioethyl.

The carboxy $C_1$–$C_6$ alkyl represented by $R^{26}$ or $R^{27}$ may include carboxymethyl, 1-carboxyethyl, and 2-carboxyethyl.

The ($C_1$–$C_6$ alkoxy)carbonyl $C_1$–$C_6$ alkyl represented by $R^{26}$ or $R^{27}$ may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

The ($C_3$–$C_8$ cycloalkoxy)carbonyl $C_1$–$C_6$ alkyl represented by $R^{26}$ or $R^{27}$ may include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, and 1-cyclohexyloxycarbonylethyl.

The {($C_1$–$C_4$ alkoxy) $C_1$–$C_4$ alkyl}carbonyl $C_1$–$C_6$ alkyl represented by $R^{26}$ or $R^{27}$ may include methoxymethylcarbonylmethyl and 1-methoxymethylcarbonylethyl.

The $C_1$–$C_6$ alkyl represented by $R^{28}$ or $R^{29}$ may include methyl, ethyl, propyl, and isopropyl.

The $C_1$–$C_6$ haloalkyl represented by $R^{28}$ or $R^{29}$ may include chloromethyl and chloroethyl.

The $C_1$–$C_6$ alkyl represented by $R^{30}$ may include methyl, ethyl, propyl, isopropyl, isobutyl, butyl, t-butyl, amyl, isoamyl, and t-amyl.

The $C_3$–$C_6$ alkenyl represented by $R^{30}$ may include allyl, 1-methyl-2-propenyl, 3-butenyl, 2-butenyl, 3-methyl-2-butenyl, and 2-methyl-3-butenyl.

The $C_3$–$C_6$ alkynyl represented by $R^{30}$ may include propargyl, 1-methyl-2-propynyl, 2-butynyl, and 1,1-dimethyl-2-propynyl.

The $C_1$–$C_6$ alkyl represented by $R^{31}$ may include methyl, ethyl, propyl, isopropyl, isobutyl, butyl, t-butyl, amyl, isoamyl, and t-amyl.

The $C_1$–$C_6$ haloalkyl represented by $R^{31}$ may include 2-chloroethyl, 2-bromoethyl, and 2,2,2-trifluoroethyl.

The $C_3$–$C_6$ alkenyl represented by $R^3$ may include allyl, 1-methyl-2-propenyl, 3-butenyl, 2-butenyl, 3-methyl-2-butenyl, and 2-methyl-3-butenyl.

The $C_3$–$C_6$ haloalkenyl represented by $R^{31}$ may include 2-chloro-2-propenyl and 3,3-dichloro-2-propenyl.

The $C_3$–$C_6$ alkynyl represented by $R^{31}$ may include propargyl, 1-methyl-2-propynyl, 2-butynyl, and 1,1-dimethyl-2-propynyl.

The cyano $C_1$–$C_6$ alkyl represented by $R^{31}$ may include cyanomethyl.

The $C_2$–$C_8$ alkoxyalkyl represented by $R^{31}$ may include methoxymethyl, methoxyethyl, ethoxymethyl, and ethoxyethyl.

The $C_2$–$C_8$ alkylthioalkyl represented by $R^{31}$ may include methylthiomethyl and methylthioethyl.

The carboxy $C_1$–$C_6$ alkyl represented by $R^{31}$ may include carboxymethyl, 1-carboxyethyl, and 2-carboxyethyl.

The ($C_1$–$C_6$ alkoxy)carbonyl Cr-$C_6$ alkyl represented by $R^{31}$ may include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

The ($C_3$–$C_8$ cycloalkoxy)carbonyl $C_1$–$C_6$ alkyl represented by $R^{31}$ may include cyclobutyloxycarbonylmethyl, cyclopentyloxycarbonylmethyl, cyclohexyloxycarbonylmethyl, cyclobutyloxycarbonylethyl, cyclopentyloxycarbonylethyl, and cyclohexyloxycarbonylethyl.

The {($C_1$–$C_4$ alkoxy) $C_1$–$C_4$ alkoxy}carbonyl $C_1$–$C_6$ alkyl represented by $R^{31}$ may include methoxymethoxycarbonylmethyl, methoxyethoxycarbonylmethyl, and 1-methoxyethoxycarbonylethyl.

The $C_1$–$C_6$ alkyl represented by $R^{32}$ may include methyl, ethyl, propyl, isopropyl, isobutyl, butyl, t-butyl, amyl, isoamyl, and t-amyl.

The $C_3$–$C_8$ cycloalkyl represented by $R^{32}$ may include cyclopropyl, cyclobutyl, cyclopentyl, and cyclohexyl.

The $C_3$–$C_6$ alkenyl represented by $R^{32}$ may include allyl, 1-methyl-2-propenyl, 3-butenyl, 2-butenyl, 3-methyl-2-butenyl, and 2-methyl-3-butenyl.

For the present compounds, there may exist geometrical isomers based on the double bond, and optical isomers or diastereomers based on the asymmetric carbon atom. These isomers and their mixtures are included in the present compounds.

In the present compounds, the substituent groups preferred in view of herbicidal activity may include fluorine-substituted methyl (e.g., trifluoromethyl, chlorodifluoromethyl) and fluorine-substituted ethyl (e.g., pentafluoroethyl, 1,1-difluoroethyl) for $R^{2;\ and\ Q\text{-}}$1, and Q-2, for Q. When Q is Q-1, compounds with hydrogen or fluorine for X and chlorine for Y are more preferred. When Q is Q-2, compounds with fluorine or hydrogen for X, oxygen for $Z^1$, hydrogen for $R^4$, and n=1 are more preferred. In these compounds, still more preferred are those which further have $C_3$–$C_6$ alkynyl for $R^5$. Compounds with a combination of the above preferred substituent groups are more preferred in view of herbicidal activity.

The following are specific examples of the preferred compounds of the present invention in view of herbicidal activity. The numbers in parentheses after the compound names are corresponding to the compound numbers in Tables 1 to 248 below.

7-Fluoro-6-[7-oxo-5-trifluoromethyl-2,3,7,8-tetrahydroimidazo[1,2-a]-pyrimidin-8-yl]-4-propargyl-3,4-dihydro-2H-1,4-benzoxadin-3-one (2–26)

6-[7-Oxo-5-trifluoromethyl-2,3,7,8-tetrahydroimidazo[1,2-a]pyrimidin-8-yl]-4-propargyl-3,4-dihydro-2H-1,4-benzoxadin-3-one (2–25)

6-Fluoro-5-[7-oxo-5-trifluoromethyl-2,3,7,8-tetrahydroimidazo[1,2-a]-pyrimidin-8-yl]-3-propargyl-2,3-dihydro-1,3-benzothiazol-2-one (2–164)

5-[7-Oxo-5-trifluoromethyl-2,3,7,8-tetrahydroimidazo[1,2-a]pyrimidin-8-yl]-3-propargyl-2,3-dihydro-1,3-benzothiazol-2-one (2–163)

8-(4-Chloro-2-fluoro-5-methoxyphenyl)-5-trifluoromethyl-2,3,7,8-tetrahydroimidazo[1,2-a]pyrimidin-7-one (1–262)

8-(4-Chloro-2-fluoro-5-ethoxyphenyl)-5-trifluoromethyl-2,3,7,8-tetra-3hydroimidazo [1,2-a] pyrimidin-7-one (1–268)

8-(4-Chloro-2-fluoro-5-isopropoxyphenyl)-5-trifluoromethyl-2,3,7,8-tetrahydroimidazo[1,2-a]pyrimidin-7-one (1–274)

8-(4-Chloro-2-fluoro-5-propargyloxyphenyl)-5-trifluoromethyl-2,3,7,8-tetrahydroimidazo[1,2-a]pyrimidin-7-one (1–340)

8-(4-Chloro-2-fluoro-5-(1-methylpropargyloxy)phenyl)-5-trifluoromethyl-2,3,7,8-tetrahydroimidazo[1,2-a]pyrimidin-7-one (1–346)

{2-Chloro-4-fluoro-5-(7-oxo-5-trifluoromethyl-2,3,7,8-tetrahydroimidazo[1,2-a]pyrimidin-8-yl)phenoxy}acetic acid methyl ester (1–400)

{2-Chloro-4-fluoro-5-(7-oxo-5-trifluoromethyl-2,3,7,8-tetrahydroimidazo[1,2-a]pyrimidin-8-yl)phenoxy} acetic acid ethyl ester (1–406)

{2-Chloro-4-fluoro-5-(7-oxo-5-trifluoromethyl-2,3,7,8-tetrahydroimidazo[1,2-a]pyrimidin-8-yl)phenoxy}acetic acid isopropyl ester (1–430)

2-{2-Chloro-4-fluoro-5-(7-oxo-5-trifluoromethyl-2,3,7,8-tetrahydroimidazo[1,2-a]pyrimidin-8-yl)phenoxy}propionic acid methyl ester (1–454)

2-{2-Chloro-4-fluoro-5-(7-oxo-5-trifluoromethyl-2,3,7,8-tetrahydroimidazo[1,2-a]pyrimidin-8-yl)phenoxy}propionic acid ethyl ester (1–460)

2-{2-Chloro-4-fluoro-5-(7-oxo-5-trifluoromethyl-2,3,7,8-tetrahydroimidazo[1,2-a]pyrimidin-8-yl)phenoxy}propionic acid isopropyl ester (1–484)

{2-Chloro-4-fluoro-5-(7-oxo-5-trifluoromethyl-2,3,7,8-tetrahydroimidazo[1,2-a]pyrimidin-8-yl)phenylthio}acetic acid methyl ester (1–706)

{2-Chloro-4-fluoro-5-(7-oxo-5-trifluoromethyl-2,3,7,8-tetrahydroimidazo[1,2-a]pyrimidin-8-yl)phenylthio}acetic acid ethyl ester (1–712) 2-{2-Chloro-4-fluoro-5-(7-oxo-5-trifluoromethyl-2,3,7,8-tetrahydroimidazo[1,2-a]pyrimidin-8-yl)phenylthio}propionic acid methyl ester (1–760)

2-{2-Chloro-4-fluoro-5-(7-oxo-5-trifluoromethyl-2,3,7,8-tetrahydroimidazo[1,2-a]pyrimidin-8-yl)phenylthio}propionic acid ethyl ester (1–766)

{2-Chloro-4-fluoro-5-(7-oxo-5-trifluoromethyl-2,3,7,8-tetrahydroimidazo[1,2-a]pyrimidin-8-yl)phenylamino}acetic acid methyl ester (1–166)

(2-Chloro-4-fluoro-5-(7-oxo-5-trifluoromethyl-2,3,7,8-tetrahydroimidazo[1,2-a]pyrimidin-8-yl)phenylamino}acetic acid ethyl ester (1–172)

2-{2-Chloro-4-fluoro-5-(7-oxo-5-trifluoromethyl-2,3,7,8-tetrahydroimidazo[1,2-a]pyrimidin-8-yl)phenylamino}propionic acid methyl ester (1–214)

2-{2-Chloro-4-fluoro-5-(7-oxo-5-trifluoromethyl-2,3,7,8-tetrahydroimidazo[1,2-a]pyrimidin-8-yl)phenylamino}propionic acid ethyl ester (1–220)

N-{2-Chloro-4-fluoro-5-(7-oxo-5-trifluoromethyl-2,3,7,8-tetrahydroimidazo[1,2-a]pyrimidin-8-yl)phenyl}methanesulfonamide (1–88)

N-{2-Chloro-4-fluoro-5-(7-oxo-5-trifluoromethyl-2,3,7,8-tetrahydroimidazo[1,2-a]pyrimidin-8-yl)phenyl}chloromethanesulfonamide (1–100)

N-{2-Chloro-5-(7-oxo-5-trifluoromethyl-2,3,7,8-tetrahydroimidazo[1,2-a]pyrimidin-8-yl)phenyl}methanesulfonamide (1–86)

2-Chloro-4-fluoro-5-(7-oxo-5-trifluoromethyl-2,3,7,8-tetrahydroimidazo[1,2-a]pyrimidin-8-yl)benzoic acid methyl ester (1–952)

2-Chloro-4-fluoro-5-(7-oxo-5-trifluoromethyl-2,3,7,8-tetrahydroimidazo[1,2-a]pyrimidin-8-yl)benzoic acid ethyl ester (1–958)

2-Chloro-5-(7-oxo-5-trifluoromethyl-2,3,7,8-tetrahydroimidazo[1,2-a]-pyrimidin-8-yl)benzoic acid methyl ester (1–950)

2-Chloro-5-(7-oxo-5-trifluoromethyl-2,3,7,8-tetrahydroimidazo[1,2-a]-pyrimidin-8-yl)benzoic acid ethyl ester (1–956)

7-Fluoro-6-[7-oxo-5-trifluoromethyl-7,8-dihydroimidazo[1,2-a]pyrimidin-8-yl]-4-propargyl-3,4-dihydro-2H-1,4-benzoxadin-3-one (7–26)

6-[7-Oxo-5-trifluoromethyl-7,8-dihydroimidazo[1,2-a]pyrimidin-8-yl]-4-propargyl-3,4-dihydro-2H-1,4-benzoxadin-3-one (7–25)

6-Fluoro-5-[7-oxo-5-trifluoromethyl-7,8-dihydroimidazo[1,2-a]pyrimidin-8-yl]-3-propargyl-2,3-dihydro-1,3-benzothiazol-2-one (7–164)

5-[7-Oxo-5-trifluoromethyl-7,8-dihydroimidazo[1,2-a]pyrimidin-8-yl]-3-propargyl-2,3-dihydro-1,3-benzothiazol-2-one (7–163)

8-(4-Chloro-2-fluoro-5-isopropoxyphenyl)-5-trifluoromethyl-7,8-dihydroimidazo[1,2-a]pyrimidin-7-one (6–274)

8-(4-Chloro-2-fluoro-5-propargyloxyphenyl)-5-trifluoromethyl-7,8-dihydroimidazo[1,2-a]pyrimidin-7-one (6–340)

8-(4-Chloro-2-fluoro-5-(1-methylpropargyloxy)phenyl)-5-trifluoromethyl-7,8-dihydroimidazo[1,2-a]pyrimidin-7-one (6–346)

{2-Chloro-4-fluoro-5-(7-oxo-5-trifluoromethyl-7,8-dihydroimidazo-[1,2-a]pyrimidin-8-yl)phenoxy}acetic acid methyl ester (6–400)

{2-Chloro-4-fluoro-5-(7-oxo-5-trifluoromethyl-7,8-dihydroimidazo-[1,2-a]pyrimidin-8-yl)phenoxy}acetic acid ethyl ester (6–406)

{2-Chloro-4-fluoro-5-(7-oxo-5-trifluoromethyl-7,8-dihydroimidazo-[1,2-a]pyrimidin-8-yl)phenoxy}acetic acid isopropyl ester (6–430)

2-{2-Chloro-4-fluoro-5-(7-oxo-5-trifluoromethyl-7,8-dihydroimidazo-[1,2-a]pyrimidin-8-yl)phenoxy}propionic acid methyl ester (6–454) 2-{2-Chloro-4-fluoro-5-(7-oxo-5-trifluoromethyl-7,8-dihydroimidazo-[1,2-a]pyrimidin-8-yl)phenoxy}propionic acid ethyl ester (6–460)

2-{2-Chloro-4-fluoro-5-(7-oxo-5-trifluoromethyl-7,8-dihydroimidazo-[1,2-a]pyrimidin-8-yl)phenoxy}propionic acid isopropyl ester (6–484)

{2-Chloro-4-fluoro-5-(7-oxo-5-trifluoromethyl-7,8-dihydroimidazo-[1,2-a]pyrimidin-8-yl)phenylthio}acetic acid methyl ester (6–706)

{2-Chloro-4-fluoro-5-(7-oxo-5-trifluoromethyl-7,8-dihydroimidazo-[1,2-a]pyrimidin-8-yl)phenylthio}acetic acid ethyl ester (6–712)

2-{2-Chloro-4-fluoro-5-(7-oxo-5-trifluoromethyl-7,8-dihydroimidazo-[1,2-a]pyrimidin-8-yl)phenylthio}propionic acid methyl ester (6–760)

2-{2-Chloro-4-fluoro-5-(7-oxo-5-trifluoromethyl-7,8-dihydroimidazo-[1,2-a]pyrimidin-8-yl)phenylthio}propionic acid ethyl ester (6–766)

(2-Chloro-4-fluoro-5-(7-oxo-5-trifluoromethyl-7,8-dihydroimidazo-[1,2-a]pyrimidin-8-yl)phenylamino}acetic acid methyl ester (6–166)

{2-Chloro-4-fluoro-5-(7-oxo-5-trifluoromethyl-7,8-dihydroimidazo-[1,2-a]pyrimidin-8-yl)phenylamino}acetic acid ethyl ester (6–172)

2-{2-Chloro-4-fluoro-5-(7-oxo-5-trifluoromethyl-7,8-dihydroimidazo-[1,2-a]pyrimidin-8-yl)phenylamino}propionic acid methyl ester (6–214)

2-{2-Chloro-4-fluoro-5-(7-oxo-5-trifluoromethyl-7,8-dihydroimidazo-[1,2-a]pyrimidin-8-yl)phenylamino}propionic acid ethyl ester (6–220)

N-{2-Chloro-4-fluoro-5-(7-oxo-5-trifluoromethyl-7,8-dihydroimidazo-[1,2-a]pyrimidin-8-yl)phenyl}methanesulfonamide (6–88)

N-{2-Chloro-4-fluoro-5-(7-oxo-5-trifluoromethyl-7,8-dihydroimidazo-[1,2-a]pyrimidin-8-yl)phenyl}chloromethanesulfonamide (6–100)

N-{2-Chloro-5-(7-oxo-5-trifluoromethyl-7,8-dihydroimidazo[1,2-a]-pyrimidin-8-yl)phenyl}methanesulfonamide (6–86)

2-Chloro-4-fluoro-5-(7-oxo-5-trifluoromethyl-7,8-dihydroimidazo-[1,2-a]pyrimidin-8-yl)benzoic acid methyl ester (6–952)

2-Chloro-4-fluoro-5-(7-oxo-5-trifluoromethyl-7,8-dihydroimidazo-[1,2-a]pyrimidin-8-yl)benzoic acid ethyl ester (6–958)

2-Chloro-5-(7-oxo-5-trifluoromethyl-7,8-dihydroimidazo[1,2-a]-pyrimidin-8-yl)benzoic acid methyl ester (6–950)

2-Chloro-5-(7-oxo-5-trifluoromethyl-7,8-dihydroimidazo[1,2-a]-pyrimidin-8-yl)benzoic acid ethyl ester (6–956)

The present compounds can be produced, for example, according to the following production processes 1 to 16.

Production Process 1

This is the production process in which an aniline derivative of the general formula:

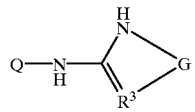

wherein G, Q, and $R^3$ are as defined above, is reacted with an ester derivative of the general formula:

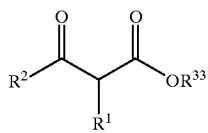

wherein $R^1$ and $R^2$ are as defined above and $R^{33}$ is $C_1$–$C_6$ alky, or an acrylic acid derivative of the general formula:

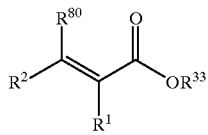

wherein $R^1$, $R^2$, and $R^{33}$ are as defined above and $R^{80}$ is a leaving group such as $C_1$–$C_6$ alkoxy, $C_1$–$C_6$ alkylthio, di($C_1$–$C_3$ alkyl)amino, halogen, $C_1$–$C_6$ alkylsulfonyl, or arylsulfonyl.

The reaction is usually effected without any solvent or in a solvent. The reaction temperature is usually in the range of 50° C. to 200° C. The reaction time is usually in the range of 1 to 100 hours.

The amounts of reagents to be used in the reaction are stoichiometrically 1 mole of the ester derivative or acrylic acid derivative of the above general formula for 1 mole of the aniline derivative of the above general formula, although they may suitably be changed with the reaction conditions.

The solvent which can be used may include aliphatic hydrocarbons such as hexane, heptane, octane, and ligroin; aromatic hydrocarbons such as benzene, toluene, ethylbenzene, xylene, and mesitylene; halogenated hydrocarbons such as chlorobenzene, dichlorobenzene, and trichlorobenzene;

ethers such as 1,4-dioxane, tetrahydrofuran, ethylene glycol dimethyl ether, and methyl t-butyl ether; nitro compounds such as nitromethane and nitrobenzene; acid amides such as N,N-dimethylformamide; sulfur compounds such as dimethylsulfoxide and sulforane; and mixtures thereof. Furthermore, acids such as p-toluenesulfonic acid may be used as the catalyst in the reaction.

After completion of the reaction, the reaction mixture is concentrated without further treatment, or the reaction mixture is poured into water, which is extracted with an organic solvent, and the organic layer is subjected to ordinary post-treatments such as drying and concentration. If necessary, purification may be carried out by an ordinary technique such as recrystallization or column chromatography. Thus the desired present compound can be obtained.

Production Process 2

This is the production process according to the following scheme:

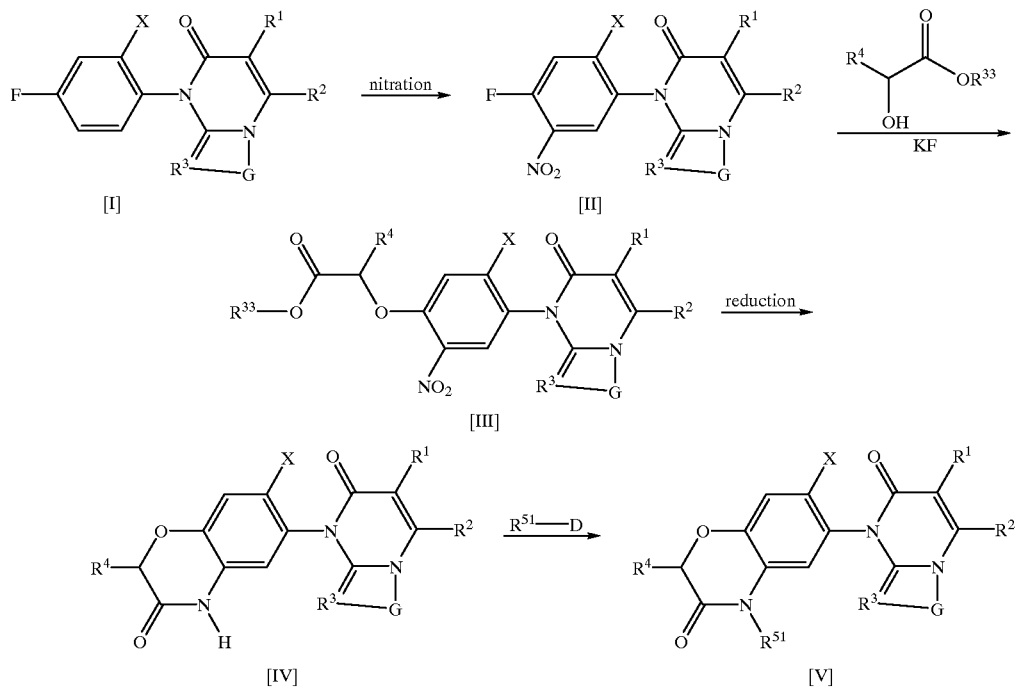

wherein $R^{51}$ is as defined for $R^5$ but not hydrogen; $R^1$, $R^2$, $R^3$, $R^4$, $R^{33}$, X, and G are as defined above; and D is chlorine, bromine, iodine, methanesulfonyloxy, or p-toluenesulfonyloxy.

The reactions in the respective steps can be effected, for example, by the procedures as described in the Japanese Laid-open Patent Publication No. 1-301679, or by the following procedures.

1) Procedure for preparing compound [II] from compound [I]

Compound [II] can be prepared by reacting compound [I] with a nitrating agent in a solvent.

Nitrating agent: nitric acid or the like

Amount of nitrating agent: 1 to 10 moles for 1 mole of compound [I]

Solvent: sulfuric acid or the like

Temperature: −10° C. to room temperature

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [III] from compound [II]

Compound [III] can be prepared by reacting compound [II] with a compound of HOCH($R^4$)COO$R^{33}$ (wherein $R^4$ and $R^{33}$ are as defined above) in the presence of potassium fluoride in a solvent.

Amount of compound of HOCH($R^4$)COO$R^{33}$: 1 to 50 moles for 1 mole of compound [II]

Amount of potassium fluoride: 1 to 50 moles for 1 mole of compound

Solvent: 1,4-dioxane or the like

Temperature: room temperature to heating temperature under reflux

Time: a moment to 96 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

3) Procedure for preparing compound [IV] from compound [III]

Compound [IV] can be prepared by reducing compound [III] with iron powder or the like in the presence of an acid in a solvent.

Amount of iron powder or the like: 3 moles to an excessive amount for 1 mole of compound [III]

Acid: acetic acid or the like

Amount of acid: 1 to 10 moles for 1 mole of compound [III]

Solvent: water, ethyl acetate, or the like

Temperature: room temperature to heating temperature under reflux

Time: a moment to 24 hours

After completion of the reaction, the iron powder or the like is removed by filtration, and the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

4) Procedure for preparing compound [V] from compound [IV]

Compound [V] can be prepared by reacting compound [IV] with a compound of $R^{5'}$-D (wherein $R^{51}$ and D are as defined as above).

The reaction is usually effected in the presence of a base in a solvent.

The reaction temperature is usually in the range of −20° C. to 150° C., preferably 0° C. to 50° C. The reaction time is usually in the range of a moment to 48 hours.

The amounts of reagents to be used in the reaction are usually 1 to 3 moles of the compound of $R^{51}$-D and usually 1 to 2 moles of the base, both for 1 mole of compound [IV].

nary post-treatments such as extraction with an organic solvent and concentration. If necessary, purification may be carried out by an ordinary technique such as column chromatography or recrystallization. Thus the present compound [V] can be isolated.

Compound [III] can also be prepared according to the following scheme:

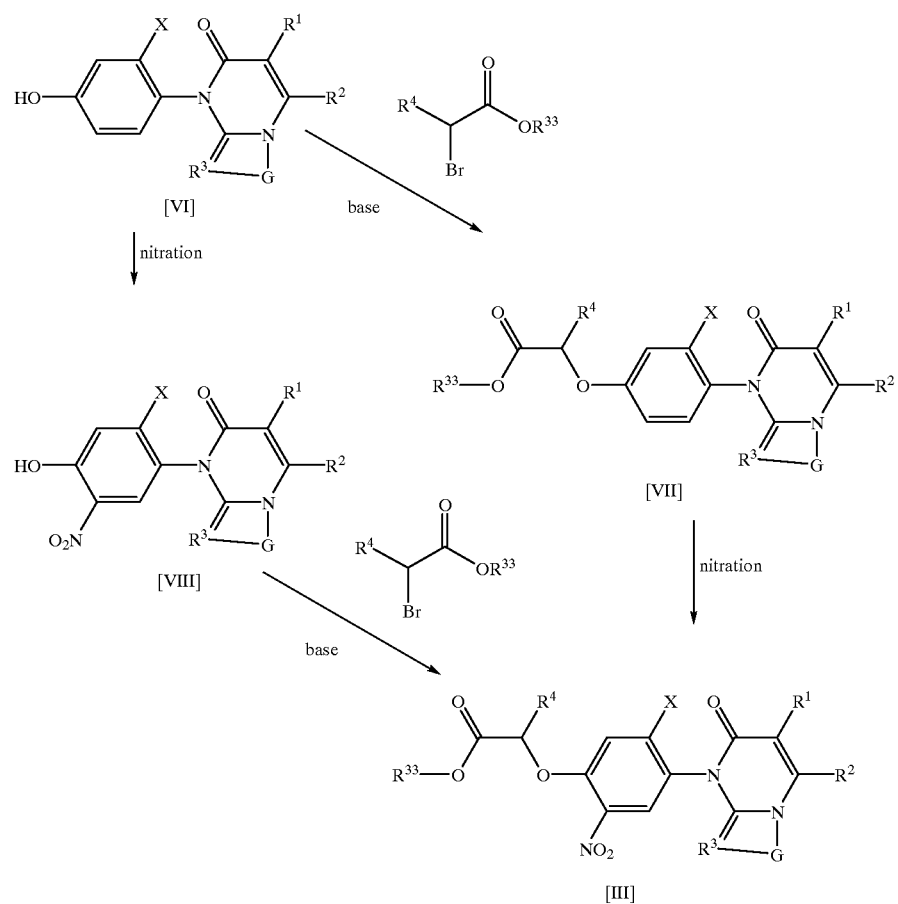

The base which can be used in the reaction may include, for example, inorganic bases such as sodium hydride, potassium hydride, sodium hydroxide, potassium hydroxide, potassium carbonate, and sodium carbonate; and organic bases such as triethylamine, diisopropylethylamine, pyridine, 4-dimethylaminopyridine, N,N-dimethylaniline, and N,N-diethylaniline.

The solvent which can be used in the reaction may include aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, THF, and ethylene glycol adimethyl ether; nitro compounds such as nitrobenzene; acid amides such as N,N-dimethylformamide; tertiary amines such as pyridine, triethylamine, diisopropylethylamine, N,N-dimethylaniline, N,N-diethylaniline, and N-methylmorpholine; and mixtures thereof.

After completion of the reaction, the reaction mixture is poured into water, if necessary, and then subjected to ordiwherein $R^1$, $R^2$, $R^3$, $R^4$, X, G, and $R^3$ are as defined above.

The reaction conditions in the respective steps are, for example, as follows:

1) Procedure for preparing compound [VII] from compound [VI]

Compound [VII] can be prepared by reacting compound [VI] with a compound of $BrCH(R^4)COOR^{33}$ (wherein $R^4$ and $R^3$ are as defined above) in the presence of a base in a solvent.

Amount of compound of $BrCH(R^4)COOR^{33}$: 1 to 2 moles for 1 mole of compound [VI]

Base: sodium hydride, potassium carbonate, or the like

Amount of base: 1 to 2 moles for 1 mole of compound [VI]

Solvent: 1,4-dioxane, N,N-dimethylformamide, or the like

Temperature: 0° C. to 100° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallzation. Thus the desired compound can be isolated.

2) Procedure for preparing compound [III] from compound [VII]

Compound [III] can be prepared by reacting compound [VII] with a nitrating agent in a solvent Nitrating agent: nitric acid or the like Amount of nitrating agent: 1 to 10 moles for 1 mole of compound [VII]

Solvent: sulfuric acid, acetic acid, or the like

Temperature: −10° C. to room temperature

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

3) Procedure for preparing compound [VIII] from compound [VI]

Compound [VIII] can be prepared by reacting compound [VI] with a nitrating agent in a solvent.

Nitrating agent: nitric acid or the like

Amount of nitrating agent: 1 to 10 moles for 1 mole of compound [VI]

Solvent: nitric acid, acetic acid, or the like

Temperature: −10° C. to room temperature

Time: a moment to 24 hours

After completion of the reaction, the crystals precipitated, if necessary, by the addition of water, are collected by filtration, or the reaction mixture is subjected to ordinary post-treatments such as extraction with an -p organic solvent and concentration. If necessary, purification may be carried out by an ordinary technique such as chromatography or recrystallization. Thus the desired compound can be isolated.

4) Procedure for preparing compound [III] from compound [VIII]

Compound [III] can be prepared by reacting compound [VII] with a compound of $BrCH(R^4)COOR^{33}$ (wherein $R^4$ and $R^{33}$ are as defined above) in the presence of a base in a solvent.

Amount of compound of $BrCHR^4)COOR^{33}$: 1 to 2 moles for 1 mole of compound [VIII]

Base: sodium hydride, potassium carbonate, or the like

Amount of base: 1 to 2 moles for 1 mole of compound [VIII]

Solvent: 1,4-dioxane, N,N-dimethylformamide, or the like

Temperature: 0° C. to 100° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 3

This is the production process according to the following scheme:

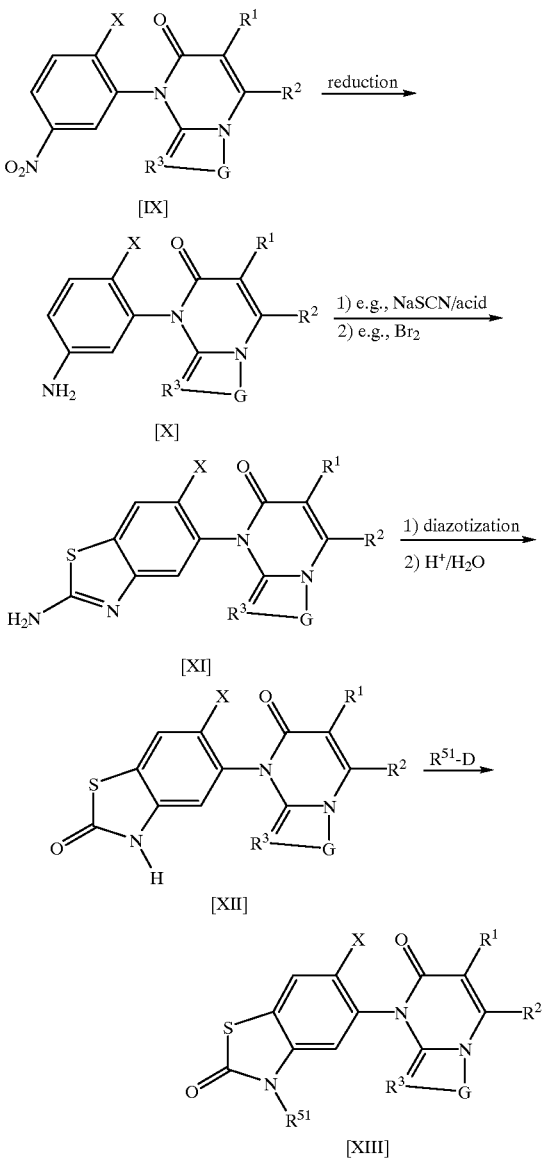

wherein X, $R^1$, $R^2$, $R^3$, G, $R^{51}$, and D are as defined above.

The reactions in the respective steps can be effected, for example, by the procedures as described in the Japanese Laid-open Patent Publication No. 62-252787, or by the following procedures.

1) Procedure for preparing compound M] from compound [IX]

Compound [X] can be prepared by reducing compound [IX] with iron powder or the like in the presence of an acid in a solvent.

Amount of iron powder or the like: 3 moles to an excessive amount for 1 mole of compound [IX]

Acid: acetic acid or the like

Amount of acid: 1 to 10 moles for 1 mole of compound [IX]

Solvent: water, ethyl acetate, or the like

Temperature: room temperature to heating temperature under reflux

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [XI] from compound [X]

Compound [XI] can be prepared by reacting compound [X] with sodium thiocyanate, potassium thiocyanate, or the like in a solvent, and then with bromine or chlorine in a solvent.

Amount of sodium thiocyanate, potassium thiocyanate, or the like: 1 to 10 moles for 1 mole of compound []

Amount of bromine or chlorine: 1 to 10 moles for 1 mole of compound [X]

Solvent: aqueous hydrochloric acid, aqueous acetic acid, aqueous sulfuric acid, or the like Temperature: 0° C. to 50° C.

Time: a moment to 150 hours

After completion of the reaction, the reaction mixture is poured into water, which is neutralized with an alkali, if necessary, and then extracted with an organic solvent. The organic layer is subjected to post-treatments such as drying and concentration. If necessary, purification may be carried out by an ordinary technique such as recrystallization or column chromatography. Thus the desired present compound can be obtained.

3) Procedure for preparing compound XII] from compound [XI]

Compound [XII] can be prepared by i) reacting compound [XI] with sodium nitrite, potassium nitrite, or the like in a solvent (reaction 1), and ii) subsequently heating in an acidic solution (reaction 2).

Reaction 1

Amount of sodium nitrite, potassium nitrite, or the like: 1 to 2 moles for 1 mole of compound [XI]

Solvent: aqueous hydrochloric acid or aqueous sulfuric acid

Temperature: −10° C. to 10° C.

Time: a moment to 5 hours

Reaction 2

Acidic solution: aqueous hydrochloric acid, aqueous sulfuric acid, or the like

Temperature: 70° C. to heating temperature under reflux

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

4) Procedure for preparing compound [XIII] from compound

Compound [XIII] can be prepared by reacting compound [XII] with a compound of $R^{5'}$-D (wherein $R^{51}$ and D are as defined above) in the presence of a base in a solvent.

Amount of compound of $R^{51}$-D: 1 to 3 moles for 1 mole of compound [XII]

Base: sodium hydride, potassium carbonate, or the like

Amount of base: 1 to 2 moles for 1 mole of compound [XII]

Solvent: 1,4-dioxane, N,N-dimethylformamide, or the like

Temperature: 0° C. to 100° C.

Time: a moment to 48 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 4

This is the production process according to the following scheme:

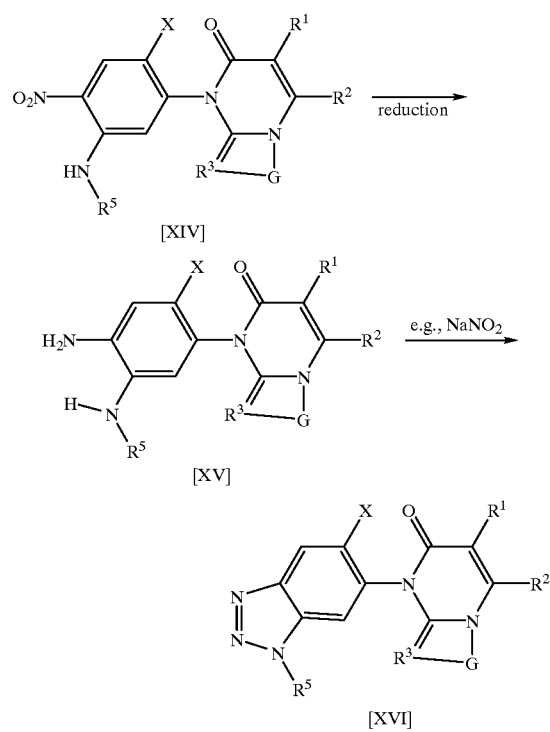

wherein X, $R^1$, $R^2$, $R^3$, G, and $R^5$ are as defined above.

The reactions in the respective steps can be effected, for example, by the procedures as described in the Japanese Laid-open Patent Publication No. 61-165384, or by the following procedures.

1) Procedure for preparing compound [XV] from compound

Compound [XV] can be prepared by reducing compound [XIV] with iron powder or the like in the presence of an acid in a solvent.

Amount of iron powder or the like: 3 moles to an excessive amount for 1 mole of compound [XIV]

Acid: acetic acid or the like

Amount of acid: 1 to 10 moles for 1 mole of compound [XIV]

Solvent: water, ethyl acetate, or the like

Temperature: room temperature to heating temperature under reflux

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [XI] from compound [XV]

Compound [XVI] can be prepared by i) reacting compound [XV] with a nitrite in a solvent to give a diazonium salt (reaction 1), and ii) subsequently raising the temperature to cause circularization of the diazonium salt in a solvent (reaction 2).

Reaction 1

Nitrite: sodium nitrite, potassium nitrite, or the like

Solvent: aqueous hydrochloric acid, aqueous sulfuric acid, or the like

Temperature: −10° C. to 10° C.

Time: a moment to 5 hours

Reaction 2

Solvent: aqueous hydrochloric acid, aqueous sulfuric acid, or the like

Temperature: room temperature to 80° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 5

This is the production process according to the following scheme:

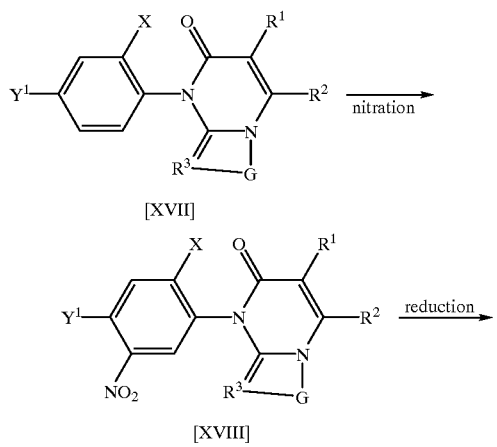

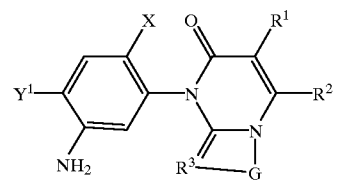

wherein $Y^1$ is as defined for Y but not nitro, and X, Y, $R^1$, $R^2$, $R^3$, and G are as defined above.

The reactions in the respective steps can be effected, for example, by the procedures as described in the Japanese Laid-open Patent Publication No. 63-41466 or Published Specification of International Patent Application, No. WO92/11244, or by the following procedures. 1) Procedure for preparing compound P[VIII] from compound [XVII]

Compound [XVIII] can be prepared by adding nitric acid to compound [XVII] in a solvent (see Organic Synthesis Collective Vol. 1, p. 372).

The reaction temperature is usually in the range of 0° C. to 100° C. The reaction time is usually in the range of a moment to 24 hours.

The amounts of reagents to be used in the reaction are stoichiometrically 1 mole of the nitric acid for 1 mole of compound [XVII], although they may suitably be changed with the reaction conditions.

The solvent which can be used may include acidic solvents such as sulfuric acid.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [XIX] from compound [XVIII]

Compound [XIX] can be prepared by reducing compound [XVIII] in a solvent (see Organic Synthesis Collective Vol. 2, p. 471, Vol. 5, p. 829.

The reaction can be effected, for example, by adding compound [XVIII] neat or dissolved in a solvent such as ethyl acetate to a mixture of acetic acid, iron powder, and water. The reaction temperature is usually in the range of 0° C. to 100° C. The reaction time is usually in the range of a moment to 24 hours.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 6

This is the production process according to the following scheme:

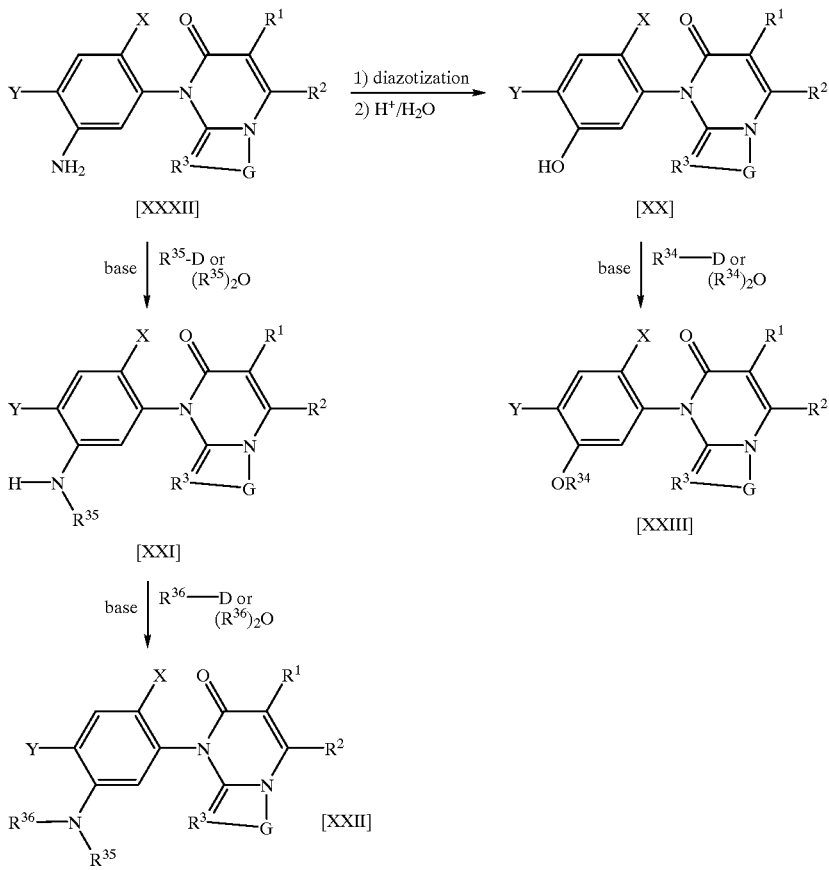

wherein X, Y, $R^1$, $R^2$, $R^3$, G, and D are as defined above; $R^{34}$ is as defined for $R^{10}$ but not hydrogen; $R^{35}$ and $R^{36}$ are the same or different and are as defined for $R^{12}$ but not hydrogen, for $COR^9$, for $SOR^{28}$, for $SO_2R^{29}$, or for $COOR^{11}$ but not carboxyl; the wordings "$R^{35}$-D or $(R^{35})_2O$", "$R^{36}$-D or $(R^{36})_2O$", and "$R^{34}$-D or $(R^{34})_2O$" mean that the reaction can be effected with either of the compounds recited, depending upon the reaction conditions.

1) Procedure for preparing compound [XX] from compound [XXXII]

Compound [XX] can be prepared by i) reacting compound [XXXII] with a nitrite in a solvent (reaction 1), and ii) subsequently heating in an acidic solvent (reaction 2).

Reaction 1
Nitrite: sodium nitrite, potassium nitrite, or the like
Amount of nitrite: 1 to 2 moles for 1 mole of compound [XXII]
Solvent: aqueous hydrochloric acid, aqueous sulfuric acid, or the like
Temperature: –10° C. to 10° C.
Time: a moment to 5 hours Reaction 2
Acid solvent: aqueous hydrochloric acid, aqueous sulfuric acid, or the like
Temperature: 70° C. to heating temperature under reflux
Time: a moment to 24 hours After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [XXIII] from compound [XX]

Compound [XXIII] can be prepared by reacting compound [XX] with a compound of $R^{34}$-D or $(R^{34})_2O$ (wherein $R^{34}$ and D are as defined as above) in the presence of a base in a solvent.

The reaction is usually effected in a solvent. The reaction temperature is usually in the range of –20° C. to 150° C., preferably 0° C. to 100° C. The reaction time is usually in the range of a moment to 72 hours.

The amounts of reagents to be used in the reaction are stoichiometrically 1 mole of the compound of $R^{34}$-D or the compound of $(R^{34})_2O$ and 1 mole of the base, both for 1 mole of compound [XX], although they may suitably be changed with the reaction conditions.

The base which can be used in the reaction may include organic bases and inorganic bases such as potassium carbonate, sodium hydroxide, and sodium hydride.

The solvent which can be used in the reaction may include aliphatic hydrocarbons such as hexane, heptane, ligroin, cyclohexane, and petroleum ether; aromatic hydrocarbons such as benzene, toluene, and xylene; halo-genated hydrocarbons such as chloroform, carbon tetrachloride, dichloromethane, dichloroethane, chlorobenzene, and dichlorobenzene; ethers such as diethyl ether, diisopropyl ether, dioxane, THF, and ethylene glycol dimethyl ether; ketones such as acetone, methyl ethyl ketone, methyl isobutyl ketone, isophorone, and cyclohexanone; esters such as ethyl formate, ethyl acetate, butyl acetate, and diethyl carbonate; nitro compounds such as nitromethane and nitrobenzene; nitriles such as acetonitrile and isobutyronitrile; acid amides such as formamide, N,N-dimethylformamide (hereinafter referred to as DMF), and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; and mixtures thereof.

After completion of the reaction, the reaction mixture is poured into water, if necessary, and then subjected to ordinary post-treatments such as extraction with an organic solvent and concentration. If necessary, purification may be carried out by an ordinary technique such as column chromatography or recrystallization. Thus the desired compound can be isolated.

3) Procedure for preparing compound [XXI] from compound [XXXII]

Compound [XXI] can be prepared by reacting compound [XII] with a compound of $R^{35}$-D or a compound of $(R^{35})_2O$ without any solvent or in a solvent, and if necessary, in the presence of a base.

The reaction temperature is usually in the range of −20° C. to 200° C., preferably 0° C. to 180° C. The reaction time is usually in the range of a moment to 72 hours.

The amounts of reagents to be used in the reaction are stoichiometrically 1 mole of the compound of $R^{35}$-D or the compound of $(R^{35})2O$ and 1 mole of the base, both for 1 mole of compound [XXXII], although they may suitably be changed with the reaction conditions.

The base which can be used in the reaction may include organic bases such as pyridine and triethylamine and inorganic bases such as potassium carbonate.

The solvent which can be used in the reaction may include aliphatic hydrocarbons such as hexane, heptane, ligroin, cyclohexane, and petroleum ether; aromatic hydrocarbons such as benzene, toluene, and xylene; halo-genated hydrocarbons such as chloroform, carbon tetrachloride, dichloromethane, dichloroethane, chlorobenzene, and dichlorobenzene; ethers such as diethyl ether, diisopropyl ether, dioxane, THF, and ethylene glycol dimethyl ether; ketones such as acetone, methyl ethyl ketone, methyl isobutyl ketone, isophorone, and cyclohexanone; esters such as ethyl formate, ethyl acetate, butyl acetate, and diethyl carbonate; nitro compounds such as nitromethane and nitrobenzene; nitriles such as acetonitrile and isobutyronitrile; acid amides such as formamide, DMF, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; and mixtures thereof.

After completion of the reaction, the precipitated crystals are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

4) Procedure for preparing compound [XXII] from compound [XXI]

Compound [XXII] can be prepared by reacting compound [XXI] with a compound of $R^{36}$-D or a compound of $(R^{36})_2O$. The reaction can be effected by the above procedure for preparing compound [XXI] from compound Production Process 7

This is the production process according to the following scheme:

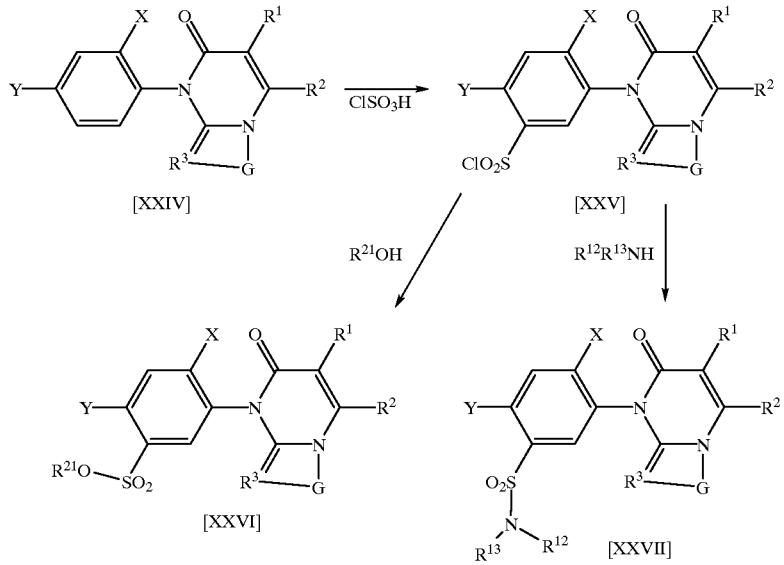

wherein X, Y, $R^1$, $R^2$, $R^3$, G, $R^{12}$, $R^{13}$, and $R^{21}$ are as defined above.

The reaction conditions in the respective steps are, for example, as follows:

1) Procedure for preparing compound [XXV] from compound [XXIV]

Compound [XXV] can be prepared by reacting compound [XXIV] with chlorosulfonic acid without any solvent or in a solvent (see Organic Synthesis Collective Vol. 1, 8 (1941)).

Amount of chlorosulfonic acid: 1 mole to an excessive amount for 1 mole of compound [XXIV]

Solvent: sulfuric acid

Temperature: 0° C. to 70° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [XXVI] from compound [XXV]

Compound [XXVI] can be prepared by reacting compound [XXVI] with a compound of $R^{21}$-OH (wherein $R^{21}$ is as defined above) in the presence of a base without any solvent or in a solvent.

Amount of compound of $R^{21}$-OH: 1 mole to an excessive amount for 1 mole of compound [XXV]

Base: tertiary amines such as triethylamine, inorganic bases such as potassium carbonate Amount of base: 1 to 2 moles for 1 mole of compound [XXV]

Solvent: DMF, 1,4-dioxane, or the like

Temperature: 0° C. to 100° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

3) Procedure for preparing compound [XXVII] from compound [XXV]

Compound [VII] can be prepared by reacting compound [XXV] with a compound of $R^{12}R^{13}NH$ (wherein $R^{12}$ and $R^{13}$ are as defined above) in the presence or absence of a base without any solvent or in a solvent.

Amount of compound of $R^{12}R^{13}NH$: 1 mole to an excessive amount for 1 mole of compound [XXV]

Base: tertiary amines such as triethylamine, inorganic bases such as potassium carbonate Amount of base: 1 to 2 moles for 1 mole of compound [XXV]

Solvent: DMF, 1,4-dioxane, or the like

Temperature: 0° C. to 100° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 8

This is the production process according to the following scheme:

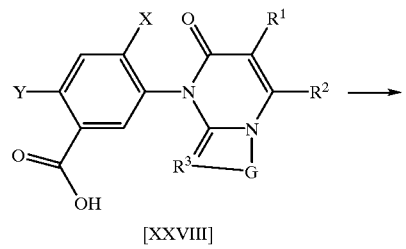

[XXVIII]

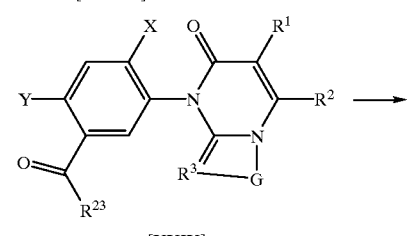

[XXIX]

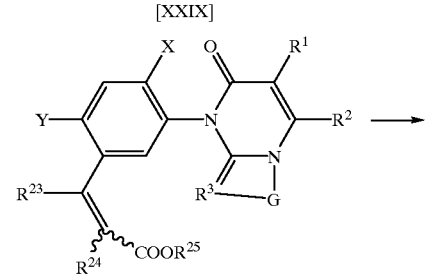

[XXX]

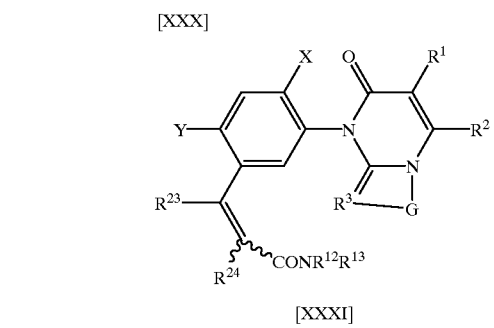

[XXXI]

wherein X, Y, G, $R^1$, $R^2$, $R^3$, $R^{23}$, $R^{24}$, $R^{25}$, $R^{12}$, and $R^{13}$ are as defined above.

The reaction conditions in the respective steps are, for example, as follows:

1) Procedure for preparing compound [XXIX] from compound [XIII]

Compound [XXIX] can be prepared from compound [XXVIII] by the procedures as described in the Japanese Laid-open Patent Publication No. 5-294920.

2) Procedure for preparing compound [XXX] from compound [XXIX]

Compound [XXX] can be prepared by reacting compound [XXIX] with a compound of $(C_6H_5)_3P=CR^{24}COOR^{25}$ or a compound of $(C_2H_5O)_2P(O)CHR^{24}$—$COOR^{25}$ (wherein $R^{24}$ and $R^{25}$ are as defined above) in a solvent, and when the compound of $(C_2H_5O)_2P(O)CHR^{24}COOR^{25}$ is used, the reaction is effected in the presence of a base.

Amount of compound of $(C_6H_5)_3P=CR^{24}COOR^{25}$ or compound of $(C_2H_5O)_2P(O)CHR^{24}COOR^{25}$: 1 to 2 moles for 1 mole of compound [XXIX]

Solvent: THF, toluene, or the like

Base: sodium hydride or the like

Amount of base: 1 to 2 moles for 1 mole of compound [XXIX]

Temperature: 0° C. to 50° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

3) Procedure for preparing compound [XXXI] from compound [XXX]

Compound [XXI] can be prepared by reacting compound [XXX] with a compound of $R^{12}R^{13}NH$.

Amount of compound of $R^{12}R^{13}NH$: 1 mole to an excessive amount for 1 mole of compound Solvent: THF or the like Temperature: 0° C. to 100° C.

Time: a moment to 24 hours

After completion of the reaction, the reaction mixture is poured into water, if necessary, and then subjected to ordinary post-treatments such as extraction with an organic solvent and concentration. If necessary, purification may be carried out by an ordinary technique such as column chromatography or recrystallization. Thus the desired compound can be isolated.

Production Process 9

This is the production process according to the following scheme:

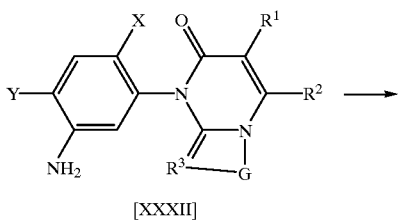

[XXXII]

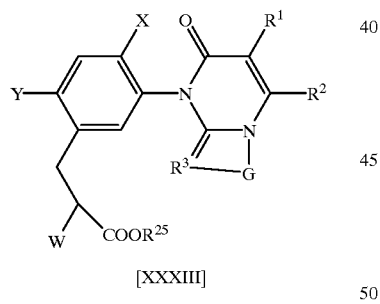

[XXXIII]

wherein X, Y, G, $R^1$, $R^2$, $R^3$, and $R^{25}$ are as defined above and W is chlorine or bromine.

1) Procedure for preparing compound [XXXIII] from compound [XXXII]

The reactions in the respective steps can be effected, for example, by the procedures as described in the specification of U.S. Pat. No. 5,208,212, or by the following procedures.

Compound [XXXIII] can be prepared by i) converting compound [XXXII] into a diazonium salt by the ordinary method in a solvent such as aqueous hydrochloric acid, aqueous hydrobromic acid,, and aqueous sulfuric acid (reaction 1), and ii) subsequently reacting the diazonium slat with a compound of $CH_2=CHCO_2R^{25}$ (wherein $R^{25}$ is as defined above) in the presence of a copper salt such as copper(II) chloride or copper(II) bromide in a solvent such as acetonitrile (reaction 2).

Reaction 1

Diazotizing agent: sodium nitrite, potassium nitrite, or the like

Amount of diazotizing agent: 1 to 2 moles for 1 mole of compound [XXXII]

Temperature: −10° C. to 10° C.

Time: a moment to 5 hours

Reaction 2

Amount of compound of $CH_2=CHCO_2R^{25}$: 1 to 2 moles for 1 mole of compound [XXXII]

Amount of copper(II) chloride or copper(II) bromide: 1 mole to an excessive amount for 1 mole of compound [XXXII]

Temperature: −20° C. to 150° C., preferably 0° C. to 60° C.

Time: a moment to 72 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 10

This is the production process according to the following scheme:

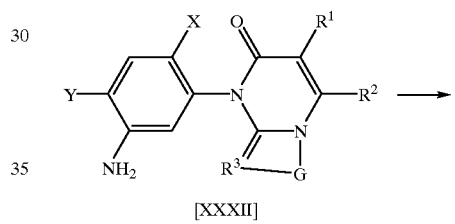

[XXXII]

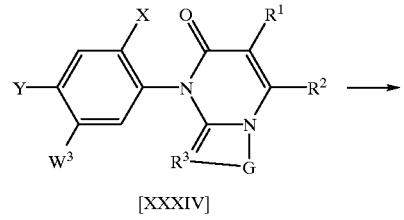

[XXXIV]

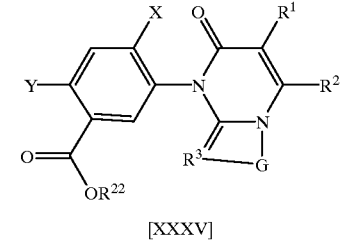

[XXXV]

wherein $W^3$ is bromine or iodine, and X, Y, G, $R^1$, $R^2$, $R^3$, and $R^{22}$ are as defined above.

The reaction conditions in the respective steps are, for example, as follows:

1) Procedure for preparing compound [XXXIV] from compound [XXXII]

Compound [XXXIV] can be prepared by i) diazotizing compound [XXXII] in a solvent (reaction 1), and ii) subsequently reacting the diazonium salt with potassium iodide or copper(I) bromide in a solvent (reaction 2) (see Organic Synthesis Collective Vol. 2, 604 (1943), Vol. 1, 136 (1932)).

Reaction 1

Diazotizing agent: sodium nitrite, potassium nitrite, or the like

Amount of diazotizing agent: 1 to 2 moles for 1 mole of compound

Solvent: aqueous hydrogen bromide, aqueous sulfuric acid, or the like

Temperature: −10° C. to 10° C.

Time: a moment to 5 hours

Reaction 2

Amount of potassium iodide or copper(I) bromide: 1 mole to an excessive amount for 1 mole of compound [XXXII]

Solvent: aqueous hydrogen bromide, aqueous sulfuric acid, or the like

Temperature: 0° C. to 80° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [XXXV] from compound [XXXIV]

Compound [XXXV] can be prepared by reacting compound [XXXIV] with carbon monoxide and a compound of $R^{22}$—OH (wherein $R^{22}$ is as defined above) in the presence of a transition metal catalysis and a base in a solvent under an atmosphere of carbon monoxide (see Bull. Chem. Soc. Jpn., 48(7), 2075(1975)).

Catalyst: $PdCl_2(PPh_3)_2$ (wherein Ph is phenyl) or the like

Amount of catalyst: a catalytic amount to 0.5 mole for 1 mole of compound [XXXIV]

Amount of compound of $R^{22}$—OH: 1 mole to an excessive amount for 1 mole of compound [XXXIV]

Base: organic bases such as diethylamine

Amount of base: 1 to 2 moles for 1 mole of compound [XXXIV]

Solvent: DMF or the like

Pressure of carbon monoxide: 1 atm to 150 atm

Temperature: 0° C. to 100° C.

Time: a moment to 72 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 11

This is the production process according to the following scheme:

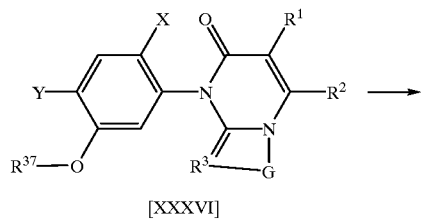

[XXXVI]

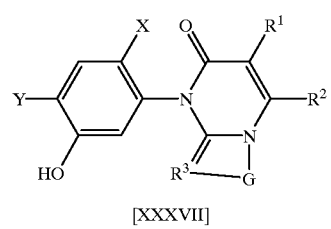

[XXXVII]

wherein X, Y, G, $R^1$, $R^2$, and $R^3$ are as defined above and $R^{37}$ is $C_1$–$C_6$ alkyl.

Compound [XXXVII] can be prepared by hydrolyzing compound [XXXVI] in the presence of an acid such as sulfuric acid, or by treating compound [XXXVI] with an acid such as boron tribromide in a solvent such as methylene chloride and then with water.

The reaction temperature is usually in the range of −20° C. to 150° C., preferably 0° C. to 100° C. The reaction time is usually in the range of a moment to 72 hours.

The amount of acid to be used in the reaction is stoichiometrically 1 mole for 1 mole of compound [XXXVI], although it may suitably be changed with the reaction conditions.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 12

This is the production process according to the following scheme:

[XXXVIII]

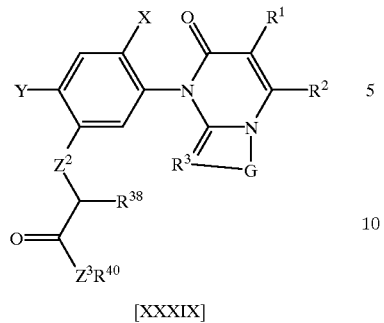

[XXXIX]

wherein X, Y, G. $R^1$, $R^2$, $R^3$, and $Z^2$ are as defined above; $R^{38}$ is hydrogen or $C_1$–$C_6$ alkyl; $R^{39}$ is hydrogen or $C_1$–$C_6$ alkyl; $Z^3$ is oxygen or sulfur; $R^{40}$ is $C_1$–$C_6$ alkyl, $C_3$–$C_6$ alkenyl, or $C_3$–$C_6$ alkynyl.

Compound [XXXIX] can be prepared by reacting compound [XXXVIII] with a compound of $R^{40}Z^3H$ (wherein $R^{40}$ and $Z^3$ are as defined above) in the presence or absence of a catalyst and usually in a solvent.

The amount of the compound of $R^{40}Z^3H$ to be used in the reaction is stoichiometrically 1 mole for 1 mole of compound [XXXVIII], although it may suitably be changed with the reaction conditions.

The catalyst which can be used may include p-toluenesulfonic acid. The solvent which can be used may include toluene, xylene, and compounds of $R^{40}Z^3H$.

The reaction temperature is usually in the range of 0° C. to 200° C., preferably 50° C. to 150° C. The reaction time is usually in the range of a moment to 72 hours.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 13

This is the production process according to the following scheme:

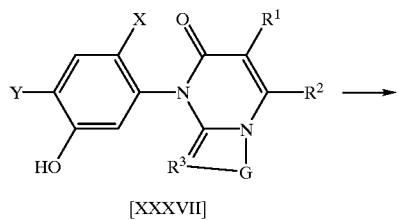

[XXXVII]

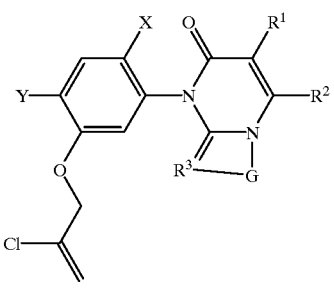

[XL]

wherein X, Y, G, $R^1$, $R^2$, and $R^3$ are as defined above.

The reaction conditions in the respective steps are, for example, as follows:

1) Procedure for preparing compound [XL] from compound [XXXVII]

Compound [XL] can be prepared by reacting compound [XXXII] with 2,3-dichloropropene in the presence of a base in a solvent.

Amount of 2,3-dichloropropene: 1 to 3 moles for 1 mole of compound [XXXVII]

Base: inorganic bases such as potassium carbonate

Amount of base: 1 to 2 moles for 1 mole of compound [XXXVII]

Solvent: DMF or the like

Temperature: 0° C. to 70° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 14

This is the production process according to the following scheme:

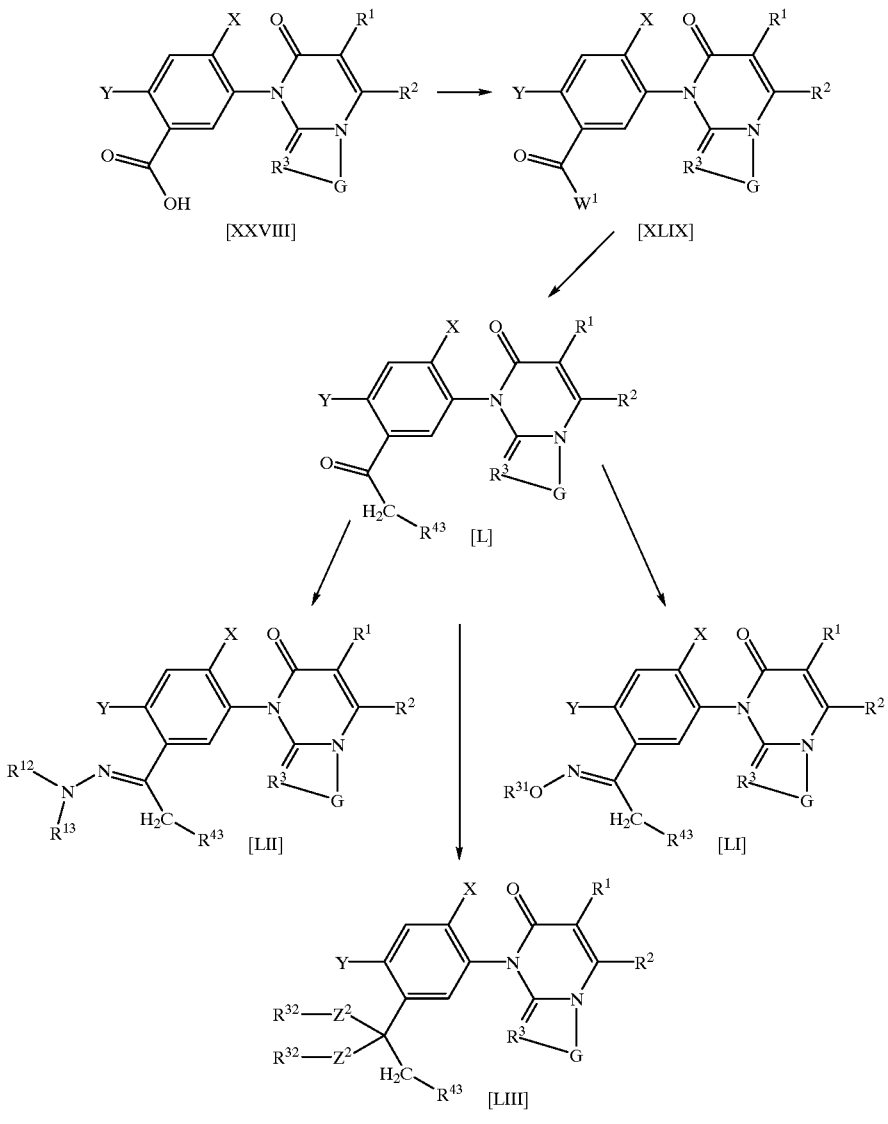

wherein $W^1$ is halogen, preferably chlorine; $R^{43}$ is hydrogen or $C_1$–$C_5$ alkyl; and X, Y, G, $Z^2$, $R^1$, $R^2$, $R^3$, $R^{12}$, $R^{13}$, $R^{31}$, and $R^{32}$ are as defined above.

The reaction conditions in the respective steps are, for example, as follows:

1) Procedure for preparing compound CLIXI from compound [XXVIII]

Compound [XLIX] can be prepared by reacting compound [XXVIII] with a halogenating agent such as thionyl chloride by the ordinary method in a solvent.

2) Procedure for preparing compound [L] from compound [XLIX]

Compound [L] can be prepared by reacting compound [XLIX] with a compound of the general formula:

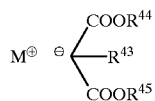

wherein $M^+$ is an alkali metal cation, preferably lithium cation or sodium cation; $R^{44}$ and $R^{45}$ are independently $C_1$–$C_6$ alkyl; and $R^{43}$ is as defined above to give a compound of the general formula:

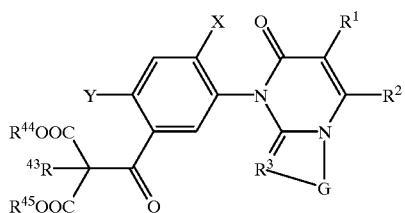

wherein X, Y, $R^1$, $R^2$, $R^3$, G, $R^{43}$, $R^{44}$, and $R^{45}$ are as defined above (reaction 1), and then hydrolyzing and decarboxylating this compound (reaction 2).

Reaction 1 is usually effected in a solvent. The reaction temperature is usually in the range of −20° C. to 50° C., preferably room temperature. The reaction time is usually in the range of a moment to 72 hours.

The solvent which can be used may include aliphatic hydrocarbons such as hexane, heptane, ligroin, cyclohexane, and petroleum ether; ethers such as diethyl ether, diisopropyl ether, dioxane, THF, and ethylene glycol dimethyl ether; acid amides such as formamide, DMF, and acetamide; sulfur compounds such as dimethylsulfoxide and sulforane; and mixtures thereof.

After completion of the reaction, the reaction mixture is concentrated, and the residue is subjected to reaction 2.

Reaction 2 is effected in the presence of sulfuric acid, hydrobromic acid, or the like in a solvent, e.g., lower carboxylic acids such as acetic acid, or without any solvent.

The reaction temperature is usually in the range of 80° C. to 140° C., preferably 100° C. to 120° C. The reaction time is usually in the range of a moment to 72 hours.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

3) Procedure for preparing compound [LI] from compound [L]

Compound [LI] can be prepared by reacting compound [L] with $H_2N$—O—$R^{31}$ (wherein $R^{31}$ is as defined above).

The reaction is effected in a lower alcohol (e.g., methanol, ethanol, isopropanol) or in a mixed solution of a lower alcohol and water. The reaction temperature is usually in the range of 0° C. to 80° C. The reaction time is usually in the range of a moment to 72 hours.

The amount of the compound of $H_2N$—O—$R^{31}$ to be used in the reaction is stoichiometrically 1 mole for 1 mole of compound [L], although it may suitably be changed with the reaction conditions.

The compound of $H_2N$—O—$R^{31}$ can be used in the form of a free base or in the form of an acid addition salt such as hydrochloride salt or sulfate salt.

The reaction can also be effected with the addition of an organic base such as pyridine; an alkali metal carbonate such as sodium carbonate or potassium carbonate; an alkali metal hydrogencarbonate such as sodium hydrogencarbonate; or alkaline earth metal carbonate such as calcium carbonate.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Compound [LI] can also be prepared by reacting a compound of the general formula:

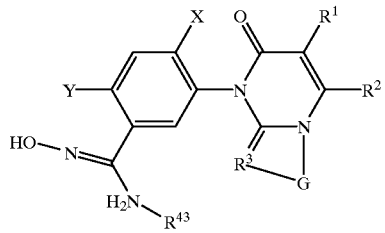

wherein G, X, Y, $R^1$, $R^2$, $R^3$, and $R^{43}$ are as defined above, which is prepared by the procedure as described in the section 3) of Production Process 15, with a compound of $R^{49}$-D (wherein $R^{49}$ is as defined for $R^{31}$ but not hydrogen and D is as defined above) in the presence of a base and usually in a solvent.

The base which can be used may include alkali metal alcoholates and alkali metal hydrides (e.g., sodium hydride).

The amounts of reagents to be used in the reaction are stoichiometrically 1 mole of the compound of $R^{49}$-D and 1 to 2 moles of base, both for 1 mole of the compound of the above general formula, although they may suitably be changed with the reaction conditions.

The solvent which can be used may include ethers such as diethyl ether, diisopropyl ether, dioxane, THF, and ethylene glycol dimethyl ether; acid amides such as formamide, DMF, and acetamide; sulfur compounds such as dimethylsulfoxide and sulforane; alcohols such as methanol, ethanol, ethylene glycol, and isopropanol; and mixtures thereof The reaction temperature is usually an integer of –10° C. to 100° C., preferably 0° C. to 80° C. The reaction time is usually an integer of a moment to 72 hours.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

4) Procedure for preparing compound [LII] from compound [L]

Compound [LII] can be prepared by reacting compound [L] with a compound of $H_2N$—N($R^{12}$)$R^{13}$ (wherein $R^{12}$ and $R^{13}$ are as defined above).

The reaction is effected in a lower alcohol (e.g., methanol, ethanol, isopropanol) or in a mixed solution of a lower alcohol and water. The reaction temperature is usually in the range of 0° C. to 80° C. The reaction time is usually in the range of a moment to 72 hours.

The amount of the compound of $H_2N$—N($R^{12}$)$R^{13}$ to be used in the reaction is stoichiometrically 1 mole for 1 mole of compound [L], although it may suitably be changed with the reaction conditions.

The compound of $H_2N$—N($R^{12}$)$R^{13}$ can be used in the form of a free base or in the form of an acid addition salt such as hydrochloride salt or sulfate salt.

The reaction can also be effected with the addition of a basic catalyst, e.g., an organic base such as pyridine; an alkali metal carbonate such as sodium carbonate or potassium carbonate; an alkali metal hydrogencarbonate such as sodium hydrogencarbonate; or alkaline earth metal carbonate such as calcium carbonate.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

5) Procedure for preparing compound [LIII] from compound [L]

Compound [LIII] can be prepared by reacting compound [L] with a compound of $R^{32}Z^2H$ (wherein $Z^2$ and $R^{32}$ are as defined above) usually in the presence of a catalytic amount to an excessive amount of an acid such as p-toluenesulfonic acid, hydrochloric acid, or sulfuric acid in an organic solvent such as benzene or chloroform.

The amount of the compound of $R^{32}Z^2H$ to be used in the reaction is stoichiometrically 2 moles for 1 mole of compound [L], although it may suitably be changed with the reaction conditions.

The reaction temperature is usually in the range of −30° C. to a boiling point of the reaction mixture. The reaction time is usually in the range of a moment to 72 hours.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 15

This is the production process according to the following scheme:

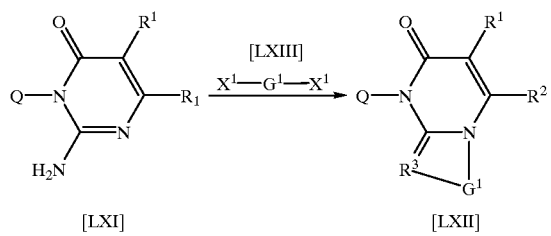

wherein Q, $R^1$, and $R^2$ are as defined above; $G^1$ is G-1 or G-2 as defined above; and $X^1$ is iodine, bromine, or chlorine.

1) Procedure for preparing compound [LXII] from compound [LXI]

Compound [LXII] can be prepared by reacting compound [LXI] with compound [LXIII] in the presence of a base in a solvent.

Amount of compound [LXIII]: 1 mole to an excessive amount for 1 mole of compound [LXI]

Solvent: ethers such as dioxane, alcohols such as ethanol, water, or the like

Temperature: 0° C. to heating temperature under reflux

Time: a moment to 48 hours

Base: alcoholates such as sodium ethoxide, organic bases such as triethylamine, or inorganic bases such as potassium carbonate Amount of base: 2 moles to an excessive amount for 1 mole of compound [LXI]

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 16

This is the production process according to the following scheme:

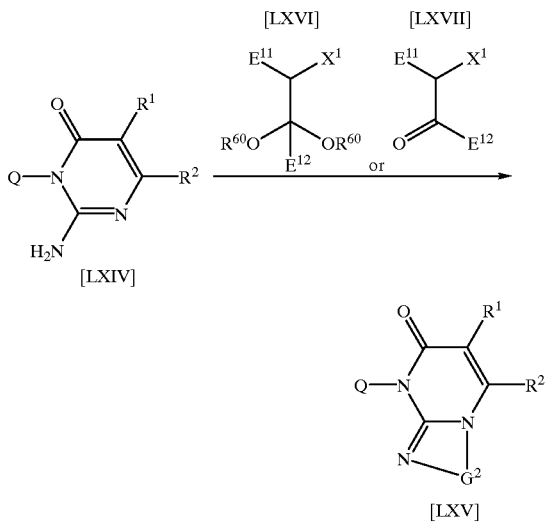

wherein Q, $X^1$, $R^1$, $R^2$, $E^{11}$, and $E^{12}$ are as defined above; $G^2$ is G-3 as defined above; and $R^{60}$ hydrogen or $C_1$–$C_5$ alkyl.

1) Procedure for preparing compound [LXV] from compound [LXIV]

Compound [LXV] can be prepared by reacting compound [LIV] with compound [IXVl] or compound [LXVII] in a solvent and if necessary, in the presence of an acid.

Amount of compound [LXVI] or compound [LXVII]: 1 mole to an excessive amount for 1 mole of compound [LXIV]

Solvent: ethers such as dioxane, alcohols such as ethanol, organic acids such as acetic acid, water, or the like Temperature: 0° C. to heating temperature under reflux Time: a moment to 168 hours Acid: inorganic acids such as hydrochloric acid Amount of acid: a catalytic amount to an excessive amount After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

The following are production processes for intermediates or starting compounds used in the production of the present compounds.

In the aniline derivatives of the general formula:

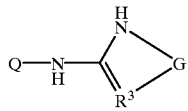

wherein Q, G, and $R^3$ are as defined above, which are the starting compounds in the production of the present compounds, the compounds of the general formula:

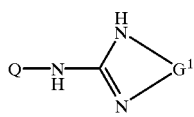

wherein Q and $G^1$ are as defined above, can be prepared, for example, by the following production process 17 or 18, and the compounds of the general formula:

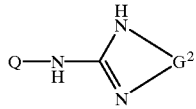

wherein Q and $G^2$ are as defined above, can be prepared, for example, by the following production process 19.

Production Process 17

This is the production process in which a carbamate derivative of the general formula:

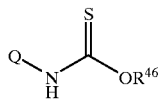

wherein Q is as defined above and $R^{46}$ is $C_1$–$C_6$ alkyl, is reacted with an amine derivative of the general formula:

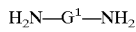

wherein $G^1$ is as defined above.

The reaction is usually effected without any solvent or in a solvent. The reaction temperature is usually in the range of 20° C. to 200° C. The reaction time is usually in the range of a moment to 24 hours.

The amounts of reagents to be used in the reaction are stoichiometrically 1 mole of the amine derivative of the above general formula for 1 mole of the carbamate compound of the above general formula, although they may suitably be changed with the reaction conditions.

The solvent which can be used may include aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, THF, and ethylene glycol dimethyl ether; nitro compounds such as nitromethane and nitrobenzene; nitrites such as acetonitrile and isobutyronitrile; acid amides such as DMF; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; water; and mixtures thereof. The amine derivatives of the above general formula can also be used as the solvents.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

The carbamate derivatives of the above general formula can be prepared by the known methods, for example, by reacting an isothiocyanate of Q-NCS (wherein Q is as defined above) with $R^{46}$OH (wherein $R^4$ is as defined above).

The isothiocyanate of Q-NCS (wherein Q is as defined above) is commercially available or can be prepared, for example, by the procedures as described in the "Jikken Kagaku Kohza" (Maruzen Kabushiki Kaisha), 4th ed., vol. 20, pp. 483–489.

Production Process 18

This is the production process in which an isothiocyanate derivative of Q-NCS (wherein Q is as defined above) is reacted with an amine derivative of the above general formula.

The reaction is usually effected without any solvent or in a solvent.

The reaction temperature is usually in the range of 20° C. to 200° C. The reaction time is usually in the range of a moment to 24 hours.

The amounts of reagents to be used in the reaction are stoichiometrically 1 mole of the amine derivative of the above general formula for 1 mole of the isothiocyanate derivative of Q-NCS, although they may suitably be changed with the reaction conditions.

The solvent which can be used may include aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, THF, and ethylene glycol dimethyl ether; nitro compounds such as nitromethane and nitrobenzene; nitrites such as acetonitrile and isobutyronitrile; acid amides such as DMF; tertiary amines such as pyridine, triethylamine, diisopropylethylamine, N,N-dimethylaniline, N,N-diethylaniline, and N-methylmorpholine; sulfur compounds such as dimethylsulfoxide and sulforane; water; and mixtures thereof The amine derivatives of the above general formula can also be used as the solvents.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 19

This is the production process according to the following scheme:

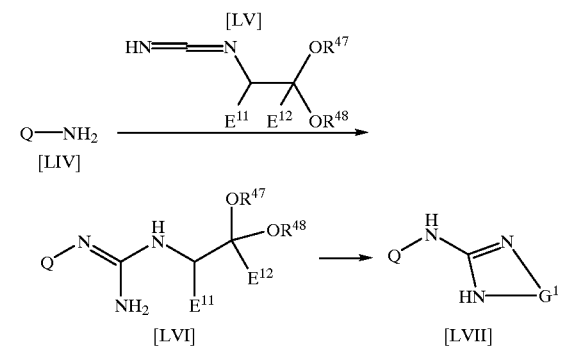

wherein $R^{47}$ an $R^{48}$ are independently $C_1$–$C_6$ alkyl; and Q, $E^{11}$, $E^{12}$, and $G^2$ are as defined above (see J. Med. Chem., 1997, 40, 18–23).

1) Procedure for preparing compound [LVI] from compound [LIV]

Compound [LVI] can be prepared by reacting compound [LIV] with compound [LV] in the presence of an acid in a solvent.

Amount of compound [LV]: 1 mole to an excessive amount for 1 mole of compound [LIV]
Solvent: ethanol or the like
Temperature: 0° C. to heating temperature under reflux
Time: a moment to 24 hours
Acid: organic acids such as methanesulfonic acid
Amount of acid: a catalytic amount to an excessive amount After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [LVII] from compound [LVI]

Compound [LVII] can be prepared by reacting compound [LVI] in the presence of an acid in a solvent.

Solvent: water or the like
Temperature: 0° C. to heating temperature under reflux
Time: a moment to 24 hours
Acid: inorganic acids such as hydrochloric acid
Amount of acid: a catalytic amount to an excessive amount After completion of the reaction, the crystals precipitated by the addition of water are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

The aniline derivatives of Q-NH2 (wherein Q is as defined above) are known in the art, for example, in the published specification of European Patent Application, EP-61741-A; and the specifications of U.S. Pat. No. 4,770,695, No. 4,709,049, and No. 4,720,297, or can be prepared by the procedures as described therein.

Production Process 20

The 2-aminopyrimidine derivatives used in the production processes 15 and 16 can be prepared by the following scheme:

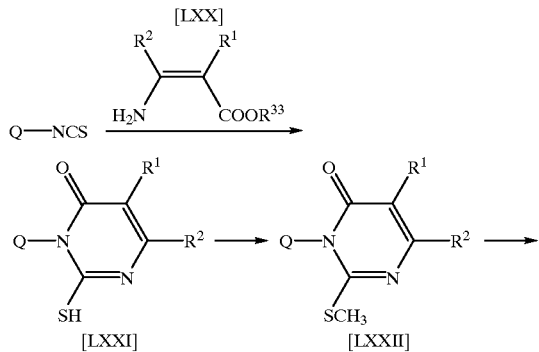

-continued

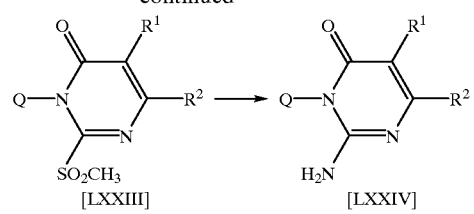

wherein Q, $R^1$, $R^2$, and $R^{33}$ are as defined above (see the published specification of European Patent Application EP-0396250).

1) Procedure for preparing compound [LXXI] from isothiocyanate derivative

Compound [LXXI] can be prepared by reacting compound [LXX] with an isothiocyanate derivative in the presence of a base in a solvent.

Amount of compound [LXX]: 1 mole to an excessive amount for 1 mole of isothiocyanate derivative
Solvent: N,N-dimethylformamide or the like
Temperature: 0° C. to 100° C.
Time: a moment to 24 hours
Base: inorganic bases such as sodium hydride
Amount of base: 1 mole to an excessive amount for 1 mole of isothiocyanate derivative After completion of the reaction, the crystals precipitated, if necessary, by the addition of aqueous hydrochloric acid, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [LXXII] from compound Compound [LXII] can be prepared by methylating compound [LXXI] in the presence of a base in a solvent.

Amount of methylating agent: 1 mole to an excessive amount for 1 mole of compound [LXXI]
Methylating agent: iodomethane, dimethyl sulfate, or the like
Solvent: N,N-dimethylformamide or the like
Temperature: −10° C. to 100° C.
Time: a moment to 24 hours
Base: organic bases such as triethylamine, or inorganic bases such as potassium carbonate
Amount of base: 1 mole to an excessive amount for 1 mole of compound [LXXI]

After completion of the reaction, the crystals precipitated by the addition of water are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

3) Procedure for preparing compound [LXXIII] from compound [LXXII]

Compound [XIII] can be prepared by oxidizing compound [LXXII] in a solvent.

Amount of oxidizing agent: 2 moles to an excessive amount for 1 mole of compound [LXXII]
Oxidizing agent: m-chloroperbenzoic acid or the like
Solvent: chloroform or the like
Temperature: −10° C. to refluxing temperature Time: a moment to 48 hours After completion of the reaction, the reaction mixture is washed with an aqueous solution of sodium hydrogensulfite or the like and then subjected to ordinary post-treatments such as extraction with an organic solvent and concentration. If necessary, purification may be carried out by an ordinary technique such as chromatography or recrystallization. Thus the desired compound can be isolated.

4) Procedure for preparing compound [LXXIV] from compound [LXXIII]

Compound [LXXIX] can be prepared by reacting compound [LXXIII] with ammonia in a solvent.

Amount of ammonia: 1 mole to an excessive amount for 1 mole of compound [LXXIII]

Solvent: 2-propanol, 2-methyl-2-propanol, or the like

Temperature: −10° C. to refluxing temperature

Time: a moment to 48 hours

After completion of the reaction, the reaction mixture is poured into water and the precipitated crystals are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

The presence compounds have excellent herbicidal activity and some of them exhibit excellent selectivity between crops and weeds. More particularly, the present compounds have herbicidal activity against various weeds which may cause some trouble in the foliar treatment and soil treatment on upland fields, such as listed below.

Polygonaceous weeds:

wild buckwheat (*Polygonum convolvulus*), pale smartweed (*Polygonum lapathifolium*), Pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)

Portulacaceous weeds:

common purslane (*Portulaca oleracea*)

Caryophyllaceous weeds:

common chickweed (*Stellaria media*)

Chenopodiaceous weeds:

common lambsquarters (*Chenopodium album*), kochia (*Kochia scoparia*)

Amaranthaceous weeds:

redroot pigweed (*Amaranthus retroflexus*), smooth pigweed (*Amaranthus hybridus*)

Cruciferous (brassicaceous) weeds:

wild radish (*Raphanus raphanistrum*), wild mustard (*Sinapis arvensis*), shepherdpurse (*Capsella bursa-pastoris*)

Leguminous (fabaceous) weeds:

hemp sesbania (*Sesbania exaltata*), sicklepod (*Cassia obtusifolia*), Florida beggarweed (*Desmodium tortuosum*), white clover (*Trifolium repens*)

Malvaceous weeds:

velvetleaf (*Abutilon theophrasti*), prickly sida (*Sida spinosa*)

Violaceous weeds:

field pansy (*Viola arvensis*), wild pansy (*Viola tricolor*)

Rubiaceous weeds:

catchweed bedstraw (cleavers) (*Galium aparine*)

Convolvulaceous weeds:

ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)

Labiate weeds:

red deadnettle (*Lamium purpureum*), henbit (*Lamium amplexicaule*)

Solanaceous weeds:

jimsonweed (*Datura stramonium*), black nightshade (*Solanum nigrum*)

Scrophulariaceous weeds:

birdseye speedwell (*Veronica persica*), ivyleaf speedwell (*Veronica hederaefolia*)

Composite weeds:

common cocklebur (*Xanthium pensylvanicum*), common sunflower (*Helianthus annuus*), scentless chamomile (*Matricaria perforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)

Boraginaceous weeds:

forget-me-not (*Myosotis arvensis*)

Asclepiadaceous weeds:

common milkweed (*Asclepias syriaca*)

Euphorbiaceous weeds:

sun spurge (*Euphorbia helioscopia*), spotted spurge (*Euphorbia maculata*)

Graminaceous weeds:

barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oats (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomifiorum*), Texas panicum (*Panicum texanum*), shattercane (*Sorghum vulgare*)

Commelinaceous weeds:

common dayflower (*Commelina communis*)

Equisetaceous weeds:

field horsetail (*Equisetum arvense*)

Cyperaceous weeds:

rice flatsedge (*Cyperus iria*), purple nutsedge (*Cyperus rotundus*), yellow nutsedge (*Cyperus esculentus*)

Furthermore, some of the present compounds exhibit no significant phytotoxicity on the main crops such as corn (*Zea mays*), wheat (*Triticum aestivum*), barley (*Hordeum vulgare*), rice (*Oryza saliva*), sorghum (*Sorghum bicoloz*), soybean (*Glycine max*), cotton (Gossypium spp.), sugar beet (*Beta vulgaris*), peanut (*Arachis hypogaea*), sunflower (*Helianthus annuus*), and canola (*Brassica napus*); horticultural crops such as flowers and ornamental plants; and vegetable crops.

The present compounds can also attain the effective control of various weeds which may cause some trouble in the no-tillage cultivation of soybean (*Glycine max*), corn (*Zea mays*), wheat (*liticum aestivum*), and other crops. Furthermore, some of them exhibit no significant phytotoxicity on the crops.

The present compounds also have herbicidal activity against various weeds which may cause some trouble in the flooding treatment on paddy fields, such as listed below.

Graminaceous weeds:
barnyardgrass (*Echinochloa oryzicola*)
Scrophulariaceous weeds:
common falsepimpernel (*Lindernia procumbens*)
Lythraceous weeds:
Indian toothcup (*Rotala indica*), red stem (*Ammannia multiflora*)
Elatinaceous weeds:
waterwort (*Elatine triandra*)
Cyperaceous weeds:
smallflower umbrella sedge (*Cyperus dfformis*), hardstem bulrush (*Scirpus juncoides*), needle spikerush (*Eleocharis acicularis*), water nutgrass (*Cyperus serotinus*), water chestnut (*Eleocharis kuroguwai*)
Pontederiaceous weeds:
monochoria (*Monochoria vaginalis*)
Alismataceous weeds:
arrowhead (*Sagittaria pygmaea*), arrowhead (*Sagittaria trifolia*),
waterplantain (*Alisma canaliculatum*)
Potamogetonaceous weeds:
roundleaf pondweed (*Potamogeton distinctus*)
Umbelloferous weeds:
watercelery sp. (*Oenanthe javanica*)

Furthermore, some of the present compounds exhibit no significant phytotoxicity on transplanted paddy rice.

The present compounds can also attain the control of a wide variety of weeds which grow or will grow in the orchards, grasslands, lawns, forests, waterways, canals, or other non-cultivated lands.

The present compounds also have herbicidal activity against various aquatic weeds, such as water hyacinth (*Eichhornia crassipes*), which grow or will grow at the waterside such as waterways or canals.

The present compounds have substantially the same characteristics as those of the herbicidal compounds disclosed in the published specification of International Patent Application, WO95/34659. In the case where crops with tolerance imparted by introducing a herbicide tolerance gene described in the published specification are cultivated, the present compounds can be used at larger rates than those used when ordinary crops without tolerance are cultivated, which makes it possible to control other unfavorable weeds more effectively.

When the present compounds are used as the active ingredients of herbicides, they are usually mixed with solid or liquid carriers or diluents, surfactants, and other auxiliary agents to give emulsifiable concentrates, wettable powders, flowables, granules, concentrated emulsions, water-dispersible granules, or other formulations.

These formulations may contain any of the present compounds as an active ingredient at an amount of 0.001 to 80% by weight, preferably 0.005 to 70% by weight, based on the total weight of the formulation.

The solid carrier or diluent which can be used may include, for example, fine powders or granules of the following materials: mineral matters such as kaolin clay, attapulgite clay, bentonite, acid clay, pyrophyllite, talc, diatomaceous earth, and calcite; organic substances such as walnut shell powder; water-soluble organic substances such as urea; inorganic salts such as ammonium sulfate; and synthetic hydrated silicon oxide. The liquid carrier or diluent which can be used may include, for example, aromatic hydrocarbons such as methylnaphthalene, phenylxylylethane, and alkylbenzene (e.g., xylene); alcohols'such as isopropanol, ethylene glycol, and 2-ethoxyethanol; esters such as phthalic acid dialkyl esters; ketones such as acetone, cyclohexanone, and isophorone; mineral oils such as machine oil; vegetable oils such as soybean oil and cottonseed oil; dimethylsulfoxide, N,N-dimethylformamide, acetonitrile, N-methylpyrrolidone, and water.

The surfactant used for emulsification, dispersing, or spreading may include surfactants of the anionic type, such as alkylsulfates, alkylsulfonates, alkylarylsulfonates, dialkylsulfosuccinates, and phosphates of polyoxyethylene alkyl aryl ethers; and surfactants of the nonionic type, such as polyoxyethylene alkyl ethers, polyoxyethylene alkyl aryl ethers, polyoxyethylene polyoxypropylene block copolymers, sorbitan fatty acid esters, and polyoxyethylene sorbitan fatty acid esters.

The auxiliary agent may include lignin sulfonates, alginates, polyvinyl alcohol, gum arabic, CMC (carboxymethylcellulose), and PAP (isopropyl acid phosphate).

The present compounds are usually formulated as described above and then used for pre- or post-emergence soil, foliar, or flooding treatment of weeds. The soil treatment may include soil surface treatment and soil incorporation. The foliar treatment may include application over the plants and directed application in which a chemical is applied only to weeds so as to keep off the crop plants.

The present compounds may often exhibit the enhancement of herbicidal activity when used in admixture with other herbicides. They can also be used in admixture with insecticides, acaricides, nematocides, fungicides, bactericides, plant growth regulators, fertilizers, and soil conditioners. Examples of the herbicide which can be used in admixture with the present compounds are atrazine, cyanazine, dimethametryn, metribuzin, prometryn, simazine, simetryn, chlorotoluron, diuron, dymron, fluometuron, isoproturon, linuron, methabenzthiazuron, bromoxynil, ioxynil, ethalfluralin, pendimethalin, trifluralin, acifluorfen, acifluorfen-sodium, bifenox, chlomethoxynil, fomesafen, lactofen, oxadiazon, oxadiargyl, oxyfluorfen, carfentrazone, flumiclorac-pentyl, flumioxazine, fluthiacet-methyl, sulfentrazone, thidiazimin, difenzoquat, diquat, paraquat, 2,4-D, 2,4-DB, DCPA, MCPA, MCPB, clomeprop, clopyralid, dicamba, dithiopyr, fluroxypyr, mecoprop, napronilide, phenothiol, quinclorac, triclopyr, acetochlor, alachlor, butachlor, diethatyl-ethyl, metolachlor, pretilachlor, propachlor, bensulfuron-methyl, chlorsulfuron, chlorimuron-ethyl, halosulfuron-methyl, metsulfuron-methyl, nicosulfuron, primisulfuron, pyrazosulfuron-ethyl, sulfometuron-ethyl, thifensulfuron-methyl, triasulfuron, tribenuron-methyl, azimsulfuron, cloransulam-methyl, cyclosulfamuron, flumetsulam, flupyrsulfuron, flazasulfuron, imazosulfuron, metosulam, prosulfuron, rimsulfuron, triflusulfuron-methyl, imazamethabenzmethyl, imazapyr, imazaquin, imazethapyr, imazameth, imazamox, bispyribac-sodium, pyriminobac-methyl, pyrithiobac-sodium, alloxydim-sodium, clethodim, sethoxydim, tralkoxydim, dichlofop-methyl, fenoxaprop-ethyl, fenoxaprop-p-ethyl, fluazifop-butyl, fluazifop-p-butyl, haloxyfop-methyl, quizalofop-p-ethyl, cyhalofopbutyl, clodinafoppropargyl, benzofenap, clomazone, diflufenican, norflurazon, pyrazolate, pyrazoxyfen, isoxaflutole, sulcotrione, glufosinate-ammonium, glyphosate, bentazon, benthiocarb, bromobutide, butamifos, butylate, dimepiperate, dimethenamid, DSMA, EPTC, esprocarb, isoxaben, mefenacet, molinate, MSMA, piperophos, pyributicarb, propanil, pyridate, triallate, cafenstrol, flupoxam, and fluthiamide.

These compounds are described in the catalog of Farm Chemicals Handbook, 1995 (published by Meister Publishing Company); AG CHEM NEW COMPOUND REVIEW, VOL. 13, 1995 (published by AG CHEM INFORMATION SERVICES); and "Josouzai Kenkyu Souran" (published by Hakuyu-sha).

When the present compounds are used as the active ingredients of herbicides, the application amount, although it may vary with the weather conditions, formulation types, application times, application methods, soil conditions, crops to be protected, weeds to be controlled, and other factors, is usually in the range of 0.01 to 10,000 g, preferably 1 to 8000 g, per hectare. In the case of emulsifiable concentrates, wettable powders, flowables, concentrated emulsions, water-dispersible granules, or other similar formulations, they are usually applied after diluted in their prescribed amounts with water (if necessary, containing an adjuvant such as a spreading agent) at a ratio of 10 to 1000 liters per hectare. In the case of granules or some types of flowables, they are usually applied as such without any dilution.

The adjuvant which can be used herein, if necessary, may include, in addition to the surfactants as described above, polyoxyethylene resin acids (esters), lignin sulfonates, abietates, dinaphthylmethanedisulfonates, crop oil concentrates, and vegetable oils such as soybean oil, corn oil, cottonseed oil, and sunflower oil.

The present compounds can also be used as the active ingredients of harvesting aids such as defoliants and desiccants for cotton (Gossipyum spp.), and desiccants for potato (*Solanum tuberosum*). In these cases, the present compounds are usually formulated in the same manner as the case where they are used as the active ingredients of herbicides, and used alone or in admixture with other harvesting aids for foliar treatment before the harvesting of crops.

EXAMPLES

The present invention will be further illustrated by the following production examples, formulation examples, and test examples; however, the present invention is not limited to these examples.

Production Example 1
(Production of Present Compound 1-2)

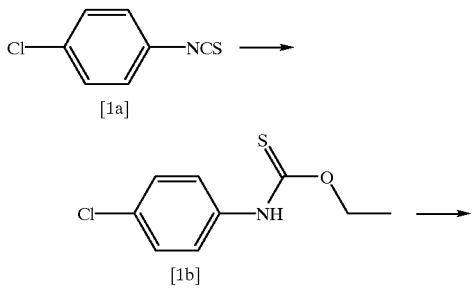

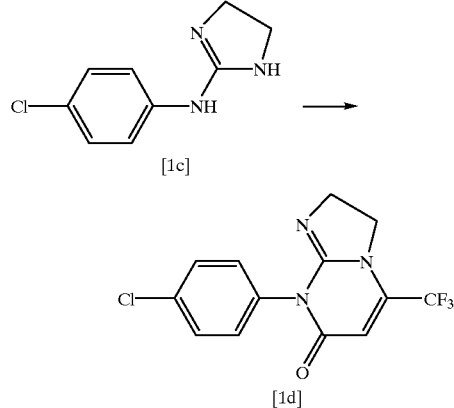

First, 6.0 g of ethanol was added to 3.0 g of compound [1a], which was heated under reflux for 5.5 hours. The reaction mixture was cooled to room temperature, and the precipitated crystals were collected by filtration. The crystals were washed with ethanol and then with hexane to give 2.2 g of compound [1b] (m.p., 93.9° C.).

Then, 1.9 g of ethylenediamine was added to 2.2 g of compound [1b], which was heated under reflux for 1.5 hours. The reaction mixture was concentrated under reduced pressure, and the precipitated crystals were collected by filtration. The crystals were washed with water and recrystallized from a mixed solvent of ethanol and water (1:1) to give 0.8 g of compound [1c] (m.p., 160.3° C.).

Finally, 2 ml of toluene and 0.6 g of ethyl 4,4,4-trifluoroacetoacetate were added to 0.40 g of compound [1c], which was heated under reflux for 5.5 hours. The reaction mixture was concentrated under reduced pressure, and the residue was subjected to silica gel column chromatography, which afforded 0.43 g of compound [1d] (present compound 1-2).

$^1$H-NMR (300 MHz, CDCl$_3$, TMS) δ (ppm): 3.88–3.97 (2H, m), 4.08–4.16 (2H, m), 5.90 (1H, s), 7.21–7.27 (2H, m), 7.44–7.50 (2H, m)

Production Example 2
(Production of Present Compound 2-26)

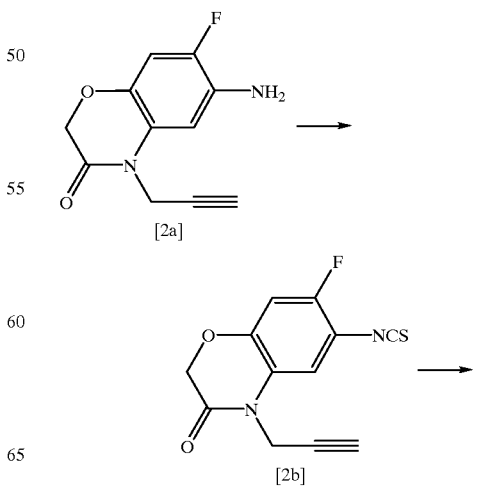

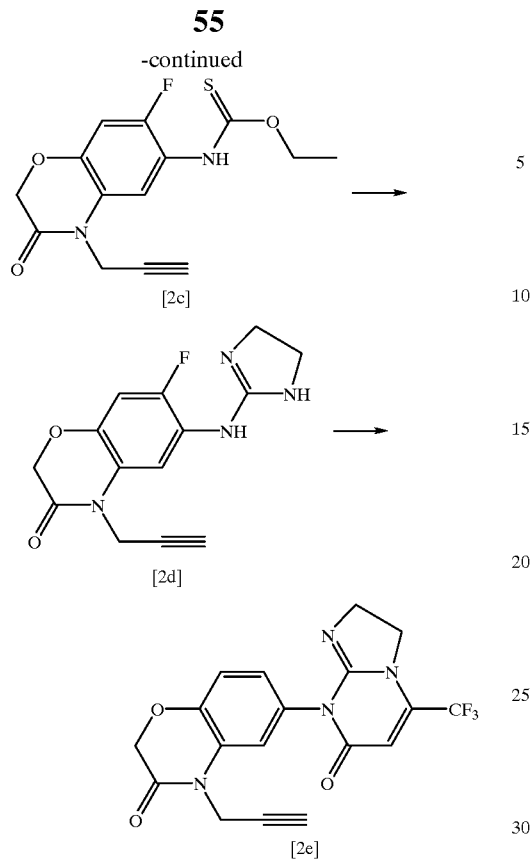

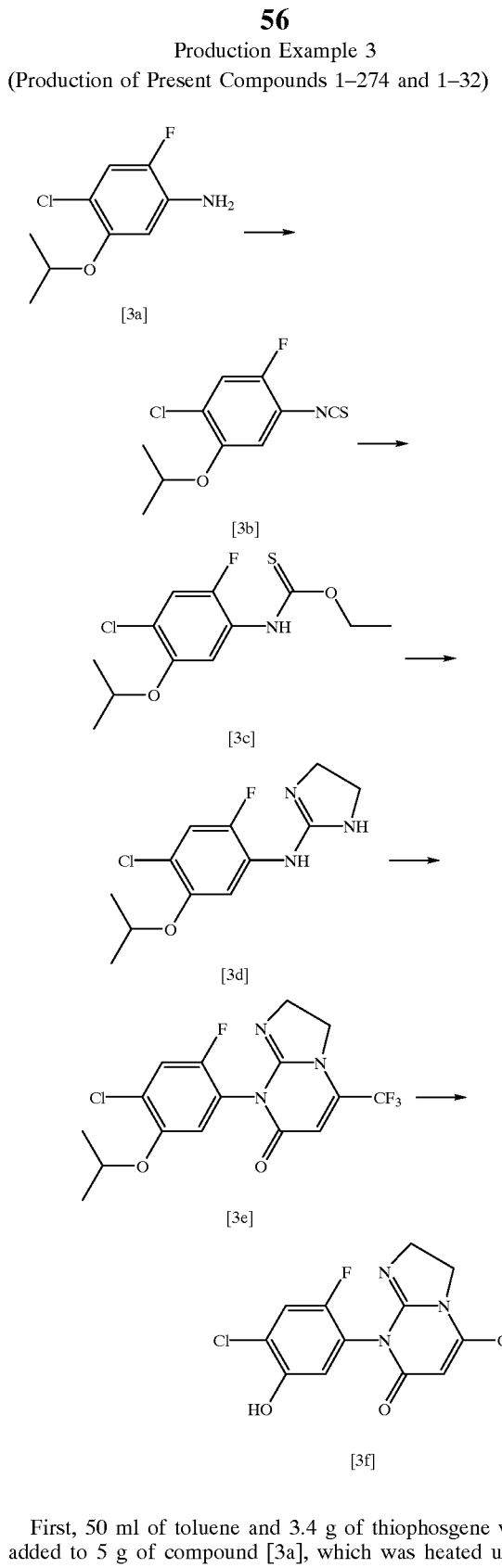

Production Example 3
(Production of Present Compounds 1–274 and 1–32)

First, 90 g of pyridine was added to 20 g of compound [2a], to which 28 g of triethylamine and 55 g of carbon disulfide were added dropwise under ice cooling, followed by stirring at room temperature for 2 hours. Then, 17 g of methyl chloroformate was added dropwise under ice cooling, which was stirred at room temperature for 2 hours. The reaction mixture was made acidic by the addition of diluted hydrochloric acid, which was extracted with ethyl acetate. The organic layer was dried over magnesium sulfate and then concentrated to give 24 g of compound [2b].

$^1$H-NMR (300 MHz, CDCl$_3$, TMS) δ (ppm): 2.32 (1H, t, J=2.7 Hz), 4.65 (2H, d, J=2.7 Hz), 4.66 (2H, s), 6.84 (1H, d, J=9.7 Hz), 7.00 (1H, d, J=7.0 Hz)

Then, 10 g of ethanol was added to 1.0 g of compound [2b], which was heated under reflux for 3 hours. The reaction mixture was concentrated under reduced pressure, and the residue was recrystallized by the addition of ethanol to give 1.1 g of compound [2c] (m.p., 189.3° C.).

Then, 0.65 g of ethylenediamine was added to 1.1 g of compound [2c], which was heated under reflux for 1.5 hours. The reaction mixture was concentrated under reduced pressure, and the precipitated crystals were collected by filtration. The crystals were washed with 2-propanol and then with hexane to give 0.35 g of compound [2d] (m.p., 146.9° C.).

Finally, 10 ml of toluene and 3.4 g of ethyl 4,4,4-trifluoroacetoacetate were added to 1.7 g of compound [2d], which was heated under reflux for 5.0 hours. The reaction mixture was concentrated under reduced pressure, and the residue was subjected to silica gel column chromatography, which afforded 0.30 g of compound [2e] present compound 2–26).

$^1$H-NMR (300 MHz, CDCl$_3$, TMS) δ (ppm): 2.29 (1H, t, J=2.4 Hz), 3.91–3.98 (2H, m), 4.08–4.19 (2H, m), 4.57 (1H, dd, J=2.4, 17.7 Hz), 4.65–4.67 (2H, m), 4.72 (1H, dd, J=2.4, 17.7 Hz), 5.90 (1H, s), 6.91 (1H, d, J=9.8 Hz), 7.11 (1H, d, J=6.8 Hz)

First, 50 ml of toluene and 3.4 g of thiophosgene were added to 5 g of compound [3a], which was heated under reflux for 1 hour. The reaction mixture was concentrated under reduced pressure to give compound [3b].

Then, 50 ml of ethanol was added to compound [3b], which was heated under reflux for 2 hours. The reaction mixture was concentrated under reduced pressure, and the residue was recrystallized by the addition of ethanol. The crystals were washed with hexane to give 2.8 g of compound [3c].

$^{1}$H-NMR (300 MHz, CDCl$_3$, TMS) δ (ppm): 1.37–1.47 (9H, m), 4.40-4.50 (1H, m), 4.60 (2H, q, J=6.9 Hz), 7.14 (1H, d, J=10.1 Hz), 7.90–8.25 (1H, br)

Then, 40 ml of toluene and 1.5 g of ethylenediamine were added to 2.7 g of compound [3c], which was heated under reflux for 7 hours. The reaction mixture was concentrated under reduced pressure, and the precipitated crystals were collected by filtration, and washed with water and then with hexane to give 2.2 g of compound [3d] (m.p., 162.8° C.).

Then, 30 ml of toluene and 3.2 ml of ethyl 4,4,4-trifluoroacetoacetate were added to 2.0 g of compound [3d]? which was heated under reflux for 5 hours. The reaction mixture was concentrated under reduced pressure, and the residue was subjected to silica gel column chromatography, which afforded 0.80 g of compound [3e] (present compound 1-274) (m.p., 158.2° C.).

Then, 2 ml of concentrated sulfuric acid was added to 100 mg of compound [3e] under ice cooling, which was stirred for 10 minutes. The reaction mixture was returned to room temperature and then neutralized with aqueous sodium hydrogencarbonate solution, which was extracted with ethyl acetate. The organic layer was dried over magnesium sulfate and then concentrated under reduced pressure, which afforded 75 mg of compound [3f] (present compound 1-32).

$^{1}$H-NMR (300 MHz, CDCl$_3$, TMS) δ (ppm): 3.95–4.27 (4H, m), 5.96 (1H, s), 6.49 (1H, d, J=6.7 Hz), 7.20 (1H, d, J=9.0 Hz).

Production Example 4
(Production of Present Compound 1–406)

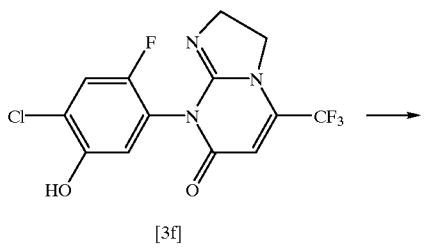

First, 1 ml of N,N-dimethylformamide, 40 mg of potassium carbonate, and 50 mg of ethyl bromoacetate were added to 75 mg of compound [3f], which was stirred at robm temperature for 2 hours. Then, water was added to the reaction mixture, and the precipitated crystals were collected by filtration and washed with hexane, which afforded 70 mg of compound [4a] (present compound 1-406).

$^{1}$H-NMR (300 MHz, CDCl$_3$, TMS) δ ppm): 1.28 (3H, t, J=7.1 Hz), 3.88–3.97 (2H, m), 4.08–4.17 (2H, m), 4.25 (2H, q, J=7.1 Hz), 4.65 (2H, s), 5.87 (1H, s), 6.88 (1H, d, J=6.3 Hz), 7.32 (1H, d, J=8.8 Hz)

Production Example 5
(Production of Present Compound 1–460)

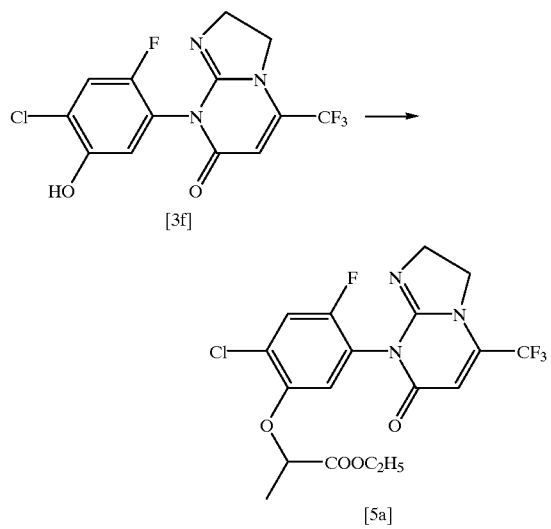

In the same manner as described in Production Example 4, except that ethyl 2-bromopropionate was substituted for ethyl bromoacetate, 0.10 g of compound [5a] (present compound 1-460) was obtained from 0.10 g of compound [31].

$^{1}$H-NMR (300 MHz, CDCl$_3$, TMS) δ (ppm): 1.19–1.29 (3H, m), 1.66 (3H, d, J=6.8 Hz), 3.87–3.97 (2H, m), 4.08–4.27 (4H, m), 4.62–4.72 (1H, m), 5.86 (1H, s), 6.83–6.93 (1H, m), 7.28–7.32 (1H, m)

Production Example 6
(Production of Present Compound 1–340)

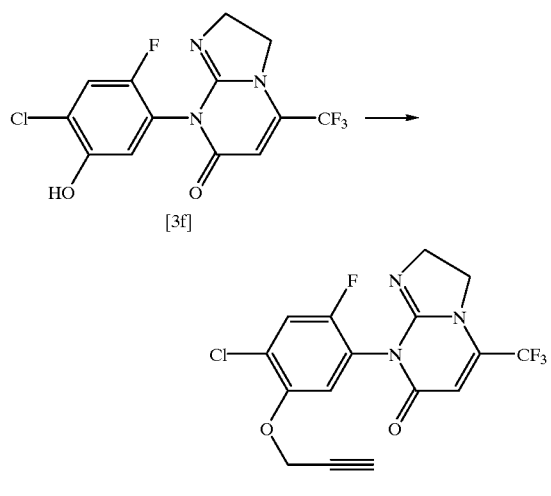

In the same manner as described in Production Example 4, except that propargyl bromide was substituted for ethyl bromoacetate, 0.10 g of compound [6a] (present compound 1-340) was obtained from 0.10 g of compound [3f].

$^{1}$H-NMR (300 MHz, CDCl$_3$, TMS) δ (ppm): 2.56 (1H, t, J=2.3 Hz), 3.90–3.98 (2H, m), 4.08–4.18 (2H, m), 4.74 (2H, d, J=2.3 Hz), 5.88 (1H, s), 7.03 (1H, d, J=6.4 Hz), 7.31 (1H, d, J=9.1 Hz)

Production Example 7

(Production of Present Compound 1-346)

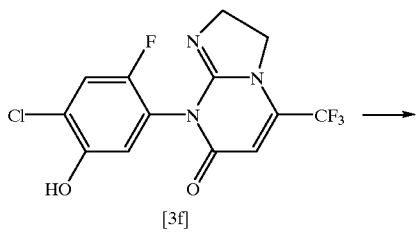

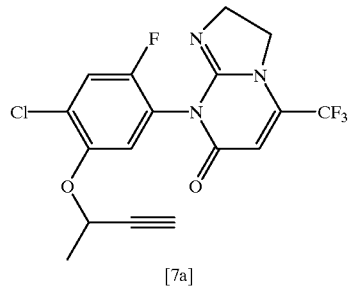

In the same manner as described in Production Example 4, except that 1-methyl-2-propynyl bromide was substituted for ethyl bromoacetate, 0.10 g of compound [7a] (present compound 1-346) (m.p., 137.6° C.) was obtained from 0.11 g of compound [3f].

Production Example 8

(Production of Present Compounds 1-454, 1-448, and 1-562)

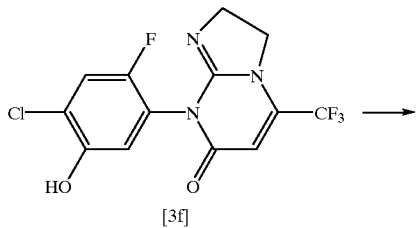

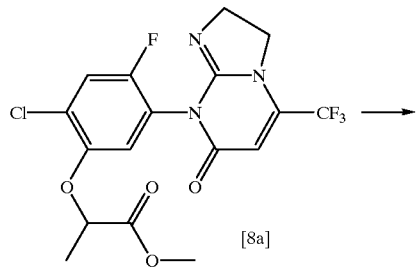

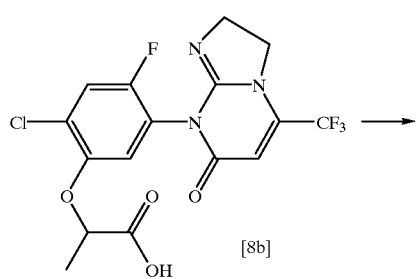

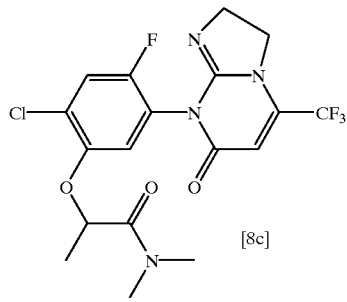

In the same manner as described in Production Example 4, except that methyl 2-bromopropionate was substituted for ethyl bromoacetate, 2.7 g of compound [8a] (present compound 1-454) (m.p., 99.7° C.) was obtained from 2.5 g of compound [3f].

Then, 10 ml of 36% hydrochloric acid was added to 1.8 g of compound [8a], which was heated at 70° C. under stirring for 5 hours. The reaction mixture was concentrated under reduced pressure, and the residue was subjected to silica gel column chromatography, which afforded 1.6 g of compound [8b] (present compound 1-448) (m.p., 185.4° C.).

Then, 2 ml of dimethylsulfoxide, 2 ml of tetrahydrofuran, and 0.40 g of N,N-carbonyldiimidazole were added to 0.40 g of compound [8b], which was heated under stirring for 2 hours. Dimethylamine was blown into the reaction mixture. Then, the reaction mixture was subjected to silica gel column chromatography, which afforded 0.45 g of compound [8c] (present compound 1-562).

$^1$H-NMR (250 MHz, CDCl$_3$, TMS) δ (ppm): 1.67 (3H, d, J=6.8 Hz), 2.91 (3H, s), 3.11 (3H, s), 3.87–3.99 (2H, m), 4.08–4.18 (2H, m), 4.86–4.98 (1H, m),5.85 (1H, s), 6.90 (0.6H, d, J=6.5 Hz), 6.93 (0.4H, d, J=6.6 Hz), 7.31 (1H, d,J=8.9 Hz)

Production Example 9

(Production of Present Compound 1-514)

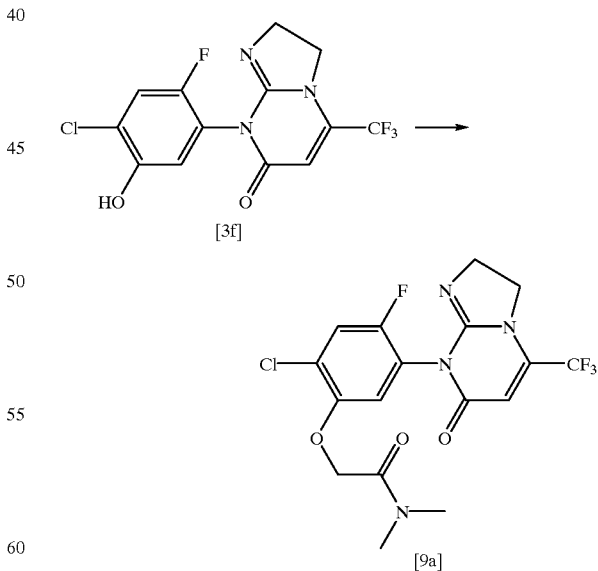

In the same manner as described in Production Example 4, except that 2-chloro-N,N-diemthylacetamide was substituted for ethyl bromoacetate, 0.54 g of compound [9a] (present compound 1-514) was obtained from 0.50 g of compound [3f].

¹H-NMR (250 MHz, CDCl₃, TMS) δ (ppm): 2.95 (3H, s), 3.12 (3H, s), 3.89–3.96 (2H, m), 4.07–4.16 (2H, m), 4.73 (2H, s), 5.86 (1H, s), 7.05 (1H, d, J=6.4 Hz), 7.30 (1H, d, J=8.8 Hz)

Production Example 10

(Production of Present Compound 1-262)

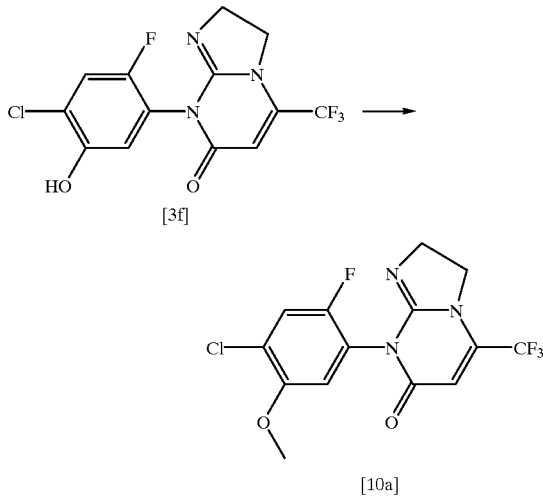

In the same manner as described in Production Example 4, except that methyl iodide was substituted for ethyl bromoacetate, 0.40 g of compound [10a] (present compound 1-262) (m.p., 149.2° C.) was obtained from 0.51 g of compound [3f].

Production Example 11

(Production of Present Compound 1-268)

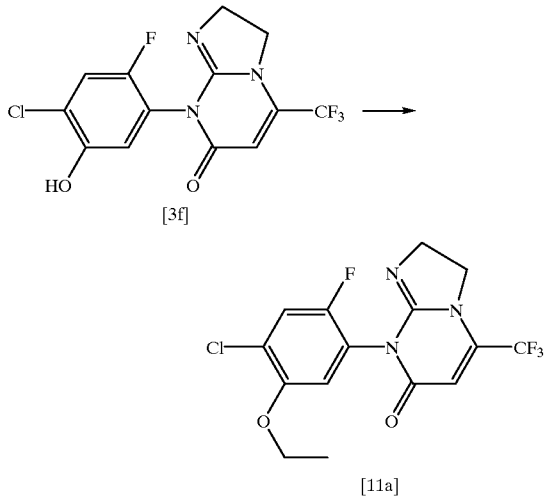

In the same manner as described in Production Example 4, except that ethyl bromide was substituted for ethyl bromoacetate, 0.44 g of compound [11a] (present compound 1-268) (m.p., 142.2° C.) was obtained from 0.51 g of compound [3f].

Production Example 12

(Production of Present Compound 1-280)

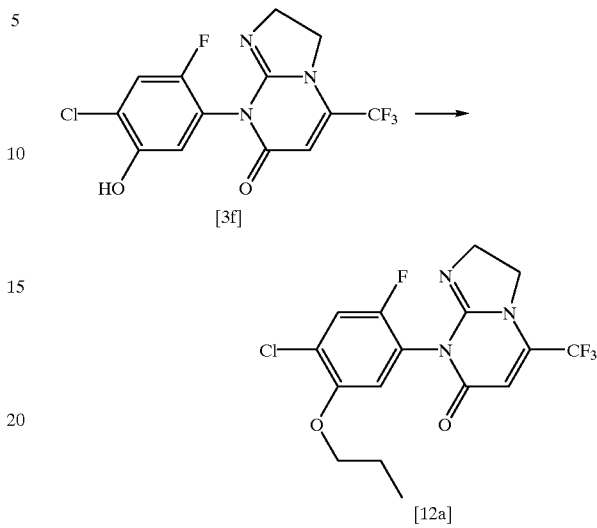

In the same manner as described in Production Example 4, except that propyl bromide was substituted for ethyl bromoacetate, 0.35 g of compound [12a] (present compound 1-280) (m.p., 171.0° C.) was obtained from 0.40 g of compound [3f].

Production Example 13

(Production of Present Compound 1-1246)

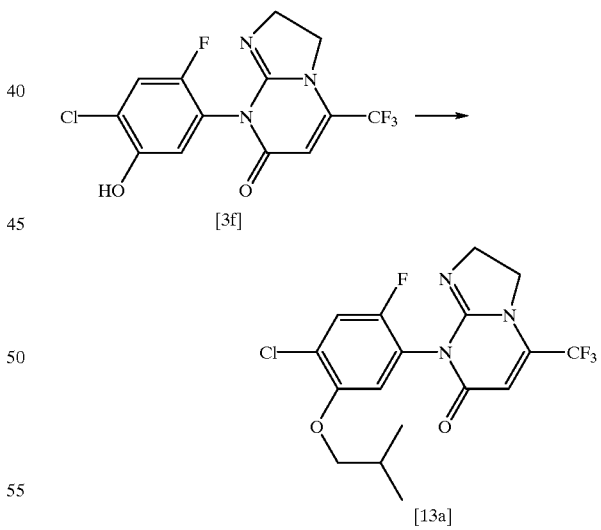

In the same manner as described in Production Example 4, except hat isobutyl bromide was substituted for ethyl bromoacetate, 0.15 g of compound [13a] (present compound 1-1246) was obtained from 0.50 g of compound [3f].

¹H-NMR (300 MHz, CDCl₃, TMS) δ (ppm): 1.02 (1H, s), 1.04 (1H, s), 2.03–2.22 (1H, m), 3.73 (2H, d, J=6.5 Hz), 3.90–4.01 (2H, m), 4.09–4.18 (2H, m), 5.88 (1H, s), 6.81 (1H, d, J=6.4 Hz), 7.29 (1H, d, J=9.0 Hz)

Production Example 14

(Production of Present Compound 1-310)

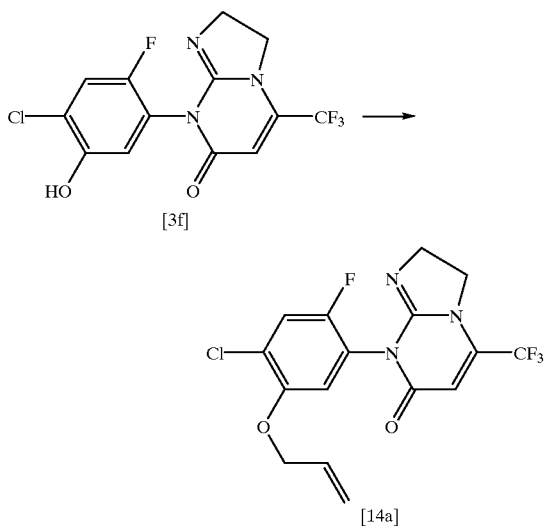

In the same manner as described in Production Example 4, except that allyl bromide was substituted for ethyl bromoacetate, 0.46 g of compound [14a] (present compound 1-310) (m.p., 146.6° C.) was obtained from 0.50 g of compound [3f].

Production Example 15

(Production of Present Compound 1-370)

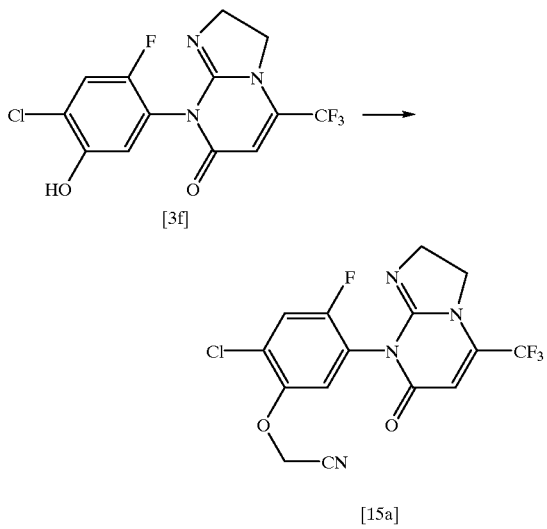

In the same manner as described in Production Example 4, except that bromoacetonitrile was substituted for ethyl bromoacetate, 0.13 g of compound [15a] (present compound 1-370) was obtained from 0.50 g of compound [3f].

$^1$H-NMR (300 MHz, CDCl$_3$, TMS) δ (ppm): 3.89–3.98 (2H, m), 4.09–4.19 (2H, m), 4.79 (2H, s), 5.88 (1H, s), 7.09 (1H, d, J=6.2 Hz), 7.35 (1H, d, J=8.8 Hz)

Production Example 16

(Production of Present Compounds 1-5, 1-14, and 1-23)

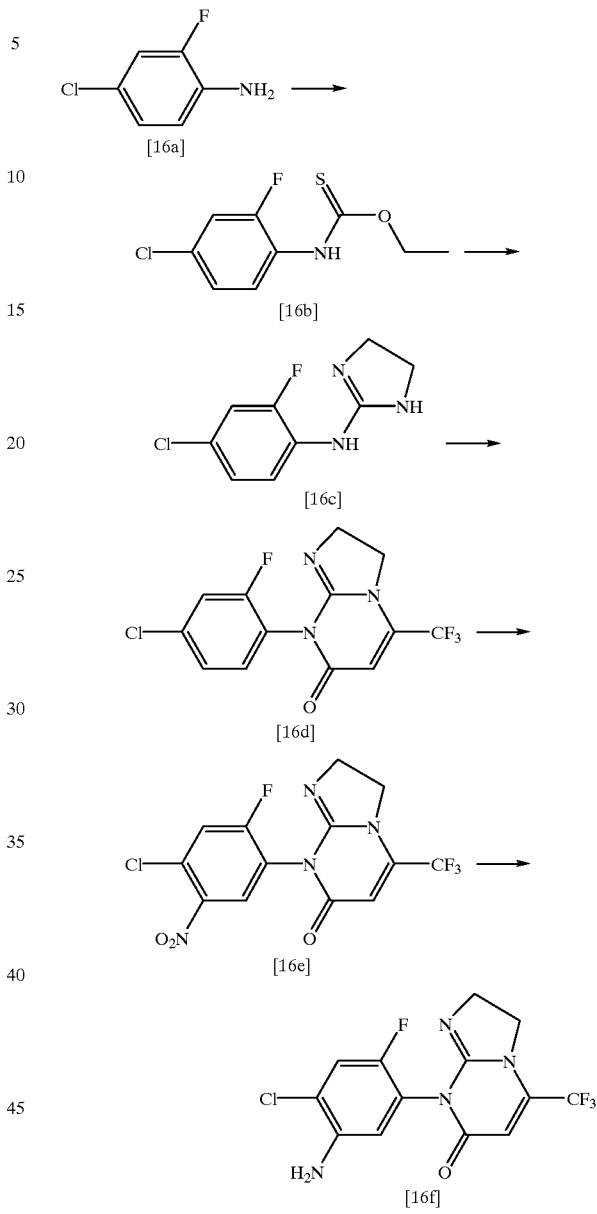

First, 27.2 g of compound [16a] was dissolved in 300 ml of toluene, to which 23.6 g of thiophosgene was added. The reaction mixture was heated under reflux for 3 hours and then concentrated to give 2-chloro-4-fluorophenylisothiocyanate. Then, 100 ml of ethanol was added to the 2-chloro-4-fluorophenylisothiocyanate. The reaction mixture was heated under reflux for 3 hours and then concentrated to give 37.5 g of compound [16b] (m.p., 87.9° C).

Then, 37 g of compound [16b] was dissolved in 50 ml of toluene, to which 14.3 g of ethylenediamine was added. The reaction mixture was heated under reflux for 2.5 hours and then poured into water, which was extracted with ethyl acetate. The organic layer was washed with water, dried over magnesium sulfate, and then concentrated. The precipitated crystals were washed with a mixed solution of hexane and diethyl ether (1:1) to give 28 g of compound [16c] (m.p., 127.8° C.).

Then, 27 g of compound [16c] and 25.6 g of ethyl 4,4,4-trifluoroacetoacetate were heated under reflux in 140 ml of toluene for 2.5 hours. The reaction mixture was concentrated, and the residue was subjected to silica gel chromatography (eluent, hexane : ethyl acetate=2:1), which afforded 10.3 g of compound [16d] (present compound 1-5) (m.p., 112.6° C.).

Then, 8.4 g of compound [16d] was dissolved in 30 ml of concentrated sulfuric acid, followed by ice cooling, to which a mixed acid of 1.7 g of fuming nitric acid and 1.5 ml of concentrated sulfuric acid was added dropwise at 0° C. to 5° C. After completion of the addition, the reaction mixture was stirred at room temperature for 1 hour and then poured onto ice, which was neutralized with saturated aqueous sodium hydrogencarbonate solution, while keeping the reaction mixture below 10° C. The precipitated crystals were collected by filtration, washed with water, and dried, which afforded 7.6 g of compound [16e] (present compound 1-14) (m.p., 178.1° C.).

Then, 3.3 g of iron powder, and a mixed solution of 6 ml of acetic acid and 12 ml of water were stirred at 25° C. for 30 minutes. While keeping the reaction mixture below 35° C., a solution of 3.3 g of compound [16e] in 40 ml of ethyl acetate was added dropwise to the reaction mixture. After completion of the addition, stirring was continued for a while. The reaction mixture was poured into water, which was then extracted with ethyl acetate. The organic layer was washed with water, neutralized, dried, and concentrated. The residue was subjected to silica gel chromatography (eluent, hexane:ethyl acetate=1:2), which afforded 1.05 g of compound [16f] (present compound 1-23).

$^1$H-NMR (250 MHz, CDCl$_3$, TMS) δ (ppm): 3.90–4.17 (6H, m), 5.87 (1H, s), 6.68 (1H, d, J=6.6 Hz), 7.19 (1H, d, J=9.0 Hz)

Production Example 17
(Production of Present Compound 1–88)

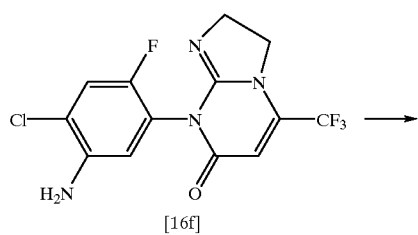

First, 0.25 g of compound [16f] was dissolved in 3 g of pyridine, to which 0.1 g of methanesulfonyl chloride was added. The reaction mixture was stirred for 4 hours and then poured into water, which was extracted with ethyl acetate. The organic layer was washed with water, dried, and concentrated. The precipitated crystals were washed with isopropanol, which afforded 0.15 g of compound [17a] (present compound 1-88) (m.p., 259.8° C.; decomposition).

Production Example 18
(Production of Present Compound 1–220)

First, 2.0 g of ethyl 2-bromopropionate was added to 0.3 g of compound [16f], which was heated at 130° C. for 3 hours. Excessive ethyl 2-bromopropionate was removed by distillation, and the residue was dissolved in ethyl acetate, which was washed with aqueous sodium hydrogencarbonate. The organic layer was dried and concentrated, and the precipitated crystals were washed with a mixed solvent of hexane and diethyl ether (1:2), which afforded 0.14 g of compound [18a] (present compound 1-220) (m.p., 99.1° C.).

Production example 19
(Present Compound 1–1096)

First, a solution of 0.2 g of compound [16f] in 10 ml of acetonitrile was added dropwise to a solution of 1.5 g of methyl acrylate, 0.1 g of amyl nitrite, and 0.08 g of copper (II) chloride at room temperature. After completion of the addition, the reaction mixture was stirred for 10 hours and then poured into water, which was extracted with ethyl acetate. The organic layer was washed with water, dried, and concentrated, and the residue was subjected to silica gel column chromatography (eluent, hexane: ethyl acetate=3:1), which afforded 0.2 g of compound [19a] (present compound 1-1096).

$^1$H-NMR (250 MHz, CDCl$_3$, TMS) δ (ppm): 3.22–3.49 (2H, m), 3.73 (1.5H, s), 3.76 (1.5H, s), 3.89–3.98 (2H, m), 4.10–4.16 (2H, m), 4.50–4.57 (1H, m), 5.85 (0.5H, s), 5.87 (0.5H, s), 7.24–7.46 (2H, m)

Production Example 20
(Production of Present Compound 1-712)

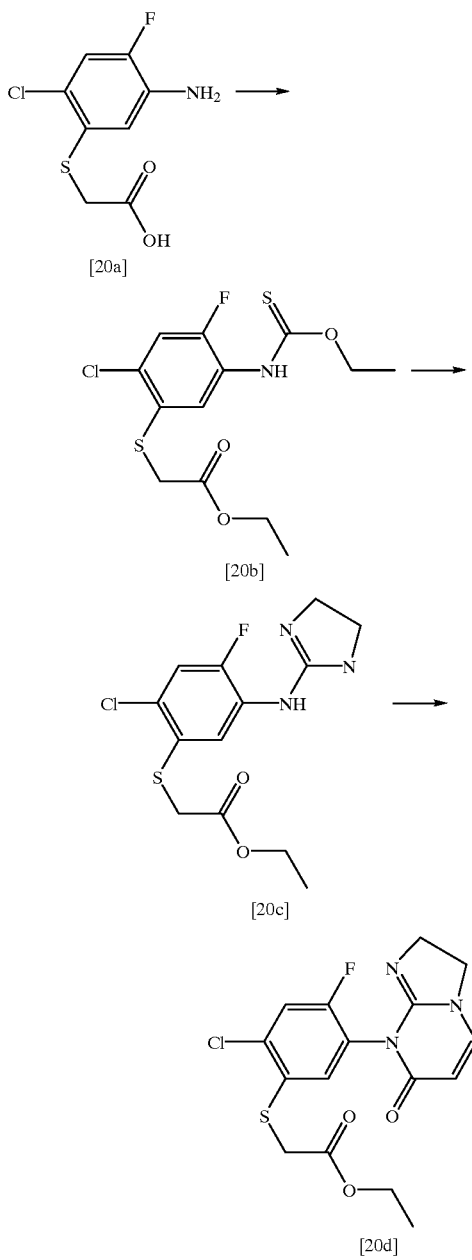

First, 7.1 g of compound [20a] was suspended in 50 ml of toluene, to which 3.9 g of thiophosgene was added. The reaction mixture was heated under reflux for 3 hours and then concentrated. Then, 50 ml of ethanol was added to the residue. The reaction mixture was heated under reflux for another 3 hours and then concentrated. The precipitated crystals were washed with a mixed solvent of hexane and diethyl ether (1:1) to give 10.1 g of compound [20b].

$^1$H-NMR (250 MHz, CDCl$_3$, TMS) δ (ppm): 1.25 (3H, t, J=7.1 Hz), 1.43 (3H, t, J=7.1 Hz), 3.66 (2H, s), 4.18 (2H, q, J=7.1 Hz), 4.62 (2H, q, J=7.1 Hz), 7.20 (1H, d, J=10.1 Hz), 7.80–8.38 (1H, br) Then, 10.1 g of compound [20b] was dissolved in 100 ml of toluene, to which 1.9 g of ethylenediamine was added at room temperature. The reaction mixture was stirred for 30 minutes, heated under reflux for 2 hours and then concentrated. The precipitated crystals were washed with diethyl ether to give 5.9 g of compound [20c].

$^1$H-NMR (250 MHz, CDCl$_3$, TMS) δ (ppm): 1.24 (3H, t, J=7.2 Hz), 3.56 (2H, s), 3.57 (4H, s), 4.14 (2H, q, J=7.2 Hz), 7.12 (1H, d, J=10.1 Hz), 7.21 (1H, d, J=8.6 Hz)

A solution of 5.9 g of compound [20c] and 3.3 g of ethyl 4,4,4-trifluoroacetoacetate in 20 ml of toluene was heated under reflux for 6 hours. The reaction mixture was concentrated, and the residue was subjected to silica gel chromatography (eluent, hexane: ethyl acetate=1:1), which afforded 2.9 g of compound [20d] (present compound 1-712). $^1$H-NMR (250 MHz, CDCl$_3$, TMS) δ (ppm): 1.23 (3H, t, J=7.1 Hz), 3.64 (2H, s), 3.89–3.96 (2H, m), 4.10–4.20 (4H, m), 5.87 (1H, s), 7.34 (1H, d, J=9.1 Hz), 7.47 (1H, d, J=7.3 Hz)

Production Example 21
(Production of Present Compounds 1-1255 and 1-1257)

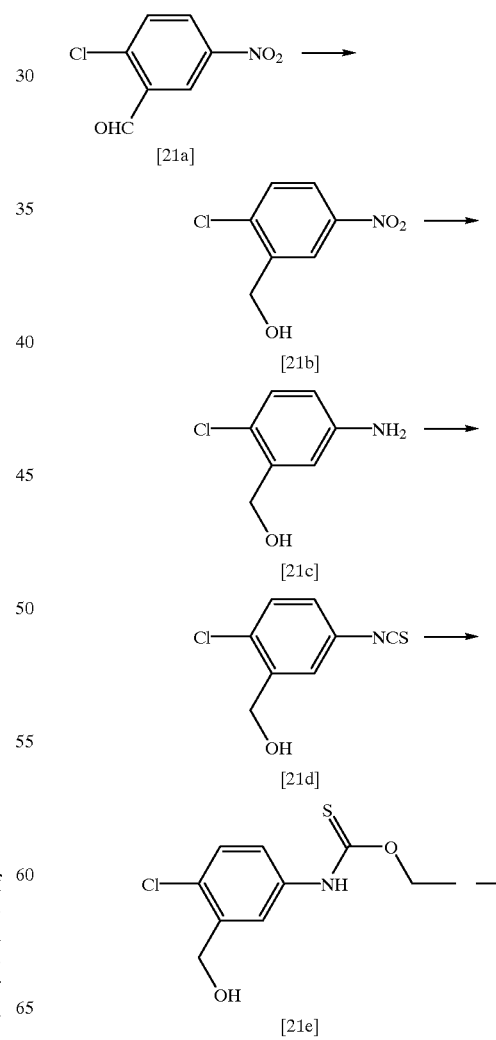

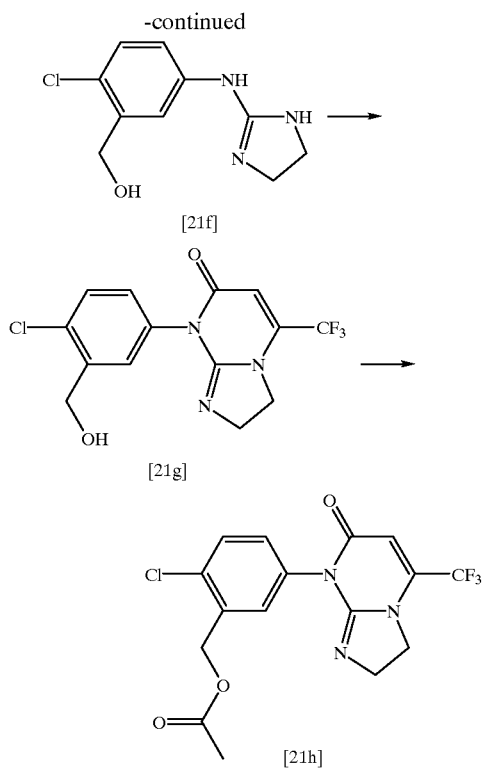

First, 10.4 g of sodium borohydride was added to a solution of 101 g of compound [21a] in 700 ml of methanol under ice cooling. The reaction mixture was stirred at room temperature for 30 minutes, into which diluted hydrochloric acid was poured. The precipitated crystals were collected by filtration to give 140 g of crude compound [21b].

$^1$H-NMR (300 MHz, CDCl$_3$, TMS) δ (ppm): 4.86 (2H, s), 7.52 (1H, d, J=8.7 Hz), 8.09 (1H, dd, J=2.8, 8.7 Hz), 8.45 (1H, d, J=2.8 Hz)

A mixture of 1000 ml of water, 100 ml of acetic acid, and 158 g of iron was heated to 60° C., to which a solution of 140 g of crude compound [21b] in 60 ml of ethyl acetate was added dropwise. The reaction mixture was stirred until it came to room temperature, and then extracted with ethyl acetate. The organic layer was dried over magnesium sulfate and then concentrated to give 59 g of compound [21c].

$^1$H-NMR (300 MHz, CDCl$_3$, TMS) δ (ppm): 3.73 (2H, br), 4.67 (2H, s), 6.53 (1H, dd, J=2.8, 8.4 Hz), 6.83 (1H, d, J=2.8 Hz), 7.09 (1H, d, J=8.4 Hz) Then, 5.6 ml of thiophosgene was added dropwise to a solution of 10.6 g of compound [21c] in 100 ml of toluene. The reaction mixture was heated under reflux for 1 hour and then concentrated to give 12 g of crude compound [21d].

$^1$H-NMR (250 MHz, CDCl$_3$, TMS) t (ppm): 2.00 (1H, t, J=6.0 Hz), 4.76 (2H, d, J=6.0 Hz), 7.08 (1H, dd, J=2.5, 8.5 Hz), 7.32 (1H, d, J=8.5 Hz), 7.42 (1H, d, J=2.5 Hz)

Then, 50 ml of ethanol was added to 12 g of crude compound [21d]. The reaction mixture was heated under reflux for 1 hour and then concentrated. The residue was subjected to silica gel column chromatography, which afforded 2.6 g of compound [21e].

Then, 100 ml of toluene and 1.7 ml of ethylenediamine were added to 2.3 g of compound [21e]. The reaction mixture was heated under reflux for 5 hours and then poured into water, which was extracted with ethyl acetate. The organic layer was dried over magnesium sulfate and then concentrated to give 1.3 g of crude compound [21f]

Then, 10 ml of toluene and 1.6 g of ethyl 3-methoxy-4,4,4-trifluorochrotonate were added to 1.3 g of crude compound [21f]. The reaction mixture was heated under reflux for 8.5 hours and then concentrated to give a crude compound [21g]. This crude product was subjected to silica gel column chromatography, which afforded 0.12 g of compound [21g] (present compound 1-1255) (m.p., 184.3° C.).

Then, 2 ml of anhydrous acetic acid and 2 ml of pyridine were added 180 mg of crude compound [21g], and the reaction was allowed to proceed at room temperature overnight. The reaction mixture was poured into water, which was then extracted with ethyl acetate. The organic layer was dried over magnesium sulfate and then concentrated under reduced pressure. The residue was subjected to silica gel column chromatography, which afforded 20 mg of compound [21h] (present compound 1-1257).

$^1$H-NMR (300 MHz, CDCl$_3$, TMS) δ (ppm): 2.13 (3H, s), 3.89–3.96 (2H, m), 4.09–4.16 (2H, m), 5.22 (2H, s), 5.90 (1H, s), 7.21 (1H, dd, J=2.5, 8.5 Hz), 7.39 (1H, d, J=2.5 Hz), 7.52 (1H, d, J=8.5 Hz)

Production Example 22
(Production of Present Compound 6-2)

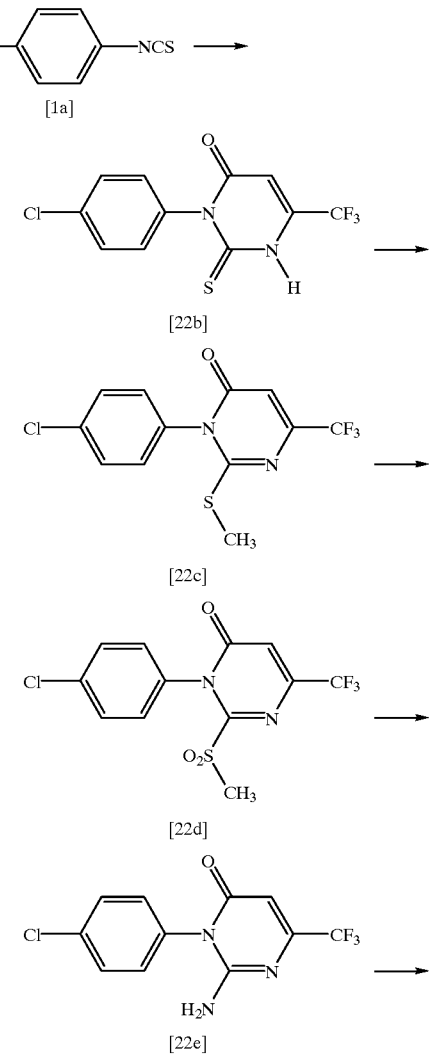

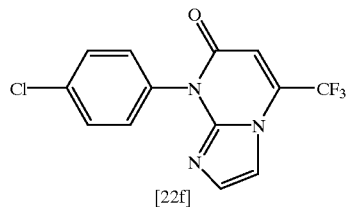

[22f]

First, 12.0 g of ethyl 3-amino-4,4,4-trifluorocrotonate was added to a suspension of 2.6 g of sodium hydride in 50 ml of N,N-dimethylformamide, while keeping the reaction mixture below 10° C. The reaction mixture was then stirred at room temperature for 30 minutes, to which a solution of 10.0 g of compound [1a] in 30 ml of toluene was added dropwise, while keeping the reaction mixture below 40° C. After completion of the addition, the reaction mixture was stirred at room temperature for 2 hours and then poured into water, which was neutralized with diluted hydrochloric acid and then extracted with diethyl ether. The organic layer was dried over magnesium sulfate and then concentrated. The crystals thus obtained were washed with a mixed solvent of hexane and diethyl ether (1:1) to give 11.3 g of compound [22b].

$^1$H-NMR (250 MHz, CDCl$_3$, TMS) δ (ppm): 6.43 (1H, s), 7.12–7.15 (2H, m), 7.49–7.51 (2H, m), 9.38–10.2 (1H, br)

Then, 4.0 g of triethylamine was added to a solution of 10.0 g of compound [22b] in 50 ml of N,N-dimethylformamide, followed by stirring for 30 minutes and addition of 5.6 g of iodomethane. The reaction mixture was stirred for 1 hour and then poured into water, which was neutralized with diluted hydrochloric acid and then extracted with diethyl ether. The organic layer was dried over magnesium sulfate and then concentrated to give 9.8 g of compound [22c] (m.p., 109.7° C.).

Then, 13 g of m-chloroperbenzoic acid was added to a solution of 6.0 g of compound [22c] in 40 ml of chloroform. The reaction mixture was stirred for 12 hours and then filtered. The filtrate was washed with aqueous sodium thiosulfate solution and then with aqueous potassium carbonate solution, dried over magnesium sulfate, and then concentrated to give 5.8 g of compound [22d].

$^1$H-NMR (250 MHz, CDCl$_3$, TMS)δ (ppm): 3.38 (3H, s), 7.04 (1H, s), 7.26–7.30 (2H, m), 7.51–7.55 (2H, m) Then, 3.5 g of compound [22d] was suspended in 20 ml of 2-methyl-2-propanol, into which ammonia gas was blown for 30 minutes, and the reaction mixture was poured into water. The precipitated crystals were collected by filtration, washed with water, and then dried to give 1.4 g of compound [22e] (m.p., 214.3° C.).

Then, 0.5 g of 2-bromo-1,1-diethoxyethane was added to a mixed solution of 1.0 g of concentrated hydrochloric acid and 2.0 g of acetic acid, followed by stirring at room temperature for 15 minutes and addition of 0.5 g of compound [22e]. The reaction mixture was heated under reflux for 10 hours and then poured into water, which was extracted with diethyl ether. The organic layer was washed with saturated aqueous sodium hydrogen-carbonate solution, dried over magnesium sulfate, and then concentrated. The residue was subjected to silica gel chromatography (eluent, hexane ethyl acetate=4 1), which afforded 0.24 g of compound [22f] (present compound 6-2) (m.p., 221.4° C.).

Production Example 23

(Present Compounds 6–32 and 6–274)

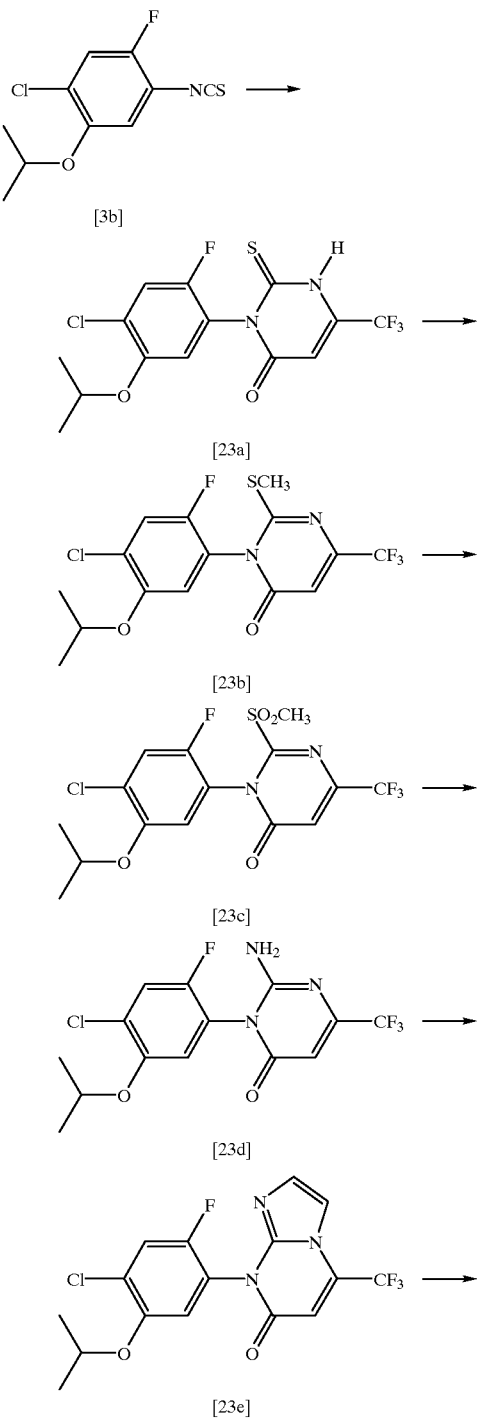

-continued

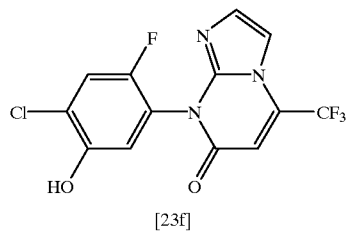

[23f]

First, 25.0 g of ethyl 3-amino-4,4,4-trifluorocrotonate was added to a suspension of 5.4 g of sodium hydride in 100 ml of N,N-dimethylformamide, while keeping the reaction mixture below 10° C. The reaction mixture was then stirred at room temperature for 30 minutes, to which a solution of 30.0 g of compound [3b] in 150 ml of toluene was added dropwise, while keeping the reaction mixture below 40° C. After completion of the addition, the reaction mixture was stirred at room temperature for 2 hours and then poured into water, which was neutralized with diluted hydrochloric acid and then extracted with diethyl ether. The organic layer was dried over magnesium sulfate and then concentrated. The crystals thus obtained were washed with a mixed solvent of hexane and diethyl ether (1 : 1) to give 16.0 g of compound [23a] (m.p., 224.9° C.).

Then, 5.0 g of triethylamine was added to a solution of 16.0 g of compound [23a] in 100 ml of N,N-dimethylformamide, followed by stirring for 30 minutes and addition of 6.0 g of iodomethane. The reaction mixture was stirred for another 1 hour and then poured into water, which was neutralized with diluted hydrochloric acid and then extracted with diethyl ether. The organic layer was dried over magnesium sulfate and then concentrated to give 16.4 g of compound [23b] (m.p., 88.4° C.).

Then, 28.6 g of m-chloroperbenzoic acid was added to a solution of 16.0 g of compound [23b] in 150 ml of chloroform. The reaction mixture was stirred for 12 hours and then filtered. The filtrate was washed with aqueous sodium thiosulfate solution and then with aqueous potassium carbonate solution, dried over magnesium sulfate, and then concentrated to give 16.5 g of compound [23c] (m.p., 164.8° C.).

Then, 16.2 g of compound [23c] was suspended in 150 ml of 2-methyl-2-propanol, into which ammonia gas was blown for 30 minutes, and the reaction mixture was poured into water. The precipitated crystals were collected by filtration, washed with water, and then dried to give 11.2 g of compound [23d] (m.p., 260.4° C.).

Then, 13.0 g of 2-bromo-1,1-dimethoxyethane was added to a mixed solution of 5.0 g of concentrated hydrochloric acid and 26.0 g of acetic acid, followed by stirring at room temperature for 15 minutes and addition of 11.0 g of compound [23d]. The reaction mixture was heated under reflux for 10 hours and then poured into water, which was extracted with diethyl ether. The organic layer was washed with saturated aqueous sodium hydrogencarbonate solution, dried over magnesium sulfate, and then concentrated. The residue was subjected to silica gel chromatography (eluent, hexane ethyl acetate=5:1), which afforded 6.7 g of compound [23e] (present compound 6–32) (m.p., 132.1° C.).

Finally, 6.0 g of compound [23e] was added to 50 ml of concentrated sulfuric acid. The reaction mixture was stirred for 3 hours and then poured into ice water, which was stirred for another 1 hour and then extracted with diethyl ether. The organic layer was dried over magnesium sulfate and then concentrated. The residue was subjected to silica gel chromatography (eluent, hexane:ethyl acetate=3:1), which afforded 2.4 g of compound [23f] (present compound 6–274).

$^1$H-NMR (250 MHz, CDCl$_3$, TMS) δ (ppm): 6.73 (1H, s), 6.74 (1H, d, J=6.5 Hz), 7.19 (1H, d, J=1.9 Hz), 7.29 (1H, d, J=1.9 Hz), 7.32 (1H, d, J=9.0 Hz)

Production Example 24

(Production of Present Compounds 16–32 and 16–274)

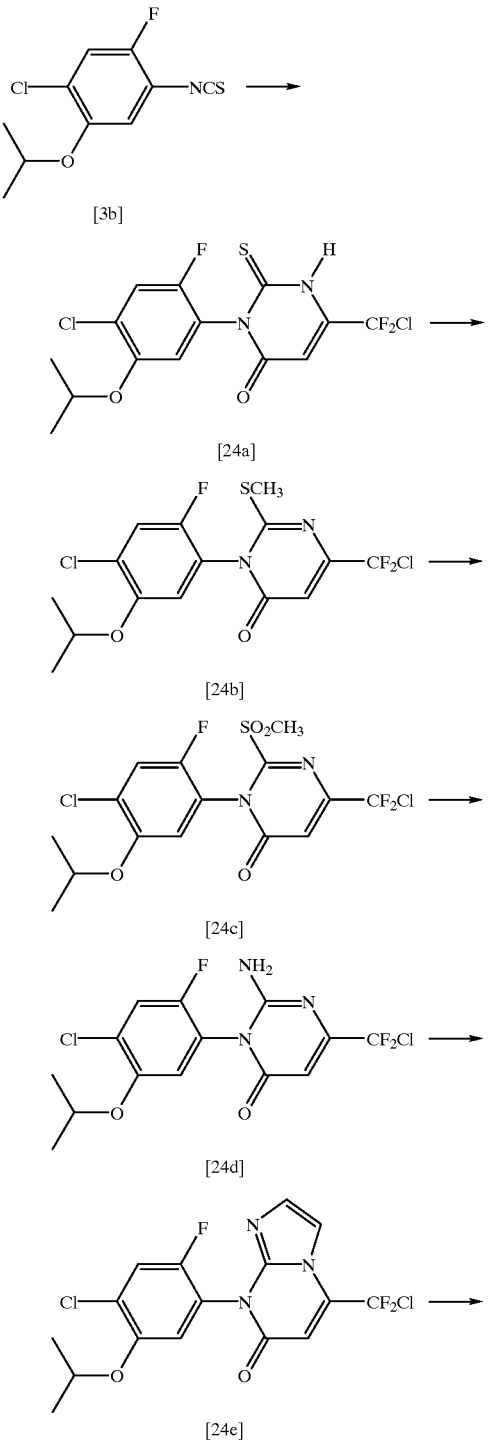

-continued

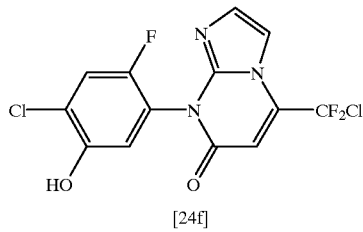

[24f]

First, 18.4 g of ethyl 3-amino-4-chloro-4,4-difluorochlotonate was added to a suspension of 3.6 g of sodium hydride in 50 ml of N,N-dimethylformamide, while keeping the reaction mixture below 10° C. The reaction mixture was stirred at room temperature for 30 minutes, to which a solution of 20.0 g of compound [3b] in 100 ml of toluene was added dropwise, while keeping the reaction mixture below 40° C. After completion of the addition, the reaction mixture was stirred at room temperature for 2 hours and then poured into water, which was neutralized with diluted hydrochloric acid and then extracted with diethyl ether. The organic layer was dried over magnesium sulfate and then concentrated. The crystals thus obtained were washed with a mixed solvent of hexane and diethyl ether (1:1) to give 8.2 g of compound [24a] (m.p., 213.7° C.).

Then, 2.5 g of triethylamine was added to a solution of 8.2 g of compound [24a] in 50 ml of N,N-dimethylformamide, followed by stirring for 30 minutes and addition of 4.4 g of iodomethane. The reaction mixture was stirred for 1 hour and then poured into water, which was neutralized with diluted hydrochloric acid and then extracted with diethyl ether. The organic layer was dried over magnesium sulfate and then concentrated to give 8.3 g of compound [24b] (m.p., 109.3° C.).

Then, 14.0 g of m-chloroperbenzoic acid was added to a solution of 8.2 g of compound [24b] in 100 ml of chloroform. The reaction mixture was stirred for 18 hours and then filtered. The filtrate was washed with aqueous sodium thiosulfate solution and then with aqueous potassium carbonate solution, dried over magnesium sulfate, and then concentrated to give 8.1 g of compound [24c] (m.p., 131.4° C.).

Then, 8.2 g of compound [24c] was suspended in 75 ml of 2-methyl-2-propanol, into which ammonia gas was blown for 30 minutes, and the reaction mixture was poured into water. The precipitated crystals were collected by filtration, washed with water, and then dried to give 5.4 g of compound [24d] (m.p., 261.3° C.).

Then, 6.0 g of 2-bromo-1,1-dimethoxyethane was added to a mixed solution of 3.0 g of concentrated hydrochloric acid and 12.0 g of acetic acid, followed by stirring at room temperature for 15 minutes and addition of 5.4 g of compound [24d]. The reaction mixture was heated under reflux for 14 hours and then poured into water, which was extracted with diethyl ether. The organic layer was washed with saturated aqueous sodium hydrogencarbonate solution, dried over magnesium sulfate, and then concentrated. The residue was subjected to silica gel chromatography (eluent, hexane ethyl acetate=5:1), which afforded 2.9 g of compound [24e] (present compound 16–32) (m.p., 112.6° C.).

Finally, 2.5 g of compound [24e] was added to 50 ml of concentrated sulfuric acid. The reaction mixture was stirred for 2 hours and then poured into ice water, which was stirred for another 1 hour and then extracted with diethyl ether. The organic layer was dried over magnesium sulfate and then concentrated, which afforded 1.4 g of compound [24f] (present compound 16–274).

$^1$H-NMR (250 MHz, CDCl$_3$, TMS) δ (ppm): 6.68 (1H, s), 6.75 (1H, d, J=6.5 Hz), 7.20 (1H, d, J=1.9 Hz), 7.32 (1H, d, J=9.0 Hz), 7.38 (1H, d, J=1.9 Hz)

Production Example 25

(Production of Present Compound 11–2)

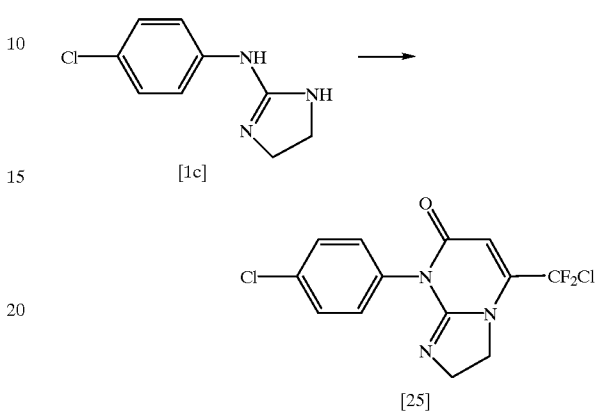

First, 2 ml of toluene and 1.0 g of ethyl 4-chloro-4,4-difluoro-3-methoxychrotonate were added to 1.0 g of compound [1c]. The reaction mixture was heated under reflux for 5 hours and then concentrated under reduced pressure. The residue was subjected to silica gel column chromatography, which afforded 0.4 g of compound [25] (Present Compound 11–2).

$^1$H-NMR (250 MHz, CDCl$_3$, TMS) δ (ppm): 3.88–3.96 (2H, m), 4.15–4.24 (2H, m), 5.85 (1H, s), 7.20–7.27 (2H, m), 7.44–7.51 (2H, m)

Production Example 26

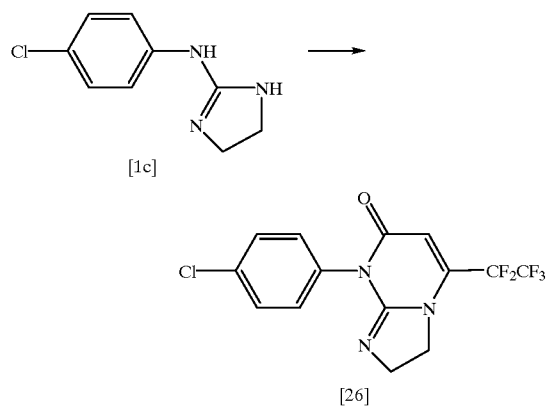

In the same manner as described in Production Example 25, except that 1.0 g of ethyl 4,4,5,5,5-pentafluoro-3-methoxy-3-methoxy-2-pentenate was substituted for 1.0 g of ethyl 4-chloro-4,4-difluoro-3-methoxychrotonate, 0.2 g of compound [26] was obtained.

$^1$H-NMR (250 MHz, CDCl$_3$, TMS) δ (ppm): 3.88 (2H, t, J=7.5 Hz), 4.11 (2H, t, J=7.5 Hz), 5.87 (1H, s), 7.24 (2H, d, J=7.5 Hz), 7.48 (2H, d, J=7.5 Hz)

Production Example 27

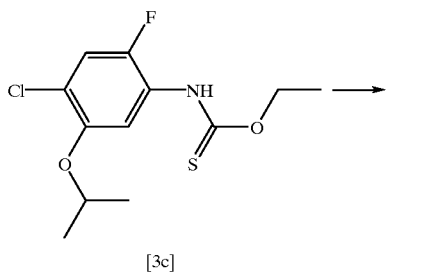

[3c]

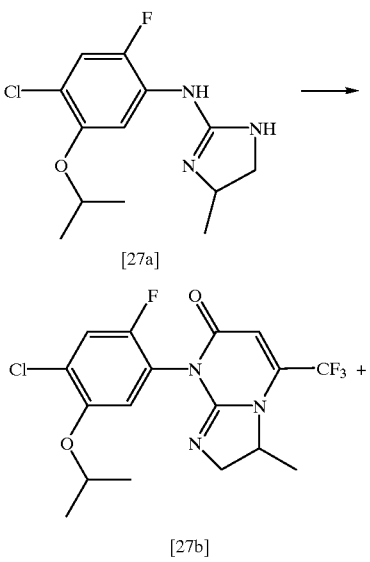

[27a]

[27b]

[27c]

First, 50 ml of toluene and 2 ml of 1,2-diaminopropane were added to 1.5 g of compound [3c]. The reaction mixture was heated under reflux for 2 hours and then concentrated to give 1.8 g of crude compound [27a]. Then, 1.0 g of ethyl 4,4,4-trifluoro-3-methoxychrotonate and 10 ml of toluene were added to 1.8 g of crude product. The reaction mixture was heated under reflux for 6 hours and then concentrated. The residue was subjected to silica gel column chromatography, which afforded 0.40 g of 1:1 mixture of compounds [27b] and [27c].

$^1$H-NMR (300 MHz, CDCl$_3$, TMS) δ (ppm): 1.19–1.31 (3H, m), 1.32–1.40 (6H, m), 3.60–3.70 (1H, m), 4.17–4.30 (2H, m), 4.38–4.49 (1H, m), 5.86 (0.5H, s), 5.87 (0.5H, s), 6.82–6.88 (1H, m), 7.27 (1H, d, J=9.0)

Production Example 28

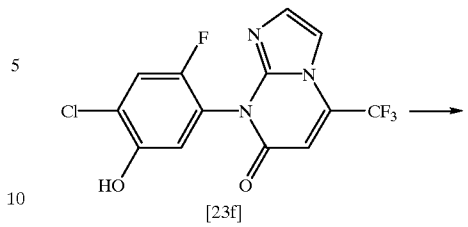

[23f]

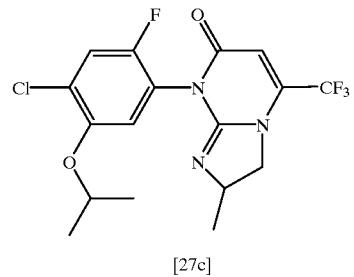

[28a]

First, 2.3 ml of N,N-dimethylformamide, 239 mg of potassium carbonate, and 154 mg of allyl bromide were added to 400 mg of compound [23f] (present compound 6–274), followed by stirring at room temperature for 1.5 hours. Then, water was added to the reaction mixture, which was extracted with ethyl acetate. The organic layer was washed with saturated aqueous sodium chloride solution, dried over anhydrous magnesium sulfate, and then concentrated. The residue was subjected to silica gel column chromatography (eluent, hexane : ethyl acetate=3:1), which afforded 366 mg of compound [28a] present compound 6–310) (m.p., 103.3° C.).

Production Example 29

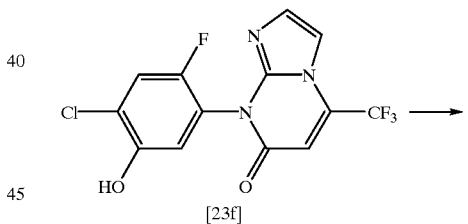

[23f]

[29a]

First, 4.0 ml of N,N-dimethylformamide, 419 mg of potassium carbonate, and 201 mg of methallyl chloride were added to 700 mg of compound [23f] (present compound 6–274), followed by stirring at 60° C. for 4 hours. Then, water was added to the reaction mixture, which was extracted with ethyl acetate. The organic layer was washed with saturated aqueous sodium chloride solution, dried over anhydrous magnesium sulfate, and then concentrated. The residue was subjected to silica gel column chromatography (eluent, hexane:ethyl acetate 3:1), which afforded 490 mg of compound [29a] (present compound 6–334).

¹H-NMR (300 MHz, CDCl₃, TMS) δ (ppm): 1.84 (3H, s), 4.45 (2H, s), 5.01 (1H, s), 5.13 (1H, s), 6.69 (1H, s), 6.95 (1H, d, J 6.2 Hz), 7.15 (1H, d, J=1.8 Hz), 7.26 (1H, d, J=1.8 Hz), 7.39 (1H, d, J=9.0 Hz)

Production Example 30

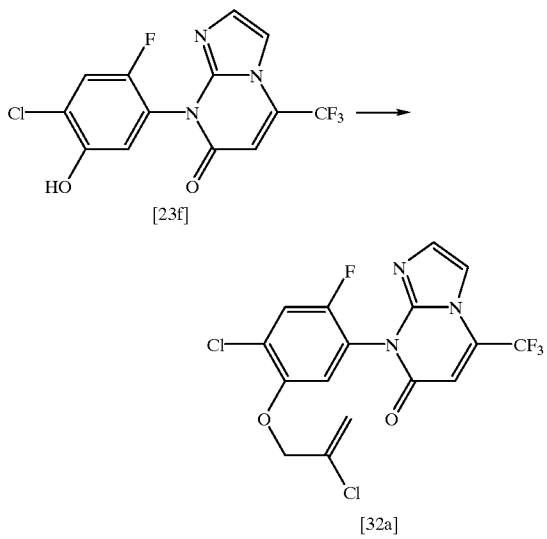

First, 4.6 ml of N,N-dimethylformamide, 478 mg of potassium carbonate, and 282 mg of 2-chloroallyl chloride were added to 800 mg of compound [23f] (present compound 6–274), followed by stirring at 60° C. for 3 hours. Then, water was added to the reaction mixture, which was extracted with ethyl acetate. The organic layer was washed with saturated aqueous sodium chloride solution, dried over anhydrous magnesium sulfate, and then concentrated. The residue was subjected to silica gel column chromatography (eluent, hexane: ethyl acetate=3:1), which afforded 551 mg of compound [32a] (present compound 6–316).

¹H-NMR (300 MHz, CDCl₃, TMS) δ (ppm): 4.60 (2H, s), 5.48 (1H, s), 5.66–5.67 (1H, m), 6.69 (1H, s), 6.98 (1H, d, J=6.2 Hz), 7.14 (1H, s), 7.26 (1H, s), 7.40 (1H, d, J=8.9 Hz)

Production Example 31

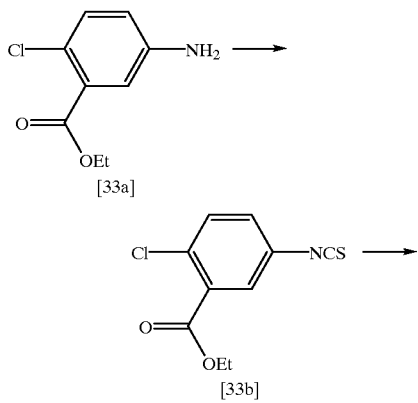

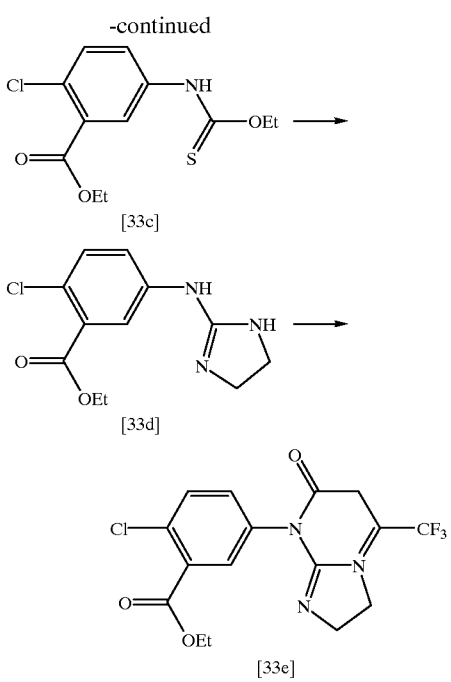

First, 12.5 ml of thiophosgene was added dropwise to a solution of 29 g of compound [33a] in 300 ml of toluene, which was heated under reflux for 2 hours. After completion of the reaction, the reaction mixture was concentrated to give 31 g of crude compound [33b].

Then, 50 ml of ethanol was added to 12 g of crude compound [33b], which was heated under reflux for 2 hours. After completion of the reaction, the reaction mixture was concentrated. The precipitated crystals were washed with hexane and then recrystallized from 2-propanol to give 6.1 g of compound [33c] (m.p., 83.8° C.).

Then, 1.7 ml of ethylenediamine was added to a solution of 6.1 g of compound [33c] in 60 ml of toluene, which was heated under reflux for 4 hours. After completion of the reaction, the reaction mixture was concentrated. The precipitated crystals were washed with 2-propanol to give 4.2 g of compound [33d] (m.p., 148.0° C.).

Finally, 2.0 g of compound [33d], 20 ml of toluene, and 1.6 g of ethyl 3-trifluoromethyl-3-methoxyacrylate were mixed and heated under reflux for 7.5 hours. After completion of the reaction, water was added to the reaction mixture, which was extracted with ethyl acetate. The organic layer was dried over magnesium sulfate and then concentrated. The residue was subjected to column chromatography, which afforded 0.3 g of compound [33e].

Some examples of the present compounds are shown, together with their compound numbers, in Tables 1 to 248. In these tables, "n", "i", "s", and "c" means "normal-", "iso-", "secondary-", and "cyclo-", respectively.

Compounds of the general formula:

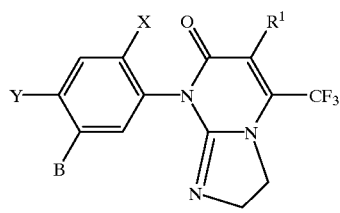

TABLE 1

|  | X | Y | R¹ | B |
|---|---|---|---|---|
| 1-1 | H | F | H | H |
| 1-2 | H | Cl | H | H |
| 1-3 | H | Br | H | H |
| 1-4 | F | F | H | H |
| 1-5 | F | Cl | H | H |
| 1-6 | F | Br | H | H |
| 1-7 | Cl | F | H | H |
| 1-8 | Cl | Cl | H | H |
| 1-9 | Cl | Br | H | H |
| 1-10 | H | F | H | $NO_2$ |
| 1-11 | H | Cl | H | $NO_2$ |
| 1-12 | H | Br | H | $NO_2$ |
| 1-13 | F | F | H | $NO_2$ |
| 1-14 | F | Cl | H | $NO_2$ |
| 1-15 | F | Br | H | $NO_2$ |
| 1-16 | Cl | F | H | $NO_2$ |
| 1-17 | Cl | Cl | H | $NO_2$ |
| 1-18 | Cl | Br | H | $NO_2$ |
| 1-19 | H | F | H | $NH_2$ |
| 1-20 | H | Cl | H | $NH_2$ |
| 1-21 | H | Br | H | $NH_2$ |
| 1-22 | F | F | H | $NH_2$ |
| 1-23 | F | Cl | H | $NH_2$ |
| 1-24 | F | Br | H | $NH_2$ |
| 1-25 | Cl | F | H | $NH_2$ |

TABLE 2

|  | X | Y | R¹ | B |
|---|---|---|---|---|
| 1-26 | Cl | Cl | H | $NH_2$ |
| 1-27 | Cl | Br | H | $NH_2$ |
| 1-28 | H | F | H | OH |
| 1-29 | H | Cl | H | OH |
| 1-30 | H | Br | H | OH |
| 1-31 | F | F | H | OH |
| 1-32 | F | Cl | H | OH |
| 1-33 | F | Br | H | OH |
| 1-34 | Cl | F | H | OH |
| 1-35 | Cl | Cl | H | OH |
| 1-36 | Cl | Br | H | OH |
| 1-37 | H | F | H | SH |
| 1-38 | H | Cl | H | SH |
| 1-39 | H | Br | H | SH |
| 1-40 | F | F | H | SH |
| 1-41 | F | Cl | H | SH |
| 1-42 | F | Br | H | SH |
| 1-43 | Cl | F | H | SH |
| 1-44 | Cl | Cl | H | SH |
| 1-45 | Cl | Br | H | SH |
| 1-46 | H | F | H | $SO_2Cl$ |
| 1-47 | H | Cl | H | $SO_2Cl$ |
| 1-48 | H | Br | H | $SO_2Cl$ |
| 1-49 | F | F | H | $SO_2Cl$ |
| 1-50 | F | Cl | H | $SO_2Cl$ |

TABLE 3

|  | X | Y | R¹ | B |
|---|---|---|---|---|
| 1-51 | F | Br | H | $SO_2Cl$ |
| 1-52 | Cl | F | H | $SO_2Cl$ |
| 1-53 | Cl | Cl | H | $SO_2Cl$ |
| 1-54 | Cl | Br | H | $SO_2Cl$ |
| 1-55 | H | F | H | $NHCH_3$ |
| 1-56 | H | Cl | H | $NHCH_3$ |
| 1-57 | F | F | H | $NHCH_3$ |
| 1-58 | F | Cl | H | $NHCH_3$ |
| 1-59 | Cl | F | H | $NHCH_3$ |
| 1-60 | Cl | Cl | H | $NHCH_3$ |
| 1-61 | H | F | H | $NHC_2H_5$ |
| 1-62 | H | Cl | H | $NHC_2H_5$ |
| 1-63 | F | F | H | $NHC_2H_5$ |
| 1-64 | F | Cl | H | $NHC_2H_5$ |
| 1-65 | Cl | F | H | $NHC_2H_5$ |
| 1-66 | Cl | Cl | H | $NHC_2H_5$ |
| 1-67 | H | F | H | $NHCH_2CH=CH_2$ |
| 1-68 | H | Cl | H | $NHCH_2CH=CH_2$ |
| 1-69 | F | F | H | $NHCH_2CH=CH_2$ |
| 1-70 | F | Cl | H | $NHCH_2CH=CH_2$ |
| 1-71 | Cl | F | H | $NHCH_2CH=CH_2$ |
| 1-72 | Cl | Cl | H | $NHCH_2CH=CH_2$ |
| 1-73 | H | F | H | $NHCH_2C\equiv CH$ |
| 1-74 | H | Cl | H | $NHCH_2C\equiv CH$ |
| 1-75 | F | F | H | $NHCH_2C\equiv CH$ |

TABLE 4

|  | X | Y | R¹ | B |
|---|---|---|---|---|
| 1-76 | F | Cl | H | $NHCH_2C\equiv CH$ |
| 1-77 | Cl | F | H | $NHCH_2C\equiv CH$ |
| 1-78 | Cl | Cl | H | $NHCH_2C\equiv CH$ |
| 1-79 | H | F | H | $NHCH(CH_3)C\equiv CH$ |
| 1-80 | H | Cl | H | $NHCH(CH_3)C\equiv CH$ |
| 1-81 | F | F | H | $NHCH(CH_3)C\equiv CH$ |
| 1-82 | F | Cl | H | $NHCH(CH_3)C\equiv CH$ |
| 1-83 | Cl | F | H | $NHCH(CH_3)C\equiv CH$ |
| 1-84 | Cl | Cl | H | $NHCH(CH_3)C\equiv CH$ |
| 1-85 | H | F | H | $NHSO_2CH_3$ |
| 1-86 | H | Cl | H | $NHSO_2CH_3$ |
| 1-87 | F | F | H | $NHSO_2CH_3$ |
| 1-88 | F | Cl | H | $NHSO_2CH_3$ |
| 1-89 | Cl | F | H | $NHSO_2CH_3$ |
| 1-90 | Cl | Cl | H | $NHSO_2CH_3$ |
| 1-91 | H | F | H | $NHSO_2C_2H_5$ |
| 1-92 | H | Cl | H | $NHSO_2C_2H_5$ |
| 1-93 | F | F | H | $NHSO_2C_2H_5$ |
| 1-94 | F | Cl | H | $NHSO_2C_2H_5$ |
| 1-95 | Cl | F | H | $NHSO_2C_2H_5$ |
| 1-96 | Cl | Cl | H | $NHSO_2C_2H_5$ |
| 1-97 | H | F | H | $NHSO_2CH_2Cl$ |
| 1-98 | H | Cl | H | $NHSO_2CH_2Cl$ |
| 1-99 | F | F | H | $NHSO_2CH_2Cl$ |
| 1-100 | F | Cl | H | $NHSO_2CH_2Cl$ |

TABLE 5

|  | X | Y | R¹ | B |
|---|---|---|---|---|
| 1-101 | Cl | F | H | $NHSO_2CH_2Cl$ |
| 1-102 | Cl | Cl | H | $NHSO_2CH_2Cl$ |
| 1-103 | H | F | H | $NHSO_2CF_3$ |
| 1-104 | H | Cl | H | $NHSO_2CF_3$ |
| 1-105 | F | F | H | $NHSO_2CF_3$ |
| 1-106 | F | Cl | H | $NHSO_2CF_3$ |
| 1-107 | Cl | F | H | $NHSO_2CF_3$ |
| 1-108 | Cl | Cl | H | $NHSO_2CF_3$ |
| 1-109 | H | F | H | $N(SO_2CH_3)_2$ |
| 1-110 | H | Cl | H | $N(SO_2CH_3)_2$ |
| 1-111 | F | F | H | $N(SO_2CH_3)_2$ |
| 1-112 | F | Cl | H | $N(SO_2CH_3)_2$ |

TABLE 5-continued

| | X | Y | R¹ | B |
|---|---|---|---|---|
| 1-113 | Cl | F | H | N(SO$_2$CH$_3$)$_2$ |
| 1-114 | Cl | Cl | H | N(SO$_2$CH$_3$)$_2$ |
| 1-115 | H | F | H | N(CH$_3$)SO$_2$CH$_3$ |
| 1-116 | H | Cl | H | N(CH$_3$)SO$_2$CH$_3$ |
| 1-117 | F | F | H | N(CH$_3$)SO$_2$CH$_3$ |
| 1-118 | F | Cl | H | N(CH$_3$)SO$_2$CH$_3$ |
| 1-119 | Cl | F | H | N(CH$_3$)SO$_2$CH$_3$ |
| 1-120 | Cl | Cl | H | N(CH$_3$)SO$_2$CH$_3$ |
| 1-121 | H | F | H | N(CH$_2$C≡CH)SO$_2$CH$_3$ |
| 1-122 | H | Cl | H | N(CH$_2$C≡CH)SO$_2$CH$_3$ |
| 1-123 | F | F | H | N(CH$_2$C≡CH)SO$_2$CH$_3$ |
| 1-124 | F | Cl | H | N(CH$_2$C≡CH)SO$_2$CH$_3$ |
| 1-125 | Cl | F | H | N(CH$_2$C≡CH)SO$_2$CH$_3$ |

TABLE 6

| | X | Y | R¹ | B |
|---|---|---|---|---|
| 1-126 | Cl | Cl | H | N(CH$_2$C≡CH)SO$_2$CH$_3$ |
| 1-127 | H | F | H | NHCOOCH$_3$ |
| 1-128 | H | Cl | H | NHCOOCH$_3$ |
| 1-129 | F | F | H | NHCOOCH$_3$ |
| 1-130 | F | Cl | H | NHCOOCH$_3$ |
| 1-131 | Cl | F | H | NHCOOCH$_3$ |
| 1-132 | Cl | Cl | H | NHCOOCH$_3$ |
| 1-133 | H | F | H | NHCOOC$_2$H$_5$ |
| 1-134 | H | Cl | H | NHCOOC$_2$H$_5$ |
| 1-135 | F | F | H | NHCOOC$_2$H$_5$ |
| 1-136 | F | Cl | H | NHCOOC$_2$H$_5$ |
| 1-137 | Cl | F | H | NHCOOC$_2$H$_5$ |
| 1-138 | Cl | Cl | H | NHCOOC$_2$H$_5$ |
| 1-139 | H | F | H | NHCOOnC$_3$H$_7$ |
| 1-140 | H | Cl | H | NHCOOnC$_3$H$_7$ |
| 1-141 | F | F | H | NHCOOnC$_3$H$_7$ |
| 1-142 | F | Cl | H | NHCOOnC$_3$H$_7$ |
| 1-143 | Cl | F | H | NHCOOnC$_3$H$_7$ |
| 1-144 | Cl | Cl | H | NHCOOnC$_3$H$_7$ |
| 1-145 | H | F | H | NHCOOiC$_3$H$_7$ |
| 1-146 | H | Cl | H | NHCOOiC$_3$H$_7$ |
| 1-147 | F | F | H | NHCOOiC$_3$H$_7$ |
| 1-148 | F | Cl | H | NHCOOiC$_3$H$_7$ |
| 1-149 | Cl | F | H | NHCOOiC$_3$H$_7$ |
| 1-150 | Cl | Cl | H | NHCOOiC$_3$H$_7$ |

TABLE 7

| | X | Y | R¹ | B |
|---|---|---|---|---|
| 1-151 | H | F | H | NHCOOnC$_4$H$_9$ |
| 1-152 | H | Cl | H | NHCOOnC$_4$H$_9$ |
| 1-153 | F | F | H | NHCOOnC$_4$H$_9$ |
| 1-154 | F | Cl | H | NHCOOnC$_4$H$_9$ |
| 1-155 | Cl | F | H | NHCOOnC$_4$H$_9$ |
| 1-156 | Cl | Cl | H | NHCOOnC$_4$H$_9$ |
| 1-157 | H | F | H | NHCOOnC$_5$H$_{11}$ |
| 1-158 | H | Cl | H | NHCOOnC$_5$H$_{11}$ |
| 1-159 | F | F | H | NHCOOnC$_5$H$_{11}$ |
| 1-160 | F | Cl | H | NHCOOnC$_5$H$_{11}$ |
| 1-161 | Cl | F | H | NHCOOnC$_5$H$_{11}$ |
| 1-162 | Cl | Cl | H | NHCOOnC$_5$H$_{11}$ |
| 1-163 | H | F | H | NHCH$_2$COOCH$_3$ |
| 1-164 | H | Cl | H | NHCH$_2$COOCH$_3$ |
| 1-165 | F | F | H | NHCH$_2$COOCH$_3$ |
| 1-166 | F | Cl | H | NHCH$_2$COOCH$_3$ |
| 1-167 | Cl | F | H | NHCH$_2$COOCH$_3$ |
| 1-168 | Cl | Cl | H | NHCH$_2$COOCH$_3$ |
| 1-169 | H | F | H | NHCH$_2$COOC$_2$H$_5$ |
| 1-170 | H | Cl | H | NHCH$_2$COOC$_2$H$_5$ |
| 1-171 | F | F | H | NHCH$_2$COOC$_2$H$_5$ |
| 1-172 | F | Cl | H | NHCH$_2$COOC$_2$H$_5$ |

TABLE 7-continued

| | X | Y | R¹ | B |
|---|---|---|---|---|
| 1-173 | Cl | F | H | NHCH$_2$COOC$_2$H$_5$ |
| 1-174 | Cl | Cl | H | NHCH$_2$COOC$_2$H$_5$ |
| 1-175 | H | F | H | NHCH$_2$COOnC$_3$H$_7$ |

TABLE 8

| | X | Y | R¹ | B |
|---|---|---|---|---|
| 1-176 | H | Cl | H | NHCH$_2$COOnC$_3$H$_7$ |
| 1-177 | F | F | H | NHCH$_2$COOnC$_3$H$_7$ |
| 1-178 | F | Cl | H | NHCH$_2$COOnC$_3$H$_7$ |
| 1-179 | Cl | F | H | NHCH$_2$COOnC$_3$H$_7$ |
| 1-180 | Cl | Cl | H | NHCH$_2$COOnC$_3$H$_7$ |
| 1-181 | H | F | H | NHCH$_2$COOnC$_4$H$_9$ |
| 1-182 | H | Cl | H | NHCH$_2$COOnC$_4$H$_9$ |
| 1-183 | F | F | H | NHCH$_2$COOnC$_4$H$_9$ |
| 1-184 | F | Cl | H | NHCH$_2$COOnC$_4$H$_9$ |
| 1-185 | Cl | F | H | NHCH$_2$COOnC$_4$H$_9$ |
| 1-186 | Cl | Cl | H | NHCH$_2$COOnC$_4$H$_9$ |
| 1-187 | H | F | H | NHCH$_2$COOnC$_5$H$_{11}$ |
| 1-188 | H | Cl | H | NHCH$_2$COOnC$_5$H$_{11}$ |
| 1-189 | F | F | H | NHCH$_2$COOnC$_5$H$_{11}$ |
| 1-190 | F | Cl | H | NHCH$_2$COOnC$_5$H$_{11}$ |
| 1-191 | Cl | F | H | NHCH$_2$COOnC$_5$H$_{11}$ |
| 1-192 | Cl | Cl | H | NHCH$_2$COOnC$_5$H$_{11}$ |
| 1-193 | H | F | H | NHCH$_2$COOiC$_3$H$_7$ |
| 1-194 | H | Cl | H | NHCH$_2$COOiC$_3$H$_7$ |
| 1-195 | F | F | H | NHCH$_2$COOiC$_3$H$_7$ |
| 1-196 | F | Cl | H | NHCH$_2$COOiC$_3$H$_7$ |
| 1-197 | Cl | F | H | NHCH$_2$COOiC$_3$H$_7$ |
| 1-198 | Cl | Cl | H | NHCH$_2$COOiC$_3$H$_7$ |
| 1-199 | H | F | H | NHCH$_2$COOcC$_5$H$_9$ |
| 1-200 | H | Cl | H | NHCH$_2$COOcC$_5$H$_9$ |

TABLE 9

| | X | Y | R¹ | B |
|---|---|---|---|---|
| 1-201 | F | F | H | NHCH$_2$COOcC$_5$H$_9$ |
| 1-202 | F | Cl | H | NHCH$_2$COOcC$_5$H$_9$ |
| 1-203 | Cl | F | H | NHCH$_2$COOcC$_5$H$_9$ |
| 1-204 | Cl | Cl | H | NHCH$_2$COOcC$_5$H$_9$ |
| 1-205 | H | F | H | NHCH$_2$COOcC$_6$H$_{11}$ |
| 1-206 | H | Cl | H | NHCH$_2$COOcC$_6$H$_{11}$ |
| 1-207 | F | F | H | NHCH$_2$COOcC$_6$H$_{11}$ |
| 1-208 | F | Cl | H | NHCH$_2$COOcC$_6$H$_{11}$ |
| 1-209 | Cl | F | H | NHCH$_2$COOcC$_6$H$_{11}$ |
| 1-210 | Cl | Cl | H | NHCH$_2$COOcC$_6$H$_{11}$ |
| 1-211 | H | F | H | NHCH(CH$_3$)COOCH$_3$ |
| 1-212 | H | Cl | H | NHCH(CH$_3$)COOCH$_3$ |
| 1-213 | F | F | H | NHCH(CH$_3$)COOCH$_3$ |
| 1-214 | F | Cl | H | NHCH(CH$_3$)COOCH$_3$ |
| 1-215 | Cl | F | H | NHCH(CH$_3$)COOCH$_3$ |
| 1-216 | Cl | Cl | H | NHCH(CH$_3$)COOCH$_3$ |
| 1-217 | H | F | H | NHCH(CH$_3$)COOC$_2$H$_5$ |
| 1-218 | H | Cl | H | NHCH(CH$_3$)COOC$_2$H$_5$ |
| 1-219 | F | F | H | NHCH(CH$_3$)COOC$_2$H$_5$ |
| 1-220 | F | Cl | H | NHCH(CH$_3$)COOC$_2$H$_5$ |
| 1-221 | Cl | F | H | NHCH(CH$_3$)COOC$_2$H$_5$ |
| 1-222 | Cl | Cl | H | NHCH(CH$_3$)COOC$_2$H$_5$ |
| 1-223 | H | F | H | NHCH(CH$_3$)COOnC$_3$H$_7$ |
| 1-224 | H | Cl | H | NHCH(CH$_3$)COOnC$_3$H$_7$ |
| 1-225 | F | F | H | NHCH(CH$_3$)COOnC$_3$H$_7$ |

TABLE 10

| | X | Y | R¹ | B |
|---|---|---|---|---|
| 1-226 | F | Cl | H | NHCH(CH$_3$)COOnC$_3$H$_7$ |
| 1-227 | Cl | F | H | NHCH(CH$_3$)COOnC$_3$H$_7$ |

TABLE 10-continued

| | X | Y | R¹ | B |
|---|---|---|---|---|
| 1-228 | Cl | Cl | H | NHCH($CH_3$)COOn$C_3H_7$ |
| 1-229 | H | F | H | NHCH($CH_3$)COOn$C_4H_9$ |
| 1-230 | H | Cl | H | NHCH($CH_3$)COOn$C_4H_9$ |
| 1-231 | F | F | H | NHCH($CH_3$)COOn$C_4H_9$ |
| 1-232 | F | Cl | H | NHCH($CH_3$)COOn$C_4H_9$ |
| 1-233 | Cl | F | H | NHCH($CH_3$)COOn$C_4H_9$ |
| 1-234 | Cl | Cl | H | NHCH($CH_3$)COOn$C_4H_9$ |
| 1-235 | H | F | H | NHCH($CH_3$)COOn$C_5H_{11}$ |
| 1-236 | H | Cl | H | NHCH($CH_3$)COOn$C_5H_{11}$ |
| 1-237 | F | F | H | NHCH($CH_3$)COOn$C_5H_{11}$ |
| 1-238 | F | Cl | H | NHCH($CH_3$)COOn$C_5H_{11}$ |
| 1-239 | Cl | F | H | NHCH($CH_3$)COOn$C_5H_{11}$ |
| 1-240 | Cl | Cl | H | NHCH($CH_3$)COOn$C_5H_{11}$ |
| 1-241 | H | F | H | NHCH($CH_3$)COOi$C_3H_7$ |
| 1-242 | H | Cl | H | NHCH($CH_3$)COOi$C_3H_7$ |
| 1-243 | F | F | H | NHCH($CH_3$)COOi$C_3H_7$ |
| 1-244 | F | Cl | H | NHCH($CH_3$)COOi$C_3H_7$ |
| 1-245 | Cl | F | H | NHCH($CH_3$)COOi$C_3H_7$ |
| 1-246 | Cl | Cl | H | NHCH($CH_3$)COOi$C_3H_7$ |
| 1-247 | H | F | H | NHCH($CH_3$)COOc$C_5H_9$ |
| 1-248 | H | Cl | H | NHCH($CH_3$)COOc$C_5H_9$ |
| 1-249 | F | F | H | NHCH($CH_3$)COOc$C_5H_9$ |
| 1-250 | F | Cl | H | NHCH($CH_3$)COOc$C_5H_9$ |

TABLE 11

| | X | Y | R¹ | B |
|---|---|---|---|---|
| 1-251 | Cl | F | H | NHCH($CH_3$)COOc$C_5H_9$ |
| 1-252 | Cl | Cl | H | NHCH($CH_3$)COOc$C_5H_9$ |
| 1-253 | H | F | H | NHCH($CH_3$)COOc$C_6H_{11}$ |
| 1-254 | H | Cl | H | NHCH($CH_3$)COOc$C_6H_{11}$ |
| 1-255 | F | F | H | NHCH($CH_3$)COOc$C_6H_{11}$ |
| 1-256 | F | Cl | H | NHCH($CH_3$)COOc$C_6H_{11}$ |
| 1-257 | Cl | F | H | NHCH($CH_3$)COOc$C_6H_{11}$ |
| 1-258 | Cl | Cl | H | NHCH($CH_3$)COOc$C_6H_{11}$ |
| 1-259 | H | F | H | O$CH_3$ |
| 1-260 | H | Cl | H | O$CH_3$ |
| 1-261 | F | F | H | O$CH_3$ |
| 1-262 | F | Cl | H | O$CH_3$ |
| 1-263 | Cl | F | H | O$CH_3$ |
| 1-264 | Cl | Cl | H | O$CH_3$ |
| 1-265 | H | F | H | O$C_2H_5$ |
| 1-266 | H | Cl | H | O$C_2H_5$ |
| 1-267 | F | F | H | O$C_2H_5$ |
| 1-268 | F | Cl | H | O$C_2H_5$ |
| 1-269 | Cl | F | H | O$C_2H_5$ |
| 1-270 | Cl | Cl | H | O$C_2H_5$ |
| 1-271 | H | F | H | Oi$C_3H_7$ |
| 1-272 | H | Cl | H | Oi$C_3H_7$ |
| 1-273 | F | F | H | Oi$C_3H_7$ |
| 1-274 | F | Cl | H | Oi$C_3H_7$ |
| 1-275 | Cl | F | H | Oi$C_3H_7$ |

TABLE 12

| | X | Y | R¹ | B |
|---|---|---|---|---|
| 1-276 | Cl | Cl | H | Oi$C_3H_7$ |
| 1-277 | H | F | H | On$C_3H_7$ |
| 1-278 | H | Cl | H | On$C_3H_7$ |
| 1-279 | F | F | H | On$C_3H_7$ |
| 1-280 | F | Cl | H | On$C_3H_7$ |
| 1-281 | Cl | F | H | On$C_3H_7$ |
| 1-282 | Cl | Cl | H | On$C_3H_7$ |
| 1-283 | H | F | H | O$CH_2CH_2$Cl |
| 1-284 | H | Cl | H | O$CH_2CH_2$Cl |
| 1-285 | F | F | H | O$CH_2CH_2$Cl |
| 1-286 | F | Cl | H | O$CH_2CH_2$Cl |
| 1-287 | Cl | F | H | O$CH_2CH_2$Cl |
| 1-288 | Cl | Cl | H | O$CH_2CH_2$Cl |
| 1-289 | H | F | H | O$CF_2CF_2$H |
| 1-290 | H | Cl | H | O$CF_2CF_2$H |
| 1-291 | F | F | H | O$CF_2CF_2$H |
| 1-292 | F | Cl | H | O$CF_2CF_2$H |
| 1-293 | Cl | F | H | O$CF_2CF_2$H |
| 1-294 | Cl | Cl | H | O$CF_2CF_2$H |
| 1-295 | H | F | H | Oc$C_5H_9$ |
| 1-296 | H | Cl | H | Oc$C_5H_9$ |
| 1-297 | F | F | H | Oc$C_5H_9$ |
| 1-298 | F | Cl | H | Oc$C_5H_9$ |
| 1-299 | Cl | F | H | Oc$C_5H_9$ |
| 1-300 | Cl | Cl | H | Oc$C_5H_9$ |

TABLE 13

| | X | Y | R¹ | B |
|---|---|---|---|---|
| 1-301 | H | F | H | Oc$C_6H_{11}$ |
| 1-302 | H | Cl | H | Oc$C_6H_{11}$ |
| 1-303 | F | F | H | Oc$C_6H_{11}$ |
| 1-304 | F | Cl | H | Oc$C_6H_{11}$ |
| 1-305 | Cl | F | H | Oc$C_6H_{11}$ |
| 1-306 | Cl | Cl | H | Oc$C_6H_{11}$ |
| 1-307 | H | F | H | O$CH_2$CH=$CH_2$ |
| 1-308 | H | Cl | H | O$CH_2$CH=$CH_2$ |
| 1-309 | F | F | H | O$CH_2$CH=$CH_2$ |
| 1-310 | F | Cl | H | O$CH_2$CH=$CH_2$ |
| 1-311 | Cl | F | H | O$CH_2$CH=$CH_2$ |
| 1-312 | Cl | Cl | H | O$CH_2$CH=$CH_2$ |
| 1-313 | H | F | H | O$CH_2$CCl=$CH_2$ |
| 1-314 | H | Cl | H | O$CH_2$CCl=$CH_2$ |
| 1-315 | F | F | H | O$CH_2$CCl=$CH_2$ |
| 1-316 | F | Cl | H | O$CH_2$CCl=$CH_2$ |
| 1-317 | Cl | F | H | O$CH_2$CCl=$CH_2$ |
| 1-318 | Cl | Cl | H | O$CH_2$CCl=$CH_2$ |
| 1-319 | H | F | H | O$CH_2$CCl=CHCl |
| 1-320 | H | Cl | H | O$CH_2$CCl=CHCl |
| 1-321 | F | F | H | O$CH_2$CCl=CHCl |
| 1-322 | F | Cl | H | O$CH_2$CCl=CHCl |
| 1-323 | Cl | F | H | O$CH_2$CCl=CHCl |
| 1-324 | Cl | Cl | H | O$CH_2$CCl=CHCl |
| 1-325 | H | F | H | OCH($CH_3$)CH=$CH_2$ |

TABLE 14

| | X | Y | R¹ | B |
|---|---|---|---|---|
| 1-326 | H | Cl | H | OCH($CH_3$)CH=$CH_2$ |
| 1-327 | F | F | H | OCH($CH_3$)CH=$CH_2$ |
| 1-328 | F | Cl | H | OCH($CH_3$)CH=$CH_2$ |
| 1-329 | Cl | F | H | OCH($CH_3$)CH=$CH_2$ |
| 1-330 | Cl | Cl | H | OCH($CH_3$)CH=$CH_2$ |
| 1-331 | H | F | H | O$CH_2$C($CH_3$)=$CH_2$ |
| 1-332 | H | Cl | H | O$CH_2$C($CH_3$)=$CH_2$ |
| 1-333 | F | F | H | O$CH_2$C($CH_3$)=$CH_2$ |
| 1-334 | F | Cl | H | O$CH_2$C($CH_3$)=$CH_2$ |
| 1-335 | Cl | F | H | O$CH_2$C($CH_3$)=$CH_2$ |
| 1-336 | Cl | Cl | H | O$CH_2$C($CH_3$)=$CH_2$ |
| 1-337 | H | F | H | O$CH_2$C≡CH |
| 1-338 | H | Cl | H | O$CH_2$C≡CH |
| 1-339 | F | F | H | O$CH_2$C≡CH |
| 1-340 | F | Cl | H | O$CH_2$C≡CH |
| 1-341 | Cl | F | H | O$CH_2$C≡CH |
| 1-342 | Cl | Cl | H | O$CH_2$C≡CH |
| 1-343 | H | F | H | OCH($CH_3$)C≡CH |
| 1-344 | H | Cl | H | OCH($CH_3$)C≡CH |
| 1-345 | F | F | H | OCH($CH_3$)C≡CH |
| 1-346 | F | Cl | H | OCH($CH_3$)C≡CH |
| 1-347 | Cl | F | H | OCH($CH_3$)C≡CH |
| 1-348 | Cl | Cl | H | OCH($CH_3$)C≡CH |
| 1-349 | H | F | H | O$CH_2$C≡CBr |
| 1-350 | H | Cl | H | O$CH_2$C≡CBr |

TABLE 15

| | X | Y | R$^1$ | B |
|---|---|---|---|---|
| 1-351 | F | F | H | OCH$_2$C≡CBr |
| 1-352 | F | Cl | H | OCH$_2$C≡CBr |
| 1-353 | Cl | F | H | OCH$_2$C≡CBr |
| 1-354 | Cl | Cl | H | OCH$_2$C≡CBr |
| 1-355 | H | F | H | OCH$_2$C≡CCl |
| 1-356 | H | Cl | H | OCH$_2$C≡CCl |
| 1-357 | F | F | H | OCH$_2$C≡CCl |
| 1-358 | F | Cl | H | OCH$_2$C≡CCl |
| 1-359 | Cl | F | H | OCH$_2$C≡CCl |
| 1-360 | Cl | Cl | H | OCH$_2$C≡CCl |
| 1-361 | H | F | H | OCH$_2$C≡CCH$_2$Cl |
| 1-362 | H | Cl | H | OCH$_2$C≡CCH$_2$Cl |
| 1-363 | F | F | H | OCH$_2$C≡CCH$_2$Cl |
| 1-364 | F | Cl | H | OCH$_2$C≡CCH$_2$Cl |
| 1-365 | Cl | F | H | OCH$_2$C≡CCH$_2$Cl |
| 1-366 | Cl | Cl | H | OCH$_2$C≡CCH$_2$Cl |
| 1-367 | H | F | H | OCH$_2$CN |
| 1-368 | H | Cl | H | OCH$_2$CN |
| 1-369 | F | F | H | OCH$_2$CN |
| 1-370 | F | Cl | H | OCH$_2$CN |
| 1-371 | Cl | F | H | OCH$_2$CN |
| 1-372 | Cl | Cl | H | OCH$_2$CN |
| 1-373 | H | F | H | OCH$_2$OCH$_3$ |
| 1-374 | H | Cl | H | OCH$_2$OCH$_3$ |
| 1-375 | F | F | H | OCH$_2$OCH$_3$ |

TABLE 16

| | X | Y | R$^1$ | B |
|---|---|---|---|---|
| 1-376 | F | Cl | H | OCH$_2$OCH$_3$ |
| 1-377 | Cl | F | H | OCH$_2$OCH$_3$ |
| 1-378 | Cl | Cl | H | OCH$_2$OCH$_3$ |
| 1-379 | H | F | H | OCH$_2$OC$_2$H$_5$ |
| 1-380 | H | Cl | H | OCH$_2$OC$_2$H$_5$ |
| 1-381 | F | F | H | OCH$_2$OC$_2$H$_5$ |
| 1-382 | F | Cl | H | OCH$_2$OC$_2$H$_5$ |
| 1-383 | Cl | F | H | OCH$_2$OC$_2$H$_5$ |
| 1-384 | Cl | Cl | H | OCH$_2$OC$_2$H$_5$ |
| 1-385 | H | F | H | OCH$_2$SCH$_3$ |
| 1-386 | H | Cl | H | OCH$_2$SCH$_3$ |
| 1-387 | F | F | H | OCH$_2$SCH$_3$ |
| 1-388 | F | Cl | H | OCH$_2$SCH$_3$ |
| 1-389 | Cl | F | H | OCH$_2$SCH$_3$ |
| 1-390 | Cl | Cl | H | OCH$_2$SCH$_3$ |
| 1-391 | H | F | H | OCH$_2$COOH |
| 1-392 | H | Cl | H | OCH$_2$COOH |
| 1-393 | F | F | H | OCH$_2$COOH |
| 1-394 | F | Cl | H | OCH$_2$COOH |
| 1-395 | Cl | F | H | OCH$_2$COOH |
| 1-396 | Cl | Cl | H | OCH$_2$COOH |
| 1-397 | H | F | H | OCH$_2$COOCH$_3$ |
| 1-398 | H | Cl | H | OCH$_2$COOCH$_3$ |
| 1-399 | F | F | H | OCH$_2$COOCH$_3$ |
| 1-400 | F | Cl | H | OCH$_2$COOCH$_3$ |

TABLE 17

| | X | Y | R$^1$ | B |
|---|---|---|---|---|
| 1-401 | Cl | F | H | OCH$_2$COOCH$_3$ |
| 1-402 | Cl | Cl | H | OCH$_2$COOCH$_3$ |
| 1-403 | H | F | H | OCH$_2$COOC$_2$H$_5$ |
| 1-404 | H | Cl | H | OCH$_2$COOC$_2$H$_5$ |
| 1-405 | F | F | H | OCH$_2$COOC$_2$H$_5$ |
| 1-406 | F | Cl | H | OCH$_2$COOC$_2$H$_5$ |
| 1-407 | Cl | F | H | OCH$_2$COOC$_2$H$_5$ |
| 1-408 | Cl | Cl | H | OCH$_2$COOC$_2$H$_5$ |
| 1-409 | H | F | H | OCH$_2$COO$_n$C$_3$H$_7$ |
| 1-410 | H | Cl | H | OCH$_2$COO$_n$C$_3$H$_7$ |
| 1-411 | F | F | H | OCH$_2$COO$_n$C$_3$H$_7$ |
| 1-412 | F | Cl | H | OCH$_2$COO$_n$C$_3$H$_7$ |

TABLE 17-continued

| | X | Y | R$^1$ | B |
|---|---|---|---|---|
| 1-413 | Cl | F | H | OCH$_2$COO$_n$C$_3$H$_7$ |
| 1-414 | Cl | Cl | H | OCH$_2$COO$_n$C$_3$H$_7$ |
| 1-415 | H | F | H | OCH$_2$COO$_n$C$_4$H$_9$ |
| 1-416 | H | Cl | H | OCH$_2$COO$_n$C$_4$H$_9$ |
| 1-417 | F | F | H | OCH$_2$COO$_n$C$_4$H$_9$ |
| 1-418 | F | Cl | H | OCH$_2$COO$_n$C$_4$H$_9$ |
| 1-419 | Cl | F | H | OCH$_2$COO$_n$C$_4$H$_9$ |
| 1-420 | Cl | Cl | H | OCH$_2$COO$_n$C$_4$H$_9$ |
| 1-421 | H | F | H | OCH$_2$COO$_n$C$_5$H$_{11}$ |
| 1-422 | H | Cl | H | OCH$_2$COO$_n$C$_5$H$_{11}$ |
| 1-423 | F | F | H | OCH$_2$COO$_n$C$_5$H$_{11}$ |
| 1-424 | F | Cl | H | OCH$_2$COO$_n$C$_5$H$_{11}$ |
| 1-425 | Cl | F | H | OCH$_2$COO$_n$C$_5$H$_{11}$ |

TABLE 18

| | X | Y | R$^1$ | B |
|---|---|---|---|---|
| 1-426 | Cl | Cl | H | OCH$_2$COO$_n$C$_5$H11 |
| 1-427 | H | F | H | OCH$_2$COO$_i$C$_3$H$_7$ |
| 1-428 | H | Cl | H | OCH$_2$COO$_i$C$_3$H$_7$ |
| 1-429 | F | F | H | OCH$_2$COO$_i$C$_3$H$_7$ |
| 1-430 | F | Cl | H | OCH$_2$COO$_i$C$_3$H$_7$ |
| 1-431 | Cl | F | H | OCH$_2$COO$_i$C$_3$H$_7$ |
| 1-432 | Cl | Cl | H | OCH$_2$COO$_i$C$_3$H$_7$ |
| 1-433 | H | F | H | OCH$_2$COO$_c$C$_5$H$_9$ |
| 1-434 | H | Cl | H | OCH$_2$COO$_c$C$_5$H$_9$ |
| 1-435 | F | F | H | OCH$_2$COO$_c$C$_5$H$_9$ |
| 1-436 | F | Cl | H | OCH$_2$COO$_c$C$_5$H$_9$ |
| 1-437 | Cl | F | H | OCH$_2$COO$_c$C$_5$H$_9$ |
| 1-438 | Cl | Cl | H | OCH$_2$COO$_c$C$_5$H$_9$ |
| 1-439 | H | F | H | OCH$_2$COO$_c$C$_6$H$_{11}$ |
| 1-440 | H | Cl | H | OCH$_2$COO$_c$C$_6$H$_{11}$ |
| 1-441 | F | F | H | OCH$_2$COO$_c$C$_6$H$_{11}$ |
| 1-442 | F | Cl | H | OCH$_2$COO$_c$C$_6$H$_{11}$ |
| 1-443 | Cl | F | H | OCH$_2$COO$_c$C$_6$H$_{11}$ |
| 1-444 | Cl | Cl | H | OCH$_2$COO$_c$C$_6$H$_{11}$ |
| 1-445 | H | F | H | OCH(CH$_3$)COOH |
| 1-446 | H | Cl | H | OCH(CH$_3$)COOH |
| 1-447 | F | F | H | OCH(CH$_3$)COOH |
| 1-448 | F | Cl | H | OCH(CH$_3$)COOH |
| 1-449 | Cl | F | H | OCH(CH$_3$)COOH |
| 1-450 | Cl | Cl | H | OCH(CH$_3$)COOH |

TABLE 19

| | X | Y | R$^1$ | B |
|---|---|---|---|---|
| 1-451 | H | F | H | OCH(CH$_3$)COOCH$_3$ |
| 1-452 | H | Cl | H | OCH(CH$_3$)COOCH$_3$ |
| 1-453 | F | F | H | OCH(CH$_3$)COOCH$_3$ |
| 1-454 | F | Cl | H | OCH(CH$_3$)COOCH$_3$ |
| 1-455 | Cl | F | H | OCH(CH$_3$)COOCH$_3$ |
| 1-456 | Cl | Cl | H | OCH(CH$_3$)COOCH$_3$ |
| 1-457 | H | F | H | OCH(CH$_3$)COOC$_2$H$_5$ |
| 1-458 | H | Cl | H | OCH(CH$_3$)COOC$_2$H$_5$ |
| 1-459 | F | F | H | OCH(CH$_3$)COOC$_2$H$_5$ |
| 1-460 | F | Cl | H | OCH(CH$_3$)COOC$_2$H$_5$ |
| 1-461 | Cl | F | H | OCH(CH$_3$)COOC$_2$H$_5$ |
| 1-462 | Cl | Cl | H | OCH(CH$_3$)COOC$_2$H$_5$ |
| 1-463 | H | F | H | OCH(CH$_3$)COO$_n$C$_3$H$_7$ |
| 1-464 | H | Cl | H | OCH(CH$_3$)COO$_n$C$_3$H$_7$ |
| 1-465 | F | F | H | OCH(CH$_3$)COO$_n$C$_3$H$_7$ |
| 1-466 | F | Cl | H | OCH(CH$_3$)COO$_n$C$_3$H$_7$ |
| 1-467 | Cl | F | H | OCH(CH$_3$)COO$_n$C$_3$H$_7$ |
| 1-468 | Cl | Cl | H | OCH(CH$_3$)COO$_n$C$_3$H$_7$ |
| 1-469 | H | F | H | OCH(CH$_3$)COO$_n$C$_4$H$_9$ |
| 1-470 | H | Cl | H | OCH(CH$_3$)COO$_n$C$_4$H$_9$ |
| 1-471 | F | F | H | OCH(CH$_3$)COO$_n$C$_4$H$_9$ |
| 1-472 | F | Cl | H | OCH(CH$_3$)COO$_n$C$_4$H$_9$ |
| 1-473 | Cl | F | H | OCH(CH$_3$)COO$_n$C$_4$H$_9$ |

TABLE 19-continued

|  | X | Y | R¹ | B |
|---|---|---|---|---|
| 1-474 | Cl | Cl | H | OCH(CH$_3$)COO$_n$C$_4$H$_9$ |
| 1-475 | H | F | H | OCH(CH$_3$)COO$_n$C$_5$H$_{11}$ |

TABLE 20

|  | X | Y | R¹ |  | B |
|---|---|---|---|---|---|
| 1-476 | H | Cl | 0 | H | OCH(CH$_3$)COO$_n$C$_5$H$_{11}$ |
| 1-477 | F | F | H |  | OCH(CH$_3$)COO$_n$C$_5$H$_{11}$ |
| 1-478 | F | Cl | H |  | OCH(CH$_3$)COO$_n$C$_5$H$_{11}$ |
| 1-479 | Cl | F | H |  | OCH(CH$_3$)COO$_n$C$_5$H$_{11}$ |
| 1-480 | Cl | Cl | H |  | OCH(CH$_3$)COO$_n$C$_5$H$_{11}$ |
| 1-481 | H | F | H |  | OCH(CH$_3$)COO$_i$C$_3$H$_7$ |
| 1-482 | H | Cl | H |  | OCH(CH$_3$)COO$_i$C$_3$H$_7$ |
| 1-483 | F | F | H |  | OCH(CH$_3$)COO$_i$C$_3$H$_7$ |
| 1-484 | F | Cl | H |  | OCH(CH$_3$)COO$_i$C$_3$H$_7$ |
| 1-485 | Cl | F | H |  | OCH(CH$_3$)COO$_i$C$_3$H$_7$ |
| 1-486 | Cl | Cl | H |  | OCH(CH$_3$)COO$_i$C$_3$H$_7$ |
| 1-487 | H | F | H |  | OCH(CH$_3$)COO$_c$C$_5$H$_9$ |
| 1-488 | H | Cl | H |  | OCH(CH$_3$)COO$_c$C$_5$H$_9$ |
| 1-489 | F | F | H |  | OCH(CH$_3$)COO$_c$C$_5$H$_9$ |
| 1-490 | F | Cl | H |  | OCH(CH$_3$)COO$_c$C$_5$H$_9$ |
| 1-491 | Cl | F | H |  | OCH(CH$_3$)COO$_c$C$_5$H$_9$ |
| 1-492 | Cl | Cl | H |  | OCH(CH$_3$)COO$_c$C$_5$H$_9$ |
| 1-493 | H | F | H |  | OCH(CH$_3$)COO$_c$C$_6$H$_{11}$ |
| 1-494 | H | Cl | H |  | OCH(CH$_3$)COO$_c$C$_6$H$_{11}$ |
| 1-495 | F | F | H |  | OCH(CH$_3$)COO$_c$C$_6$H$_{11}$ |
| 1-496 | F | Cl | H |  | OCH(CH$_3$)COO$_c$C$_6$H$_{11}$ |
| 1-497 | Cl | F | H |  | OCH(CH$_3$)COO$_c$C$_6$H$_{11}$ |
| 1-498 | Cl | Cl | H |  | OCH(CH$_3$)COO$_c$C$_6$H$_{11}$ |
| 1-499 | H | F | H |  | OCH$_2$CONH$_2$ |
| 1-500 | H | Cl | H |  | OCH$_2$CONH$_2$ |

TABLE 21

|  | X | Y | R¹ | B |
|---|---|---|---|---|
| 1-501 | F | F | H | OCH$_2$CONH$_2$ |
| 1-502 | F | Cl | H | OCH$_2$CONH$_2$ |
| 1-503 | Cl | F | H | OCH$_2$CONH$_2$ |
| 1-504 | Cl | Cl | H | OCH$_2$CONH$_2$ |
| 1-505 | H | F | H | OCH$_2$CONHCH$_3$ |
| 1-506 | H | Cl | H | OCH$_2$CONHCH$_3$ |
| 1-507 | F | F | H | OCH$_2$CONHCH$_3$ |
| 1-508 | F | Cl | H | OCH$_2$CONHCH$_3$ |
| 1-509 | Cl | F | H | OCH$_2$CONHCH$_3$ |
| 1-510 | Cl | Cl | H | OCH$_2$CONHCH$_3$ |
| 1-511 | H | F | H | OCH$_2$CON(CH$_3$)$_2$ |
| 1-512 | H | Cl | H | OCH$_2$CON(CH$_3$)$_2$ |
| 1-513 | F | F | H | OCH$_2$CON(CH$_3$)$_2$ |
| 1-514 | F | Cl | H | OCH$_2$CON(CH$_3$)$_2$ |
| 1-515 | Cl | F | H | OCH$_2$CON(CH$_3$)$_2$ |
| 1-516 | Cl | Cl | H | OCH$_2$CON(CH$_3$)$_2$ |
| 1-517 | H | F | H | OCH$_2$CON(C$_2$H$_5$)$_2$ |
| 1-518 | H | Cl | H | OCH$_2$CON(C$_2$H$_5$)$_2$ |
| 1-519 | F | F | H | OCH$_2$CON(C$_2$H$_5$)$_2$ |
| 1-520 | F | Cl | H | OCH$_2$CON(C$_2$H$_5$)$_2$ |
| 1-521 | Cl | F | H | OCH$_2$CON(C$_2$H$_5$)$_2$ |
| 1-522 | Cl | Cl | H | OCH$_2$CON(C$_2$H$_5$)$_2$ |
| 1-523 | H | F | H | OCH$_2$CON(CH$_3$)C$_2$H$_5$ |
| 1-524 | H | Cl | H | OCH$_2$CON(CH$_3$)C$_2$H$_5$ |
| 1-525 | F | F | H | OCH$_2$CON(CH$_3$)C$_2$H$_5$ |

TABLE 22

|  | X | Y | R¹ | B |
|---|---|---|---|---|
| 1-526 | F | Cl | H | OCH$_2$CON(CH$_3$)C$_2$H$_5$ |
| 1-527 | Cl | F | H | OCH$_2$CON(CH$_3$)C$_2$H$_5$ |
| 1-528 | Cl | Cl | H | OCH$_2$CON(CH$_3$)C$_2$H$_5$ |

TABLE 22-continued

|  | X | Y | R¹ | B |
|---|---|---|---|---|
| 1-529 | H | F | H | OCH$_2$CON(tetramethylene) |
| 1-530 | H | Cl | H | OCH$_2$CON(tetramethylene) |
| 1-531 | F | F | H | OCH$_2$CON(tetramethylene) |
| 1-532 | F | Cl | H | OCH$_2$CON(tetramethylene) |
| 1-533 | Cl | F | H | OCH$_2$CON(tetramethylene) |
| 1-534 | Cl | Cl | H | OCH$_2$CON(tetramethylene) |
| 1-535 | H | F | H | OCH$_2$CON(pentamethylene) |
| 1-536 | H | Cl | H | OCH$_2$CON(pentamethylene) |
| 1-537 | F | F | H | OCH$_2$CON(pentamethylene) |
| 1-538 | F | Cl | H | OCH$_2$CON(pentamethylene) |
| 1-539 | Cl | F | H | OCH$_2$CON(pentamethylene) |
| 1-540 | Cl | Cl | H | OCH$_2$CON(pentamethylene) |
| 1-541 | H | F | H | OCH$_2$CON(ethyleneoxyethylene) |
| 1-542 | H | Cl | H | OCH$_2$CON(ethyleneoxyethylene) |
| 1-543 | F | F | H | OCH$_2$CON(ethyleneoxyethylene) |
| 1-544 | F | Cl | H | OCH$_2$CON(ethyleneoxyethylene) |
| 1-545 | Cl | F | H | OCH$_2$CON(ethyleneoxyethylene) |
| 1-546 | Cl | Cl | H | OCH$_2$CON(ethyleneoxyethylene) |
| 1-547 | H | F | H | OCH(CH$_3$)CONH$_2$ |
| 1-548 | H | Cl | H | OCH(CH$_3$)CONH$_2$ |
| 1-549 | F | F | H | OCH(CH$_3$)CONH$_2$ |
| 1-550 | F | Cl | H | OCH(CH$_3$)CONH$_2$ |

TABLE 23

|  | X | Y | R¹ | B |
|---|---|---|---|---|
| 1-551 | Cl | F | H | OCH(CH$_3$)CONH$_2$ |
| 1-552 | Cl | Cl | H | OCH(CH$_3$)CONH$_2$ |
| 1-553 | H | F | H | OCH(CH$_3$)CONHCH$_3$ |
| 1-554 | H | Cl | H | OCH(CH$_3$)CONHCH$_3$ |
| 1-555 | F | F | H | OCH(CH$_3$)CONHCH$_3$ |
| 1-556 | F | Cl | H | OCH(CH$_3$)CONHCH$_3$ |
| 1-557 | Cl | F | H | OCH(CH$_3$)CONHCH$_3$ |
| 1-558 | Cl | Cl | H | OCH(CH$_3$)CONHCH$_3$ |
| 1-559 | H | F | H | OCH(CH$_3$)CON(CH$_3$)$_2$ |
| 1-560 | H | Cl | H | OCH(CH$_3$)CON(CH$_3$)$_2$ |
| 1-561 | F | F | H | OCH(CH$_3$)CON(CH$_3$)$_2$ |
| 1-562 | F | Cl | H | OCH(CH$_3$)CON(CH$_3$)$_2$ |
| 1-563 | Cl | F | H | OCH(CH$_3$)CON(CH$_3$)$_2$ |
| 1-564 | Cl | Cl | H | OCH(CH$_3$)CON(CH$_3$)$_2$ |
| 1-565 | H | F | H | OCH(CH$_3$)CON(C$_2$H$_5$)$_2$ |
| 1-566 | H | Cl | H | OCH(CH$_3$)CON(C$_2$H$_5$)$_2$ |
| 1-567 | F | F | H | OCH(CH$_3$)CON(C$_2$H$_5$)$_2$ |
| 1-568 | F | Cl | H | OCH(CH$_3$)CON(C$_2$H$_5$)$_2$ |
| 1-569 | Cl | F | H | OCH(CH$_3$)CON(C$_2$H$_5$)$_2$ |
| 1-570 | Cl | Cl | H | OCH(CH$_3$)CON(C$_2$H$_5$)$_2$ |
| 1-571 | H | F | H | OCH(CH$_3$)CON(CH$_3$)C$_2$H$_5$ |
| 1-572 | H | Cl | H | OCH(CH$_3$)CON(CH$_3$)C$_2$H$_5$ |
| 1-573 | F | F | H | OCH(CH$_3$)CON(CH$_3$)C$_2$H$_5$ |
| 1-574 | F | Cl | H | OCH(CH$_3$)CON(CH$_3$)C$_2$H$_5$ |
| 1-575 | Cl | F | H | OCH(CH$_3$)CON(CH$_3$)C$_2$H$_5$ |

TABLE 24

|  | X | Y | R¹ | B |
|---|---|---|---|---|
| 1-576 | Cl | Cl | H | OCH(CH$_3$)CON(CH$_3$)C$_2$H$_5$ |
| 1-577 | H | F | H | OCH(CH$_3$)CON(tetramethylene) |
| 1-578 | H | Cl | H | OCH(CH$_3$)CON(tetramethylene) |
| 1-579 | F | F | H | OCH(CH$_3$)CON(tetramethylene) |
| 1-580 | F | Cl | H | OCH(CH$_3$)CON(tetramethylene) |
| 1-581 | Cl | F | H | OCH(CH$_3$)CON(tetramethylene) |
| 1-582 | Cl | Cl | H | OCH(CH$_3$)CON(tetramethylene) |
| 1-583 | H | F | H | OCH(CH$_3$)CON(pentamethylene) |
| 1-584 | H | Cl | H | OCH(CH$_3$)CON(pentamethylene) |
| 1-585 | F | F | H | OCH(CH$_3$)CON(pentamethylene) |
| 1-586 | F | Cl | H | OCH(CH$_3$)CON(pentamethylene) |
| 1-587 | Cl | F | H | OCH(CH$_3$)CON(pentamethylene) |
| 1-588 | Cl | Cl | H | OCH(CH$_3$)CON(pentamethylene) |
| 1-589 | H | F | H | OCH(CH$_3$)CON(ethyleneoxyethylene) |
| 1-590 | H | Cl | H | OCH(CH$_3$)CON(ethyleneoxyethylene) |

TABLE 24-continued

| | X | Y | R¹ | B |
|---|---|---|---|---|
| 1-591 | F | F | H | OCH(CH₃)CON(ethyleneoxyethylene) |
| 1-592 | F | Cl | H | OCH(CH₃)CON(ethyleneoxyethylene) |
| 1-593 | Cl | F | H | OCH(CH₃)CON(ethyleneoxyethylene) |
| 1-594 | Cl | Cl | H | OCH(CH₃)CON(ethyleneoxyethylene) |
| 1-595 | H | F | H | OCH₂COON(CH₃)₂ |
| 1-596 | H | Cl | H | OCH₂COON(CH₃)₂ |
| 1-597 | F | F | H | OCH₂COON(CH₃)₂ |
| 1-598 | F | Cl | H | OCH₂COON(CH₃)₂ |
| 1-599 | Cl | F | H | OCH₂COON(CH₃)₂ |
| 1-600 | Cl | Cl | H | OCH₂COON(CH₃)₂ |

TABLE 25

| | X | Y | R¹ | B |
|---|---|---|---|---|
| 1-601 | H | F | H | OCH₂COON(C₂H₅)₂ |
| 1-602 | H | Cl | H | OCH₂COON(C₂H₅)₂ |
| 1-603 | F | F | H | OCH₂COON(C₂H₅)₂ |
| 1-604 | F | Cl | H | OCH₂COON(C₂H₅)₂ |
| 1-605 | Cl | F | H | OCH₂COON(C₂H₅)₂ |
| 1-606 | Cl | Cl | H | OCH₂COON(C₂H₅)₂ |
| 1-607 | H | F | H | OCH(CH₃)COON(CH₃)₂ |
| 1-608 | H | Cl | H | OCH(CH₃)COON(CH₃)₂ |
| 1-609 | F | F | H | OCH(CH₃)COON(CH₃)₂ |
| 1-610 | F | Cl | H | OCH(CH₃)COON(CH₃)₂ |
| 1-611 | Cl | F | H | OCH(CH₃)COON(CH₃)₂ |
| 1-612 | Cl | Cl | H | OCH(CH₃)COON(CH₃)₂ |
| 1-613 | H | F | H | OCH(CH₃)COON(C₂H₅)₂ |
| 1-614 | H | Cl | H | OCH(CH₃)COON(C₂H₅)₂ |
| 1-615 | F | F | H | OCH(CH₃)COON(C₂H₅)₂ |
| 1-616 | F | Cl | H | OCH(CH₃)COON(C₂H₅)₂ |
| 1-617 | Cl | F | H | OCH(CH₃)COON(C₂H₅)₂ |
| 1-618 | Cl | Cl | H | OCH(CH₃)COON(C₂H₅)₂ |
| 1-619 | H | F | H | SCH₃ |
| 1-620 | H | Cl | H | SCH₃ |
| 1-621 | F | F | H | SCH₃ |
| 1-622 | F | Cl | H | SCH₃ |
| 1-623 | Cl | F | H | SCH₃ |
| 1-624 | Cl | Cl | H | SCH₃ |
| 1-625 | H | F | H | SC₂H₅ |

TABLE 26

| | X | Y | R¹ | B |
|---|---|---|---|---|
| 1-626 | H | Cl | H | SC₂H₅ |
| 1-627 | F | F | H | SC₂H₅ |
| 1-628 | F | Cl | H | SC₂H₅ |
| 1-629 | Cl | F | H | SC₂H₅ |
| 1-630 | Cl | Cl | H | SC₂H₅ |
| 1-631 | H | F | H | SiC₃H₇ |
| 1-632 | H | Cl | H | SiC₃H₇ |
| 1-633 | F | F | H | SiC₃H₇ |
| 1-634 | F | Cl | H | SiC₃H₇ |
| 1-635 | Cl | F | H | SiC₃H₇ |
| 1-636 | Cl | Cl | H | SiC₃H₇ |
| 1-637 | H | F | H | SnC₃H₇ |
| 1-638 | H | Cl | H | SnC₃H₇ |
| 1-639 | F | F | H | SnC₃H₇ |
| 1-640 | F | Cl | H | SnC₃H₇ |
| 1-641 | Cl | F | H | SnC₃H₇ |
| 1-642 | Cl | Cl | H | SnC₃H₇ |
| 1-643 | H | F | H | SCH₂CH₂Cl |
| 1-644 | H | Cl | H | SCH₂CH₂Cl |
| 1-645 | F | F | H | SCH₂CH₂Cl |
| 1-646 | F | Cl | H | SCH₂CH₂Cl |
| 1-647 | Cl | F | H | SCH₂CH₂Cl |
| 1-648 | Cl | Cl | H | SCH₂CH₂Cl |
| 1-649 | H | F | H | ScC₅H₉ |
| 1-650 | H | Cl | H | ScC₅H₉ |

TABLE 27

| | X | Y | R¹ | B |
|---|---|---|---|---|
| 1-651 | F | F | H | ScC₅H₉ |
| 1-652 | F | Cl | H | ScC₅H₉ |
| 1-653 | Cl | F | H | ScC₅H₉ |
| 1-654 | Cl | Cl | H | ScC₅H₉ |
| 1-655 | H | F | H | ScC₆H₁₁ |
| 1-656 | H | Cl | H | ScC₆H₁₁ |
| 1-657 | F | F | H | ScC₆H₁₁ |
| 1-658 | F | Cl | H | ScC₆H₁₁ |
| 1-659 | Cl | F | H | ScC₆H₁₁ |
| 1-660 | Cl | Cl | H | ScC₆H₁₁ |
| 1-661 | H | F | H | SCH₂CH=CH₂ |
| 1-662 | H | Cl | H | SCH₂CH=CH₂ |
| 1-663 | F | F | H | SCH₂CH=CH₂ |
| 1-664 | F | Cl | H | SCH₂CH=CH₂ |
| 1-665 | Cl | F | H | SCH₂CH=CH₂ |
| 1-666 | Cl | Cl | H | SCH₂CH=CH₂ |
| 1-667 | H | F | H | SCH₂CCl=CH₂ |
| 1-668 | H | Cl | H | SCH₂CCl=CH₂ |
| 1-669 | F | F | H | SCH₂CCl=CH₂ |
| 1-670 | F | Cl | H | SCH₂CCl=CH₂ |
| 1-671 | Cl | F | H | SCH₂CCl=CH₂ |
| 1-672 | Cl | Cl | H | SCH₂CCl=CH₂ |
| 1-673 | H | F | H | SCH₂CCl=CHCl |
| 1-674 | H | Cl | H | SCH₂CCl=CHCl |
| 1-675 | F | F | H | SCH₂CCl=CHCl |

TABLE 28

| | X | Y | R¹ | B |
|---|---|---|---|---|
| 1-676 | F | Cl | H | SCH₂CCl=CHCl |
| 1-677 | Cl | F | H | SCH₂CCl=CHCl |
| 1-678 | Cl | Cl | H | SCH₂CCl=CHCl |
| 1-679 | H | F | H | SCH(CH₃)CH=CH₂ |
| 1-680 | H | Cl | H | SCH(CH₃)CH=CH₂ |
| 1-681 | F | F | H | SCH(CH₃)CH=CH₂ |
| 1-682 | F | Cl | H | SCH(CH₃)CH=CH₂ |
| 1-683 | Cl | F | H | SCH(CH₃)CH=CH₂ |
| 1-684 | Cl | Cl | H | SCH(CH₃)CH=CH₂ |
| 1-685 | H | F | H | SCH₂C≡CH |
| 1-686 | H | Cl | H | SCH₂C≡CH |
| 1-687 | F | F | H | SCH₂C≡CH |
| 1-688 | F | Cl | H | SCH₂C≡CH |
| 1-689 | Cl | F | H | SCH₂C≡CH |
| 1-690 | Cl | Cl | H | SCH₂C≡CH |
| 1-691 | H | F | H | SCH(CH₃)C≡CH |
| 1-692 | H | Cl | H | SCH(CH₃)C≡CH |
| 1-693 | F | F | H | SCH(CH₃)C≡CH |
| 1-694 | F | Cl | H | SCH(CH₃)C≡CH |
| 1-695 | Cl | F | H | SCH(CH₃)C≡CH |
| 1-696 | Cl | Cl | H | SCH(CH₃)C≡CH |
| 1-697 | H | F | H | SCH₂COOH |
| 1-698 | H | Cl | H | SCH₂COOH |
| 1-699 | F | F | H | SCH₂COOH |
| 1-700 | F | Cl | H | SCH₂COOH |

TABLE 29

| | X | Y | R¹ | B |
|---|---|---|---|---|
| 1-701 | Cl | F | H | SCH₂COOH |
| 1-702 | Cl | Cl | H | SCH₂COOH |
| 1-703 | H | F | H | SCH₂COOCH₃ |
| 1-704 | H | Cl | H | SCH₂COOCH₃ |
| 1-705 | F | F | H | SCH₂COOCH₃ |
| 1-706 | F | Cl | H | SCH₂COOCH₃ |
| 1-707 | Cl | F | H | SCH₂COOCH₃ |
| 1-708 | Cl | Cl | H | SCH₂COOCH₃ |
| 1-709 | H | F | H | SCH₂COOC₂H₅ |
| 1-710 | H | Cl | H | SCH₂COOC₂H₅ |
| 1-711 | F | F | H | SCH₂COOC₂H₅ |
| 1-712 | F | Cl | H | SCH₂COOC₂H₅ |

TABLE 29-continued

|  | X | Y | R$^1$ | B |
|---|---|---|---|---|
| 1-713 | Cl | F | H | SCH$_2$COOC$_2$H$_5$ |
| 1-714 | Cl | Cl | H | SCH$_2$COOC$_2$H$_5$ |
| 1-715 | H | F | H | SCH$_2$COO$_n$C$_3$H$_7$ |
| 1-716 | H | Cl | H | SCH$_2$COO$_n$C$_3$H$_7$ |
| 1-717 | F | F | H | SCH$_2$COO$_n$C$_3$H$_7$ |
| 1-718 | F | Cl | H | SCH$_2$COO$_n$C$_3$H$_7$ |
| 1-719 | Cl | F | H | SCH$_2$COO$_n$C$_3$H$_7$ |
| 1-720 | Cl | Cl | H | SCH$_2$COO$_n$C$_3$H$_7$ |
| 1-721 | H | F | H | SCH$_2$COO$_n$C$_4$H$_9$ |
| 1-722 | H | Cl | W | SCH$_2$COO$_n$C$_4$H$_9$ |
| 1-723 | F | F | H | SCH$_2$COO$_n$C$_4$H$_9$ |
| 1-724 | F | Cl | H | SCH$_2$COO$_n$C$_4$H$_9$ |
| 1-725 | Cl | F | H | SCH$_2$COO$_n$C$_4$H$_9$ |

TABLE 30

|  | X | Y | R$^1$ | B |
|---|---|---|---|---|
| 1-726 | Cl | Cl | H | SCH$_2$COO$_n$C$_4$H$_9$ |
| 1-727 | H | F | H | SCH$_2$COO$_n$C$_5$H$_{11}$ |
| 1-728 | H | Cl | H | SCH$_2$COO$_n$C$_5$H$_{11}$ |
| 1-729 | F | F | H | SCH$_2$COO$_n$C$_5$H$_{11}$ |
| 1-730 | F | Cl | H | SCH$_2$COO$_n$C$_5$H$_{11}$ |
| 1-731 | Cl | F | H | SCH$_2$COO$_n$C$_5$H$_{11}$ |
| 1-732 | Cl | Cl | H | SCH$_2$COO$_n$C$_5$H$_{11}$ |
| 1-733 | H | F | H | SCH$_2$COO$_i$C$_3$H$_7$ |
| 1-734 | H | Cl | H | SCH$_2$COO$_i$C$_3$H$_7$ |
| 1-735 | F | F | H | SCH$_2$COO$_i$C$_3$H$_7$ |
| 1-736 | F | Cl | H | SCH$_2$COO$_i$C$_3$H$_7$ |
| 1-737 | Cl | F | H | SCH$_2$COO$_i$C$_3$H$_7$ |
| 1-738 | Cl | Cl | H | SCH$_2$COO$_i$C$_3$H$_7$ |
| 1-739 | H | F | H | SCH$_2$COO$_c$C$_5$H$_9$ |
| 1-740 | H | Cl | H | SCH$_2$COO$_c$C$_5$H$_9$ |
| 1-741 | F | F | H | SCH$_2$COO$_c$C$_5$H$_9$ |
| 1-742 | F | Cl | H | SCH$_2$COO$_c$C$_5$H$_9$ |
| 1-743 | Cl | F | H | SCH$_2$COO$_c$C$_5$H$_9$ |
| 1-744 | Cl | Cl | H | SCH$_2$COO$_c$C$_5$H$_9$ |
| 1-745 | H | F | H | SCH$_2$COO$_c$C$_6$H$_{11}$ |
| 1-746 | H | Cl | H | SCH$_2$COO$_c$C$_6$H$_{11}$ |
| 1-747 | F | F | H | SCH$_2$COO$_c$C$_6$H$_{11}$ |
| 1-748 | F | Cl | H | SCH$_2$COO$_c$C$_6$H$_{11}$ |
| 1-749 | Cl | F | H | SCH$_2$COO$_c$C$_6$H$_{11}$ |
| 1-750 | Cl | Cl | H | SCH$_2$COO$_c$C$_6$H$_{11}$ |

TABLE 31

|  | X | Y | R$^1$ | B |
|---|---|---|---|---|
| 1-751 | H | F | H | SCH(CH$_3$)COOH |
| 1-752 | H | Cl | H | SCH(CH$_3$)COOH |
| 1-753 | F | F | H | SCH(CH$_3$)COOH |
| 1-754 | F | Cl | H | SCH(CH$_3$)COOH |
| 1-755 | Cl | F | H | SCH(CH$_3$)COOH |
| 1-756 | Cl | Cl | H | SCH(CH$_3$)COOH |
| 1-757 | H | F | H | SCH(CH$_3$)COOCH$_3$ |
| 1-758 | H | Cl | H | SCH(CH$_3$)COOCH$_3$ |
| 1-759 | F | F | H | SCH(CH$_3$)COOCH$_3$ |
| 1-760 | F | Cl | H | SCH(CH$_3$)COOCH$_3$ |
| 1-761 | Cl | F | H | SCH(CH$_3$)COOCH$_3$ |
| 1-762 | Cl | Cl | H | SCH(CH$_3$)COOCH$_3$ |
| 1-763 | H | F | H | SCH(CH$_3$)COOC$_2$H$_5$ |
| 1-764 | H | Cl | H | SCH(CH$_3$)COOC$_2$H$_5$ |
| 1-765 | F | F | H | SCH(CH$_3$)COOC$_2$H$_5$ |
| 1-766 | F | Cl | H | SCH(CH$_3$)COOC$_2$H$_5$ |
| 1-767 | Cl | F | H | SCH(CH$_3$)COOC$_2$H$_5$ |
| 1-768 | Cl | Cl | H | SCH(CH$_3$)COOC$_2$H$_5$ |
| 1-769 | H | F | H | SCH(CH$_3$)COO$_n$C$_3$H$_7$ |
| 1-770 | H | Cl | H | SCH(CH$_3$)COO$_n$C$_3$H$_7$ |
| 1-771 | F | F | H | SCH(CH$_3$)COO$_n$C$_3$H$_7$ |
| 1-772 | F | Cl | H | SCH(CH$_3$)COO$_n$C$_3$H$_7$ |
| 1-773 | Cl | F | H | SCH(CH$_3$)COO$_n$C$_3$H$_7$ |

TABLE 31-continued

|  | X | Y | R$^1$ | B |
|---|---|---|---|---|
| 1-774 | Cl | Cl | H | SCH(CH$_3$)COO$_n$C$_3$H$_7$ |
| 1-775 | H | F | H | SCH(CH$_3$)COO$_n$C$_4$H$_9$ |

TABLE 32

|  | X | Y | R$^1$ | B |
|---|---|---|---|---|
| 1-776 | H | Cl | H | SCH(CH$_3$)COO$_n$C$_4$H$_9$ |
| 1-777 | F | F | H | SCH(CH$_3$)COO$_n$C$_4$H$_9$ |
| 1-778 | F | Cl | H | SCH(CH$_3$)COO$_n$C$_4$H$_9$ |
| 1-779 | Cl | F | H | SCH(CH$_3$)COO$_n$C$_4$H$_9$ |
| 1-780 | Cl | Cl | H | SCH(CH$_3$)COO$_n$C$_4$H$_9$ |
| 1-781 | H | F | H | SCH(CH$_3$)COO$_n$C$_5$H$_{11}$ |
| 1-782 | H | Cl | H | SCH(CH$_3$)COO$_n$C$_5$H$_{11}$ |
| 1-783 | F | F | H | SCH(CH$_3$)COO$_n$C$_5$H$_{11}$ |
| 1-784 | F | Cl | H | SCH(CH$_3$)COO$_n$C$_5$H$_{11}$ |
| 1-785 | Cl | F | H | SCH(CH$_3$)COO$_n$C$_5$H$_{11}$ |
| 1-786 | Cl | Cl | H | SCH(CH$_3$)COO$_n$C$_5$H$_{11}$ |
| 1-787 | H | F | H | SCH(CH$_3$)COO$_i$C$_3$H$_7$ |
| 1-788 | H | Cl | H | SCH(CH$_3$)COO$_i$C$_3$H$_7$ |
| 1-789 | F | F | H | SCH(CH$_3$)COO$_i$C$_3$H$_7$ |
| 1-790 | F | Cl | H | SCH(CH$_3$)COO$_i$C$_3$H$_7$ |
| 1-791 | Cl | F | H | SCH(CH$_3$)COO$_i$C$_3$H$_7$ |
| 1-792 | Cl | Cl | H | SCH(CH$_3$)COO$_i$C$_3$H$_7$ |
| 1-793 | H | F | H | SCH(CH$_3$)COO$_c$C$_5$H$_9$ |
| 1-794 | H | Cl | H | SCH(CH$_3$)COO$_c$C$_5$H$_9$ |
| 1-795 | F | F | H | SCH(CH$_3$)COO$_c$C$_5$H$_9$ |
| 1-796 | F | Cl | H | SCH(CH$_3$)COO$_c$C$_5$H$_9$ |
| 1-797 | Cl | F | H | SCH(CH$_3$)COO$_c$C$_5$H$_9$ |
| 1-798 | Cl | Cl | H | SCH(CH$_3$)COO$_c$C$_5$H$_9$ |
| 1-799 | H | F | H | SCH(CH$_3$)COO$_c$C$_6$H$_{11}$ |
| 1-800 | H | Cl | H | SCH(CH$_3$)COO$_c$C$_6$H$_{11}$ |

TABLE 33

|  | X | Y | R$^1$ | B |
|---|---|---|---|---|
| 1-801 | F | F | H | SCH(CH$_3$)COO$_c$C$_6$H$_{11}$ |
| 1-802 | F | Cl | H | SCH(CH$_3$)COO$_c$C$_6$H$_{11}$ |
| 1-803 | Cl | F | H | SCH(CH$_3$)COO$_c$C$_6$H$_{11}$ |
| 1-804 | Cl | Cl | H | SCH(CH$_3$)COO$_c$C$_6$H$_{11}$ |
| 1-805 | H | F | H | SCH$_2$CONH$_2$ |
| 1-806 | H | Cl | H | SCH$_2$CONH$_2$ |
| 1-807 | F | F | H | SCH$_2$CONH$_2$ |
| 1-808 | F | Cl | H | SCH$_2$CONH$_2$ |
| 1-809 | Cl | F | H | SCH$_2$CONH$_2$ |
| 1-810 | Cl | Cl | H | SCH$_2$CONH$_2$ |
| 1-811 | H | F | H | SCH$_2$CONHCH$_3$ |
| 1-812 | H | Cl | H | SCH$_2$CONHCH$_3$ |
| 1-813 | F | F | H | SCH$_2$CONHCH$_3$ |
| 1-814 | F | Cl | H | SCH$_2$CONHCH$_3$ |
| 1-815 | Cl | F | H | SCH$_2$CONHCH$_3$ |
| 1-816 | Cl | Cl | H | SCH$_2$CONHCH$_3$ |
| 1-817 | H | F | H | SCH$_2$CON(CH$_3$)$_2$ |
| 1-818 | H | Cl | H | SCH$_2$CON(CH$_3$)$_2$ |
| 1-819 | F | F | H | SCH$_2$CON(CH$_3$)$_2$ |
| 1-820 | F | Cl | H | SCH$_2$CON(CH$_3$)$_2$ |
| 1-821 | Cl | F | H | SCH$_2$CON(CH$_3$)$_2$ |
| 1-822 | Cl | Cl | H | SCH$_2$CON(CH$_3$)$_2$ |
| 1-823 | H | F | H | SCH$_2$CON(C$_2$H$_5$)$_2$ |
| 1-824 | H | Cl | H | SCH$_2$CON(C$_2$H$_5$)$_2$ |
| 1-825 | F | F | H | SCH$_2$CON(C$_2$H$_5$)$_2$ |

TABLE 34

|  | X | Y | R$^1$ | B |
|---|---|---|---|---|
| 1-826 | F | Cl | H | SCH$_2$CON(C$_2$H$_5$)$_2$ |
| 1-827 | Cl | F | H | SCH$_2$CON(C$_2$H$_5$)$_2$ |
| 1-828 | Cl | Cl | H | SCH$_2$CON(C$_2$H$_5$)$_2$ |

TABLE 34-continued

| | X | Y | R$^1$ | B |
|---|---|---|---|---|
| 1-829 | H | F | H | SCH$_2$CON(CH$_3$)C$_{2H5}$ |
| 1-830 | H | Cl | H | SCH$_2$CON(CH$_3$)C$_{2H5}$ |
| 1-831 | F | F | H | SCH$_2$CON(CH$_3$)C$_{2H5}$ |
| 1-832 | F | Cl | H | SCH$_2$CON(CH$_3$)C$_{2H5}$ |
| 1-833 | Cl | F | H | SCH$_2$CON(CH$_3$)C$_{2H5}$ |
| 1-834 | Cl | Cl | H | SCH$_2$CON(CH$_3$)C$_{2H5}$ |
| 1-835 | H | F | H | SCH$_2$CON(tetramethylene) |
| 1-836 | H | Cl | H | SCH$_2$CON(tetramethylene) |
| 1-837 | F | F | H | SCH$_2$CON(tetramethylene) |
| 1-838 | F | Cl | H | SCH$_2$CON(tetramethylene) |
| 1-839 | Cl | F | H | SCH$_2$CON(tetramethylene) |
| 1-840 | Cl | Cl | H | SCH$_2$CON(tetramethylene) |
| 1-841 | H | F | H | SCH$_2$CON(pentamethylene) |
| 1-842 | H | Cl | H | SCH$_2$CON(pentamethylene) |
| 1-843 | F | F | H | SCH$_2$CON(pentamethylene) |
| 1-844 | F | Cl | H | SCH$_2$CON(pentamethylene) |
| 1-845 | Cl | F | H | SCH$_2$CON(pentamethylene) |
| 1-846 | Cl | Cl | H | SCH$_2$CON(pentamethylene) |
| 1-847 | H | F | H | SCH$_2$CON(ethyleneoxyethylene) |
| 1-848 | H | Cl | H | SCH$_2$CON(ethyleneoxyethylene) |
| 1-849 | F | F | H | SCH$_2$CON(ethyleneoxyethylene) |
| 1-850 | F | Cl | H | SCH$_2$CON(ethyleneoxyethylene) |

TABLE 35

| | X | Y | R$^1$ | B |
|---|---|---|---|---|
| 1-851 | Cl | F | H | SCH$_2$CON(ethyleneoxyethylene) |
| 1-852 | Cl | Cl | H | SCH$_2$CON(ethyleneoxyethylene) |
| 1-853 | H | F | H | SCH(CH$_3$)CONH$_2$ |
| 1-854 | H | Cl | H | SCH(CH$_3$)CONH$_2$ |
| 1-855 | F | F | H | SCH(CH$_3$)CONH$_2$ |
| 1-856 | F | Cl | H | SCH(CH$_3$)CONH$_2$ |
| 1-857 | Cl | F | H | SCH(CH$_3$)CONH$_2$ |
| 1-858 | Cl | Cl | H | SCH(CH$_3$)CONH$_2$ |
| 1-859 | H | F | H | SCH(CH$_3$)CONHCH$_3$ |
| 1-860 | H | Cl | H | SCH(CH$_3$)CONHCH$_3$ |
| 1-861 | F | F | H | SCH(CH$_3$)CONHCH$_3$ |
| 1-862 | F | Cl | H | SCH(CH$_3$)CONHCH$_3$ |
| 1-863 | Cl | F | H | SCH(CH$_3$)CONHCH$_3$ |
| 1-864 | Cl | Cl | H | SCH(CH$_3$)CONHCH$_3$ |
| 1-865 | H | F | H | SCH(CH$_3$)CON(CH$_3$)$_2$ |
| 1-866 | H | Cl | H | SCH(CH$_3$)CON(CH$_3$)$_2$ |
| 1-867 | F | F | H | SCH(CH$_3$)CON(CH$_3$)$_2$ |
| 1-868 | F | Cl | H | SCH(CH$_3$)CON(CH$_3$)$_2$ |
| 1-869 | Cl | F | H | SCH(CH$_3$)CON(CH$_3$)$_2$ |
| 1-870 | Cl | Cl | H | SCH(CH$_3$)CON(CH$_3$)$_2$ |
| 1-871 | H | F | H | SCH(CH$_3$)CON(C$_2$H$_5$)$_2$ |
| 1-872 | H | Cl | H | SCH(CH$_3$)CON(C$_2$H$_5$)$_2$ |
| 1-873 | F | F | H | SCH(CH$_3$)CON(C$_2$H$_5$)$_2$ |
| 1-874 | F | Cl | H | SCH(CH$_3$)CON(C$_2$H$_5$)$_2$ |
| 1-875 | Cl | F | H | SCH(CH$_3$)CON(C$_2$H$_5$)$_2$ |

TABLE 36

| | X | Y | R$^1$ | B |
|---|---|---|---|---|
| 1-876 | Cl | Cl | H | SCH(CH$_3$)CON(C$_2$H$_5$)$_2$ |
| 1-877 | H | F | H | SCH(CH$_3$)CON(CH$_3$)C$_2$H$_5$ |
| 1-878 | H | Cl | H | SCH(CH$_3$)CON(CH$_3$)C$_2$H$_5$ |
| 1-879 | F | F | H | SCH(CH$_3$)CON(CH$_3$)C$_2$H$_5$ |
| 1-880 | F | Cl | H | SCH(CH$_3$)CON(CH$_3$)C$_2$H$_5$ |
| 1-881 | Cl | F | H | SCH(CH$_3$)CON(CH$_3$)C$_2$H$_5$ |
| 1-882 | Cl | Cl | H | SCH(CH$_3$)CON(CH$_3$)C$_2$H$_5$ |
| 1-883 | H | F | H | SCH(CH$_3$)CON(CH$_3$)C$_2$H$_5$ |
| 1-884 | H | Cl | H | SCH(CH$_3$)CON(CH$_3$)C$_2$H$_5$ |
| 1-885 | F | F | H | SCH(CH$_3$)CON(CH$_3$)C$_2$H$_5$ |
| 1-886 | F | Cl | H | SCH(CH$_3$)CON(CH$_3$)C$_2$H$_5$ |
| 1-887 | Cl | F | H | SCH(CH$_3$)CON(CH$_3$)C$_2$H$_5$ |
| 1-888 | Cl | Cl | H | SCH(CH$_3$)CON(CH$_3$)C$_2$H$_5$ |
| 1-889 | H | F | H | SCH(CH$_3$)CON(tetramethylene) |
| 1-890 | H | Cl | H | SCH(CH$_3$)CON(tetramethylene) |

TABLE 36-continued

| | X | Y | R$^1$ | B |
|---|---|---|---|---|
| 1-891 | F | F | H | SCH(CH$_3$)CON(tetramethylene) |
| 1-892 | F | Cl | H | SCH(CH$_3$)CON(tetramethylene) |
| 1-893 | Cl | F | H | SCH(CH$_3$)CON(tetramethylene) |
| 1-894 | Cl | Cl | H | SCH(CH$_3$)CON(tetramethylene) |
| 1-895 | H | F | H | SCH(CH$_3$)CON(pentamethylene) |
| 1-896 | H | Cl | H | SCH(CH$_3$)CON(pentamethylene) |
| 1-897 | F | F | H | SCH(CH$_3$)CON(pentamethylene) |
| 1-898 | F | Cl | H | SCH(CH$_3$)CON(pentamethylene) |
| 1-899 | Cl | F | H | SCH(CH$_3$)CON(pentamethylene) |
| 1-900 | Cl | Cl | H | SCH(CH$_3$)CON(pentamethylene) |

TABLE 37

| | X | Y | R$^1$ | B |
|---|---|---|---|---|
| 1-901 | H | F | H | SCH(CH$_3$)CON(ethyleneoxyethylene) |
| 1-902 | H | Cl | H | SCH(CH$_3$)CON(ethyleneoxyethylene) |
| 1-903 | F | F | H | SCH(CH$_3$)CON(ethyleneoxyethylene) |
| 1-904 | F | Cl | H | SCH(CH$_3$)CON(ethyleneoxyethylene) |
| 1-905 | Cl | F | H | SCH(CH$_3$)CON(ethyleneoxyethylene) |
| 1-906 | Cl | Cl | H | SCH(CH$_3$)CON(ethyleneoxyethylene) |
| 1-907 | H | F | H | SO$_2$OCH$_3$ |
| 1-908 | H | Cl | H | SO$_2$OCH$_3$ |
| 1-909 | F | F | H | SO$_2$OCH$_3$ |
| 1-910 | F | Cl | H | SO$_2$OCH$_3$ |
| 1-911 | Cl | F | H | SO$_2$OCH$_3$ |
| 1-912 | Cl | Cl | H | SO$_2$OCH$_3$ |
| 1-913 | H | F | H | SO$_2$OC$_2$H$_5$ |
| 1-914 | H | Cl | H | SO$_2$OC$_2$H$_5$ |
| 1-915 | F | F | H | SO$_2$OC$_2$H$_5$ |
| 1-916 | F | Cl | H | SO$_2$OC$_2$H$_5$ |
| 1-917 | Cl | F | H | SO$_2$OC$_2$H$_5$ |
| 1-918 | Cl | Cl | H | SO$_2$OC$_2$H$_5$ |
| 1-919 | H | F | H | SO$_2$OiC$_3$H$_7$ |
| 1-920 | H | Cl | H | SO$_2$OiC$_3$H$_7$ |
| 1-921 | F | F | H | SO$_2$OiC$_3$H$_7$ |
| 1-922 | F | Cl | H | SO$_2$OiC$_3$H$_7$ |
| 1-923 | Cl | F | H | SO$_2$OiC$_3$H$_7$ |
| 1-924 | Cl | Cl | H | SO$_2$OiC$_3$H$_7$ |
| 1-925 | H | F | H | SO$_2$OCH$_2$CH=CH$_2$ |

TABLE 38

| | X | Y | R$^1$ | B |
|---|---|---|---|---|
| 1-926 | H | Cl | H | SO$_2$OCH$_2$CH=CH$_2$ |
| 1-927 | F | F | H | SO$_2$OCH$_2$CH=CH$_2$ |
| 1-928 | F | Cl | H | SO$_2$OCH$_2$CH=CH$_2$ |
| 1-929 | Cl | F | H | SO$_2$OCH$_2$CH=CH$_2$ |
| 1-930 | Cl | Cl | H | SO$_2$OCH$_2$CH=CH$_2$ |
| 1-931 | H | F | H | SO$_2$N(CH$_3$)$_2$ |
| 1-932 | H | Cl | H | SO$_2$N(CH$_3$)$_2$ |
| 1-933 | F | F | H | SO$_2$N(CH$_3$)$_2$ |
| 1-934 | F | Cl | H | SO$_2$N(CH$_3$)$_2$ |
| 1-935 | Cl | F | H | SO$_2$N(CH$_3$)$_2$ |
| 1-936 | Cl | Cl | H | SO$_2$N(CH$_3$)$_2$ |
| 1-937 | H | F | H | SO$_2$N(C$_2$H$_5$)$_2$ |
| 1-938 | H | Cl | H | SO$_2$N(C$_2$H$_5$)$_2$ |
| 1-939 | F | F | H | SO$_2$N(C$_2$H$_5$)$_2$ |
| 1-940 | F | Cl | H | SO$_2$N(C$_2$H$_5$)$_2$ |
| 1-941 | Cl | F | H | SO$_2$N(C$_2$H$_5$)$_2$ |
| 1-942 | Cl | Cl | H | SO$_2$N(C$_2$H$_5$)$_2$ |
| 1-943 | H | F | H | COOH |
| 1-944 | H | Cl | H | COOH |
| 1-945 | F | F | H | COOH |
| 1-946 | F | Cl | H | COOH |
| 1-947 | Cl | F | H | COOH |
| 1-948 | Cl | Cl | H | COOH |
| 1-949 | H | F | H | COOCH$_3$ |
| 1-950 | H | Cl | H | COOCH$_3$ |

TABLE 39

| | X | Y | R¹ | B |
|---|---|---|---|---|
| 1-951 | F | F | H | COOCH₃ |
| 1-952 | F | Cl | H | COOCH₃ |
| 1-953 | Cl | F | H | COOCH₃ |
| 1-954 | Cl | Cl | H | COOCH₃ |
| 1-955 | H | F | H | COOC₂H₅ |
| 1-956 | H | Cl | H | COOC₂H₅ |
| 1-957 | F | F | H | COOC₂H₅ |
| 1-958 | F | Cl | H | COOC₂H₅ |
| 1-959 | Cl | F | H | COOC₂H₅ |
| 1-960 | Cl | Cl | H | COOC₂H₅ |
| 1-961 | H | F | H | COOnC₃H₇ |
| 1-962 | H | Cl | H | COOnC₃H₇ |
| 1-963 | F | F | H | COOnC₃H₇ |
| 1-964 | F | Cl | H | COOnC₃H₇ |
| 1-965 | Cl | F | H | COOnC₃H₇ |
| 1-966 | Cl | Cl | H | COOnC₃H₇ |
| 1-967 | H | F | H | COOnC₄H₉ |
| 1-968 | H | Cl | H | COOnC₄H₉ |
| 1-969 | F | F | H | COOnC₄H₉ |
| 1-970 | F | Cl | H | COOnC₄H₉ |
| 1-971 | Cl | F | H | COOnC₄H₉ |
| 1-972 | Cl | Cl | H | COOnC₄H₉ |
| 1-973 | H | F | H | COOnC₅H₁₁ |
| 1-974 | H | Cl | H | COOnC₅H₁₁ |
| 1-975 | F | F | H | COOnC₅H₁₁ |

TABLE 40

| | X | Y | R¹ | B |
|---|---|---|---|---|
| 1-976 | F | Cl | H | COOnC₅H₁₁ |
| 1-977 | Cl | F | H | COOnC₅H₁₁ |
| 1-978 | Cl | Cl | H | COOnC₅H₁₁ |
| 1-979 | H | F | H | COOiC₃H₇ |
| 1-980 | H | Cl | H | COOiC₃H₇ |
| 1-981 | F | F | H | COOiC₃H₇ |
| 1-982 | F | Cl | H | COOiC₃H₇ |
| 1-983 | Cl | F | H | COOiC₃H₇ |
| 1-984 | Cl | Cl | H | COOiC₃H₇ |
| 1-985 | H | F | H | COOcC₅H₉ |
| 1-986 | H | Cl | H | COOcC₅H₉ |
| 1-987 | F | F | H | COOcC₅H₉ |
| 1-988 | F | Cl | H | COOcC₅H₉ |
| 1-989 | Cl | F | H | COOcC₅H₉ |
| 1-990 | Cl | Cl | H | COOcC₅H₉ |
| 1-991 | H | F | H | COOcC₆H₁₁ |
| 1-992 | H | Cl | H | COOcC₆H₁₁ |
| 1-993 | F | F | H | COOcC₆H₁₁ |
| 1-994 | F | Cl | H | COOcC₆H₁₁ |
| 1-995 | Cl | F | H | COOcC₆H₁₁ |
| 1-996 | Cl | Cl | H | COOcC₆H₁₁ |
| 1-997 | H | F | H | COOCH₂C₆H₅ |
| 1-998 | H | Cl | H | COOCH₂C₆H₅ |
| 1-999 | F | F | H | COOCH₂C₆H₅ |
| 1-1000 | F | Cl | H | COOCH₂C₆H₅ |

TABLE 41

| | X | Y | R¹ | B |
|---|---|---|---|---|
| 1-1001 | Cl | F | H | COOCH₂C₆H₅ |
| 1-1002 | Cl | Cl | H | COOCH₂C₆H₅ |
| 1-1003 | H | F | H | COOCH₂CH₂Cl |
| 1-1004 | H | Cl | H | COOCH₂CH₂Cl |
| 1-1005 | F | F | H | COOCH₂CH₂Cl |
| 1-1006 | F | Cl | H | COOCH₂CH₂Cl |
| 1-1007 | Cl | F | H | COOCH₂CH₂Cl |
| 1-1008 | Cl | Cl | H | COOCH₂CH₂Cl |
| 1-1009 | H | F | H | COOCH₂CH₂Br |
| 1-1010 | H | Cl | H | COOCH₂CH₂Br |
| 1-1011 | F | F | H | COOCH₂CH₂Br |
| 1-1012 | F | Cl | H | COOCH₂CH₂Br |

TABLE 41-continued

| | X | Y | R¹ | B |
|---|---|---|---|---|
| 1-1013 | Cl | F | H | COOCH₂CH₂Br |
| 1-1014 | Cl | Cl | H | COOCH₂CH₂Br |
| 1-1015 | H | F | H | CONH₂ |
| 1-1016 | H | Cl | H | CONH₂ |
| 1-1017 | F | F | H | CONH₂ |
| 1-1018 | F | Cl | H | CONH₂ |
| 1-1019 | Cl | F | H | CONH₂ |
| 1-1020 | Cl | Cl | H | CONH₂ |
| 1-1021 | H | F | H | CONHCH₃ |
| 1-1022 | H | Cl | H | CONHCH₃ |
| 1-1023 | F | F | H | CONHCH₃ |
| 1-1024 | F | Cl | H | CONHCH₃ |
| 1-1025 | Cl | F | H | CONHCH₃ |

TABLE 42

| | X | Y | R¹ | B |
|---|---|---|---|---|
| 1-1026 | Cl | Cl | H | CONHCH₃ |
| 1-1027 | H | F | H | CONHC₂H₅ |
| 1-1028 | H | Cl | H | CONHC₂H₅ |
| 1-1029 | F | F | H | CONHC₂H₅ |
| 1-1030 | F | Cl | H | CONHC₂H₅ |
| 1-1031 | Cl | F | H | CONHC₂H₅ |
| 1-1032 | Cl | Cl | H | CONHC₂H₅ |
| 1-1033 | H | F | H | CON(CH₃)₂ |
| 1-1034 | H | Cl | H | CON(CH₃)₂ |
| 1-1035 | F | F | H | CON(CH₃)₂ |
| 1-1036 | F | Cl | H | CON(CH₃)₂ |
| 1-1037 | Cl | F | H | CON(CH₃)₂ |
| 1-1038 | Cl | Cl | H | CON(CH₃)₂ |
| 1-1039 | H | F | H | CON(C₂H₅)₂ |
| 1-1040 | H | Cl | H | CON(C₂H₅)₂ |
| 1-1041 | F | F | H | CON(C₂H₅)₂ |
| 1-1042 | F | Cl | H | CON(C₂H₅)₂ |
| 1-1043 | Cl | F | H | CON(C₂H₅)₂ |
| 1-1044 | Cl | Cl | H | CON(C₂H₅)₂ |
| 1-1045 | H | F | H | CON(CH₃)(C₂H₅) |
| 1-1046 | H | Cl | H | CON(CH₃)(C₂H₅) |
| 1-1047 | F | F | H | CON(CH₃)(C₂H₅) |
| 1-1048 | F | Cl | H | CON(CH₃)(C₂H₅) |
| 1-1049 | Cl | F | H | CON(CH₃)(C₂H₅) |
| 1-1050 | Cl | Cl | H | CON(CH₃)(C₂H₅) |

TABLE 43

| | X | Y | R¹ | B |
|---|---|---|---|---|
| 1-1051 | H | F | H | COCH₃ |
| 1-1052 | H | Cl | H | COCH₃ |
| 1-1053 | F | F | H | COCH₃ |
| 1-1054 | F | Cl | H | COCH₃ |
| 1-1055 | Cl | F | H | COCH₃ |
| 1-1056 | Cl | Cl | H | COCH₃ |
| 1-1057 | H | F | H | COC₂H₅ |
| 1-1058 | H | Cl | H | COC₂H₅ |
| 1-1059 | F | F | H | COC₂H₅ |
| 1-1060 | F | Cl | H | COC₂H₅ |
| 1-1061 | Cl | F | H | COC₂H₅ |
| 1-1062 | Cl | Cl | H | COC₂H₅ |
| 1-1063 | H | F | H | COCH₂Cl |
| 1-1064 | H | Cl | H | COCH₂Cl |
| 1-1065 | F | F | H | COCH₂Cl |
| 1-1066 | F | Cl | H | COCH₂Cl |
| 1-1067 | Cl | F | H | COCH₂Cl |
| 1-1068 | Cl | Cl | H | COCH₂Cl |
| 1-1069 | H | F | H | CHO |
| 1-1070 | H | Cl | H | CHO |
| 1-1071 | F | F | H | CHO |
| 1-1072 | F | Cl | H | CHO |
| 1-1073 | Cl | F | H | CHO |

TABLE 43-continued

| | X | Y | R¹ | B |
|---|---|---|---|---|
| 1-1074 | Cl | Cl | H | CHO |
| 1-1075 | H | F | H | CH₂CH₂COOH |

TABLE 44

| | X | Y | R¹ | B |
|---|---|---|---|---|
| 1-1076 | H | Cl | H | CH₂CH₂COOH |
| 1-1077 | F | F | H | CH₂CH₂COOH |
| 1-1078 | F | Cl | H | CH₂CH₂COOH |
| 1-1079 | Cl | F | H | CH₂CH₂COOH |
| 1-1080 | Cl | Cl | H | CH₂CH₂COOH |
| 1-1081 | H | F | H | CH₂CH₂COOCH₃ |
| 1-1082 | H | Cl | H | CH₂CH₂COOCH₃ |
| 1-1083 | F | F | H | CH₂CH₂COOCH₃ |
| 1-1084 | F | Cl | H | CH₂CH₂COOCH₃ |
| 1-1085 | Cl | F | H | CH₂CH₂COOCH₃ |
| 1-1086 | Cl | Cl | H | CH₂CH₂COOCH₃ |
| 1-1087 | H | F | H | CH₂CH₂COOC₂H₅ |
| 1-1088 | H | Cl | H | CH₂CH₂COOC₂H₅ |
| 1-1089 | F | F | H | CH₂CH₂COOC₂H₅ |
| 1-1090 | F | Cl | H | CH₂CH₂COOC₂H₅ |
| 1-1091 | Cl | F | H | CH₂CH₂COOC₂H₅ |
| 1-1092 | Cl | Cl | H | CH₂CH₂COOC₂H₅ |
| 1-1093 | H | F | H | CH₂CHClCOOCH₃ |
| 1-1094 | H | Cl | H | CH₂CHClCOOCH₃ |
| 1-1095 | F | F | H | CH₂CHClCOOCH₃ |
| 1-1096 | F | Cl | H | CH₂CHClCOOCH₃ |
| 1-1097 | Cl | F | H | CH₂CHClCOOCH₃ |
| 1-1098 | Cl | Cl | H | CH₂CHClCOOCH₃ |
| 1-1099 | H | F | H | CH₂CHClCOOC₂H₅ |
| 1-1100 | H | Cl | H | CH₂CHClCOOC₂H₅ |

TABLE 45

| | X | Y | R¹ | B |
|---|---|---|---|---|
| 1-1101 | F | F | H | CH₂CHClCOOC₂H₅ |
| 1-1102 | F | Cl | H | CH₂CHClCOOC₂H₅ |
| 1-1103 | Cl | F | H | CH₂CHClCOOC₂H₅ |
| 1-1104 | Cl | Cl | H | CH₂CHClCOOC₂H₅ |
| 1-1105 | H | F | H | CH=CHCOOCH₃ |
| 1-1106 | H | Cl | H | CH=CHCOOCH₃ |
| 1-1107 | F | F | H | CH=CHCOOCH₃ |
| 1-1108 | F | Cl | H | CH=CHCOOCH₃ |
| 1-1109 | Cl | F | H | CH=CHCOOCH₃ |
| 1-1110 | Cl | Cl | H | CH=CHCOOCH₃ |
| 1-1111 | H | F | H | CH=CHCOOC₂H₅ |
| 1-1112 | H | Cl | H | CH=CHCOOC₂H₅ |
| 1-1113 | F | F | H | CH=CHCOOC₂H₅ |
| 1-1114 | F | Cl | H | CH=CHCOOC₂H₅ |
| 1-1115 | Cl | F | H | CH=CHCOOC₂H₅ |
| 1-1116 | Cl | Cl | H | CH=CHCOOC₂H₅ |
| 1-1117 | H | F | H | C(CH₃)=NOH |
| 1-1118 | H | Cl | H | C(CH₃)=NOH |
| 1-1119 | F | F | H | C(CH₃)=NOH |
| 1-1120 | F | Cl | H | C(CH₃)=NOH |
| 1-1121 | Cl | F | H | C(CH₃)=NOH |
| 1-1122 | Cl | Cl | H | C(CH₃)=NOH |
| 1-1123 | H | F | H | C(CH₃)=NOCH₃ |
| 1-1124 | H | Cl | H | C(CH₃)=NOCH₃ |
| 1-1125 | F | F | H | C(CH₃)=NOCH₃ |

TABLE 46

| | X | Y | R¹ | B |
|---|---|---|---|---|
| 1-1126 | F | Cl | H | C(CH₃)=NOCH₃ |
| 1-1127 | Cl | F | H | C(CH₃)=NOCH₃ |
| 1-1128 | Cl | Cl | H | C(CH₃)=NOCH₃ |

TABLE 46-continued

| | X | Y | R¹ | B |
|---|---|---|---|---|
| 1-1129 | H | F | H | C(CH₃)=NOC₂H₅ |
| 1-1130 | H | Cl | H | C(CH₃)=NOC₂H₅ |
| 1-1131 | F | F | H | C(CH₃)=NOC₂H₅ |
| 1-1132 | F | Cl | H | C(CH₃)=NOC₂H₅ |
| 1-1133 | Cl | F | H | C(CH₃)=NOC₂H₅ |
| 1-1134 | Cl | Cl | H | C(CH₃)=NOC₂H₅ |
| 1-1135 | H | F | H | C(CH₃)=NOiC₃H₇ |
| 1-1136 | H | Cl | H | C(CH₃)=NOiC₃H₇ |
| 1-1137 | F | F | H | C(CH₃)=NOiC₃H₇ |
| 1-1138 | F | Cl | H | C(CH₃)=NOiC₃H₇ |
| 1-1139 | Cl | F | H | C(CH₃)=NOiC₃H₇ |
| 1-1140 | Cl | Cl | H | C(CH₃)=NOiC₃H₇ |
| 1-1141 | H | F | H | C(CH₃)=NNH₂ |
| 1-1142 | H | Cl | H | C(CH₃)=NNH₂ |
| 1-1143 | F | F | H | C(CH₃)=NNH₂ |
| 1-1144 | F | Cl | H | C(CH₃)=NNH₂ |
| 1-1145 | Cl | F | H | C(CH₃)=NNH₂ |
| 1-1146 | Cl | Cl | H | C(CH₃)=NNH₂ |
| 1-1147 | H | F | H | C(CH₃)=NNHCH₃ |
| 1-1148 | H | Cl | H | C(CH₃)=NNHCH₃ |
| 1-1149 | F | F | H | C(CH₃)=NNHCH₃ |
| 1-1150 | F | Cl | H | C(CH₃)=NNHCH₃ |

TABLE 47

| | X | Y | R¹ | B |
|---|---|---|---|---|
| 1-1151 | Cl | F | H | C(CH₃)=NNHCH₃ |
| 1-1152 | Cl | Cl | H | C(CH₃)=NNHCH₃ |
| 1-1153 | H | F | H | C(CH₃)=NN(CH₃)₂ |
| 1-1154 | H | Cl | H | C(CH₃)=NN(CH₃)₂ |
| 1-1155 | F | F | H | C(CH₃)=NN(CH₃)₂ |
| 1-1156 | F | Cl | H | C(CH₃)=NN(CH₃)₂ |
| 1-1157 | Cl | F | H | C(CH₃)=NN(CH₃)₂ |
| 1-1158 | Cl | Cl | H | C(CH₃)=NN(CH₃)₂ |
| 1-1159 | H | F | H | C(CH₃)=NNHC₂H₅ |
| 1-1160 | H | Cl | H | C(CH₃)=NNHC₂H₅ |
| 1-1161 | F | F | H | C(CH₃)=NNHC₂H₅ |
| 1-1162 | F | Cl | H | C(CH₃)=NNHC₂H₅ |
| 1-1163 | Cl | F | H | C(CH₃)=NNHC₂H₅ |
| 1-1164 | Cl | Cl | H | C(CH₃)=NNHC₂H₅ |
| 1-1165 | H | F | H | C(CH₃)=NN(C₂H₅)₂ |
| 1-1166 | H | Cl | H | C(CH₃)=NN(C₂H₅)₂ |
| 1-1167 | F | F | H | C(CH₃)=NN(C₂H₅)₂ |
| 1-1168 | F | Cl | H | C(CH₃)=NN(C₂H₅)₂ |
| 1-1169 | Cl | F | H | C(CH₃)=NN(C₂H₅)₂ |
| 1-1170 | Cl | Cl | H | C(CH₃)=NN(C₂H₅)₂ |
| 1-1171 | H | F | H | C(C₂H₅)=NNH₂ |
| 1-1172 | H | Cl | H | C(C₂H₅)=NNH₂ |
| 1-1173 | F | F | H | C(C₂H₅)=NNH₂ |
| 1-1174 | F | Cl | H | C(C₂H₅)=NNH₂ |
| 1-1175 | Cl | F | H | C(C₂H₅)=NNH₂ |

TABLE 48

| | X | Y | R¹ | B |
|---|---|---|---|---|
| 1-1176 | Cl | Cl | H | C(C₂H₅)=NNH₂ |
| 1-1177 | H | F | H | C(C₂H₅)=NNHCH₃ |
| 1-1178 | H | Cl | H | C(C₂H₅)=NNHCH₃ |
| 1-1179 | F | F | H | C(C₂H₅)=NNHCH₃ |
| 1-1180 | F | Cl | H | C(C₂H₅)=NNHCH₃ |
| 1-1181 | Cl | F | H | C(C₂H₅)=NNHCH₃ |
| 1-1182 | Cl | Cl | H | C(C₂H₅)=NNHCH₃ |
| 1-1183 | H | F | H | C(C₂H₅)=NN(CH₃)₂ |
| 1-1184 | H | Cl | H | C(C₂H₅)=NN(CH₃)₂ |
| 1-1185 | F | F | H | C(C₂H₅)=NN(CH₃)₂ |
| 1-1186 | F | Cl | H | C(C₂H₅)=NN(CH₃)₂ |
| 1-1187 | Cl | F | H | C(C₂H₅)=NN(CH₃)₂ |
| 1-1188 | Cl | Cl | H | C(C₂H₅)=NN(CH₃)₂ |
| 1-1189 | H | F | H | C(C₂H₅)=NNHC₂H₅ |
| 1-1190 | H | Cl | H | C(C₂H₅)=NNHC₂H₅ |

TABLE 48-continued

| | X | Y | R$^1$ | B |
|---|---|---|---|---|
| 1-1191 | F | F | H | C(C$_2$H$_5$)=NNHC$_2$H$_5$ |
| 1-1192 | F | Cl | H | C(C$_2$H$_5$)=NNHC$_2$H$_5$ |
| 1-1193 | Cl | F | H | C(C$_2$H$_5$)=NNHC$_2$H$_5$ |
| 1-1194 | Cl | Cl | H | C(C$_2$H$_5$)=NNHC$_2$H$_5$ |
| 1-1195 | H | F | H | C(C$_2$H$_5$)=NN(C$_2$H$_5$)$_2$ |
| 1-1196 | H | Cl | H | C(C$_2$H$_5$)=NN(C$_2$H$_5$)$_2$ |
| 1-1197 | F | F | H | C(C$_2$H$_5$)=NN(C$_2$H$_5$)$_2$ |
| 1-1198 | F | Cl | H | C(C$_2$H$_5$)=NN(C$_2$H$_5$)$_2$ |
| 1-1199 | Cl | F | H | C(C$_2$H$_5$)=NN(C$_2$H$_5$)$_2$ |
| 1-1200 | Cl | Cl | H | C(C$_2$H$_5$)=NN(C$_2$H$_5$)$_2$ |

TABLE 49

| | X | Y | R$^1$ | B |
|---|---|---|---|---|
| 1-1201 | H | F | H | C(CH$_3$)(OCH$_3$)$_2$ |
| 1-1202 | H | Cl | H | C(CH$_3$)(OCH$_3$)$_2$ |
| 1-1203 | F | F | H | C(CH$_3$)(OCH$_3$)$_2$ |
| 1-1204 | F | Cl | H | C(CH$_3$)(OCH$_3$)$_2$ |
| 1-1205 | Cl | F | H | C(CH$_3$)(OCH$_3$)$_2$ |
| 1-1206 | Cl | Cl | H | C(CH$_3$)(OCH$_3$)$_2$ |
| 1-1207 | H | F | H | C(CH$_3$)(OC$_2$H$_5$)$_2$ |
| 1-1208 | H | Cl | H | C(CH$_3$)(OC$_2$H$_5$)$_2$ |
| 1-1209 | F | F | H | C(CH$_3$)(OC$_2$H$_5$)$_2$ |
| 1-1210 | F | Cl | H | C(CH$_3$)(OC$_2$H$_5$)$_2$ |
| 1-1211 | Cl | F | H | C(CH$_3$)(OC$_2$H$_5$)$_2$ |
| 1-1212 | Cl | Cl | H | C(CH$_3$)(OC$_2$H$_5$)$_2$ |
| 1-1213 | H | F | H | C(CH$_3$)(OiC$_3$H$_7$)$_2$ |
| 1-1214 | H | Cl | H | C(CH$_3$)(OiC$_3$H$_7$)$_2$ |
| 1-1215 | F | F | H | C(CH$_3$)(OiC$_3$H$_7$)$_2$ |
| 1-1216 | F | Cl | H | C(CH$_3$)(OiC$_3$H$_7$)$_2$ |
| 1-1217 | Cl | F | H | C(CH$_3$)(OiC$_3$H$_7$)$_2$ |
| 1-1218 | Cl | Cl | H | C(CH$_3$)(OiC$_3$H$_7$)$_2$ |
| 1-1219 | H | F | H | C(CH$_3$)(OCH$_2$CH$_2$O) |
| 1-1220 | H | Cl | H | C(CH$_3$)(OCH$_2$CH$_2$O) |
| 1-1221 | F | F | H | C(CH$_3$)(OCH$_2$CH$_2$O) |
| 1-1222 | F | Cl | H | C(CH$_3$)(OCH$_2$CH$_2$O) |
| 1-1223 | Cl | F | H | C(CH$_3$)(OCH$_2$CH$_2$O) |
| 1-1224 | Cl | Cl | H | C(CH$_3$)(OCH$_2$CH$_2$O) |
| 1-1225 | H | F | H | C(CH$_3$)(OCH$_2$CH$_2$CH$_2$O) |

TABLE 50

| | X | Y | R$^1$ | B |
|---|---|---|---|---|
| 1-1226 | H | Cl | H | C(CH$_3$)(OCH$_2$CH$_2$CH$_2$O) |
| 1-1227 | F | F | H | C(CH$_3$)(OCH$_2$CH$_2$CH$_2$O) |
| 1-1228 | F | Cl | H | C(CH$_3$)(OCH$_2$CH$_2$CH$_2$O) |
| 1-1229 | Cl | F | H | C(CH$_3$)(OCH$_2$CH$_2$CH$_2$O) |
| 1-1230 | Cl | Cl | H | C(CH$_3$)(OCH$_2$CH$_2$CH$_2$O) |
| 1-1231 | H | F | H | C(C$_2$H$_5$)(OCH$_2$CH$_2$O) |
| 1-1232 | H | Cl | H | C(C$_2$H$_5$)(OCH$_2$CH$_2$O) |
| 1-1233 | F | F | H | C(C$_2$H$_5$)(OCH$_2$CH$_2$O) |
| 1-1234 | F | Cl | H | C(C$_2$H$_5$)(OCH$_2$CH$_2$O) |
| 1-1235 | Cl | F | H | C(C$_2$H$_5$)(OCH$_2$CH$_2$O) |
| 1-1236 | Cl | Cl | H | C(C$_2$H$_5$)(OCH$_2$CH$_2$O) |
| 1-1237 | H | F | H | C(C$_2$H$_5$)(OCH$_2$CH$_2$CH$_2$O) |
| 1-1238 | H | Cl | H | C(C$_2$H$_5$)(OCH$_2$CH$_2$CH$_2$O) |
| 1-1239 | F | F | H | C(C$_2$H$_5$)(OCH$_2$CH$_2$CH$_2$O) |
| 1-1240 | F | Cl | H | C(C$_2$H$_5$)(OCH$_2$CH$_2$CH$_2$O) |
| 1-1241 | Cl | F | H | C(C$_2$H$_5$)(OCH$_2$CH$_2$CH$_2$O) |
| 1-1242 | Cl | Cl | H | C(C$_2$H$_5$)(OCH$_2$CH$_2$CH$_2$O) |
| 1-1243 | H | F | H | OCH$_2$CH(CH$_3$)$_2$ |
| 1-1244 | H | Cl | H | OCH$_2$CH(CH$_3$)$_2$ |
| 1-1245 | F | F | H | OCH$_2$CH(CH$_3$)$_2$ |
| 1-1246 | F | Cl | H | OCH$_2$CH(CH$_3$)$_2$ |
| 1-1247 | Cl | F | H | OCH$_2$CH(CH$_3$)$_2$ |
| 1-1248 | Cl | Cl | H | OCH$_2$CH(CH$_3$)$_2$ |
| 1-1249 | H | F | H | OCH$_2$CH$_2$F |
| 1-1250 | H | Cl | H | OCH$_2$CH$_2$F |

TABLE 51

| | X | Y | R$^1$ | B |
|---|---|---|---|---|
| 1-1251 | F | F | H | OCH$_2$CH$_2$F |
| 1-1252 | F | Cl | H | OCH$_2$CH$_2$F |
| 1-1253 | Cl | F | H | OCH$_2$CH$_2$F |
| 1-1254 | Cl | Cl | H | OCH$_2$CH$_2$F |
| 1-1255 | H | Cl | H | CH$_2$OH |
| 1-1256 | F | Cl | H | CH$_2$OH |
| 1-1257 | H | Cl | H | CH$_2$OCOCH$_3$ |
| 1-1258 | F | Cl | H | CH$_2$OCOCH$_3$ |

Compounds of the general formula:

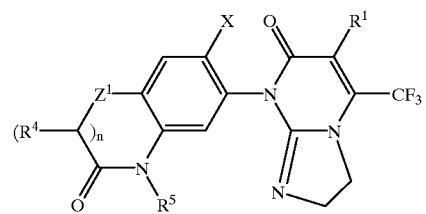

TABLE 52

| | X | Z$^1$ | n | R$^1$ | R$^4$ | R$^5$ |
|---|---|---|---|---|---|---|
| 2-1 | H | O | 1 | H | H | H |
| 2-2 | F | O | 1 | H | H | H |
| 2-3 | H | O | 1 | H | H | CH$_3$ |
| 2-4 | F | O | 1 | H | H | CH$_3$ |
| 2-5 | H | O | 1 | H | H | C$_2$H$_5$ |
| 2-6 | F | O | 1 | H | H | C$_2$H$_5$ |
| 2-7 | H | O | 1 | H | H | nC$_3$H$_7$ |
| 2-8 | F | O | 1 | H | H | nC$_3$H$_7$ |
| 2-9 | H | O | 1 | H | H | nC$_4$H$_9$ |
| 2-10 | F | O | 1 | H | H | nC$_4$H$_9$ |
| 2-11 | H | O | 1 | H | H | nC$_5$H$_{11}$ |
| 2-12 | F | O | 1 | H | H | nC$_5$H$_{11}$ |
| 2-13 | H | O | 1 | H | H | iC$_3$H$_7$ |
| 2-14 | F | O | 1 | H | H | iC$_3$H$_7$ |
| 2-15 | H | O | 1 | H | H | CH$_2$CH$_2$Cl |
| 2-16 | F | O | 1 | H | H | CH$_2$CH$_2$Cl |
| 2-17 | H | O | 1 | H | H | CH$_2$CH$_2$Br |
| 2-18 | F | O | 1 | H | H | CH$_2$CH$_2$Br |
| 2-19 | H | O | 1 | H | H | CH$_2$CH=CH$_2$ |
| 2-20 | F | O | 1 | H | H | CH$_2$CH=CH$_2$ |
| 2-21 | H | O | 1 | H | H | CH(CH$_3$)CH=CH$_2$ |
| 2-22 | F | O | 1 | H | H | CH(CH$_3$)CH=CH$_2$ |
| 2-23 | H | O | 1 | H | H | CH$_2$CCl=CH$_2$ |
| 2-24 | F | O | 1 | H | H | CH$_2$CCl=CH$_2$ |
| 2-25 | H | O | 1 | H | H | CH$_2$C≡CH |

TABLE 53

| | X | Z$^1$ | n | R$^1$ | R$^4$ | R$^5$ |
|---|---|---|---|---|---|---|
| 2-26 | F | O | 1 | H | H | CH$_2$C≡CH |
| 2-27 | H | O | 1 | H | H | CH(CH$_3$)C≡CH |
| 2-28 | F | O | 1 | H | H | CH(CH$_3$)C≡CH |
| 2-29 | H | O | 1 | H | H | CH$_2$CN |
| 2-30 | F | O | 1 | H | H | CH$_2$CN |
| 2-31 | H | O | 1 | H | H | CH$_2$OCH$_3$ |
| 2-32 | F | O | 1 | H | H | CH$_2$OCH$_3$ |
| 2-33 | H | O | 1 | H | H | CH$_2$OC$_2$H$_5$ |
| 2-34 | F | O | 1 | H | H | CH$_2$OC$_2$H$_5$ |
| 2-35 | H | O | 1 | H | H | CH$_2$COOH |
| 2-36 | F | O | 1 | H | H | CH$_2$COOH |
| 2-37 | H | O | 1 | H | H | CH$_2$COOCH$_3$ |
| 2-38 | F | O | 1 | H | H | CH$_2$COOCH$_3$ |
| 2-39 | H | O | 1 | H | H | CH$_2$COOC$_2$H$_5$ |

TABLE 53-continued

| | X | $Z^1$ | n | $R^1$ | $R^4$ | $R^5$ |
|---|---|---|---|---|---|---|
| 2-40 | F | O | 1 | H | H | $CH_2COOC_2H_5$ |
| 2-41 | H | O | 1 | H | H | $CH_2COOnC_3H_7$ |
| 2-42 | F | O | 1 | H | H | $CH_2COOnC_3H_7$ |
| 2-43 | H | O | 1 | H | H | $CH_2COOnC_4H_9$ |
| 2-44 | F | O | 1 | H | H | $CH_2COOnC_4H_9$ |
| 2-45 | H | O | 1 | H | H | $CH_2COOnC_5H_{11}$ |
| 2-46 | F | O | 1 | H | H | $CH_2COOnC_5H_{11}$ |
| 2-47 | H | O | 1 | H | H | $CH_2COOiC_3H_7$ |
| 2-48 | F | O | 1 | H | H | $CH_2COOiC_3H_7$ |
| 2-49 | H | O | 1 | H | H | $CH_2COOcC_5H_9$ |
| 2-50 | F | O | 1 | H | H | $CH_2COOcC_5H_9$ |

TABLE 54

| | X | $Z^1$ | n | $R^1$ | $R^4$ | $R^5$ |
|---|---|---|---|---|---|---|
| 2-51 | H | O | 1 | H | H | $CH_2COOcC_6H_{11}$ |
| 2-52 | F | O | 1 | H | H | $CH_2COOcC_6H_{11}$ |
| 2-53 | H | O | 1 | H | H | $CH(CH_3)COOH$ |
| 2-54 | F | O | 1 | H | H | $CH(CH_3)COOH$ |
| 2-55 | H | O | 1 | H | H | $CH(CH_3)COOCH_3$ |
| 2-56 | F | O | 1 | H | H | $CH(CH_3)COOCH_3$ |
| 2-57 | H | O | 1 | H | H | $CH(CH_3)COOC_2H_5$ |
| 2-58 | F | O | 1 | H | H | $CH(CH_3)COOC_2H_5$ |
| 2-59 | H | O | 1 | H | H | $CH(CH_3)COOnC_3H_7$ |
| 2-60 | F | O | 1 | H | H | $CH(CH_3)COOnC_3H_7$ |
| 2-61 | H | O | 1 | H | H | $CH(CH_3)COOnC_4H_9$ |
| 2-62 | F | O | 1 | H | H | $CH(CH_3)COOnC_4H_9$ |
| 2-63 | H | O | 1 | H | H | $CH(CH_3)COOnC_5H_{11}$ |
| 2-64 | F | O | 1 | H | H | $CH(CH_3)COOnC_5H_{11}$ |
| 2-65 | H | O | 1 | H | H | $CH(CH_3)COOiC_3H_7$ |
| 2-66 | F | O | 1 | H | H | $CH(CH_3)COOiC_3H_7$ |
| 2-67 | H | O | 1 | H | H | $CH(CH_3)COOcC_5H_9$ |
| 2-68 | F | O | 1 | H | H | $CH(CH_3)COOcC_5H_9$ |
| 2-69 | H | O | 1 | H | H | $CH(CH_3)COOcC_6H_{11}$ |
| 2-70 | F | O | 1 | H | H | $CH(CH_3)COOcC_6H_{11}$ |
| 2-71 | H | O | 1 | H | $CH_3$ | H |
| 2-72 | F | O | 1 | H | $CH_3$ | H |
| 2-73 | H | O | 1 | H | $CH_3$ | $CH_3$ |
| 2-74 | F | O | 1 | H | $CH_3$ | $CH_3$ |
| 2-75 | H | O | 1 | H | $CH_3$ | $C_2H_5$ |

TABLE 55

| | X | $Z^1$ | n | $R^1$ | $R^4$ | $R^5$ |
|---|---|---|---|---|---|---|
| 2-76 | F | O | 1 | H | $CH_3$ | $C_2H_5$ |
| 2-77 | H | O | 1 | H | $CH_3$ | $nC_3H_7$ |
| 2-78 | F | O | 1 | H | $CH_3$ | $nC_3H_7$ |
| 2-79 | H | O | 1 | H | $CH_3$ | $nC_4H_9$ |
| 2-80 | F | O | 1 | H | $CH_3$ | $nC_4H_9$ |
| 2-81 | H | O | 1 | H | $CH_3$ | $nC_5H_{11}$ |
| 2-82 | F | O | 1 | H | $CH_3$ | $nC_5H_{11}$ |
| 2-83 | H | O | 1 | H | $CH_3$ | $iC_3H_7$ |
| 2-84 | F | O | 1 | H | $CH_3$ | $iC_3H_7$ |
| 2-85 | H | O | 1 | H | $CH_3$ | $CH_2CH_2Cl$ |
| 2-86 | F | O | 1 | H | $CH_3$ | $CH_2CH_2Cl$ |
| 2-87 | H | O | 1 | H | $CH_3$ | $CH_2CH_2Br$ |
| 2-88 | F | O | 1 | H | $CH_3$ | $CH_2CH_2Br$ |
| 2-89 | H | O | 1 | H | $CH_3$ | $CH_2CH=CH_2$ |
| 2-90 | F | O | 1 | H | $CH_3$ | $CH_2CH=CH_2$ |
| 2-91 | H | O | 1 | H | $CH_3$ | $CH(CH_3)CH=CH_2$ |
| 2-92 | F | O | 1 | H | $CH_3$ | $CH(CH_3)CH=CH_2$ |
| 2-93 | H | O | 1 | H | $CH_3$ | $CH_2CCl=CH_2$ |
| 2-94 | F | O | 1 | H | $CH_3$ | $CH_2CCl=CH_2$ |
| 2-95 | H | O | 1 | H | $CH_3$ | $CH_2C\equiv CH$ |
| 2-96 | F | O | 1 | H | $CH_3$ | $CH_2C\equiv CH$ |
| 2-97 | H | O | 1 | H | $CH_3$ | $CH(CH_3)C\equiv CH$ |
| 2-98 | F | O | 1 | H | $CH_3$ | $CH(CH_3)C\equiv CH$ |
| 2-99 | H | O | 1 | H | $CH_3$ | $CH_2CN$ |
| 2-100 | F | O | 1 | H | $CH_3$ | $CH_2CN$ |

TABLE 56

| | X | $Z^1$ | n | $R^1$ | $R^4$ | $R^5$ |
|---|---|---|---|---|---|---|
| 2-101 | H | O | 1 | H | $CH_3$ | $CH_2OCH_3$ |
| 2-102 | F | O | 1 | H | $CH_3$ | $CH_2OCH_3$ |
| 2-103 | H | O | 1 | H | $CH_3$ | $CH_2OC_2H_5$ |
| 2-104 | F | O | 1 | H | $CH_3$ | $CH_2OC_2H_5$ |
| 2-105 | H | O | 0 | H | — | H |
| 2-106 | F | O | 0 | H | — | H |
| 2-107 | H | O | 0 | H | — | $CH_3$ |
| 2-108 | F | O | 0 | H | — | $CH_3$ |
| 2-109 | H | O | 0 | H | — | $C_2H_5$ |
| 2-110 | F | O | 0 | H | — | $C_2H_5$ |
| 2-111 | H | O | 0 | H | — | $nC_3H_7$ |
| 2-112 | F | O | 0 | H | — | $nC_3H_7$ |
| 2-113 | H | O | 0 | H | — | $nC_4H_9$ |
| 2-114 | F | O | 0 | H | — | $nC_4H_9$ |
| 2-115 | H | O | 0 | H | — | $nC_5H_{11}$ |
| 2-116 | F | O | 0 | H | — | $nC_5H_{11}$ |
| 2-117 | H | O | 0 | H | — | $iC_3H_7$ |
| 2-118 | F | O | 0 | H | — | $iC_3H_7$ |
| 2-119 | H | O | 0 | H | — | $CH_2CH_2Cl$ |
| 2-120 | F | O | 0 | H | — | $CH_2CH_2Cl$ |
| 2-121 | H | O | 0 | H | — | $CH_2CH_2Br$ |
| 2-122 | F | O | 0 | H | — | $CH_2CH_2Br$ |
| 2-123 | H | O | 0 | H | — | $CH_2CH=CH_2$ |
| 2-124 | F | O | 0 | H | — | $CH_2CH=CH_2$ |
| 2-125 | H | O | 0 | H | — | $CH(CH_3)CH=CH_2$ |

TABLE 57

| | X | $Z^1$ | n | $R^1$ | $R^4$ | $R^5$ |
|---|---|---|---|---|---|---|
| 2-126 | F | O | 0 | H | — | $CH(CH_3)CH=CH_2$ |
| 2-127 | H | O | 0 | H | — | $CH_2CCl=CH_2$ |
| 2-128 | F | O | 0 | H | — | $CH_2CCl=CH_2$ |
| 2-129 | H | O | 0 | H | — | $CH_2C\equiv CH$ |
| 2-130 | F | O | 0 | H | — | $CH_2C\equiv CH$ |
| 2-131 | H | O | 0 | H | — | $CH(CH_3)C\equiv CH$ |
| 2-132 | F | O | 0 | H | — | $CH(CH_3)C\equiv CH$ |
| 2-133 | H | O | 0 | H | — | $CH_2CN$ |
| 2-134 | F | O | 0 | H | — | $CH_2CN$ |
| 2-135 | H | O | 0 | H | — | $CH_2OCH_3$ |
| 2-136 | F | O | 0 | H | — | $CH_2OCH_3$ |
| 2-137 | H | O | 0 | H | — | $CH_2OC_2H_5$ |
| 2-138 | F | O | 0 | H | — | $CH_2OC_2H_5$ |
| 2-139 | H | S | 0 | H | — | H |
| 2-140 | F | S | 0 | H | — | H |
| 2-141 | H | S | 0 | H | — | $CH_3$ |
| 2-142 | F | S | 0 | H | — | $CH_3$ |
| 2-143 | H | S | 0 | H | — | $C_2H_5$ |
| 2-144 | F | S | 0 | H | — | $C_2H_5$ |
| 2-145 | H | S | 0 | H | — | $nC_3H_7$ |
| 2-146 | F | S | 0 | H | — | $nC_3H_7$ |
| 2-147 | H | S | 0 | H | — | $nC_4H_9$ |
| 2-148 | F | S | 0 | H | — | $nC_4H_9$ |
| 2-149 | H | S | 0 | H | — | $nC_5H_{11}$ |
| 2-150 | F | S | 0 | H | — | $nC_5H_{11}$ |

TABLE 58

| | X | $Z^1$ | n | $R^1$ | $R^4$ | $R^5$ |
|---|---|---|---|---|---|---|
| 2-151 | H | S | 0 | H | — | $iC_3H_7$ |
| 2-152 | F | S | 0 | H | — | $iC_3H_7$ |
| 2-153 | H | S | 0 | H | — | $CH_2CH_2Cl$ |
| 2-154 | F | S | 0 | H | — | $CH_2CH_2Cl$ |
| 2-155 | H | S | 0 | H | — | $CH_2CH_2Br$ |
| 2-156 | F | S | 0 | H | — | $CH_2CH_2Br$ |
| 2-157 | H | S | 0 | H | — | $CH_2CH=CH_2$ |
| 2-158 | F | S | 0 | H | — | $CH_2CH=CH_2$ |
| 2-159 | H | S | 0 | H | — | $CH(CH_3)CH=CH_2$ |
| 2-160 | F | S | 0 | H | — | $CH(CH_3)CH=CH_2$ |
| 2-161 | H | S | 0 | H | — | $CH_2CCl=CH_2$ |
| 2-162 | F | S | 0 | H | — | $CH_2CCl=CH_2$ |

TABLE 58-continued

| | X | $Z^1$ | n | $R^1$ | $R^4$ | $R^5$ |
|---|---|---|---|---|---|---|
| 2-163 | H | S | 0 | H | — | $CH_2C\equiv CH$ |
| 2-164 | F | S | 0 | H | — | $CH_2C\equiv CH$ |
| 2-165 | H | S | 0 | H | — | $CH(CH_3)C\equiv CH$ |
| 2-166 | F | S | 0 | H | — | $CH(CH_3)C\equiv CH$ |
| 2-167 | H | S | 0 | H | — | $CH_2CN$ |
| 2-168 | F | S | 0 | H | — | $CH_2CN$ |
| 2-169 | H | S | 0 | H | — | $CH_2OCH_3$ |
| 2-170 | F | S | 0 | H | — | $CH_2OCH_3$ |
| 2-171 | H | S | 0 | H | — | $CH_2OC_2H_5$ |
| 2-172 | F | S | 0 | H | — | $CH_2OC_2H_5$ |
| 2-173 | H | S | 0 | H | — | $CH_2COOH$ |
| 2-174 | F | S | 0 | H | — | $CH_2COOH$ |
| 2-175 | H | S | 0 | H | — | $CH_2COOCH_3$ |

TABLE 59

| | X | $Z^1$ | n | $R^1$ | $R^4$ | $R^5$ |
|---|---|---|---|---|---|---|
| 2-176 | F | S | 0 | H | — | $CH_2COOCH_3$ |
| 2-177 | H | S | 0 | H | — | $CH_2COOC_2H_5$ |
| 2-178 | F | S | 0 | H | — | $CH_2COOC_2H_5$ |
| 2-179 | H | S | 0 | H | — | $CH_2COOnC_3H_7$ |
| 2-180 | F | S | 0 | H | — | $CH_2COOnC_3H_7$ |
| 2-181 | H | S | 0 | H | — | $CH_2COOnC_4H_9$ |
| 2-182 | F | S | 0 | H | — | $CH_2COOnC_4H_9$ |
| 2-183 | H | S | 0 | H | — | $CH_2COOnC_5H_{11}$ |
| 2-184 | F | S | 0 | H | — | $CH_2COOnC_5H_{11}$ |
| 2-185 | H | S | 0 | H | — | $CH_2COOiC_3H_7$ |
| 2-186 | F | S | 0 | H | — | $CH_2COOiC_3H_7$ |
| 2-187 | H | S | 0 | H | — | $CH_2COOcC_5H_9$ |
| 2-188 | F | S | 0 | H | — | $CH_2COOcC_5H_9$ |
| 2-189 | H | S | 0 | H | — | $CH_2COOcC_6H_{11}$ |
| 2-190 | F | S | 0 | H | — | $CH_2COOcC_6H_{11}$ |
| 2-191 | H | S | 0 | H | — | $CH(CH_3)COOH$ |
| 2-192 | F | S | 0 | H | — | $CH(CH_3)COOH$ |
| 2-193 | H | S | 0 | H | — | $CH(CH_3)COOCH_3$ |
| 2-194 | F | S | 0 | H | — | $CH(CH_3)COOCH_3$ |
| 2-195 | H | S | 0 | H | — | $CH(CH_3)COOC_2H_5$ |
| 2-196 | F | S | 0 | H | — | $CH(CH_3)COOC_2H_5$ |
| 2-197 | H | S | 0 | H | — | $CH(CH_3)COOnC_3H_7$ |
| 2-198 | F | S | 0 | H | — | $CH(CH_3)COOnC_3H_7$ |
| 2-199 | H | S | 0 | H | — | $CH(CH_3)COOnC_4H_9$ |
| 2-200 | F | S | 0 | H | — | $CH(CH_3)COOnC_4H_9$ |

TABLE 60

| | X | $Z^1$ | n | $R^1$ | $R^4$ | $R^5$ |
|---|---|---|---|---|---|---|
| 2-201 | H | S | 0 | H | — | $CH(CH_3)COOnC_5H_{11}$ |
| 2-202 | F | S | 0 | H | — | $CH(CH_3)COOnC_5H_{11}$ |
| 2-203 | H | S | 0 | H | — | $CH(CH_3)COOiC_3H_7$ |
| 2-204 | F | S | 0 | H | — | $CH(CH_3)COOiC_3H_7$ |
| 2-205 | H | S | 0 | H | — | $CH(CH_3)COOcC_5H_9$ |
| 2-206 | F | S | 0 | H | — | $CH(CH_3)COOcC_5H_9$ |
| 2-207 | H | S | 0 | H | — | $CH(CH_3)COOcC_6H_{11}$ |
| 2-208 | F | S | 0 | H | — | $CH(CH_3)COOcC_6H_{11}$ |

Compounds of the general formula:

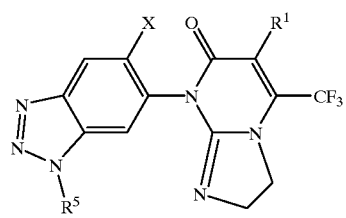

TABLE 61

| | X | $R^1$ | $R^5$ |
|---|---|---|---|
| 5-1 | H | H | $CH_3$ |
| 5-2 | F | H | $CH_3$ |
| 5-3 | Cl | H | $CH_3$ |
| 5-4 | H | H | $C_2H_5$ |
| 5-5 | F | H | $C_2H_5$ |
| 5-6 | Cl | H | $C_2H_5$ |
| 5-7 | H | H | $nC_3H_7$ |
| 5-8 | F | H | $nC_3H_7$ |
| 5-9 | Cl | H | $nC_3H_7$ |
| 5-10 | H | H | $nC_4H_9$ |
| 5-11 | F | H | $nC_4H_9$ |
| 5-12 | Cl | H | $nC_4H_9$ |
| 5-13 | H | H | $iC_4H_9$ |
| 5-14 | F | H | $iC_4H_9$ |
| 5-15 | Cl | H | $iC_4H_9$ |
| 5-16 | H | H | $CH_2CH=CH_2$ |
| 5-17 | F | H | $CH_2CH=CH_2$ |
| 5-18 | Cl | H | $CH_2CH=CH_2$ |
| 5-19 | H | H | $CH(CH_3)CH=CH_2$ |
| 5-20 | F | H | $CH(CH_3)CH=CH_2$ |
| 5-21 | Cl | H | $CH(CH_3)CH=CH_2$ |
| 5-22 | H | H | $CH_2C\equiv CH$ |
| 5-23 | F | H | $CH_2C\equiv CH$ |
| 5-24 | Cl | H | $CH_2C\equiv CH$ |
| 5-25 | H | H | $CH(CH_3)C\equiv CH$ |

TABLE 62

| | X | $R^1$ | $R^5$ |
|---|---|---|---|
| 5-26 | F | H | $CH(CH_3)C\equiv CH$ |
| 5-27 | Cl | H | $CH(CH_3)C\equiv CH$ |

Compounds of the general formula:

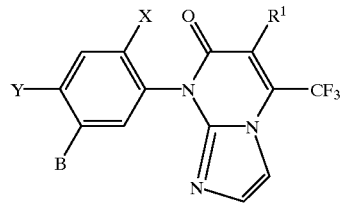

TABLE 63

| | X | Y | $R^1$ | B |
|---|---|---|---|---|
| 6-1 | H | F | H | H |
| 6-2 | H | Cl | H | H |
| 6-3 | H | Br | H | H |
| 6-4 | F | F | H | H |
| 6-5 | F | Cl | H | H |
| 6-6 | F | Br | H | H |
| 6-7 | Cl | F | H | H |
| 6-8 | Cl | Cl | H | H |
| 6-9 | Cl | Br | H | H |
| 6-10 | H | F | H | $NO_2$ |
| 6-11 | H | Cl | H | $NO_2$ |
| 6-12 | H | Br | H | $NO_2$ |
| 6-13 | F | F | H | $NO_2$ |
| 6-14 | F | Cl | H | $NO_2$ |
| 6-15 | F | Br | H | $NO_2$ |
| 6-16 | Cl | F | H | $NO_2$ |
| 6-17 | Cl | Cl | H | $NO_2$ |
| 6-18 | Cl | Br | H | $NO_2$ |
| 6-19 | H | F | H | $NH_2$ |
| 6-20 | H | Cl | H | $NH_2$ |

TABLE 63-continued

|  | X | Y | R$^1$ | B |
|---|---|---|---|---|
| 6-21 | H | Br | H | NH$_2$ |
| 6-22 | F | F | H | NH$_2$ |
| 6-23 | F | Cl | H | NH$_2$ |
| 6-24 | F | Br | H | NH$_2$ |
| 6-25 | Cl | F | H | NH$_2$ |

TABLE 64

|  | X | Y | R$^1$ | B |
|---|---|---|---|---|
| 6-26 | Cl | Cl | H | NH$_2$ |
| 6-27 | Cl | Br | H | NH$_2$ |
| 6-28 | H | F | H | OH |
| 6-29 | H | Cl | H | OH |
| 6-30 | H | Br | H | OH |
| 6-31 | F | F | H | OH |
| 6-32 | F | Cl | H | OH |
| 6-33 | F | Br | H | OH |
| 6-34 | Cl | F | H | OH |
| 6-35 | Cl | Cl | H | OH |
| 6-36 | Cl | Br | H | OH |
| 6-37 | H | F | H | SH |
| 6-38 | H | Cl | H | SH |
| 6-39 | H | Br | H | SH |
| 6-40 | F | F | H | SH |
| 6-41 | F | Cl | H | SH |
| 6-42 | F | Br | H | SH |
| 6-43 | Cl | F | H | SH |
| 6-44 | Cl | Cl | H | SH |
| 6-45 | Cl | Br | H | SH |
| 6-46 | H | F | H | SO$_2$Cl |
| 6-47 | H | Cl | H | SO$_2$Cl |
| 6-48 | H | Br | H | SO$_2$Cl |
| 6-49 | F | F | H | SO$_2$Cl |
| 6-50 | F | Cl | H | SO$_2$Cl |

TABLE 65

|  | X | Y | R$^1$ | B |
|---|---|---|---|---|
| 6-51 | F | Br | H | SO$_2$Cl |
| 6-52 | Cl | F | H | SO$_2$Cl |
| 6-53 | Cl | Cl | H | SO$_2$Cl |
| 6-54 | Cl | Br | H | SO$_2$Cl |
| 6-55 | H | F | H | NHCH$_3$ |
| 6-56 | H | Cl | H | NHCH$_3$ |
| 6-57 | F | F | H | NHCH$_3$ |
| 6-58 | F | Cl | H | NHCH$_3$ |
| 6-59 | Cl | F | H | NHCH$_3$ |
| 6-60 | Cl | Cl | H | NHCH$_3$ |
| 6-61 | H | F | H | NHC$_2$H$_5$ |
| 6-62 | H | Cl | H | NHC$_2$H$_5$ |
| 6-63 | F | F | H | NHC$_2$H$_5$ |
| 6-64 | F | Cl | H | NHC$_2$H$_5$ |
| 6-65 | Cl | F | H | NHC$_2$H$_5$ |
| 6-66 | Cl | Cl | H | NHC$_2$H$_5$ |
| 6-67 | H | F | H | NHCH$_2$CH=CH$_2$ |
| 6-68 | H | Cl | H | NHCH$_2$CH=CH$_2$ |
| 6-69 | F | F | H | NHCH$_2$CH=CH$_2$ |
| 6-70 | F | Cl | H | NHCH$_2$CH=CH$_2$ |
| 6-71 | Cl | F | H | NHCH$_2$CH=CH$_2$ |
| 6-72 | Cl | Cl | H | NHCH$_2$CH=CH$_2$ |
| 6-73 | H | F | H | NHCH$_2$C≡CH |
| 6-74 | H | Cl | H | NHCH$_2$C≡CH |
| 6-75 | F | F | H | NHCH$_2$C≡CH |

TABLE 66

|  | X | Y | R$^1$ | B |
|---|---|---|---|---|
| 6-76 | F | Cl | H | NHCH$_2$C≡CH |
| 6-77 | Cl | F | H | NHCH$_2$C≡CH |
| 6-78 | Cl | Cl | H | NHCH$_2$C≡CH |
| 6-79 | H | F | H | NHCH(CH$_3$)C≡CH |
| 6-80 | H | Cl | H | NHCH(CH$_3$)C≡CH |
| 6-81 | F | F | H | NHCH(CH$_3$)C≡CH |
| 6-82 | F | Cl | H | NHCH(CH$_3$)C≡CH |
| 6-83 | Cl | F | H | NHCH(CH$_3$)C≡CH |
| 6-84 | Cl | Cl | H | NHCH(CH$_3$)C≡CH |
| 6-85 | H | F | H | NHSO$_2$CH$_3$ |
| 6-86 | H | Cl | H | NHSO$_2$CH$_3$ |
| 6-87 | F | F | H | NHSO$_2$CH$_3$ |
| 6-88 | F | Cl | H | NHSO$_2$CH$_3$ |
| 6-89 | Cl | F | H | NHSO$_2$CH$_3$ |
| 6-90 | Cl | Cl | H | NHSO$_2$CH$_3$ |
| 6-91 | H | F | H | NHSO$_2$C$_2$H$_5$ |
| 6-92 | H | Cl | H | NHSO$_2$C$_2$H$_5$ |
| 6-93 | F | F | H | NHSO$_2$C$_2$H$_5$ |
| 6-94 | F | Cl | H | NHSO$_2$C$_2$H$_5$ |
| 6-95 | Cl | F | H | NHSO$_2$C$_2$H$_5$ |
| 6-96 | Cl | Cl | H | NHSO$_2$C$_2$H$_5$ |
| 6-97 | H | F | H | NHSO$_2$CH$_2$Cl |
| 6-98 | H | Cl | H | NHSO$_2$CH$_2$Cl |
| 6-99 | F | F | H | NHSO$_2$CH$_2$Cl |
| 6-100 | F | Cl | H | NHSO$_2$CH$_2$Cl |

TABLE 67

|  | X | Y | R$^1$ | B |
|---|---|---|---|---|
| 6-101 | Cl | F | H | NHSO$_2$CH$_2$Cl |
| 6-102 | Cl | Cl | H | NHSO$_2$CH$_2$Cl |
| 6-103 | H | F | H | NHSO$_2$CF$_3$ |
| 6-104 | H | Cl | H | NHSO$_2$CF$_3$ |
| 6-105 | F | F | H | NHSO$_2$CF$_3$ |
| 6-106 | F | Cl | H | NHSO$_2$CF$_3$ |
| 6-107 | Cl | F | H | NHSO$_2$CF$_3$ |
| 6-108 | Cl | Cl | H | NHSO$_2$CF$_3$ |
| 6-109 | H | F | H | N(SO$_2$CH$_3$)$_2$ |
| 6-110 | H | Cl | H | N(SO$_2$CH$_3$)$_2$ |
| 6-111 | F | F | H | N(SO$_2$CH$_3$)$_2$ |
| 6-112 | F | Cl | H | N(SO$_2$CH$_3$)$_2$ |
| 6-113 | Cl | F | H | N(SO$_2$CH$_3$)$_2$ |
| 6-114 | Cl | Cl | H | N(SO$_2$CH$_3$)$_2$ |
| 6-115 | H | F | H | N(CH$_3$)SO$_2$CH$_3$ |
| 6-116 | H | Cl | H | N(CH$_3$)SO$_2$CH$_3$ |
| 6-117 | F | F | H | N(CH$_3$)SO$_2$CH$_3$ |
| 6-118 | F | Cl | H | N(CH$_3$)SO$_2$CH$_3$ |
| 6-119 | Cl | F | H | N(CH$_3$)SO$_2$CH$_3$ |
| 6-120 | Cl | Cl | H | N(CH$_3$)SO$_2$CH$_3$ |
| 6-121 | H | F | H | N(CH$_2$C≡CH)SO$_2$CH$_3$ |
| 6-122 | H | Cl | H | N(CH$_2$C≡CH)SO$_2$CH$_3$ |
| 6-123 | F | F | H | N(CH$_2$C≡CH)SO$_2$CH$_3$ |
| 6-124 | F | Cl | H | N(CH$_2$C≡CH)SO$_2$CH$_3$ |
| 6-125 | Cl | F | H | N(CH$_2$C≡CH)SO$_2$CH$_3$ |

TABLE 68

|  | X | Y | R$^1$ | B |
|---|---|---|---|---|
| 6-126 | Cl | Cl | H | N(CH$_2$C≡CH)SO$_2$CH$_3$ |
| 6-127 | H | F | H | NHCOOCH$_3$ |
| 6-128 | H | Cl | H | NHCOOCH$_3$ |
| 6-129 | F | F | H | NHCOOCH$_3$ |
| 6-130 | F | Cl | H | NHCOOCH$_3$ |
| 6-131 | Cl | F | H | NHCOOCH$_3$ |
| 6-132 | Cl | Cl | H | NHCOOCH$_3$ |
| 6-133 | H | F | H | NHCOOC$_2$H$_5$ |
| 6-134 | H | Cl | H | NHCOOC$_2$H$_5$ |
| 6-135 | F | F | H | NHCOOC$_2$H$_5$ |
| 6-136 | F | Cl | H | NHCOOC$_2$H$_5$ |
| 6-137 | Cl | F | H | NHCOOC$_2$H$_5$ |

TABLE 68-continued

|  | X | Y | R¹ | B |
|---|---|---|---|---|
| 6-138 | Cl | Cl | H | NHCOOC$_2$H$_5$ |
| 6-139 | H | F | H | NHCOOnC$_3$H$_7$ |
| 6-140 | H | Cl | H | NHCOOnC$_3$H$_7$ |
| 6-141 | F | F | H | NHCOOnC$_3$H$_7$ |
| 6-142 | F | Cl | H | NHCOOnC$_3$H$_7$ |
| 6-143 | Cl | F | H | NHCOOnC$_3$H$_7$ |
| 6-144 | Cl | Cl | H | NHCOOnC$_3$H$_7$ |
| 6-145 | H | F | H | NHCOOiC$_3$H$_7$ |
| 6-146 | H | Cl | H | NHCOOiC$_3$H$_7$ |
| 6-147 | F | F | H | NHCOOiC$_3$H$_7$ |
| 6-148 | F | Cl | H | NHCOOiC$_3$H$_7$ |
| 6-149 | Cl | F | H | NHCOOiC$_3$H$_7$ |
| 6-150 | Cl | Cl | H | NHCOOiC$_3$H$_7$ |

TABLE 69

|  | X | Y | R¹ | B |
|---|---|---|---|---|
| 6-151 | H | F | H | NHCOOnC$_4$H$_9$ |
| 6-152 | H | Cl | H | NHCOOnC$_4$H$_9$ |
| 6-153 | F | F | H | NHCOOnC$_4$H$_9$ |
| 6-154 | F | Cl | H | NHCOOnC$_4$H$_9$ |
| 6-155 | Cl | F | H | NHCOOnC$_4$H$_9$ |
| 6-156 | Cl | Cl | H | NHCOOnC$_4$H$_9$ |
| 6-157 | H | F | H | NHCOOnC$_5$H$_{11}$ |
| 6-158 | H | Cl | H | NHCOOnC$_5$H$_{11}$ |
| 6-159 | F | F | H | NHCOOnC$_5$H$_{11}$ |
| 6-160 | F | Cl | H | NHCOOnC$_5$H$_{11}$ |
| 6-161 | Cl | F | H | NHCOOnC$_5$H$_{11}$ |
| 6-162 | Cl | Cl | H | NHCOOnC$_5$H$_{11}$ |
| 6-163 | H | F | H | NHCH$_2$COOCH$_3$ |
| 6-164 | H | Cl | H | NHCH$_2$COOCH$_3$ |
| 6-165 | F | F | H | NHCH$_2$COOCH$_3$ |
| 6-166 | F | Cl | H | NHCH$_2$COOCH$_3$ |
| 6-167 | Cl | F | H | NHCH$_2$COOCH$_3$ |
| 6-168 | Cl | Cl | H | NHCH$_2$COOCH$_3$ |
| 6-169 | H | F | H | NHCH$_2$COOC$_2$H$_5$ |
| 6-170 | H | Cl | H | NHCH$_2$COOC$_2$H$_5$ |
| 6-171 | F | F | H | NHCH$_2$COOC$_2$H$_5$ |
| 6-172 | F | Cl | H | NHCH$_2$COOC$_2$H$_5$ |
| 6-173 | Cl | F | H | NHCH$_2$COOC$_2$H$_5$ |
| 6-174 | Cl | Cl | H | NHCH$_2$COOC$_2$H$_5$ |
| 6-175 | H | F | H | NHCH$_2$COOnC$_3$H$_7$ |

TABLE 70

|  | X | Y | R¹ | B |
|---|---|---|---|---|
| 6-176 | H | Cl | H | NHCH$_2$COOnC$_3$H$_7$ |
| 6-177 | F | F | H | NHCH$_2$COOnC$_3$H$_7$ |
| 6-178 | F | Cl | H | NHCH$_2$COOnC$_3$H$_7$ |
| 6-179 | Cl | F | H | NHCH$_2$COOnC$_3$H$_7$ |
| 6-180 | Cl | Cl | H | NHCH$_2$COOnC$_3$H$_7$ |
| 6-181 | H | F | H | NHCH$_2$COOnC$_4$H$_9$ |
| 6-182 | H | Cl | H | NHCH$_2$COOnC$_4$H$_9$ |
| 6-183 | F | F | H | NHCH$_2$COOnC$_4$H$_9$ |
| 6-184 | F | Cl | H | NHCH$_2$COOnC$_4$H$_9$ |
| 6-185 | Cl | F | H | NHCH$_2$COOnC$_4$H$_9$ |
| 6-186 | Cl | Cl | H | NHCH$_2$COOnC$_4$H$_9$ |
| 6-187 | H | F | H | NHCH$_2$COOnC$_5$H$_{11}$ |
| 6-188 | H | Cl | H | NHCH$_2$COOnC$_5$H$_{11}$ |
| 6-189 | F | F | H | NHCH$_2$COOnC$_5$H$_{11}$ |
| 6-190 | F | Cl | H | NHCH$_2$COOnC$_5$H$_{11}$ |
| 6-191 | Cl | F | H | NHCH$_2$COOnC$_5$H$_{11}$ |
| 6-192 | Cl | Cl | H | NHCH$_2$COOnC$_5$H$_{11}$ |
| 6-193 | H | F | H | NHCH$_2$COOiC$_3$H$_7$ |
| 6-194 | H | Cl | H | NHCH$_2$COOiC$_3$H$_7$ |
| 6-195 | F | F | H | NHCH$_2$COOiC$_3$H$_7$ |
| 6-196 | F | Cl | H | NHCH$_2$COOiC$_3$H$_7$ |
| 6-197 | Cl | F | H | NHCH$_2$COOiC$_3$H$_7$ |
| 6-198 | Cl | Cl | H | NHCH$_2$COOiC$_3$H$_7$ |
| 6-199 | H | F | H | NHCH$_2$COOcC$_5$H$_9$ |
| 6-200 | H | Cl | H | NHCH$_2$COOcC$_5$H$_9$ |

TABLE 71

|  | X | Y | R¹ | B |
|---|---|---|---|---|
| 6-201 | F | F | H | NHCH$_2$COOcC$_5$H$_9$ |
| 6-202 | F | Cl | H | NHCH$_2$COOcC$_5$H$_9$ |
| 6-203 | Cl | F | H | NHCH$_2$COOcC$_5$H$_9$ |
| 6-204 | Cl | Cl | H | NHCH$_2$COOcC$_5$H$_9$ |
| 6-205 | H | F | H | NHCH$_2$COOcC$_6$H$_{11}$ |
| 6-206 | H | Cl | H | NHCH$_2$COOcC$_6$H$_{11}$ |
| 6-207 | F | F | H | NHCH$_2$COOcC$_6$H$_{11}$ |
| 6-208 | F | Cl | H | NHCH$_2$COOcC$_6$H$_{11}$ |
| 6-209 | Cl | F | H | NHCH$_2$COOcC$_6$H$_{11}$ |
| 6-210 | Cl | Cl | H | NHCH$_2$COOcC$_6$H$_{11}$ |
| 6-211 | H | F | H | NHCH(CH$_3$)COOCH$_3$ |
| 6-212 | H | Cl | H | NHCH(CH$_3$)COOCH$_3$ |
| 6-213 | F | F | H | NHCH(CH$_3$)COOCH$_3$ |
| 6-214 | F | Cl | H | NHCH(CH$_3$)COOCH$_3$ |
| 6-215 | Cl | F | H | NHCH(CH$_3$)COOCH$_3$ |
| 6-216 | Cl | Cl | H | NHCH(CH$_3$)COOCH$_3$ |
| 6-217 | H | F | H | NHCH(CH$_3$)COOC$_2$H$_5$ |
| 6-218 | H | Cl | H | NHCH(CH$_3$)COOC$_2$H$_5$ |
| 6-219 | F | F | H | NHCH(CH$_3$)COOC$_2$H$_5$ |
| 6-220 | F | Cl | H | NHCH(CH$_3$)COOC$_2$H$_5$ |
| 6-221 | Cl | F | H | NHCH(CH$_3$)COOC$_2$H$_5$ |
| 6-222 | Cl | Cl | H | NHCH(CH$_3$)COOC$_2$H$_5$ |
| 6-223 | H | F | H | NHCH(CH$_3$)COOnC$_3$H$_7$ |
| 6-224 | H | Cl | H | NHCH(CH$_3$)COOnC$_3$H$_7$ |
| 6-225 | F | F | H | NHCH(CH$_3$)COOnC$_3$H$_7$ |

TABLE 72

|  | X | Y | R¹ | B |
|---|---|---|---|---|
| 6-226 | F | Cl | H | NHCH(CH$_3$)COOnC$_3$H$_7$ |
| 6-227 | Cl | F | H | NHCH(CH$_3$)COOnC$_3$H$_7$ |
| 6-228 | Cl | Cl | H | NHCH(CH$_3$)COOnC$_3$H$_7$ |
| 6-229 | H | F | H | NHCH(CH$_3$)COOnC$_4$H$_9$ |
| 6-230 | H | Cl | H | NHCH(CH$_3$)COOnC$_4$H$_9$ |
| 6-231 | F | F | H | NHCH(CH$_3$)COOnC$_4$H$_9$ |
| 6-232 | F | Cl | H | NHCH(CH$_3$)COOnC$_4$H$_9$ |
| 6-233 | Cl | F | H | NHCH(CH$_3$)COOnC$_4$H$_9$ |
| 6-234 | Cl | Cl | H | NHCH(CH$_3$)COOnC$_4$H$_9$ |
| 6-235 | H | F | H | NHCH(CH$_3$)COOnC$_5$H$_{11}$ |
| 6-236 | H | Cl | H | NHCH(CH$_3$)COOnC$_5$H$_{11}$ |
| 6-237 | F | F | H | NHCH(CH$_3$)COOnC$_5$H$_{11}$ |
| 6-238 | F | Cl | H | NHCH(CH$_3$)COOnC$_5$H$_{11}$ |
| 6-239 | Cl | F | H | NHCH(CH$_3$)COOnC$_5$H$_{11}$ |
| 6-240 | Cl | Cl | H | NHCH(CH$_3$)COOnC$_5$H$_{11}$ |
| 6-241 | H | F | H | NHCH(CH$_3$)COOiC$_3$H$_7$ |
| 6-242 | H | Cl | H | NHCH(CH$_3$)COOiC$_3$H$_7$ |
| 6-243 | F | F | H | NHCH(CH$_3$)COOiC$_3$H$_7$ |
| 6-244 | F | Cl | H | NHCH(CH$_3$)COOiC$_3$H$_7$ |
| 6-245 | Cl | F | H | NHCH(CH$_3$)COOiC$_3$H$_7$ |
| 6-246 | Cl | Cl | H | NHCH(CH$_3$)COOiC$_3$H$_7$ |
| 6-247 | H | F | H | NHCH(CH$_3$)COOcC$_5$H$_9$ |
| 6-248 | H | Cl | H | NHCH(CH$_3$)COOcC$_5$H$_9$ |
| 6-249 | F | F | H | NHCH(CH$_3$)COOcC$_5$H$_9$ |
| 6-250 | F | Cl | H | NHCH(CH$_3$)COOcC$_5$H$_9$ |

TABLE 73

|  | X | Y | R¹ | B |
|---|---|---|---|---|
| 6-251 | Cl | F | H | NHCH(CH$_3$)COOcC$_5$H$_9$ |
| 6-252 | Cl | Cl | H | NHCH(CH$_3$)COOcC$_5$H$_9$ |
| 6-253 | H | F | H | NHCH(CH$_3$)COOcC$_6$H$_{11}$ |
| 6-254 | H | Cl | H | NHCH(CH$_3$)COOcC$_6$H$_{11}$ |

TABLE 73-continued

|   | X | Y | R¹ | B |
|---|---|---|---|---|
| 6-255 | F | F | H | NHCH(CH$_3$)COOcC$_6$H$_{11}$ |
| 6-256 | F | Cl | H | NHCH(CH$_3$)COOcC$_6$H$_{11}$ |
| 6-257 | Cl | F | H | NHCH(CH$_3$)COOcC$_6$H$_{11}$ |
| 6-258 | Cl | Cl | H | NHCH(CH$_3$)COOcC$_6$H$_{11}$ |
| 6-259 | H | F | H | OCH$_3$ |
| 6-260 | H | Cl | H | OCH$_3$ |
| 6-261 | F | F | H | OCH$_3$ |
| 6-262 | F | Cl | H | OCH$_3$ |
| 6-263 | Cl | F | H | OCH$_3$ |
| 6-264 | Cl | Cl | H | OCH$_3$ |
| 6-265 | H | F | H | OC$_2$H$_5$ |
| 6-266 | H | Cl | H | OC$_2$H$_5$ |
| 6-267 | F | F | H | OC$_2$H$_5$ |
| 6-268 | F | Cl | H | OC$_2$H$_5$ |
| 6-269 | Cl | F | H | OC$_2$H$_5$ |
| 6-270 | Cl | Cl | H | OC$_2$H$_5$ |
| 6-271 | H | F | H | OiC$_3$H$_7$ |
| 6-272 | H | Cl | H | OiC$_3$H$_7$ |
| 6-273 | F | F | H | OiC$_3$H$_7$ |
| 6-274 | F | Cl | H | OiC$_3$H$_7$ |
| 6-275 | Cl | F | H | OiC$_3$H$_7$ |

TABLE 74

|   | X | Y | R¹ | B |
|---|---|---|---|---|
| 6-276 | Cl | Cl | H | OiC$_3$H$_7$ |
| 6-277 | H | F | H | OnC$_3$H$_7$ |
| 6-278 | H | Cl | H | OnC$_3$H$_7$ |
| 6-279 | F | F | H | OnC$_3$H$_7$ |
| 6-280 | F | Cl | H | OnC$_3$H$_7$ |
| 6-281 | Cl | F | H | OnC$_3$H$_7$ |
| 6-282 | Cl | Cl | H | OnC$_3$H$_7$ |
| 6-283 | H | F | H | OCH$_2$CH$_2$Cl |
| 6-284 | H | Cl | H | OCH$_2$CH$_2$Cl |
| 6-285 | F | F | H | OCH$_2$CH$_2$Cl |
| 6-286 | F | Cl | H | OCH$_2$CH$_2$Cl |
| 6-287 | Cl | F | H | OCH$_2$CH$_2$Cl |
| 6-288 | Cl | Cl | H | OCH$_2$CH$_2$Cl |
| 6-289 | H | F | H | OCF$_2$CF$_2$H |
| 6-290 | H | Cl | H | OCF$_2$CF$_2$H |
| 6-291 | F | F | H | OCF$_2$CF$_2$H |
| 6-292 | F | Cl | H | OCF$_2$CF$_2$H |
| 6-293 | Cl | F | H | OCF$_2$CF$_2$H |
| 6-294 | Cl | Cl | H | OCF$_2$CF$_2$H |
| 6-295 | H | F | H | OcC$_5$H$_9$ |
| 6-296 | H | Cl | H | OcC$_5$H$_9$ |
| 6-297 | F | F | H | OcC$_5$H$_9$ |
| 6-298 | F | Cl | H | OcC$_5$H$_9$ |
| 6-299 | Cl | F | H | OcC$_5$H$_9$ |
| 6-300 | Cl | Cl | H | OcC$_5$H$_9$ |

TABLE 75

|   | X | Y | R¹ | B |
|---|---|---|---|---|
| 6-301 | H | F | H | OcC$_6$H$_{11}$ |
| 6-302 | H | Cl | H | OcC$_6$H$_{11}$ |
| 6-303 | F | F | H | OcC$_6$H$_{11}$ |
| 6-304 | F | Cl | H | OcC$_6$H$_{11}$ |
| 6-305 | Cl | F | H | OcC$_6$H$_{11}$ |
| 6-306 | Cl | Cl | H | OcC$_6$H$_{11}$ |
| 6-307 | H | F | H | OCH$_2$CH=CH$_2$ |
| 6-308 | H | Cl | H | OCH$_2$CH=CH$_2$ |
| 6-309 | F | F | H | OCH$_2$CH=CH$_2$ |
| 6-310 | F | Cl | H | OCH$_2$CH=CH$_2$ |
| 6-311 | Cl | F | H | OCH$_2$CH=CH$_2$ |
| 6-312 | Cl | Cl | H | OCH$_2$CH=CH$_2$ |
| 6-313 | H | F | H | OCH$_2$CCl=CH$_2$ |
| 6-314 | H | Cl | H | OCH$_2$CCl=CH$_2$ |
| 6-315 | F | F | H | OCH$_2$CCl=CH$_2$ |
| 6-316 | F | Cl | H | OCH$_2$CCl=CH$_2$ |

TABLE 75-continued

|   | X | Y | R¹ | B |
|---|---|---|---|---|
| 6-317 | Cl | F | H | OCH$_2$CCl=CH$_2$ |
| 6-318 | Cl | Cl | H | OCH$_2$CCl=CH$_2$ |
| 6-319 | H | F | H | OCH$_2$CCl=CHCl |
| 6-320 | H | Cl | H | OCH$_2$CCl=CHCl |
| 6-321 | F | F | H | OCH$_2$CCl=CHCl |
| 6-322 | F | Cl | H | OCH$_2$CCl=CHCl |
| 6-323 | Cl | F | H | OCH$_2$CCl=CHCl |
| 6-324 | Cl | Cl | H | OCH$_2$CCl=CHCl |
| 6-325 | H | F | H | OCH(CH$_3$)CH=CH$_2$ |

TABLE 76

|   | X | Y | R¹ | B |
|---|---|---|---|---|
| 6-326 | H | Cl | H | OCH(CH$_3$)CH=CH$_2$ |
| 6-327 | F | F | H | OCH(CH$_3$)CH=CH$_2$ |
| 6-328 | F | Cl | H | OCH(CH$_3$)CH=CH$_2$ |
| 6-329 | Cl | F | H | OCH(CH$_3$)CH=CH$_2$ |
| 6-330 | Cl | Cl | H | OCH(CH$_3$)CH=CH$_2$ |
| 6-331 | H | F | H | OCH$_2$C(CH$_3$)=CH$_2$ |
| 6-332 | H | Cl | H | OCH$_2$C(CH$_3$)=CH$_2$ |
| 6-333 | F | F | H | OCH$_2$C(CH$_3$)=CH$_2$ |
| 6-334 | F | Cl | H | OCH$_2$C(CH$_3$)=CH$_2$ |
| 6-335 | Cl | F | H | OCH$_2$C(CH$_3$)=CH$_2$ |
| 6-336 | Cl | Cl | H | OCH$_2$C(CH$_3$)=CH$_2$ |
| 6-337 | H | F | H | OCH$_2$C≡CH |
| 6-338 | H | Cl | H | OCH$_2$C≡CH |
| 6-339 | F | F | H | OCH$_2$C≡CH |
| 6-340 | F | Cl | H | OCH$_2$C≡CH |
| 6-341 | Cl | F | H | OCH$_2$C≡CH |
| 6-342 | Cl | Cl | H | OCH$_2$C≡CH |
| 6-343 | H | F | H | OCH(CH$_3$)C≡CH |
| 6-344 | H | Cl | H | OCH(CH$_3$)C≡CH |
| 6-345 | F | F | H | OCH(CH$_3$)C≡CH |
| 6-346 | F | Cl | H | OCH(CH$_3$)C≡CH |
| 6-347 | Cl | F | H | OCH(CH$_3$)C≡CH |
| 6-348 | Cl | Cl | H | OCH(CH$_3$)C≡CH |
| 6-349 | H | F | H | OCH$_2$C≡CBr |
| 6-350 | H | Cl | H | OCH$_2$C≡CBr |

TABLE 77

|   | X | Y | R¹ | B |
|---|---|---|---|---|
| 6-351 | F | F | H | OCH$_2$C≡CBr |
| 6-352 | F | Cl | H | OCH$_2$C≡CBr |
| 6-353 | Cl | F | H | OCH$_2$C≡CBr |
| 6-354 | Cl | Cl | H | OCH$_2$C≡CBr |
| 6-355 | H | F | H | OCH$_2$C≡CCl |
| 6-356 | H | Cl | H | OCH$_2$C≡CCl |
| 6-357 | F | F | H | OCH$_2$C≡CCl |
| 6-358 | F | Cl | H | OCH$_2$C≡CCl |
| 6-359 | Cl | F | H | OCH$_2$C≡CCl |
| 6-360 | Cl | Cl | H | OCH$_2$C≡CCl |
| 6-361 | H | F | H | OCH$_2$C≡CCH$_2$Cl |
| 6-362 | H | Cl | H | OCH$_2$C≡CCH$_2$Cl |
| 6-363 | F | F | H | OCH$_2$C≡CCH$_2$Cl |
| 6-364 | F | Cl | H | OCH$_2$C≡CCH$_2$Cl |
| 6-365 | Cl | F | H | OCH$_2$C≡CCH$_2$Cl |
| 6-366 | Cl | Cl | H | OCH$_2$C≡CCH$_2$Cl |
| 6-367 | H | F | H | OCH$_2$CN |
| 6-368 | H | Cl | H | OCH$_2$CN |
| 6-369 | F | F | H | OCH$_2$CN |
| 6-370 | F | Cl | H | OCH$_2$CN |
| 6-371 | Cl | F | H | OCH$_2$CN |
| 6-372 | Cl | Cl | H | OCH$_2$CN |
| 6-373 | H | F | H | OCH$_2$OCH$_3$ |
| 6-374 | H | Cl | H | OCH$_2$OCH$_3$ |
| 6-375 | F | F | H | OCH$_2$OCH$_3$ |

TABLE 78

|  | X | Y | R¹ | B |
|---|---|---|---|---|
| 6-376 | F | Cl | H | OCH₂OCH₃ |
| 6-377 | Cl | F | H | OCH₂OCH₃ |
| 6-378 | Cl | Cl | H | OCH₂OCH₃ |
| 6-379 | H | F | H | OCH₂OC₂H₅ |
| 6-380 | H | Cl | H | OCH₂OC₂H₅ |
| 6-381 | F | F | H | OCH₂OC₂H₅ |
| 6-382 | F | Cl | H | OCH₂OC₂H₅ |
| 6-383 | Cl | F | H | OCH₂OC₂H₅ |
| 6-384 | Cl | Cl | H | OCH₂OC₂H₅ |
| 6-385 | H | F | H | OCH₂SCH₃ |
| 6-386 | H | Cl | H | OCH₂SCH₃ |
| 6-387 | F | F | H | OCH₂SCH₃ |
| 6-388 | F | Cl | H | OCH₂SCH₃ |
| 6-389 | Cl | F | H | OCH₂SCH₃ |
| 6-390 | Cl | Cl | H | OCH₂SCH₃ |
| 6-391 | H | F | H | OCH₂COOH |
| 6-392 | H | Cl | H | OCH₂COOH |
| 6-393 | F | F | H | OCH₂COOH |
| 6-394 | F | Cl | H | OCH₂COOH |
| 6-395 | Cl | F | H | OCH₂COOH |
| 6-396 | Cl | Cl | H | OCH₂COOH |
| 6-397 | H | F | H | OCH₂COOCH₃ |
| 6-398 | H | Cl | H | OCH₂COOCH₃ |
| 6-399 | F | F | H | OCH₂COOCH₃ |
| 6-400 | F | Cl | H | OCH₂COOCH₃ |

TABLE 79

|  | X | Y | R¹ | B |
|---|---|---|---|---|
| 6-401 | Cl | F | H | OCH₂COOCH₃ |
| 6-402 | Cl | Cl | H | OCH₂COOCH₃ |
| 6-403 | H | F | H | OCH₂COOC₂H₅ |
| 6-404 | H | Cl | H | OCH₂COOC₂H₅ |
| 6-405 | F | F | H | OCH₂COOC₂H₅ |
| 6-406 | F | Cl | H | OCH₂COOC₂H₅ |
| 6-407 | Cl | F | H | OCH₂COOC₂H₅ |
| 6-408 | Cl | Cl | H | OCH₂COOC₂H₅ |
| 6-409 | H | F | H | OCH₂COOnC₃H₇ |
| 6-410 | H | Cl | H | OCH₂COOnC₃H₇ |
| 6-411 | F | F | H | OCH₂COOnC₃H₇ |
| 6-412 | F | Cl | H | OCH₂COOnC₃H₇ |
| 6-413 | Cl | F | H | OCH₂COOnC₃H₇ |
| 6-414 | Cl | Cl | H | OCH₂COOnC₃H₇ |
| 6-415 | H | F | H | OCH₂COOnC₄H₉ |
| 6-416 | H | Cl | H | OCH₂COOnC₄H₉ |
| 6-417 | F | F | H | OCH₂COOnC₄H₉ |
| 6-418 | F | Cl | H | OCH₂COOnC₄H₉ |
| 6-419 | Cl | F | H | OCH₂COOnC₄H₉ |
| 6-420 | Cl | Cl | H | OCH₂COOnC₄H₉ |
| 6-421 | H | F | H | OCH₂COOnC₅H₁₁ |
| 6-422 | H | Cl | H | OCH₂COOnC₅H₁₁ |
| 6-423 | F | F | H | OCH₂COOnC₅H₁₁ |
| 6-424 | F | Cl | H | OCH₂COOnC₅H₁₁ |
| 6-425 | Cl | F | H | OCH₂COOnC₅H₁₁ |

TABLE 80

|  | X | Y | R¹ | B |
|---|---|---|---|---|
| 6-426 | Cl | Cl | H | OCH₂COOnC₅H₁₁ |
| 6-427 | H | F | H | OCH₂COOiC₃H₇ |
| 6-428 | H | Cl | H | OCH₂COOiC₃H₇ |
| 6-429 | F | F | H | OCH₂COOiC₃H₇ |
| 6-430 | F | Cl | H | OCH₂COOiC₃H₇ |
| 6-431 | Cl | F | H | OCH₂COOiC₃H₇ |
| 6-432 | Cl | Cl | H | OCH₂COOiC₃H₇ |
| 6-433 | H | F | H | OCH₂COOcC₅H₉ |
| 6-434 | H | Cl | H | OCH₂COOcC₅H₉ |
| 6-435 | F | F | H | OCH₂COOcC₅H₉ |
| 6-436 | F | Cl | H | OCH₂COOcC₅H₉ |
| 6-437 | Cl | F | H | OCH₂COOcC₅H₉ |

TABLE 80-continued

|  | X | Y | R¹ | B |
|---|---|---|---|---|
| 6-438 | Cl | Cl | H | OCH₂COOcC₅H₉ |
| 6-439 | H | F | H | OCH₂COOcC₆H₁₁ |
| 6-440 | H | Cl | H | OCH₂COOcC₆H₁₁ |
| 6-441 | F | F | H | OCH₂COOcC₆H₁₁ |
| 6-442 | F | Cl | H | OCH₂COOcC₆H₁₁ |
| 6-443 | Cl | F | H | OCH₂COOcC₆H₁₁ |
| 6-444 | Cl | Cl | H | OCH₂COOcC₆H₁₁ |
| 6-445 | H | F | H | OCH(CH₃)COOH |
| 6-446 | H | Cl | H | OCH(CH₃)COOH |
| 6-447 | F | F | H | OCH(CH₃)COOH |
| 6-448 | F | Cl | H | OCH(CH₃)COOH |
| 6-449 | Cl | F | H | OCH(CH₃)COOH |
| 6-450 | Cl | Cl | H | OCH(CH₃)COOH |

TABLE 81

|  | X | Y | R¹ | B |
|---|---|---|---|---|
| 6-451 | H | F | H | OCH(CH₃)COOCH₃ |
| 6-452 | H | Cl | H | OCH(CH₃)COOCH₃ |
| 6-453 | F | F | H | OCH(CH₃)COOCH₃ |
| 6-454 | F | Cl | H | OCH(CH₃)COOCH₃ |
| 6-455 | Cl | F | H | OCH(CH₃)COOCH₃ |
| 6-456 | Cl | Cl | H | OCH(CH₃)COOCH₃ |
| 6-457 | H | F | H | OCH(CH₃)COOC₂H₅ |
| 6-458 | H | Cl | H | OCH(CH₃)COOC₂H₅ |
| 6-459 | F | F | H | OCH(CH₃)COOC₂H₅ |
| 6-460 | F | Cl | H | OCH(CH₃)COOC₂H₅ |
| 6-461 | Cl | F | H | OCH(CH₃)COOC₂H₅ |
| 6-462 | Cl | Cl | H | OCH(CH₃)COOC₂H₅ |
| 6-463 | H | F | H | OCH(CH₃)COOnC₃H₇ |
| 6-464 | H | Cl | H | OCH(CH₃)COOnC₃H₇ |
| 6-465 | F | F | H | OCH(CH₃)COOnC₃H₇ |
| 6-466 | F | Cl | H | OCH(CH₃)COOnC₃H₇ |
| 6-467 | Cl | F | H | OCH(CH₃)COOnC₃H₇ |
| 6-468 | Cl | Cl | H | OCH(CH₃)COOnC₃H₇ |
| 6-469 | H | F | H | OCH(CH₃)COOnC₄H₉ |
| 6-470 | H | Cl | H | OCH(CH₃)COOnC₄H₉ |
| 6-471 | F | F | H | OCH(CH₃)COOnC₄H₉ |
| 6-472 | F | Cl | H | OCH(CH₃)COOnC₄H₉ |
| 6-473 | Cl | F | H | OCH(CH₃)COOnC₄H₉ |
| 6-474 | Cl | Cl | H | OCH(CH₃)COOnC₄H₉ |
| 6-475 | H | F | H | OCH(CH₃)COOnC₅H₁₁ |

TABLE 82

|  | X | Y | R¹ | B |
|---|---|---|---|---|
| 6-476 | H | Cl | H | OCH(CH₃)COOnC₅H₁₁ |
| 6-477 | F | F | H | OCH(CH₃)COOnC₅H₁₁ |
| 6-478 | F | Cl | H | OCH(CH₃)COOnC₅H₁₁ |
| 6-479 | Cl | F | H | OCH(CH₃)COOnC₅H₁₁ |
| 6-480 | Cl | Cl | H | OCH(CH₃)COOnC₅H₁₁ |
| 6-481 | H | F | H | OCH(CH₃)COOiC₃H₇ |
| 6-482 | H | Cl | H | OCH(CH₃)COOiC₃H₇ |
| 6-483 | F | F | H | OCH(CH₃)COOiC₃H₇ |
| 6-484 | F | Cl | H | OCH(CH₃)COOiC₃H₇ |
| 6-485 | Cl | F | H | OCH(CH₃)COOiC₃H₇ |
| 6-486 | Cl | Cl | H | OCH(CH₃)COOiC₃H₇ |
| 6-487 | H | F | H | OCH(CH₃)COOcC₅H₉ |
| 6-488 | H | Cl | H | OCH(CH₃)COOcC₅H₉ |
| 6-489 | F | F | H | OCH(CH₃)COOcC₅H₉ |
| 6-490 | F | Cl | H | OCH(CH₃)COOcC₅H₉ |
| 6-491 | Cl | F | H | OCH(CH₃)COOcC₅H₉ |
| 6-492 | Cl | Cl | H | OCH(CH₃)COOcC₅H₉ |
| 6-493 | H | F | H | OCH(CH₃)COOcC₆H₁₁ |
| 6-494 | H | Cl | H | OCH(CH₃)COOcC₆H₁₁ |
| 6-495 | F | F | H | OCH(CH₃)COOcC₆H₁₁ |
| 6-496 | F | Cl | H | OCH(CH₃)COOcC₆H₁₁ |
| 6-497 | Cl | F | H | OCH(CH₃)COOcC₆H₁₁ |
| 6-498 | Cl | Cl | H | OCH(CH₃)COOcC₆H₁₁ |

TABLE 82-continued

|       | X | Y  | R¹ | B                      |
|-------|---|----|----|------------------------|
| 6-499 | H | F  | H  | OCH$_2$CONH$_2$        |
| 6-500 | H | Cl | H  | OCH$_2$CONH$_2$        |

TABLE 83

|       | X  | Y  | R¹ | B                                    |
|-------|----|----|----|--------------------------------------|
| 6-501 | F  | F  | H  | OCH$_2$CONH$_2$                      |
| 6-502 | F  | Cl | H  | OCH$_2$CONH$_2$                      |
| 6-503 | Cl | F  | H  | OCH$_2$CONH$_2$                      |
| 6-504 | Cl | Cl | H  | OCH$_2$CONH$_2$                      |
| 6-505 | H  | F  | H  | OCH$_2$CONHCH$_3$                    |
| 6-506 | H  | Cl | H  | OCH$_2$CONHCH$_3$                    |
| 6-507 | F  | F  | H  | OCH$_2$CONHCH$_3$                    |
| 6-508 | F  | Cl | H  | OCH$_2$CONHCH$_3$                    |
| 6-509 | Cl | F  | H  | OCH$_2$CONHCH$_3$                    |
| 6-510 | Cl | Cl | H  | OCH$_2$CONHCH$_3$                    |
| 6-511 | H  | F  | H  | OCH$_2$CON(CH$_3$)$_2$               |
| 6-512 | H  | Cl | H  | OCH$_2$CON(CH$_3$)$_2$               |
| 6-513 | F  | F  | H  | OCH$_2$CON(CH$_3$)$_2$               |
| 6-514 | F  | Cl | H  | OCH$_2$CON(CH$_3$)$_2$               |
| 6-515 | Cl | F  | H  | OCH$_2$CON(CH$_3$)$_2$               |
| 6-516 | Cl | Cl | H  | OCH$_2$CON(CH$_3$)$_2$               |
| 6-517 | H  | F  | H  | OCH$_2$CON(C$_2$H$_5$)$_2$           |
| 6-518 | H  | Cl | H  | OCH$_2$CON(C$_2$H$_5$)$_2$           |
| 6-519 | F  | F  | H  | OCH$_2$CON(C$_2$H$_5$)$_2$           |
| 6-520 | F  | Cl | H  | OCH$_2$CON(C$_2$H$_5$)$_2$           |
| 6-521 | Cl | F  | H  | OCH$_2$CON(C$_2$H$_5$)$_2$           |
| 6-522 | Cl | Cl | H  | OCH$_2$CON(C$_2$H$_5$)$_2$           |
| 6-523 | H  | F  | H  | OCH$_2$CON(CH$_3$)C$_2$H$_5$         |
| 6-524 | H  | Cl | H  | OCH$_2$CON(CH$_3$)C$_2$H$_5$         |
| 6-525 | F  | F  | H  | OCH$_2$CON(CH$_3$)C$_2$H$_5$         |

TABLE 84

|       | X  | Y  | R¹ | B                                    |
|-------|----|----|----|--------------------------------------|
| 6-526 | F  | Cl | H  | OCH$_2$CON(CH$_3$)C$_2$H$_5$         |
| 6-527 | Cl | F  | H  | OCH$_2$CON(CH$_3$)C$_2$H$_5$         |
| 6-528 | Cl | Cl | H  | OCH$_2$CON(CH$_3$)C$_2$H$_5$         |
| 6-529 | H  | F  | H  | OCH$_2$CON(tetramethylene)           |
| 6-530 | H  | Cl | H  | OCH$_2$CON(tetramethylene)           |
| 6-531 | F  | F  | H  | OCH$_2$CON(tetramethylene)           |
| 6-532 | F  | Cl | H  | OCH$_2$CON(tetramethylene)           |
| 6-533 | Cl | F  | H  | OCH$_2$CON(tetramethylene)           |
| 6-534 | Cl | Cl | H  | OCH$_2$CON(tetramethylene)           |
| 6-535 | H  | F  | H  | OCH$_2$CON(pentamethylene)           |
| 6-536 | H  | Cl | H  | OCH$_2$CON(pentamethylene)           |
| 6-537 | F  | F  | H  | OCH$_2$CON(pentamethylene)           |
| 6-538 | F  | Cl | H  | OCH$_2$CON(pentamethylene)           |
| 6-539 | Cl | F  | H  | OCH$_2$CON(pentamethylene)           |
| 6-540 | Cl | Cl | H  | OCH$_2$CON(pentamethylene)           |
| 6-541 | H  | F  | H  | OCH$_2$CON(ethyleneoxyethylene)      |
| 6-542 | H  | Cl | H  | OCH$_2$CON(ethyleneoxyethylene)      |
| 6-543 | F  | F  | H  | OCH$_2$CON(ethyleneoxyethylene)      |
| 6-544 | F  | Cl | H  | OCH$_2$CON(ethyleneoxyethylene)      |
| 6-545 | Cl | F  | H  | OCH$_2$CON(ethyleneoxyethylene)      |
| 6-546 | Cl | Cl | H  | OCH$_2$CON(ethyleneoxyethylene)      |
| 6-547 | H  | F  | H  | OCH(CH$_3$)CONH$_2$                  |
| 6-548 | H  | Cl | H  | OCH(CH$_3$)CONH$_2$                  |
| 6-549 | F  | F  | H  | OCH(CH$_3$)CONH$_2$                  |
| 6-550 | F  | Cl | H  | OCH(CH$_3$)CONH$_2$                  |

TABLE 85

|       | X  | Y  | R¹ | B                                    |
|-------|----|----|----|--------------------------------------|
| 6-551 | Cl | F  | H  | OCH(CH$_3$)CONH$_2$                  |
| 6-552 | Cl | Cl | H  | OCH(CH$_3$)CONH$_2$                  |
| 6-553 | H  | F  | H  | OCH(CH$_3$)CONHCH$_3$                |
| 6-554 | H  | Cl | H  | OCH(CH$_3$)CONHCH$_3$                |
| 6-555 | F  | F  | H  | OCH(CH$_3$)CONHCH$_3$                |
| 6-556 | F  | Cl | H  | OCH(CH$_3$)CONHCH$_3$                |
| 6-557 | Cl | F  | H  | OCH(CH$_3$)CONHCH$_3$                |
| 6-558 | Cl | Cl | H  | OCH(CH$_3$)CONHCH$_3$                |
| 6-559 | H  | F  | H  | OCH(CH$_3$)CON(CH$_3$)$_2$           |
| 6-560 | H  | Cl | H  | OCH(CH$_3$)CON(CH$_3$)$_2$           |
| 6-561 | F  | F  | H  | OCH(CH$_3$)CON(CH$_3$)$_2$           |
| 6-562 | F  | Cl | H  | OCH(CH$_3$)CON(CH$_3$)$_2$           |
| 6-563 | Cl | F  | H  | OCH(CH$_3$)CON(CH$_3$)$_2$           |
| 6-564 | Cl | Cl | H  | OCH(CH$_3$)CON(CH$_3$)$_2$           |
| 6-565 | H  | F  | H  | OCH(CH$_3$)CON(C$_2$H$_5$)$_2$       |
| 6-566 | H  | Cl | H  | OCH(CH$_3$)CON(C$_2$H$_5$)$_2$       |
| 6-567 | F  | F  | H  | OCH(CH$_3$)CON(C$_2$H$_5$)$_2$       |
| 6-568 | F  | Cl | H  | OCH(CH$_3$)CON(C$_2$H$_5$)$_2$       |
| 6-569 | Cl | F  | H  | OCH(CH$_3$)CON(C$_2$H$_5$)$_2$       |
| 6-570 | Cl | Cl | H  | OCH(CH$_3$)CON(C$_2$H$_5$)$_2$       |
| 6-571 | H  | F  | H  | OCH(CH$_3$)CON(CH$_3$)C$_2$H$_5$     |
| 6-572 | H  | Cl | H  | OCH(CH$_3$)CON(CH$_3$)C$_2$H$_5$     |
| 6-573 | F  | F  | H  | OCH(CH$_3$)CON(CH$_3$)C$_2$H$_5$     |
| 6-574 | F  | Cl | H  | OCH(CH$_3$)CON(CH$_3$)C$_2$H$_5$     |
| 6-575 | Cl | F  | H  | OCH(CH$_3$)CON(CH$_3$)C$_2$H$_5$     |

TABLE 86

|       | X  | Y  | R¹ | B                                         |
|-------|----|----|----|-------------------------------------------|
| 6-576 | Cl | Cl | H  | OCH(CH$_3$)CON(CH$_3$)C$_2$H$_5$          |
| 6-577 | H  | F  | H  | OCH(CH$_3$)CON(tetramethylene)            |
| 6-578 | H  | Cl | H  | OCH(CH$_3$)CON(tetramethylene)            |
| 6-579 | F  | F  | H  | OCH(CH$_3$)CON(tetramethylene)            |
| 6-580 | F  | Cl | H  | OCH(CH$_3$)CON(tetramethylene)            |
| 6-581 | Cl | F  | H  | OCH(CH$_3$)CON(tetramethylene)            |
| 6-582 | Cl | Cl | H  | OCH(CH$_3$)CON(tetramethylene)            |
| 6-583 | H  | F  | H  | OCH(CH$_3$)CON(pentamethylene)            |
| 6-584 | H  | Cl | H  | OCH(CH$_3$)CON(pentamethylene)            |
| 6-585 | F  | F  | H  | OCH(CH$_3$)CON(pentamethylene)            |
| 6-586 | F  | Cl | H  | OCH(CH$_3$)CON(pentamethylene)            |
| 6-587 | Cl | F  | H  | OCH(CH$_3$)CON(pentamethylene)            |
| 6-588 | Cl | Cl | H  | OCH(CH$_3$)CON(pentamethylene)            |
| 6-589 | H  | F  | H  | OCH(CH$_3$)CON(ethyleneoxyethylene)       |
| 6-590 | H  | Cl | H  | OCH(CH$_3$)CON(ethyleneoxyethylene)       |
| 6-591 | F  | F  | H  | OCH(CH$_3$)CON(ethyleneoxyethylene)       |
| 6-592 | F  | Cl | H  | OCH(CH$_3$)CON(ethyleneoxyethylene)       |
| 6-593 | Cl | F  | H  | OCH(CH$_3$)CON(ethyleneoxyethylene)       |
| 6-594 | Cl | Cl | H  | OCH(CH$_3$)CON(ethyleneoxyethylene)       |
| 6-595 | H  | F  | H  | OCH$_2$COON(CH$_3$)$_2$                   |
| 6-596 | H  | Cl | H  | OCH$_2$COON(CH$_3$)$_2$                   |
| 6-597 | F  | F  | H  | OCH$_2$COON(CH$_3$)$_2$                   |
| 6-598 | F  | Cl | H  | OCH$_2$COON(CH$_3$)$_2$                   |
| 6-599 | Cl | F  | H  | OCH$_2$COON(CH$_3$)$_2$                   |
| 6-600 | Cl | Cl | H  | OCH$_2$COON(CH$_3$)$_2$                   |

TABLE 87

|       | X  | Y  | R¹ | B                                     |
|-------|----|----|----|---------------------------------------|
| 6-601 | H  | F  | H  | OCH$_2$COON(C$_2$H$_5$)$_2$           |
| 6-602 | H  | Cl | H  | OCH$_2$COON(C$_2$H$_5$)$_2$           |
| 6-603 | F  | F  | H  | OCH$_2$COON(C$_2$H$_5$)$_2$           |
| 6-604 | F  | Cl | H  | OCH$_2$COON(C$_2$H$_5$)$_2$           |
| 6-605 | Cl | F  | H  | OCH$_2$COON(C$_2$H$_5$)$_2$           |
| 6-606 | Cl | Cl | H  | OCH$_2$COON(C$_2$H$_5$)$_2$           |
| 6-607 | H  | F  | H  | OCH(CH$_3$)COON(CH$_3$)$_2$           |
| 6-608 | H  | Cl | H  | OCH(CH$_3$)COON(CH$_3$)$_2$           |
| 6-609 | F  | F  | H  | OCH(CH$_3$)COON(CH$_3$)$_2$           |
| 6-610 | F  | Cl | H  | OCH(CH$_3$)COON(CH$_3$)$_2$           |
| 6-611 | Cl | F  | H  | OCH(CH$_3$)COON(CH$_3$)$_2$           |
| 6-612 | Cl | Cl | H  | OCH(CH$_3$)COON(CH$_3$)$_2$           |
| 6-613 | H  | F  | H  | OCH(CH$_3$)COON(C$_2$H$_5$)$_2$       |
| 6-614 | H  | Cl | H  | OCH(CH$_3$)COON(C$_2$H$_5$)$_2$       |
| 6-615 | F  | F  | H  | OCH(CH$_3$)COON(C$_2$H$_5$)$_2$       |

TABLE 87-continued

| | X | Y | R¹ | B |
|---|---|---|---|---|
| 6-616 | F | Cl | H | OCH(CH₃)COON(C₂H₅)₂ |
| 6-617 | Cl | F | H | OCH(CH₃)COON(C₂H₅)₂ |
| 6-618 | Cl | Cl | H | OCH(CH₃)COON(C₂H₅)₂ |
| 6-619 | H | F | H | SCH₃ |
| 6-620 | H | Cl | H | SCH₃ |
| 6-621 | F | F | H | SCH₃ |
| 6-622 | F | Cl | H | SCH₃ |
| 6-623 | Cl | F | H | SCH₃ |
| 6-624 | Cl | Cl | H | SCH₃ |
| 6-625 | H | F | H | SC₂H₅ |

TABLE 88

| | X | Y | R¹ | B |
|---|---|---|---|---|
| 6-626 | H | Cl | H | SC₂H₅ |
| 6-627 | F | F | H | SC₂H₅ |
| 6-628 | F | Cl | H | SC₂H₅ |
| 6-629 | Cl | F | H | SC₂H₅ |
| 6-630 | Cl | Cl | H | SC₂H₅ |
| 6-631 | H | F | H | SiC₃H₇ |
| 6-632 | H | Cl | H | SiC₃H₇ |
| 6-633 | F | F | H | SiC₃H₇ |
| 6-634 | F | Cl | H | SiC₃H₇ |
| 6-635 | Cl | F | H | SiC₃H₇ |
| 6-636 | Cl | Cl | H | SiC₃H₇ |
| 6-637 | H | F | H | SnC₃H₇ |
| 6-638 | H | Cl | H | SnC₃H₇ |
| 6-639 | F | F | H | SnC₃H₇ |
| 6-640 | F | Cl | H | SnC₃H₇ |
| 6-641 | Cl | F | H | SnC₃H₇ |
| 6-642 | Cl | Cl | H | SnC₃H₇ |
| 6-643 | H | F | H | SCH₂CH₂Cl |
| 6-644 | H | Cl | H | SCH₂CH₂Cl |
| 6-645 | F | F | H | SCH₂CH₂Cl |
| 6-646 | F | Cl | H | SCH₂CH₂Cl |
| 6-647 | Cl | F | H | SCH₂CH₂Cl |
| 6-648 | Cl | Cl | H | SCH₂CH₂Cl |
| 6-649 | H | F | H | ScC₅H₉ |
| 6-650 | H | Cl | H | ScC₅H₉ |

TABLE 89

| | X | Y | R¹ | B |
|---|---|---|---|---|
| 6-651 | F | F | H | ScC₅H₉ |
| 6-652 | F | Cl | H | ScC₅H₉ |
| 6-653 | Cl | F | H | ScC₅H₉ |
| 6-654 | Cl | Cl | H | ScC₅H₉ |
| 6-655 | H | F | H | ScC₆H₁₁ |
| 6-656 | H | Cl | H | ScC₆H₁₁ |
| 6-657 | F | F | H | ScC₆H₁₁ |
| 6-658 | F | Cl | H | ScC₆H₁₁ |
| 6-659 | Cl | F | H | ScC₆H₁₁ |
| 6-660 | Cl | Cl | H | ScC₆H₁₁ |
| 6-661 | H | F | H | SCH₂CH=CH₂ |
| 6-662 | H | Cl | H | SCH₂CH=CH₂ |
| 6-663 | F | F | H | SCH₂CH=CH₂ |
| 6-664 | F | Cl | H | SCH₂CH=CH₂ |
| 6-665 | Cl | F | H | SCH₂CH=CH₂ |
| 6-666 | Cl | Cl | H | SCH₂CH=CH₂ |
| 6-667 | H | F | H | SCH₂CCl=CH₂ |
| 6-668 | H | Cl | H | SCH₂CCl=CH₂ |
| 6-669 | F | F | H | SCH₂CCl=CH₂ |
| 6-670 | F | Cl | H | SCH₂CCl=CH₂ |
| 6-671 | Cl | F | H | SCH₂CCl=CH₂ |
| 6-672 | Cl | Cl | H | SCH₂CCl=CH₂ |
| 6-673 | H | F | H | SCH₂CCl=CHCl |
| 6-674 | H | Cl | H | SCH₂CCl=CHCl |
| 6-675 | F | F | H | SCH₂CCl=CHCl |

TABLE 90

| | X | Y | R¹ | B |
|---|---|---|---|---|
| 6-676 | F | Cl | H | SCH₂CCl=CHCl |
| 6-677 | Cl | F | H | SCH₂CCl=CHCl |
| 6-678 | Cl | Cl | H | SCH₂CCl=CHCl |
| 6-679 | H | F | H | SCH(CH₃)CH=CH₂ |
| 6-680 | H | Cl | H | SCH(CH₃)CH=CH₂ |
| 6-681 | F | F | H | SCH(CH₃)CH=CH₂ |
| 6-682 | F | Cl | H | SCH(CH₃)CH=CH₂ |
| 6-683 | Cl | F | H | SCH(CH₃)CH=CH₂ |
| 6-684 | Cl | Cl | H | SCH(CH₃)CH=CH₂ |
| 6-685 | H | F | H | SCH₂C≡CH |
| 6-686 | H | Cl | H | SCH₂C≡CH |
| 6-687 | F | F | H | SCH₂C≡CH |
| 6-688 | F | Cl | H | SCH₂C≡CH |
| 6-689 | Cl | F | H | SCH₂C≡CH |
| 6-690 | Cl | Cl | H | SCH₂C≡CH |
| 6-691 | H | F | H | SCH(CH₃)C≡CH |
| 6-692 | H | Cl | H | SCH(CH₃)C≡CH |
| 6-693 | F | F | H | SCH(CH₃)C≡CH |
| 6-694 | F | Cl | H | SCH(CH₃)C≡CH |
| 6-695 | Cl | F | H | SCH(CH₃)C≡CH |
| 6-696 | Cl | Cl | H | SCH(CH₃)C≡CH |
| 6-697 | H | F | H | SCH₂COOH |
| 6-698 | H | Cl | H | SCH₂COOH |
| 6-699 | F | F | H | SCH₂COOH |
| 6-700 | F | Cl | H | SCH₂COOH |

TABLE 91

| | X | Y | R¹ | B |
|---|---|---|---|---|
| 6-701 | Cl | F | H | SCH₂COOH |
| 6-702 | Cl | Cl | H | SCH₂COOH |
| 6-703 | H | F | H | SCH₂COOCH₃ |
| 6-704 | H | Cl | H | SCH₂COOCH₃ |
| 6-705 | F | F | H | SCH₂COOCH₃ |
| 6-706 | F | Cl | H | SCH₂COOCH₃ |
| 6-707 | Cl | F | H | SCH₂COOCH₃ |
| 6-708 | Cl | Cl | H | SCH₂COOCH₃ |
| 6-709 | H | F | H | SCH₂COOC₂H₅ |
| 6-710 | H | Cl | H | SCH₂COOC₂H₅ |
| 6-711 | F | F | H | SCH₂COOC₂H₅ |
| 6-712 | F | Cl | H | SCH₂COOC₂H₅ |
| 6-713 | Cl | F | H | SCH₂COOC₂H₅ |
| 6-714 | Cl | Cl | H | SCH₂COOC₂H₅ |
| 6-715 | H | F | H | SCH₂COOnC₃H₇ |
| 6-716 | H | Cl | H | SCH₂COOnC₃H₇ |
| 6-717 | F | F | H | SCH₂COOnC₃H₇ |
| 6-718 | F | Cl | H | SCH₂COOnC₃H₇ |
| 6-719 | Cl | F | H | SCH₂COOnC₃H₇ |
| 6-720 | Cl | Cl | H | SCH₂COOnC₃H₇ |
| 6-721 | H | F | H | SCH₂COOnC₄H₉ |
| 6-722 | H | Cl | H | SCH₂COOnC₄H₉ |
| 6-723 | F | F | H | SCH₂COOnC₄H₉ |
| 6-724 | F | Cl | H | SCH₂COOnC₄H₉ |
| 6-725 | Cl | F | H | SCH₂COOnC₄H₉ |

TABLE 92

| | X | Y | R¹ | B |
|---|---|---|---|---|
| 6-726 | Cl | Cl | H | SCH₂COOnC₄H₉ |
| 6-727 | H | F | H | SCH₂COOnC₅H₁₁ |
| 6-728 | H | Cl | H | SCH₂COOnC₅H₁₁ |
| 6-729 | F | F | H | SCH₂COOnC₅H₁₁ |
| 6-730 | F | Cl | H | SCH₂COOnC₅H₁₁ |
| 6-731 | Cl | F | H | SCH₂COOnC₅H₁₁ |
| 6-732 | Cl | Cl | H | SCH₂COOnC₅H₁₁ |
| 6-733 | H | F | H | SCH₂COOiC₃H₇ |
| 6-734 | H | Cl | H | SCH₂COOiC₃H₇ |
| 6-735 | F | F | H | SCH₂COOiC₃H₇ |
| 6-736 | F | Cl | H | SCH₂COOiC₃H₇ |
| 6-737 | Cl | F | H | SCH₂COOiC₃H₇ |

TABLE 92-continued

|  | X | Y | R¹ | B |
|---|---|---|---|---|
| 6-738 | Cl | Cl | H | SCH$_2$COOiC$_3$H$_7$ |
| 6-739 | H | F | H | SCH$_2$COOcC$_5$H$_9$ |
| 6-740 | H | Cl | H | SCH$_2$COOcC$_5$H$_9$ |
| 6-741 | F | F | H | SCH$_2$COOcC$_5$H$_9$ |
| 6-742 | F | Cl | H | SCH$_2$COOcC$_5$H$_9$ |
| 6-743 | Cl | F | H | SCH$_2$COOcC$_5$H$_9$ |
| 6-744 | Cl | Cl | H | SCH$_2$COOcC$_5$H$_9$ |
| 6-745 | H | F | H | SCH$_2$COOcC$_6$H$_{11}$ |
| 6-746 | H | Cl | H | SCH$_2$COOcC$_6$H$_{11}$ |
| 6-747 | F | F | H | SCH$_2$COOcC$_6$H$_{11}$ |
| 6-748 | F | Cl | H | SCH$_2$COOcC$_6$H$_{11}$ |
| 6-749 | Cl | F | H | SCH$_2$COOcC$_6$H$_{11}$ |
| 6-750 | Cl | Cl | H | SCH$_2$COOcC$_6$H$_{11}$ |

TABLE 93

|  | X | Y | R¹ | B |
|---|---|---|---|---|
| 6-751 | H | F | H | SCH(CH$_3$)COOH |
| 6-752 | H | Cl | H | SCH(CH$_3$)COOH |
| 6-753 | F | F | H | SCH(CH$_3$)COOH |
| 6-754 | F | Cl | H | SCH(CH$_3$)COOH |
| 6-755 | Cl | F | H | SCH(CH$_3$)COOH |
| 6-756 | Cl | Cl | H | SCH(CH$_3$)COOH |
| 6-757 | H | F | H | SCH(CH$_3$)COOCH$_3$ |
| 6-758 | H | Cl | H | SCH(CH$_3$)COOCH$_3$ |
| 6-759 | F | F | H | SCH(CH$_3$)COOCH$_3$ |
| 6-760 | F | Cl | H | SCH(CH$_3$)COOCH$_3$ |
| 6-761 | Cl | F | H | SCH(CH$_3$)COOCH$_3$ |
| 6-762 | Cl | Cl | H | SCH(CH$_3$)COOCH$_3$ |
| 6-763 | H | F | H | SCH(CH$_3$)COOC$_2$H$_5$ |
| 6-764 | H | Cl | H | SCH(CH$_3$)COOC$_2$H$_5$ |
| 6-765 | F | F | H | SCH(CH$_3$)COOC$_2$H$_5$ |
| 6-766 | F | Cl | H | SCH(CH$_3$)COOC$_2$H$_5$ |
| 6-767 | Cl | F | H | SCH(CH$_3$)COOC$_2$H$_5$ |
| 6-768 | Cl | Cl | H | SCH(CH$_3$)COOC$_2$H$_5$ |
| 6-769 | H | F | H | SCH(CH$_3$)COOnC$_3$H$_7$ |
| 6-770 | H | Cl | H | SCH(CH$_3$)COOnC$_3$H$_7$ |
| 6-771 | F | F | H | SCH(CH$_3$)COOnC$_3$H$_7$ |
| 6-772 | F | Cl | H | SCH(CH$_3$)COOnC$_3$H$_7$ |
| 6-773 | Cl | F | H | SCH(CH$_3$)COOnC$_3$H$_7$ |
| 6-774 | Cl | Cl | H | SCH(CH$_3$)COOnC$_3$H$_7$ |
| 6-775 | H | F | H | SCH(CH$_3$)COOnC$_4$H$_9$ |

TABLE 94

|  | X | Y | R¹ | B |
|---|---|---|---|---|
| 6-776 | H | Cl | H | SCH(CH$_3$)COOnC$_4$H$_9$ |
| 6-777 | F | F | H | SCH(CH$_3$)COOnC$_4$H$_9$ |
| 6-778 | F | Cl | H | SCH(CH$_3$)COOnC$_4$H$_9$ |
| 6-779 | Cl | F | H | SCH(CH$_3$)COOnC$_4$H$_9$ |
| 6-780 | Cl | Cl | H | SCH(CH$_3$)COOnC$_4$H$_9$ |
| 6-781 | H | F | H | SCH(CH$_3$)COOnC$_5$H$_{11}$ |
| 6-782 | H | Cl | H | SCH(CH$_3$)COOnC$_5$H$_{11}$ |
| 6-783 | F | F | H | SCH(CH$_3$)COOnC$_5$H$_{11}$ |
| 6-784 | F | Cl | H | SCH(CH$_3$)COOnC$_5$H$_{11}$ |
| 6-785 | Cl | F | H | SCH(CH$_3$)COOnC$_5$H$_{11}$ |
| 6-786 | Cl | Cl | H | SCH(CH$_3$)COOnC$_5$H$_{11}$ |
| 6-787 | H | F | H | SCH(CH$_3$)COOiC$_3$H$_7$ |
| 6-788 | H | Cl | H | SCH(CH$_3$)COOiC$_3$H$_7$ |
| 6-789 | F | F | H | SCH(CH$_3$)COOiC$_3$H$_7$ |
| 6-790 | F | Cl | H | SCH(CH$_3$)COOiC$_3$H$_7$ |
| 6-791 | Cl | F | H | SCH(CH$_3$)COOiC$_3$H$_7$ |
| 6-792 | Cl | Cl | H | SCH(CH$_3$)COOiC$_3$H$_7$ |
| 6-793 | H | F | H | SCH(CH$_3$)COOcC$_5$H$_9$ |
| 6-794 | H | Cl | H | SCH(CH$_3$)COOcC$_5$H$_9$ |
| 6-795 | F | F | H | SCH(CH$_3$)COOcC$_5$H$_9$ |
| 6-796 | F | Cl | H | SCH(CH$_3$)COOcC$_5$H$_9$ |
| 6-797 | Cl | F | H | SCH(CH$_3$)COOcC$_5$H$_9$ |
| 6-798 | Cl | Cl | H | SCH(CH$_3$)COOcC$_5$H$_9$ |

TABLE 94-continued

|  | X | Y | R¹ | B |
|---|---|---|---|---|
| 6-799 | H | F | H | SCH(CH$_3$)COOcC$_6$H$_{11}$ |
| 6-800 | H | Cl | H | SCH(CH$_3$)COOcC$_6$H$_{11}$ |

TABLE 95

|  | X | Y | R¹ | B |
|---|---|---|---|---|
| 6-801 | F | F | H | SCH(CH$_3$)COOcC$_6$H$_{11}$ |
| 6-802 | F | Cl | H | SCH(CH$_3$)COOcC$_6$H$_{11}$ |
| 6-803 | Cl | F | H | SCH(CH$_3$)COOcC$_6$H$_{11}$ |
| 6-804 | Cl | Cl | H | SCH(CH$_3$)COOcC$_6$H$_{11}$ |
| 6-805 | H | F | H | SCH$_2$CONH$_2$ |
| 6-806 | H | Cl | H | SCH$_2$CONH$_2$ |
| 6-807 | F | F | H | SCH$_2$CONH$_2$ |
| 6-808 | F | Cl | H | SCH$_2$CONH$_2$ |
| 6-809 | Cl | F | H | SCH$_2$CONH$_2$ |
| 6-810 | Cl | Cl | H | SCH$_2$CONH$_2$ |
| 6-811 | H | F | H | SCH$_2$CONHCH$_3$ |
| 6-812 | H | Cl | H | SCH$_2$CONHCH$_3$ |
| 6-813 | F | F | H | SCH$_2$CONHCH$_3$ |
| 6-814 | F | Cl | H | SCH$_2$CONHCH$_3$ |
| 6-815 | Cl | F | H | SCH$_2$CONHCH$_3$ |
| 6-816 | Cl | Cl | H | SCH$_2$CONHCH$_3$ |
| 6-817 | H | F | H | SCH$_2$CON(CH$_3$)$_2$ |
| 6-818 | H | Cl | H | SCH$_2$CON(CH$_3$)$_2$ |
| 6-819 | F | F | H | SCH$_2$CON(CH$_3$)$_2$ |
| 6-820 | F | Cl | H | SCH$_2$CON(CH$_3$)$_2$ |
| 6-821 | Cl | F | H | SCH$_2$CON(CH$_3$)$_2$ |
| 6-822 | Cl | Cl | H | SCH$_2$CON(CH$_3$)$_2$ |
| 6-823 | H | F | H | SCH$_2$CON(C$_2$H$_5$)$_2$ |
| 6-824 | H | Cl | H | SCH$_2$CON(C$_2$H$_5$)$_2$ |
| 6-825 | F | F | H | SCH$_2$CON(C$_2$H$_5$)$_2$ |

TABLE 96

|  | X | Y | R¹ | B |
|---|---|---|---|---|
| 6-826 | F | Cl | H | SCH$_2$CON(C$_2$H$_5$)$_2$ |
| 6-827 | Cl | F | H | SCH$_2$CON(C$_2$H$_5$)$_2$ |
| 6-828 | Cl | Cl | H | SCH$_2$CON(C$_2$H$_5$)$_2$ |
| 6-829 | H | F | H | SCH$_2$CON(CH$_3$)C$_2$H$_5$ |
| 6-830 | H | Cl | H | SCH$_2$CON(CH$_3$)C$_2$H$_5$ |
| 6-831 | F | F | H | SCH$_2$CON(CH$_3$)C$_2$H$_5$ |
| 6-832 | F | Cl | H | SCH$_2$CON(CH$_3$)C$_2$H$_5$ |
| 6-833 | Cl | F | H | SCH$_2$CON(CH$_3$)C$_2$H$_5$ |
| 6-834 | Cl | Cl | H | SCH$_2$CON(CH$_3$)C$_2$H$_5$ |
| 6-835 | H | F | H | SCH$_2$CON(tetramethylene) |
| 6-836 | H | Cl | H | SCH$_2$CON(tetramethylene) |
| 6-837 | F | F | H | SCH$_2$CON(tetramethylene) |
| 6-838 | F | Cl | H | SCH$_2$CON(tetramethylene) |
| 6-839 | Cl | F | H | SCH$_2$CON(tetramethylene) |
| 6-840 | Cl | Cl | H | SCH$_2$CON(tetramethylene) |
| 6-841 | H | F | H | SCH$_2$CON(pentamethylene) |
| 6-842 | H | Cl | H | SCH$_2$CON(pentamethylene) |
| 6-843 | F | F | H | SCH$_2$CON(pentamethylene) |
| 6-844 | F | Cl | H | SCH$_2$CON(pentamethylene) |
| 6-845 | Cl | F | H | SCH$_2$CON(pentamethylene) |
| 6-846 | Cl | Cl | H | SCH$_2$CON(pentamethylene) |
| 6-847 | H | F | H | SCH$_2$CON(ethyleneoxyethylene) |
| 6-848 | H | Cl | H | SCH$_2$CON(ethyleneoxyethylene) |
| 6-849 | F | F | H | SCH$_2$CON(ethyleneoxyethylene) |
| 6-850 | F | Cl | H | SCH$_2$CON(ethyleneoxyethylene) |

TABLE 97

|  | X | Y | R¹ | B |
|---|---|---|---|---|
| 6-851 | Cl | F | H | SCH$_2$CON(ethyleneoxyethylene) |
| 6-852 | Cl | Cl | H | SCH$_2$CON(ethyleneoxyethylene) |
| 6-853 | H | F | H | SCH(CH$_3$)CONH$_2$ |

TABLE 97-continued

| | X | Y | R¹ | B |
|---|---|---|---|---|
| 6-854 | H | Cl | H | SCH(CH$_3$)CONH$_2$ |
| 6-855 | F | F | H | SCH(CH$_3$)CONH$_2$ |
| 6-856 | F | Cl | H | SCH(CH$_3$)CONH$_2$ |
| 6-857 | Cl | F | H | SCH(CH$_3$)CONH$_2$ |
| 6-858 | Cl | Cl | H | SCH(CH$_3$)CONH$_2$ |
| 6-859 | H | F | H | SCH(CH$_3$)CONHCH$_3$ |
| 6-860 | H | Cl | H | SCH(CH$_3$)CONHCH$_3$ |
| 6-861 | F | F | H | SCH(CH$_3$)CONHCH$_3$ |
| 6-862 | F | Cl | H | SCH(CH$_3$)CONHCH$_3$ |
| 6-863 | Cl | F | H | SCH(CH$_3$)CONHCH$_3$ |
| 6-864 | Cl | Cl | H | SCH(CH$_3$)CONHCH$_3$ |
| 6-865 | H | F | H | SCH(CH$_3$)CON(CH$_3$)$_2$ |
| 6-866 | H | Cl | H | SCH(CH$_3$)CON(CH$_3$)$_2$ |
| 6-867 | F | F | H | SCH(CH$_3$)CON(CH$_3$)$_2$ |
| 6-868 | F | Cl | H | SCH(CH$_3$)CON(CH$_3$)$_2$ |
| 6-869 | Cl | F | H | SCH(CH$_3$)CON(CH$_3$)$_2$ |
| 6-870 | Cl | Cl | H | SCH(CH$_3$)CON(CH$_3$)$_2$ |
| 6-871 | H | F | H | SCH(CH$_3$)CON(C$_2$H$_5$)$_2$ |
| 6-872 | H | Cl | H | SCH(CH$_3$)CON(C$_2$H$_5$)$_2$ |
| 6-873 | F | F | H | SCH(CH$_3$)CON(C$_2$H$_5$)$_2$ |
| 6-874 | F | Cl | H | SCH(CH$_3$)CON(C$_2$H$_5$)$_2$ |
| 6-875 | Cl | F | H | SCH(CH$_3$)CON(C$_2$H$_5$)$_2$ |

TABLE 98

| | X | Y | R¹ | B |
|---|---|---|---|---|
| 6-876 | Cl | Cl | H | SCH(CH$_3$)CON(C$_2$H$_5$)$_2$ |
| 6-877 | H | F | H | SCH(CH$_3$)CON(CH$_3$)C$_2$H$_5$ |
| 6-878 | H | Cl | H | SCH(CH$_3$)CON(CH$_3$)C$_2$H$_5$ |
| 6-879 | F | F | H | SCH(CH$_3$)CON(CH$_3$)C$_2$H$_5$ |
| 6-880 | F | Cl | H | SCH(CH$_3$)CON(CH$_3$)C$_2$H$_5$ |
| 6-881 | Cl | F | H | SCH(CH$_3$)CON(CH$_3$)C$_2$H$_5$ |
| 6-882 | Cl | Cl | H | SCH(CH$_3$)CON(CH$_3$)C$_2$H$_5$ |
| 6-883 | H | F | H | SCH(CH$_3$)CON(CH$_3$)C$_2$H$_5$ |
| 6-884 | H | Cl | H | SCH(CH$_3$)CON(CH$_3$)C$_2$H$_5$ |
| 6-885 | F | F | H | SCH(CH$_3$)CON(CH$_3$)C$_2$H$_5$ |
| 6-886 | F | Cl | H | SCH(CH$_3$)CON(CH$_3$)C$_2$H$_5$ |
| 6-887 | Cl | F | H | SCH(CH$_3$)CON(CH$_3$)C$_2$H$_5$ |
| 6-888 | Cl | Cl | H | SCH(CH$_3$)CON(CH$_3$)C$_2$H$_5$ |
| 6-889 | H | F | H | SCH(CH$_3$)CON(tetramethylene) |
| 6-890 | H | Cl | H | SCH(CH$_3$)CON(tetramethylene) |
| 6-891 | F | F | H | SCH(CH$_3$)CON(tetramethylene) |
| 6-892 | F | Cl | H | SCH(CH$_3$)CON(tetramethylene) |
| 6-893 | Cl | F | H | SCH(CH$_3$)CON(tetramethylene) |
| 6-894 | Cl | Cl | H | SCH(CH$_3$)CON(tetramethylene) |
| 6-895 | H | F | H | SCH(CH$_3$)CON(pentamethylene) |
| 6-896 | H | Cl | H | SCH(CH$_3$)CON(pentamethylene) |
| 6-897 | F | F | H | SCH(CH$_3$)CON(pentamethylene) |
| 6-898 | F | Cl | H | SCH(CH$_3$)CON(pentamethylene) |
| 6-899 | Cl | F | H | SCH(CH$_3$)CON(pentamethylene) |
| 6-900 | Cl | Cl | H | SCH(CH$_3$)CON(pentamethylene) |

TABLE 99

| | X | Y | R¹ | B |
|---|---|---|---|---|
| 6-901 | H | F | H | SCH(CH$_3$)CON(ethyleneoxyethylene) |
| 6-902 | H | Cl | H | SCH(CH$_3$)CON(ethyleneoxyethylene) |
| 6-903 | F | F | H | SCH(CH$_3$)CON(ethyleneoxyethylene) |
| 6-904 | F | Cl | H | SCH(CH$_3$)CON(ethyleneoxyethylene) |
| 6-905 | Cl | F | H | SCH(CH$_3$)CON(ethyleneoxyethylene) |
| 6-906 | Cl | Cl | H | SCH(CH$_3$)CON(ethyleneoxyethylene) |
| 6-907 | H | F | H | SO$_2$OCH$_3$ |
| 6-908 | H | Cl | H | SO$_2$OCH$_3$ |
| 6-909 | F | F | H | SO$_2$OCH$_3$ |
| 6-910 | F | Cl | H | SO$_2$OCH$_3$ |
| 6-911 | Cl | F | H | SO$_2$OCH$_3$ |
| 6-912 | Cl | Cl | H | SO$_2$OCH$_3$ |
| 6-913 | H | F | H | SO$_2$OC$_2$H$_5$ |
| 6-914 | H | Cl | H | SO$_2$OC$_2$H$_5$ |
| 6-915 | F | F | H | SO$_2$OC$_2$H$_5$ |

TABLE 99-continued

| | X | Y | R¹ | B |
|---|---|---|---|---|
| 6-916 | F | Cl | H | SO$_2$OC$_2$H$_5$ |
| 6-917 | Cl | F | H | SO$_2$OC$_2$H$_5$ |
| 6-918 | Cl | Cl | H | SO$_2$OC$_2$H$_5$ |
| 6-919 | H | F | H | SO$_2$OiC$_3$H$_7$ |
| 6-920 | H | Cl | H | SO$_2$OiC$_3$H$_7$ |
| 6-921 | F | F | H | SO$_2$OiC$_3$H$_7$ |
| 6-922 | F | Cl | H | SO$_2$OiC$_3$H$_7$ |
| 6-923 | Cl | F | H | SO$_2$OiC$_3$H$_7$ |
| 6-924 | Cl | Cl | H | SO$_2$OiC$_3$H$_7$ |
| 6-925 | H | F | H | SO$_2$OCH$_2$CH=CH$_2$ |

TABLE 100

| | X | Y | R¹ | B |
|---|---|---|---|---|
| 6-926 | H | Cl | H | SO$_2$OCH$_2$CH=CH$_2$ |
| 6-927 | F | F | H | SO$_2$OCH$_2$CH=CH$_2$ |
| 6-928 | F | Cl | H | SO$_2$OCH$_2$CH=CH$_2$ |
| 6-929 | Cl | F | H | SO$_2$OCH$_2$CH=CH$_2$ |
| 6-930 | Cl | Cl | H | SO$_2$OCH$_2$CH=CH$_2$ |
| 6-931 | H | F | H | SO$_2$N(CH$_3$)$_2$ |
| 6-932 | H | Cl | H | SO$_2$N(CH$_3$)$_2$ |
| 6-933 | F | F | H | SO$_2$N(CH$_3$)$_2$ |
| 6-934 | F | Cl | H | SO$_2$N(CH$_3$)$_2$ |
| 6-935 | Cl | F | H | SO$_2$N(CH$_3$)$_2$ |
| 6-936 | Cl | Cl | H | SO$_2$N(CH$_3$)$_2$ |
| 6-937 | H | F | H | SO$_2$N(C$_2$H$_5$)$_2$ |
| 6-938 | H | Cl | H | SO$_2$N(C$_2$H$_5$)$_2$ |
| 6-939 | F | F | H | SO$_2$N(C$_2$H$_5$)$_2$ |
| 6-940 | F | Cl | H | SO$_2$N(C$_2$H$_5$)$_2$ |
| 6-941 | Cl | F | H | SO$_2$N(C$_2$H$_5$)$_2$ |
| 6-942 | Cl | Cl | H | SO$_2$N(C$_2$H$_5$)$_2$ |
| 6-943 | H | F | H | COOH |
| 6-944 | H | Cl | H | COOH |
| 6-945 | F | F | H | COOH |
| 6-946 | F | Cl | H | COOH |
| 6-947 | Cl | F | H | COOH |
| 6-948 | Cl | Cl | H | COOH |
| 6-949 | H | F | H | COOCH$_3$ |
| 6-950 | H | Cl | H | COOCH$_3$ |

TABLE 101

| | X | Y | R¹ | B |
|---|---|---|---|---|
| 6-951 | F | F | H | COOCH$_3$ |
| 6-952 | F | Cl | H | COOCH$_3$ |
| 6-953 | Cl | F | H | COOCH$_3$ |
| 6-954 | Cl | Cl | H | COOCH$_3$ |
| 6-955 | H | F | H | COOC$_2$H$_5$ |
| 6-956 | H | Cl | H | COOC$_2$H$_5$ |
| 6-957 | F | F | H | COOC$_2$H$_5$ |
| 6-958 | F | Cl | H | COOC$_2$H$_5$ |
| 6-959 | Cl | F | H | COOC$_2$H$_5$ |
| 6-960 | Cl | Cl | H | COOC$_2$H$_5$ |
| 6-961 | H | F | H | COOnC$_3$H$_7$ |
| 6-962 | H | Cl | H | COOnC$_3$H$_7$ |
| 6-963 | F | F | H | COOnC$_3$H$_7$ |
| 6-964 | F | Cl | H | COOnC$_3$H$_7$ |
| 6-965 | Cl | F | H | COOnC$_3$H$_7$ |
| 6-966 | Cl | Cl | H | COOnC$_3$H$_7$ |
| 6-967 | H | F | H | COOnC$_4$H$_9$ |
| 6-968 | H | Cl | H | COOnC$_4$H$_9$ |
| 6-969 | F | F | H | COOnC$_4$H$_9$ |
| 6-970 | F | Cl | H | COOnC$_4$H$_9$ |
| 6-971 | Cl | F | H | COOnC$_4$H$_9$ |
| 6-972 | Cl | Cl | H | COOnC$_4$H$_9$ |
| 6-973 | H | F | H | COOnC$_5$H$_{11}$ |
| 6-974 | H | Cl | H | COOnC$_5$H$_{11}$ |
| 6-975 | F | F | H | COOnC$_5$H$_{11}$ |

TABLE 102

|  | X | Y | R¹ | B |
|---|---|---|---|---|
| 6-976 | F | Cl | H | COOnC$_5$H$_{11}$ |
| 6-977 | Cl | F | H | COOnC$_5$H$_{11}$ |
| 6-978 | Cl | Cl | H | COOnC$_5$H$_{11}$ |
| 6-979 | H | F | H | COOiC$_3$H$_7$ |
| 6-980 | H | Cl | H | COOiC$_3$H$_7$ |
| 6-981 | F | F | H | COOiC$_3$H$_7$ |
| 6-982 | F | Cl | H | COOiC$_3$H$_7$ |
| 6-983 | Cl | F | H | COOiC$_3$H$_7$ |
| 6-984 | Cl | Cl | H | COOiC$_3$H$_7$ |
| 6-985 | H | F | H | COOcC$_5$H$_9$ |
| 6-986 | H | Cl | H | COOcC$_5$H$_9$ |
| 6-987 | F | F | H | COOcC$_5$H$_9$ |
| 6-988 | F | Cl | H | COOcC$_5$H$_9$ |
| 6-989 | Cl | F | H | COOcC$_5$H$_9$ |
| 6-990 | Cl | Cl | H | COOcC$_5$H$_9$ |
| 6-991 | H | F | H | COOcC$_6$H$_{11}$ |
| 6-992 | H | Cl | H | COOcC$_6$H$_{11}$ |
| 6-993 | F | F | H | COOcC$_6$H$_{11}$ |
| 6-994 | F | Cl | H | COOcC$_6$H$_{11}$ |
| 6-995 | Cl | F | H | COOcC$_6$H$_{11}$ |
| 6-996 | Cl | Cl | H | COOcC$_6$H$_{11}$ |
| 6-997 | H | F | H | COOCH$_2$C$_6$H$_5$ |
| 6-998 | H | Cl | H | COOCH$_2$C$_6$H$_5$ |
| 6-999 | F | F | H | COOCH$_2$C$_6$H$_5$ |
| 6-1000 | F | Cl | H | COOCH$_2$C$_6$H$_5$ |

TABLE 103

|  | X | Y | R¹ | B |
|---|---|---|---|---|
| 6-1001 | Cl | F | H | COOCH$_2$C$_6$H$_5$ |
| 6-1002 | Cl | Cl | H | COOCH$_2$C$_6$H$_5$ |
| 6-1003 | H | F | H | COOCH$_2$CH$_2$Cl |
| 6-1004 | H | Cl | H | COOCH$_2$CH$_2$Cl |
| 6-1005 | F | F | H | COOCH$_2$CH$_2$Cl |
| 6-1006 | F | Cl | H | COOCH$_2$CH$_2$Cl |
| 6-1007 | Cl | F | H | COOCH$_2$CH$_2$Cl |
| 6-1008 | Cl | Cl | H | COOCH$_2$CH$_2$Cl |
| 6-1009 | H | F | H | COOCH$_2$CH$_2$Br |
| 6-1010 | H | Cl | H | COOCH$_2$CH$_2$Br |
| 6-1011 | F | F | H | COOCH$_2$CH$_2$Br |
| 6-1012 | F | Cl | H | COOCH$_2$CH$_2$Br |
| 6-1013 | Cl | F | H | COOCH$_2$CH$_2$Br |
| 6-1014 | Cl | Cl | H | COOCH$_2$CH$_2$Br |
| 6-1015 | H | F | H | CONH$_2$ |
| 6-1016 | H | Cl | H | CONH$_2$ |
| 6-1017 | F | F | H | CONH$_2$ |
| 6-1018 | F | Cl | H | CONH$_2$ |
| 6-1019 | Cl | F | H | CONH$_2$ |
| 6-1020 | Cl | Cl | H | CONH$_2$ |
| 6-1021 | H | F | H | CONHCH$_3$ |
| 6-1022 | H | Cl | H | CONHCH$_3$ |
| 6-1023 | F | F | H | CONHCH$_3$ |
| 6-1024 | F | Cl | H | CONHCH$_3$ |
| 6-1025 | Cl | F | H | CONHCH$_3$ |

TABLE 104

|  | X | Y | R¹ | B |
|---|---|---|---|---|
| 6-1026 | Cl | Cl | H | CONHCH$_3$ |
| 6-1027 | H | F | H | CONHC$_2$H$_5$ |
| 6-1028 | H | Cl | H | CONHC$_2$H$_5$ |
| 6-1029 | F | F | H | CONHC$_2$H$_5$ |
| 6-1030 | F | Cl | H | CONHC$_2$H$_5$ |
| 6-1031 | Cl | F | H | CONHC$_2$H$_5$ |
| 6-1032 | Cl | Cl | H | CONHC$_2$H$_5$ |
| 6-1033 | H | F | H | CON(CH$_3$)$_2$ |
| 6-1034 | H | Cl | H | CON(CH$_3$)$_2$ |
| 6-1035 | F | F | H | CON(CH$_3$)$_2$ |
| 6-1036 | F | Cl | H | CON(CH$_3$)$_2$ |
| 6-1037 | Cl | F | H | CON(CH$_3$)$_2$ |

TABLE 104-continued

|  | X | Y | R¹ | B |
|---|---|---|---|---|
| 6-1038 | Cl | Cl | H | CON(CH$_3$)$_2$ |
| 6-1039 | H | F | H | CON(C$_2$H$_5$)$_2$ |
| 6-1040 | H | Cl | H | CON(C$_2$H$_5$)$_2$ |
| 6-1041 | F | F | H | CON(C$_2$H$_5$)$_2$ |
| 6-1042 | F | Cl | H | CON(C$_2$H$_5$)$_2$ |
| 6-1043 | Cl | F | H | CON(C$_2$H$_5$)$_2$ |
| 6-1044 | Cl | Cl | H | CON(C$_2$H$_5$)$_2$ |
| 6-1045 | H | F | H | CON(CH$_3$)(C$_2$H$_5$) |
| 6-1046 | H | Cl | H | CON(CH$_3$)(C$_2$H$_5$) |
| 6-1047 | F | F | H | CON(CH$_3$)(C$_2$H$_5$) |
| 6-1048 | F | Cl | H | CON(CH$_3$)(C$_2$H$_5$) |
| 6-1049 | Cl | F | H | CON(CH$_3$)(C$_2$H$_5$) |
| 6-1050 | Cl | Cl | H | CON(CH$_3$)(C$_2$H$_5$) |

TABLE 105

|  | X | Y | R¹ | B |
|---|---|---|---|---|
| 6-1051 | H | F | H | COCH$_3$ |
| 6-1052 | H | Cl | H | COCH$_3$ |
| 6-1053 | F | F | H | COCH$_3$ |
| 6-1054 | F | Cl | H | COCH$_3$ |
| 6-1055 | Cl | F | H | COCH$_3$ |
| 6-1056 | Cl | Cl | H | COCH$_3$ |
| 6-1057 | H | F | H | COC$_2$H$_5$ |
| 6-1058 | H | Cl | H | COC$_2$H$_5$ |
| 6-1059 | F | F | H | COC$_2$H$_5$ |
| 6-1060 | F | Cl | H | COC$_2$H$_5$ |
| 6-1061 | Cl | F | H | COC$_2$H$_5$ |
| 6-1062 | Cl | Cl | H | COC$_2$H$_5$ |
| 6-1063 | H | F | H | COCH$_2$Cl |
| 6-1064 | H | Cl | H | COCH$_2$Cl |
| 6-1065 | F | F | H | COCH$_2$Cl |
| 6-1066 | F | Cl | H | COCH$_2$Cl |
| 6-1067 | Cl | F | H | COCH$_2$Cl |
| 6-1068 | Cl | Cl | H | COCH$_2$Cl |
| 6-1069 | H | F | H | CHO |
| 6-1070 | H | Cl | H | CHO |
| 6-1071 | F | F | H | CHO |
| 6-1072 | F | Cl | H | CHO |
| 6-1073 | Cl | F | H | CHO |
| 6-1074 | Cl | Cl | H | CHO |
| 6-1075 | H | F | H | CH$_2$CH$_2$COOH |

TABLE 106

|  | X | Y | R¹ | B |
|---|---|---|---|---|
| 6-1076 | H | Cl | H | CH$_2$CH$_2$COOH |
| 6-1077 | F | F | H | CH$_2$CH$_2$COOH |
| 6-1078 | F | Cl | H | CH$_2$CH$_2$COOH |
| 6-1079 | Cl | F | H | CH$_2$CH$_2$COOH |
| 6-1080 | Cl | Cl | H | CH$_2$CH$_2$COOH |
| 6-1081 | H | F | H | CH$_2$CH$_2$COOCH$_3$ |
| 6-1082 | H | Cl | H | CH$_2$CH$_2$COOCH$_3$ |
| 6-1083 | F | F | H | CH$_2$CH$_2$COOCH$_3$ |
| 6-1084 | F | Cl | H | CH$_2$CH$_2$COOCH$_3$ |
| 6-1085 | Cl | F | H | CH$_2$CH$_2$COOCH$_3$ |
| 6-1086 | Cl | Cl | H | CH$_2$CH$_2$COOCH$_3$ |
| 6-1087 | H | F | H | CH$_2$CH$_2$COOC$_2$H$_5$ |
| 6-1088 | H | Cl | H | CH$_2$CH$_2$COOC$_2$H$_5$ |
| 6-1089 | F | F | H | CH$_2$CH$_2$COOC$_2$H$_5$ |
| 6-1090 | F | Cl | H | CH$_2$CH$_2$COOC$_2$H$_5$ |
| 6-1091 | Cl | F | H | CH$_2$CH$_2$COOC$_2$H$_5$ |
| 6-1092 | Cl | Cl | H | CH$_2$CH$_2$COOC$_2$H$_5$ |
| 6-1093 | H | F | H | CH$_2$CHClCOOCH$_3$ |
| 6-1094 | H | Cl | H | CH$_2$CHClCOOCH$_3$ |
| 6-1095 | F | F | H | CH$_2$CHClCOOCH$_3$ |
| 6-1096 | F | Cl | H | CH$_2$CHClCOOCH$_3$ |
| 6-1097 | Cl | F | H | CH$_2$CHClCOOCH$_3$ |
| 6-1098 | Cl | Cl | H | CH$_2$CHClCOOCH$_3$ |

TABLE 106-continued

| | X | Y | R¹ | B |
|---|---|---|---|---|
| 6-1099 | H | F | H | CH$_2$CHClCOOC$_2$H$_5$ |
| 6-1100 | H | Cl | H | CH$_2$CHClCOOC$_2$H$_5$ |

TABLE 107

| | X | Y | R¹ | B |
|---|---|---|---|---|
| 6-1101 | F | F | H | CH$_2$CHClCOOC$_2$H$_5$ |
| 6-1102 | F | Cl | H | CH$_2$CHClCOOC$_2$H$_5$ |
| 6-1103 | Cl | F | H | CH$_2$CHClCOOC$_2$H$_5$ |
| 6-1104 | Cl | Cl | H | CH$_2$CHClCOOC$_2$H$_5$ |
| 6-1105 | H | F | H | CH=CHCOOCH$_3$ |
| 6-1106 | H | Cl | H | CH=CHCOOCH$_3$ |
| 6-1107 | F | F | H | CH=CHCOOCH$_3$ |
| 6-1108 | F | Cl | H | CH=CHCOOCH$_3$ |
| 6-1109 | Cl | F | H | CH=CHCOOCH$_3$ |
| 6-1110 | Cl | Cl | H | CH=CHCOOCH$_3$ |
| 6-1111 | H | F | H | CH=CHCOOC$_2$H$_5$ |
| 6-1112 | H | Cl | H | CH=CHCOOC$_2$H$_5$ |
| 6-1113 | F | F | H | CH=CHCOOC$_2$H$_5$ |
| 6-1114 | F | Cl | H | CH=CHCOOC$_2$H$_5$ |
| 6-1115 | Cl | F | H | CH=CHCOOC$_2$H$_5$ |
| 6-1116 | Cl | Cl | H | CH=CHCOOC$_2$H$_5$ |
| 6-1117 | H | F | H | C(CH$_3$)=NOH |
| 6-1118 | H | Cl | H | C(CH$_3$)=NOH |
| 6-1119 | F | F | H | C(CH$_3$)=NOH |
| 6-1120 | F | Cl | H | C(CH$_3$)=NOH |
| 6-1121 | Cl | F | H | C(CH$_3$)=NOH |
| 6-1122 | Cl | Cl | H | C(CH$_3$)=NOH |
| 6-1123 | H | F | H | C(CH$_3$)=NOCH$_3$ |
| 6-1124 | H | Cl | H | C(CH$_3$)=NOCH$_3$ |
| 6-1125 | F | F | H | C(CH$_3$)=NOCH$_3$ |

TABLE 108

| | X | Y | R¹ | B |
|---|---|---|---|---|
| 6-1126 | F | Cl | H | C(CH$_3$)=NOCH$_3$ |
| 6-1127 | Cl | F | H | C(CH$_3$)=NOCH$_3$ |
| 6-1128 | Cl | Cl | H | C(CH$_3$)=NOCH$_3$ |
| 6-1129 | H | F | H | C(CH$_3$)=NOC$_2$H$_5$ |
| 6-1130 | H | Cl | H | C(CH$_3$)=NOC$_2$H$_5$ |
| 6-1131 | F | F | H | C(CH$_3$)=NOC$_2$H$_5$ |
| 6-1132 | F | Cl | H | C(CH$_3$)=NOC$_2$H$_5$ |
| 6-1133 | Cl | F | H | C(CH$_3$)=NOC$_2$H$_5$ |
| 6-1134 | Cl | Cl | H | C(CH$_3$)=NOC$_2$H$_5$ |
| 6-1135 | H | F | H | C(CH$_3$)=NOiC$_3$H$_7$ |
| 6-1136 | H | Cl | H | C(CH$_3$)=NOiC$_3$H$_7$ |
| 6-1137 | F | F | H | C(CH$_3$)=NOiC$_3$H$_7$ |
| 6-1138 | F | Cl | H | C(CH$_3$)=NOiC$_3$H$_7$ |
| 6-1139 | Cl | F | H | C(CH$_3$)=NOiC$_3$H$_7$ |
| 6-1140 | Cl | Cl | H | C(CH$_3$)=NOiC$_3$H$_7$ |
| 6-1141 | H | F | H | C(CH$_3$)=NNH$_2$ |
| 6-1142 | H | Cl | H | C(CH$_3$)=NNH$_2$ |
| 6-1143 | F | F | H | C(CH$_3$)=NNH$_2$ |
| 6-1144 | F | Cl | H | C(CH$_3$)=NNH$_2$ |
| 6-1145 | Cl | F | H | C(CH$_3$)=NNH$_2$ |
| 6-1146 | Cl | Cl | H | C(CH$_3$)=NNH$_2$ |
| 6-1147 | H | F | H | C(CH$_3$)=NNHCH$_3$ |
| 6-1148 | H | Cl | H | C(CH$_3$)=NNHCH$_3$ |
| 6-1149 | F | F | H | C(CH$_3$)=NNHCH$_3$ |
| 6-1150 | F | Cl | H | C(CH$_3$)=NNHCH$_3$ |

TABLE 109

| | X | Y | R¹ | B |
|---|---|---|---|---|
| 6-1151 | Cl | F | H | C(CH$_3$)=NNHCH$_3$ |
| 6-1152 | Cl | Cl | H | C(CH$_3$)=NNHCH$_3$ |
| 6-1153 | H | F | H | C(CH$_3$)=NN(CH$_3$)$_2$ |

TABLE 109-continued

| | X | Y | R¹ | B |
|---|---|---|---|---|
| 6-1154 | H | Cl | H | C(CH$_3$)=NN(CH$_3$)$_2$ |
| 6-1155 | F | F | H | C(CH$_3$)=NN(CH$_3$)$_2$ |
| 6-1156 | F | Cl | H | C(CH$_3$)=NN(CH$_3$)$_2$ |
| 6-1157 | Cl | F | H | C(CH$_3$)=NN(CH$_3$)$_2$ |
| 6-1158 | Cl | Cl | H | C(CH$_3$)=NN(CH$_3$)$_2$ |
| 6-1159 | H | F | H | C(CH$_3$)=NNHC$_2$H$_5$ |
| 6-1160 | H | Cl | H | C(CH$_3$)=NNHC$_2$H$_5$ |
| 6-1161 | F | F | H | C(CH$_3$)=NNHC$_2$H$_5$ |
| 6-1162 | F | Cl | H | C(CH$_3$)=NNHC$_2$H$_5$ |
| 6-1163 | Cl | F | H | C(CH$_3$)=NNHC$_2$H$_5$ |
| 6-1164 | Cl | Cl | H | C(CH$_3$)=NNHC$_2$H$_5$ |
| 6-1165 | H | F | H | C(CH$_3$)=NN(C$_2$H$_5$)$_2$ |
| 6-1166 | H | Cl | H | C(CH$_3$)=NN(C$_2$H$_5$)$_2$ |
| 6-1167 | F | F | H | C(CH$_3$)=NN(C$_2$H$_5$)$_2$ |
| 6-1168 | F | Cl | H | C(CH$_3$)=NN(C$_2$H$_5$)$_2$ |
| 6-1169 | Cl | F | H | C(CH$_3$)=NN(C$_2$H$_5$)$_2$ |
| 6-1170 | Cl | Cl | H | C(CH$_3$)=NN(C$_2$H$_5$)$_2$ |
| 6-1171 | H | F | H | C(C$_2$H$_5$)=NNH$_2$ |
| 6-1172 | H | Cl | H | C(C$_2$H$_5$)=NNH$_2$ |
| 6-1173 | F | F | H | C(C$_2$H$_5$)=NNH$_2$ |
| 6-1174 | F | Cl | H | C(C$_2$H$_5$)=NNH$_2$ |
| 6-1175 | Cl | F | H | C(C$_2$H$_5$)=NNH$_2$ |

TABLE 110

| | X | Y | R¹ | B |
|---|---|---|---|---|
| 6-1176 | Cl | Cl | H | C(C$_2$H$_5$)=NNH$_2$ |
| 6-1177 | H | F | H | C(C$_2$H$_5$)=NNHCH$_3$ |
| 6-1178 | H | Cl | H | C(C$_2$H$_5$)=NNHCH$_3$ |
| 6-1179 | F | F | H | C(C$_2$H$_5$)=NNHCH$_3$ |
| 6-1180 | F | Cl | H | C(C$_2$H$_5$)=NNHCH$_3$ |
| 6-1181 | Cl | F | H | C(C$_2$H$_5$)=NNHCH$_3$ |
| 6-1182 | Cl | Cl | H | C(C$_2$H$_5$)=NNHCH$_3$ |
| 6-1183 | H | F | H | C(C$_2$H$_5$)=NN(CH$_3$)$_2$ |
| 6-1184 | H | Cl | H | C(C$_2$H$_5$)=NN(CH$_3$)$_2$ |
| 6-1185 | F | F | H | C(C$_2$H$_5$)=NN(CH$_3$)$_2$ |
| 6-1186 | F | Cl | H | C(C$_2$H$_5$)=NN(CH$_3$)$_2$ |
| 6-1187 | Cl | F | H | C(C$_2$H$_5$)=NN(CH$_3$)$_2$ |
| 6-1188 | Cl | Cl | H | C(C$_2$H$_5$)=NN(CH$_3$)$_2$ |
| 6-1189 | H | F | H | C(C$_2$H$_5$)=NNHC$_2$H$_5$ |
| 6-1190 | H | Cl | H | C(C$_2$H$_5$)=NNHC$_2$H$_5$ |
| 6-1191 | F | F | H | C(C$_2$H$_5$)=NNHC$_2$H$_5$ |
| 6-1192 | F | Cl | H | C(C$_2$H$_5$)=NNHC$_2$H$_5$ |
| 6-1193 | Cl | F | H | C(C$_2$H$_5$)=NNHC$_2$H$_5$ |
| 6-1194 | Cl | Cl | H | C(C$_2$H$_5$)=NNHC$_2$H$_5$ |
| 6-1195 | H | F | H | C(C$_2$H$_5$)=NN(C$_2$H$_5$)$_2$ |
| 6-1196 | H | Cl | H | C(C$_2$H$_5$)=NN(C$_2$H$_5$)$_2$ |
| 6-1197 | F | F | H | C(C$_2$H$_5$)=NN(C$_2$H$_5$)$_2$ |
| 6-1198 | F | Cl | H | C(C$_2$H$_5$)=NN(C$_2$H$_5$)$_2$ |
| 6-1199 | Cl | F | H | C(C$_2$H$_5$)=NN(C$_2$H$_5$)$_2$ |
| 6-1200 | Cl | Cl | H | C(C$_2$H$_5$)=NN(C$_2$H$_5$)$_2$ |

TABLE 111

| | X | Y | R¹ | B |
|---|---|---|---|---|
| 6-1201 | H | F | H | C(CH$_3$)(OCH$_3$)$_2$ |
| 6-1202 | H | Cl | H | C(CH$_3$)(OCH$_3$)$_2$ |
| 6-1203 | F | F | H | C(CH$_3$)(OCH$_3$)$_2$ |
| 6-1204 | F | Cl | H | C(CH$_3$)(OCH$_3$)$_2$ |
| 6-1205 | Cl | F | H | C(CH$_3$)(OCH$_3$)$_2$ |
| 6-1206 | Cl | Cl | H | C(CH$_3$)(OCH$_3$)$_2$ |
| 6-1207 | H | F | H | C(CH$_3$)(OC$_2$H$_5$)$_2$ |
| 6-1208 | H | Cl | H | C(CH$_3$)(OC$_2$H$_5$)$_2$ |
| 6-1209 | F | F | H | C(CH$_3$)(OC$_2$H$_5$)$_2$ |
| 6-1210 | F | Cl | H | C(CH$_3$)(OC$_2$H$_5$)$_2$ |
| 6-1211 | Cl | F | H | C(CH$_3$)(OC$_2$H$_5$)$_2$ |
| 6-1212 | Cl | Cl | H | C(CH$_3$)(OC$_2$H$_5$)$_2$ |
| 6-1213 | H | F | H | C(CH$_3$)(OiC$_3$H$_7$)$_2$ |
| 6-1214 | H | Cl | H | C(CH$_3$)(OiC$_3$H$_7$)$_2$ |
| 6-1215 | F | F | H | C(CH$_3$)(OiC$_3$H$_7$)$_2$ |

TABLE 111-continued

| | X | Y | R$^1$ | B |
|---|---|---|---|---|
| 6-1216 | F | Cl | H | C(CH$_3$)(OiC$_3$H$_7$)$_2$ |
| 6-1217 | Cl | F | H | C(CH$_3$)(OiC$_3$H$_7$)$_2$ |
| 6-1218 | Cl | Cl | H | C(CH$_3$)(OiC$_3$H$_7$)$_2$ |
| 6-1219 | H | F | H | C(CH$_3$)(OCH$_2$CH$_2$O) |
| 6-1220 | H | Cl | H | C(CH$_3$)(OCH$_2$CH$_2$O) |
| 6-1221 | F | F | H | C(CH$_3$)(OCH$_2$CH$_2$O) |
| 6-1222 | F | Cl | H | C(CH$_3$)(OCH$_2$CH$_2$O) |
| 6-1223 | Cl | F | H | C(CH$_3$)(OCH$_2$CH$_2$O) |
| 6-1224 | Cl | Cl | H | C(CH$_3$)(OCH$_2$CH$_2$O) |
| 6-1225 | H | F | H | C(CH$_3$)(OCH$_2$CH$_2$CH$_2$O) |

TABLE 112

| | X | Y | R$^1$ | B |
|---|---|---|---|---|
| 6-1226 | H | Cl | H | C(CH$_3$)(OCH$_2$CH$_2$CH$_2$O) |
| 6-1227 | F | F | H | C(CH$_3$)(OCH$_2$CH$_2$CH$_2$O) |
| 6-1228 | F | Cl | H | C(CH$_3$)(OCH$_2$CH$_2$CH$_2$O) |
| 6-1229 | Cl | F | H | C(CH$_3$)(OCH$_2$CH$_2$CH$_2$O) |
| 6-1230 | Cl | Cl | H | C(CH$_3$)(OCH$_2$CH$_2$CH$_2$O) |
| 6-1231 | H | F | H | C(C$_2$H$_5$)(OCH$_2$CH$_2$O) |
| 6-1232 | H | Cl | H | C(C$_2$H$_5$)(OCH$_2$CH$_2$O) |
| 6-1233 | F | F | H | C(C$_2$H$_5$)(OCH$_2$CH$_2$O) |
| 6-1234 | F | Cl | H | C(C$_2$H$_5$)(OCH$_2$CH$_2$O) |
| 6-1235 | Cl | F | H | C(C$_2$H$_5$)(OCH$_2$CH$_2$O) |
| 6-1236 | Cl | Cl | H | C(C$_2$H$_5$)(OCH$_2$CH$_2$O) |
| 6-1237 | H | F | H | C(C$_2$H$_5$)(OCH$_2$CH$_2$CH$_2$O) |
| 6-1238 | H | Cl | H | C(C$_2$H$_5$)(OCH$_2$CH$_2$CH$_2$O) |
| 6-1239 | F | F | H | C(C$_2$H$_5$)(OCH$_2$CH$_2$CH$_2$O) |
| 6-1240 | F | Cl | H | C(C$_2$H$_5$)(OCH$_2$CH$_2$CH$_2$O) |
| 6-1241 | Cl | F | H | C(C$_2$H$_5$)(OCH$_2$CH$_2$CH$_2$O) |
| 6-1242 | Cl | Cl | H | C(C$_2$H$_5$)(OCH$_2$CH$_2$CH$_2$O) |
| 6-1243 | H | F | H | OCH$_2$CH(CH$_3$)$_2$ |
| 6-1244 | H | Cl | H | OCH$_2$CH(CH$_3$)$_2$ |
| 6-1245 | F | F | H | OCH$_2$CH(CH$_3$)$_2$ |
| 6-1246 | F | Cl | H | OCH$_2$CH(CH$_3$)$_2$ |
| 6-1247 | Cl | F | H | OCH$_2$CH(CH$_3$)$_2$ |
| 6-1248 | Cl | Cl | H | OCH$_2$CH(CH$_3$)$_2$ |
| 6-1249 | H | F | H | OCH$_2$CH$_2$F |
| 6-1250 | H | Cl | H | OCH$_2$CH$_2$F |

TABLE 113

| | X | Y | R$^1$ | B |
|---|---|---|---|---|
| 6-1251 | F | F | H | OCH$_2$CH$_2$F |
| 6-1252 | F | Cl | H | OCH$_2$CH$_2$F |
| 6-1253 | Cl | F | H | OCH$_2$CH$_2$F |
| 6-1254 | Cl | Cl | H | OCH$_2$CH$_2$F |
| 6-1255 | H | Cl | H | CH$_2$OH |
| 6-1256 | F | Cl | H | CH$_2$OH |
| 6-1257 | H | Cl | H | CH$_2$OCOCH$_3$ |
| 6-1258 | F | Cl | H | CH$_2$OCOCH$_3$ |

Compounds of the general formula:

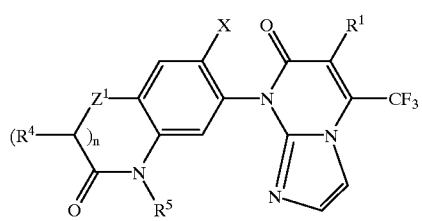

TABLE 114

| | X | Z$^1$ | n | R$^1$ | R$^4$ | R$^5$ |
|---|---|---|---|---|---|---|
| 7-1 | H | O | 1 | H | H | H |
| 7-2 | F | O | 1 | H | H | H |
| 7-3 | H | O | 1 | H | H | CH$_3$ |
| 7-4 | F | O | 1 | H | H | CH$_3$ |
| 7-5 | H | O | 1 | H | H | C$_2$H$_5$ |
| 7-6 | F | O | 1 | H | H | C$_2$H$_5$ |
| 7-7 | H | O | 1 | H | H | nC$_3$H$_7$ |
| 7-8 | F | O | 1 | H | H | nC$_3$H$_7$ |
| 7-9 | H | O | 1 | H | H | nC$_4$H$_9$ |
| 7-10 | F | O | 1 | H | H | nC$_4$H$_9$ |
| 7-11 | H | O | 1 | H | H | nC$_5$H$_{11}$ |
| 7-12 | F | O | 1 | H | H | nC$_5$H$_{11}$ |
| 7-13 | H | O | 1 | H | H | iC$_3$H$_7$ |
| 7-14 | F | O | 1 | H | H | iC$_3$H$_7$ |
| 7-15 | H | O | 1 | H | H | CH$_2$CH$_2$Cl |
| 7-16 | F | O | 1 | H | H | CH$_2$CH$_2$Cl |
| 7-17 | H | O | 1 | H | H | CH$_2$CH$_2$Br |
| 7-18 | F | O | 1 | H | H | CH$_2$CH$_2$Br |
| 7-19 | H | O | 1 | H | H | CH$_2$CH=CH$_2$ |
| 7-20 | F | O | 1 | H | H | CH$_2$CH=CH$_2$ |
| 7-21 | H | O | 1 | H | H | CH(CH$_3$)CH=CH$_2$ |
| 7-22 | F | O | 1 | H | H | CH(CH$_3$)CH=CH$_2$ |
| 7-23 | H | O | 1 | H | H | CH$_2$CCl=CH$_2$ |
| 7-24 | F | O | 1 | H | H | CH$_2$CCl=CH$_2$ |
| 7-25 | H | O | 1 | H | H | CH$_2$C≡CH |

TABLE 115

| | X | Z$^1$ | n | R$^1$ | R$^4$ | R$^5$ |
|---|---|---|---|---|---|---|
| 7-26 | F | O | 1 | H | H | CH$_2$C≡CH |
| 7-27 | H | O | 1 | H | H | CH(CH$_3$)C≡CH |
| 7-28 | F | O | 1 | H | H | CH(CH$_3$)C≡CH |
| 7-29 | H | O | 1 | H | H | CH$_2$CN |
| 7-30 | F | O | 1 | H | H | CH$_2$CN |
| 7-31 | H | O | 1 | H | H | CH$_2$OCH$_3$ |
| 7-32 | F | O | 1 | H | H | CH$_2$OCH$_3$ |
| 7-33 | H | O | 1 | H | H | CH$_2$OC$_2$H$_5$ |
| 7-34 | F | O | 1 | H | H | CH$_2$OC$_2$H$_5$ |
| 7-35 | H | O | 1 | H | H | CH$_2$COOH |
| 7-36 | F | O | 1 | H | H | CH$_2$COOH |
| 7-37 | H | O | 1 | H | H | CH$_2$COOCH$_3$ |
| 7-38 | F | O | 1 | H | H | CH$_2$COOCH$_3$ |
| 7-39 | H | O | 1 | H | H | CH$_2$COOC$_2$H$_5$ |
| 7-40 | F | O | 1 | H | H | CH$_2$COOC$_2$H$_5$ |
| 7-41 | H | O | 1 | H | H | CH$_2$COOnC$_3$H$_7$ |
| 7-42 | F | O | 1 | H | H | CH$_2$COOnC$_3$H$_7$ |
| 7-43 | H | O | 1 | H | H | CH$_2$COOnC$_4$H$_9$ |
| 7-44 | F | O | 1 | H | H | CH$_2$COOnC$_4$H$_9$ |
| 7-45 | H | O | 1 | H | H | CH$_2$COOnC$_5$H$_{11}$ |
| 7-46 | F | O | 1 | H | H | CH$_2$COOnC$_5$H$_{11}$ |
| 7-47 | H | O | 1 | H | H | CH$_2$COOiC$_3$H$_7$ |
| 7-48 | F | O | 1 | H | H | CH$_2$COOiC$_3$H$_7$ |
| 7-49 | H | O | 1 | H | H | CH$_2$COOcC$_5$H$_9$ |
| 7-50 | F | O | 1 | H | H | CH$_2$COOcC$_5$H$_9$ |

TABLE 116

| | X | Z$^1$ | n | R$^1$ | R$^4$ | R$^5$ |
|---|---|---|---|---|---|---|
| 7-51 | H | O | 1 | H | H | CH$_2$COOcC$_6$H$_{11}$ |
| 7-52 | F | O | 1 | H | H | CH$_2$COOcC$_6$H$_{11}$ |
| 7-53 | H | O | 1 | H | H | CH(CH$_3$)COOH |
| 7-54 | F | O | 1 | H | H | CH(CH$_3$)COOH |
| 7-55 | H | O | 1 | H | H | CH(CH$_3$)COOCH$_3$ |
| 7-56 | F | O | 1 | H | H | CH(CH$_3$)COOCH$_3$ |
| 7-57 | H | O | 1 | H | H | CH(CH$_3$)COOC$_2$H$_5$ |
| 7-58 | F | O | 1 | H | H | CH(CH$_3$)COOC$_2$H$_5$ |
| 7-59 | H | O | 1 | H | H | CH(CH$_3$)COOnC$_3$H$_7$ |
| 7-60 | F | O | 1 | H | H | CH(CH$_3$)COOnC$_3$H$_7$ |
| 7-61 | H | O | 1 | H | H | CH(CH$_3$)COOnC$_4$H$_9$ |
| 7-62 | F | O | 1 | H | H | CH(CH$_3$)COOnC$_4$H$_9$ |

TABLE 116-continued

|  | X | $Z^1$ | n | $R^1$ | $R^4$ | $R^5$ |
|---|---|---|---|---|---|---|
| 7-63 | H | O | 1 | H | H | $CH(CH_3)COOnC_5H_{11}$ |
| 7-64 | F | O | 1 | H | H | $CH(CH_3)COOnC_5H_{11}$ |
| 7-65 | H | O | 1 | H | H | $CH(CH_3)COOiC_3H_7$ |
| 7-66 | F | O | 1 | H | H | $CH(CH_3)COOiC_3H_7$ |
| 7-67 | H | O | 1 | H | H | $CH(CH_3)COOcC_5H_9$ |
| 7-68 | F | O | 1 | H | H | $CH(CH_3)COOcC_5H_9$ |
| 7-69 | H | O | 1 | H | H | $CH(CH_3)COOcC_6H_{11}$ |
| 7-70 | F | O | 1 | H | H | $CH(CH_3)COOcC_6H_{11}$ |
| 7-71 | H | O | 1 | H | $CH_3$ | H |
| 7-72 | F | O | 1 | H | $CH_3$ | H |
| 7-73 | H | O | 1 | H | $CH_3$ | $CH_3$ |
| 7-74 | F | O | 1 | H | $CH_3$ | $CH_3$ |
| 7-75 | H | O | 1 | H | $CH_3$ | $C_2H_5$ |

TABLE 117

|  | X | $Z^1$ | n | $R^1$ | $R^4$ | $R^5$ |
|---|---|---|---|---|---|---|
| 7-76 | F | O | 1 | H | $CH_3$ | $C_2H_5$ |
| 7-77 | H | O | 1 | H | $CH_3$ | $nC_3H_7$ |
| 7-78 | F | O | 1 | H | $CH_3$ | $nC_3H_7$ |
| 7-79 | H | O | 1 | H | $CH_3$ | $nC_4H_9$ |
| 7-80 | F | O | 1 | H | $CH_3$ | $nC_4H_9$ |
| 7-81 | H | O | 1 | H | $CH_3$ | $nC_5H_{11}$ |
| 7-82 | F | O | 1 | H | $CH_3$ | $nC_5H_{11}$ |
| 7-83 | H | O | 1 | H | $CH_3$ | $iC_3H_7$ |
| 7-84 | F | O | 1 | H | $CH_3$ | $iC_3H_7$ |
| 7-85 | H | O | 1 | H | $CH_3$ | $CH_2CH_2Cl$ |
| 7-86 | F | O | 1 | H | $CH_3$ | $CH_2CH_2Cl$ |
| 7-87 | H | O | 1 | H | $CH_3$ | $CH_2CH_2Br$ |
| 7-88 | F | O | 1 | H | $CH_3$ | $CH_2CH_2Br$ |
| 7-89 | H | O | 1 | H | $CH_3$ | $CH_2CH=CH_2$ |
| 7-90 | F | O | 1 | H | $CH_3$ | $CH_2CH=CH_2$ |
| 7-91 | H | O | 1 | H | $CH_3$ | $CH(CH_3)CH=CH_2$ |
| 7-92 | F | O | 1 | H | $CH_3$ | $CH(CH_3)CH=CH_2$ |
| 7-93 | H | O | 1 | H | $CH_3$ | $CH_2CCl=CH_2$ |
| 7-94 | F | O | 1 | H | $CH_3$ | $CH_2CCl=CH_2$ |
| 7-95 | H | O | 1 | H | $CH_3$ | $CH_2C\equiv CH$ |
| 7-96 | F | O | 1 | H | $CH_3$ | $CH_2C\equiv CH$ |
| 7-97 | H | O | 1 | H | $CH_3$ | $CH(CH_3)C\equiv CH$ |
| 7-98 | F | O | 1 | H | $CH_3$ | $CH(CH_3)C\equiv CH$ |
| 7-99 | H | O | 1 | H | $CH_3$ | $CH_2CN$ |
| 7-100 | F | O | 1 | H | $CH_3$ | $CH_2CN$ |

TABLE 118

|  | X | $Z^1$ | n | $R^1$ | $R^4$ | $R^5$ |
|---|---|---|---|---|---|---|
| 7-101 | H | O | 1 | H | $CH_3$ | $CH_2OCH_3$ |
| 7-102 | F | O | 1 | H | $CH_3$ | $CH_2OCH_3$ |
| 7-103 | H | O | 1 | H | $CH_3$ | $CH_2OC_2H_5$ |
| 7-104 | F | O | 1 | H | $CH_3$ | $CH_2OC_2H_5$ |
| 7-105 | H | O | 0 | H | — | H |
| 7-106 | F | O | 0 | H | — | H |
| 7-107 | H | O | 0 | H | — | $CH_3$ |
| 7-108 | F | O | 0 | H | — | $CH_3$ |
| 7-109 | H | O | 0 | H | — | $C_2H_5$ |
| 7-110 | F | O | 0 | H | — | $C_2H_5$ |
| 7-111 | H | O | 0 | H | — | $nC_3H_7$ |
| 7-112 | F | O | 0 | H | — | $nC_3H_7$ |
| 7-113 | H | O | 0 | H | — | $nC_4H_9$ |
| 7-114 | F | O | 0 | H | — | $nC_4H_9$ |
| 7-115 | H | O | 0 | H | — | $nC_5H_{11}$ |
| 7-116 | F | O | 0 | H | — | $nC_5H_{11}$ |
| 7-117 | H | O | 0 | H | — | $iC_3H_7$ |
| 7-118 | F | O | 0 | H | — | $iC_3H_7$ |
| 7-119 | H | O | 0 | H | — | $CH_2CH_2Cl$ |
| 7-120 | F | O | 0 | H | — | $CH_2CH_2Cl$ |
| 7-121 | H | O | 0 | H | — | $CH_2CH_2Br$ |
| 7-122 | F | O | 0 | H | — | $CH_2CH_2Br$ |
| 7-123 | H | O | 0 | H | — | $CH_2CH=CH_2$ |

TABLE 118-continued

|  | X | $Z^1$ | n | $R^1$ | $R^4$ | $R^5$ |
|---|---|---|---|---|---|---|
| 7-124 | F | O | 0 | H | — | $CH_2CH=CH_2$ |
| 7-125 | H | O | 0 | H | — | $CH(CH_3)CH=CH_2$ |

TABLE 119

|  | X | $Z^1$ | n | $R^1$ | $R^4$ | $R^5$ |
|---|---|---|---|---|---|---|
| 7-126 | F | O | 0 | H | — | $CH(CH_3)CH=CH_2$ |
| 7-127 | H | O | 0 | H | — | $CH_2CCl=CH_2$ |
| 7-128 | F | O | 0 | H | — | $CH_2CCl=CH_2$ |
| 7-129 | H | O | 0 | H | — | $CH_2C\equiv CH$ |
| 7-130 | F | O | 0 | H | — | $CH_2C\equiv CH$ |
| 7-131 | H | O | 0 | H | — | $CH(CH_3)C\equiv CH$ |
| 7-132 | F | O | 0 | H | — | $CH(CH_3)C\equiv CH$ |
| 7-133 | H | O | 0 | H | — | $CH_2CN$ |
| 7-134 | F | O | 0 | H | — | $CH_2CN$ |
| 7-135 | H | O | 0 | H | — | $CH_2OCH_3$ |
| 7-136 | F | O | 0 | H | — | $CH_2OCH_3$ |
| 7-137 | H | O | 0 | H | — | $CH_2OC_2H_5$ |
| 7-138 | F | O | 0 | H | — | $CH_2OC_2H_5$ |
| 7-139 | H | S | 0 | H | — | H |
| 7-140 | F | S | 0 | H | — | H |
| 7-141 | H | S | 0 | H | — | $CH_3$ |
| 7-142 | F | S | 0 | H | — | $CH_3$ |
| 7-143 | H | S | 0 | H | — | $C_2H_5$ |
| 7-144 | F | S | 0 | H | — | $C_2H_5$ |
| 7-145 | H | S | 0 | H | — | $nC_3H_7$ |
| 7-146 | F | S | 0 | H | — | $nC_3H_7$ |
| 7-147 | H | S | 0 | H | — | $nC_4H_9$ |
| 7-148 | F | S | 0 | H | — | $nC_4H_9$ |
| 7-149 | H | S | 0 | H | — | $nC_5H_{11}$ |
| 7-150 | F | S | 0 | H | — | $nC_5H_{11}$ |

TABLE 120

|  | X | $Z^1$ | n | $R^1$ | $R^4$ | $R^5$ |
|---|---|---|---|---|---|---|
| 7-151 | H | S | 0 | H | — | $iC_3H_7$ |
| 7-152 | F | S | 0 | H | — | $iC_3H_7$ |
| 7-153 | H | S | 0 | H | — | $CH_2CH_2Cl$ |
| 7-154 | F | S | 0 | H | — | $CH_2CH_2Cl$ |
| 7-155 | H | S | 0 | H | — | $CH_2CH_2Br$ |
| 7-156 | F | S | 0 | H | — | $CH_2CH_2Br$ |
| 7-157 | H | S | 0 | H | — | $CH_2CH=CH_2$ |
| 7-158 | F | S | 0 | H | — | $CH_2CH=CH_2$ |
| 7-159 | H | S | 0 | H | — | $CH(CH_3)CH=CH_2$ |
| 7-160 | F | S | 0 | H | — | $CH(CH_3)CH=CH_2$ |
| 7-161 | H | S | 0 | H | — | $CH_2CCl=CH_2$ |
| 7-162 | F | S | 0 | H | — | $CH_2CCl=CH_2$ |
| 7-163 | H | S | 0 | H | — | $CH_2C\equiv CH$ |
| 7-164 | F | S | 0 | H | — | $CH_2C\equiv CH$ |
| 7-165 | H | S | 0 | H | — | $CH(CH_3)C\equiv CH$ |
| 7-166 | F | S | 0 | H | — | $CH(CH_3)C\equiv CH$ |
| 7-167 | H | S | 0 | H | — | $CH_2CN$ |
| 7-168 | F | S | 0 | H | — | $CH_2CN$ |
| 7-169 | H | S | 0 | H | — | $CH_2OCH_3$ |
| 7-170 | F | S | 0 | H | — | $CH_2OCH_3$ |
| 7-171 | H | S | 0 | H | — | $CH_2OC_2H_5$ |
| 7-172 | F | S | 0 | H | — | $CH_2OC_2H_5$ |
| 7-173 | H | S | 0 | H | — | $CH_2COOH$ |
| 7-174 | F | S | 0 | H | — | $CH_2COOH$ |
| 7-175 | H | S | 0 | H | — | $CH_2COOCH_3$ |

TABLE 121

|  | X | $Z^1$ | n | $R^1$ | $R^4$ | $R^5$ |
|---|---|---|---|---|---|---|
| 7-176 | F | S | 0 | H | — | $CH_2COOCH_3$ |
| 7-177 | H | S | 0 | H | — | $CH_2COOC_2H_5$ |
| 7-178 | F | S | 0 | H | — | $CH_2COOC_2H_5$ |

TABLE 121-continued

| | X | Z¹ | n | R¹ | R⁴ | R⁵ |
|---|---|---|---|---|---|---|
| 7-179 | H | S | 0 | H | — | $CH_2COOnC_3H_7$ |
| 7-180 | F | S | 0 | H | — | $CH_2COOnC_3H_7$ |
| 7-181 | H | S | 0 | H | — | $CH_2COOnC_4H_9$ |
| 7-182 | F | S | 0 | H | — | $CH_2COOnC_4H_9$ |
| 7-183 | H | S | 0 | H | — | $CH_2COOnC_5H_{11}$ |
| 7-184 | F | S | 0 | H | — | $CH_2COOnC_5H_{11}$ |
| 7-185 | H | S | 0 | H | — | $CH_2COOiC_3H_7$ |
| 7-186 | F | S | 0 | H | — | $CH_2COOiC_3H_7$ |
| 7-187 | H | S | 0 | H | — | $CH_2COOcC_5H_9$ |
| 7-188 | F | S | 0 | H | — | $CH_2COOcC_5H_9$ |
| 7-189 | H | S | 0 | H | — | $CH_2COOcC_6H11$ |
| 7-190 | F | S | 0 | H | — | $CH_2COOcC_6H_{11}$ |
| 7-191 | H | S | 0 | H | — | $CH(CH_3)COOH$ |
| 7-192 | F | S | 0 | H | — | $CH(CH_3)COOH$ |
| 7-193 | H | S | 0 | H | — | $CH(CH_3)COOCH_3$ |
| 7-194 | F | S | 0 | H | — | $CH(CH_3)COOCH_3$ |
| 7-195 | H | S | 0 | H | — | $CH(CH_3)COOC_2H_5$ |
| 7-196 | F | S | 0 | H | — | $CH(CH_3)COOC_2H_5$ |
| 7-197 | H | S | 0 | H | — | $CH(CH_3)COOnC_3H_7$ |
| 7-198 | F | S | 0 | H | — | $CH(CH_3)COOnC_3H_7$ |
| 7-199 | H | S | 0 | H | — | $CH(CH_3)COOnC_4H_9$ |
| 7-200 | F | S | 0 | H | — | $CH(CH_3)COOnC_4H_9$ |

TABLE 122

| | X | Z¹ | n | R¹ | R⁴ | R⁵ |
|---|---|---|---|---|---|---|
| 7-201 | H | S | 0 | H | — | $CH(CH_3)COOnC_5H_{11}$ |
| 7-202 | F | S | 0 | H | — | $CH(CH_3)COOnC_5H_{11}$ |
| 7-203 | H | S | 0 | H | — | $CH(CH_3)COOiC_3H_7$ |
| 7-204 | F | S | 0 | H | — | $CH(CH_3)COOiC_3H_7$ |
| 7-205 | H | S | 0 | H | — | $CH(CH_3)COOcC_5H_9$ |
| 7-206 | F | S | 0 | H | — | $CH(CH_3)COOcC_5H_9$ |
| 7-207 | H | S | 0 | H | — | $CH(CH_3)COOcC_6H_{11}$ |
| 7-208 | F | S | 0 | H | — | $CH(CH_3)COOcC_6H_{11}$ |

Compounds of the general formula:

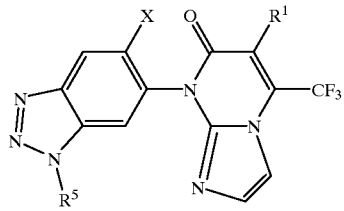

TABLE 123

| | X | R¹ | R⁵ |
|---|---|---|---|
| 10-1 | H | H | $CH_3$ |
| 10-2 | F | H | $CH_3$ |
| 10-3 | Cl | H | $CH_3$ |
| 10-4 | H | H | $C_2H_5$ |
| 10-5 | F | H | $C_2H_5$ |
| 10-6 | Cl | H | $C_2H_5$ |
| 10-7 | H | H | $nC_3H_7$ |
| 10-8 | F | H | $nC_3H_7$ |
| 10-9 | Cl | H | $nC_3H_7$ |
| 10-10 | H | H | $nC_4H_9$ |
| 10-11 | F | H | $nC_4H_9$ |
| 10-12 | Cl | H | $nC_4H_9$ |
| 10-13 | H | H | $iC_4H_9$ |
| 10-14 | F | H | $iC_4H_9$ |
| 10-15 | Cl | H | $iC_4H_9$ |
| 10-16 | H | H | $CH_2CH=CH_2$ |
| 10-17 | F | H | $CH_2CH=CH_2$ |

TABLE 123-continued

| | X | R¹ | R⁵ |
|---|---|---|---|
| 10-18 | Cl | H | $CH_2CH=CH_2$ |
| 10-19 | H | H | $CH(CH_3)CH=CH_2$ |
| 10-20 | F | H | $CH(CH_3)CH=CH_2$ |
| 10-21 | Cl | H | $CH(CH_3)CH=CH_2$ |
| 10-22 | H | H | $CH_2C\equiv CH$ |
| 10-23 | F | H | $CH_2C\equiv CH$ |
| 10-24 | Cl | H | $CH_2C\equiv CH$ |
| 10-25 | H | H | $CH(CH_3)C\equiv CH$ |

TABLE 124

| | X | R¹ | R⁵ |
|---|---|---|---|
| 10-26 | F | H | $CH(CH_3)C\equiv CH$ |
| 10-27 | Cl | H | $CH(CH_3)C\equiv CH$ |

Compounds of the general formula:

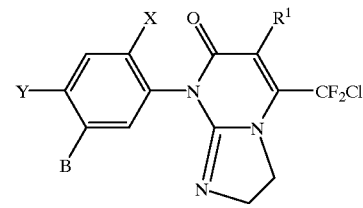

TABLE 125

| | X | Y | R¹ | B |
|---|---|---|---|---|
| 11-1 | H | F | H | H |
| 11-2 | H | Cl | H | H |
| 11-3 | H | Br | H | H |
| 11-4 | F | F | H | H |
| 11-5 | F | Cl | H | H |
| 11-6 | F | Br | H | H |
| 11-7 | Cl | F | H | H |
| 11-8 | Cl | Cl | H | H |
| 11-9 | Cl | Br | H | H |
| 11-10 | H | F | H | $NO_2$ |
| 11-11 | H | Cl | H | $NO_2$ |
| 11-12 | H | Br | H | $NO_2$ |
| 11-13 | F | F | H | $NO_2$ |
| 11-14 | F | Cl | H | $NO_2$ |
| 11-15 | F | Br | H | $NO_2$ |
| 11-16 | Cl | F | H | $NO_2$ |
| 11-17 | Cl | Cl | H | $NO_2$ |
| 11-18 | Cl | Br | H | $NO_2$ |
| 11-19 | H | F | H | $NH_2$ |
| 11-20 | H | Cl | H | $NH_2$ |
| 11-21 | H | Br | H | $NH_2$ |
| 11-22 | F | F | H | $NH_2$ |
| 11-23 | F | CL | H | $NH_2$ |
| 11-24 | F | Br | H | $NH_2$ |
| 11-25 | Cl | F | H | $NH_2$ |

TABLE 126

| | X | Y | R¹ | B |
|---|---|---|---|---|
| 11-26 | Cl | Cl | H | $NH_2$ |
| 11-27 | Cl | Br | H | $NH_2$ |
| 11-28 | H | F | H | OH |
| 11-29 | H | Cl | H | OH |
| 11-30 | H | Br | H | OH |

TABLE 126-continued

|  | X | Y | R¹ | B |
|---|---|---|---|---|
| 11-31 | F | F | H | OH |
| 11-32 | F | Cl | H | OH |
| 11-33 | F | Br | H | OH |
| 11-34 | Cl | F | H | OH |
| 11-35 | Cl | Cl | H | OH |
| 11-36 | Cl | Br | H | OH |
| 11-37 | H | F | H | SH |
| 11-38 | H | Cl | H | SH |
| 11-39 | H | Br | H | SH |
| 11-40 | F | F | H | SH |
| 11-41 | F | Cl | H | SH |
| 11-42 | F | Br | H | SH |
| 11-43 | Cl | F | H | SH |
| 11-44 | Cl | Cl | H | SH |
| 11-45 | Cl | Br | H | SH |
| 11-46 | H | F | H | SO$_2$Cl |
| 11-47 | H | Cl | H | SO$_2$Cl |
| 11-48 | H | Br | H | SO$_2$Cl |
| 11-49 | F | F | H | SO$_2$Cl |
| 11-50 | F | Cl | H | SO$_2$Cl |

TABLE 127

|  | X | Y | R¹ | B |
|---|---|---|---|---|
| 11-51 | F | Br | H | SO$_2$Cl |
| 11-52 | Cl | F | H | SO$_2$Cl |
| 11-53 | Cl | Cl | H | SO$_2$Cl |
| 11-54 | Cl | Br | H | SO$_2$Cl |
| 11-55 | H | F | H | NHCH$_3$ |
| 11-56 | H | Cl | H | NHCH$_3$ |
| 11-57 | F | F | H | NHCH$_3$ |
| 11-58 | F | Cl | H | NHCH$_3$ |
| 11-59 | Cl | F | H | NHCH$_3$ |
| 11-60 | Cl | Cl | H | NHCH$_3$ |
| 11-61 | H | F | W | NHC$_2$H$_5$ |
| 11-62 | H | Cl | H | NHC$_2$H$_5$ |
| 11-63 | F | F | H | NHC$_2$H$_5$ |
| 11-64 | F | Cl | H | NHC$_2$H$_5$ |
| 11-65 | Cl | F | H | NHC$_2$H$_5$ |
| 11-66 | Cl | Cl | H | NHC$_2$H$_5$ |
| 11-67 | H | F | H | NHCH$_2$CH=CH$_2$ |
| 11-68 | H | Cl | H | NHCH$_2$CH=CH$_2$ |
| 11-69 | F | F | H | NHCH$_2$CH=CH$_2$ |
| 11-70 | F | Cl | H | NHCH$_2$CH=CH$_2$ |
| 11-71 | Cl | F | H | NHCH$_2$CH=CH$_2$ |
| 11-72 | Cl | Cl | H | NHCH$_2$CH=CH$_2$ |
| 11-73 | H | F | H | NHCH$_2$C≡CH |
| 11-74 | H | Cl | H | NHCH$_2$C≡CH |
| 11-75 | F | F | H | NHCH$_2$C≡CH |

TABLE 128

|  | X | Y | R¹ | B |
|---|---|---|---|---|
| 11-76 | F | Cl | H | NHCH$_2$C≡CH |
| 11-77 | Cl | F | H | NHCH$_2$C≡CH |
| 11-78 | Cl | Cl | H | NHCH$_2$C≡CH |
| 11-79 | H | F | H | NHCH(CH$_3$)C≡CH |
| 11-80 | H | Cl | H | NHCH(CH$_3$)C≡CH |
| 11-81 | F | F | H | NHCH(CH$_3$)C≡CH |
| 11-82 | F | Cl | H | NHCH(CH$_3$)C≡CH |
| 11-83 | Cl | F | H | NHCH(CH$_3$)C≡CH |
| 11-84 | Cl | Cl | H | NHCH(CH$_3$)C≡CH |
| 11-85 | H | F | H | NHSO$_2$CH$_3$ |
| 11-86 | H | Cl | H | NHSO$_2$CH$_3$ |
| 11-87 | F | F | H | NHSO$_2$CH$_3$ |
| 11-88 | F | Cl | H | NHSO$_2$CH$_3$ |
| 11-89 | Cl | F | H | NHSO$_2$CH$_3$ |
| 11-90 | Cl | Cl | H | NHSO$_2$CH$_3$ |
| 11-91 | H | F | H | NHSO$_2$C$_2$H$_5$ |
| 11-92 | H | Cl | H | NHSO$_2$C$_2$H$_5$ |

TABLE 128-continued

|  | X | Y | R¹ | B |
|---|---|---|---|---|
| 11-93 | F | F | H | NHSO$_2$C$_2$H$_5$ |
| 11-94 | F | Cl | H | NHSO$_2$C$_2$H$_5$ |
| 11-95 | Cl | F | H | NHSO$_2$C$_2$H$_5$ |
| 11-96 | Cl | Cl | H | NHSO$_2$C$_2$H$_5$ |
| 11-97 | H | F | H | NHSO$_2$CH$_2$Cl |
| 11-98 | H | Cl | H | NHSO$_2$CH$_2$Cl |
| 11-99 | F | F | H | NHSO$_2$CH$_2$Cl |
| 11-100 | F | Cl | H | NHSO$_2$CH$_2$Cl |

TABLE 129

|  | X | Y | R¹ | B |
|---|---|---|---|---|
| 11-101 | Cl | F | H | NHSO$_2$CH$_2$Cl |
| 11-102 | Cl | Cl | H | NHSO$_2$CH$_2$Cl |
| 11-103 | H | F | H | NHSO$_2$CF$_3$ |
| 11-104 | H | Cl | H | NHSO$_2$CF$_3$ |
| 11-105 | F | F | H | NHSO$_2$CF$_3$ |
| 11-106 | F | Cl | H | NHSO$_2$CF$_3$ |
| 11-107 | Cl | F | H | NHSO$_2$CF$_3$ |
| 11-108 | Cl | Cl | H | NHSO$_2$CF$_3$ |
| 11-109 | H | F | H | N(SO$_2$CH$_3$)$_2$ |
| 11-110 | H | Cl | H | N(SO$_2$CH$_3$)$_2$ |
| 11-111 | F | F | H | N(SO$_2$CH$_3$)$_2$ |
| 11-112 | F | Cl | H | N(SO$_2$CH$_3$)$_2$ |
| 11-113 | Cl | F | H | N(SO$_2$CH$_3$)$_2$ |
| 11-114 | Cl | CL | H | N(SO$_2$CH$_3$)$_2$ |
| 11-115 | H | F | H | N(CH$_3$)SO$_2$CH$_3$ |
| 11-116 | H | Cl | H | N(CH$_3$)SO$_2$CH$_3$ |
| 11-117 | F | F | H | N(CH$_3$)SO$_2$CH$_3$ |
| 11-118 | F | Cl | H | N(CH$_3$)SO$_2$CH$_3$ |
| 11-119 | Cl | F | H | N(CH$_3$)SO$_2$CH$_3$ |
| 11-120 | Cl | Cl | H | N(CH$_3$)SO$_2$CH$_3$ |
| 11-121 | H | F | H | N(CH$_2$C=CH)SO$_2$CH$_3$ |
| 11-122 | H | Cl | H | N(CH$_2$C=CH)SO$_2$CH$_3$ |
| 11-123 | F | F | H | N(CH$_2$C=CH)SO$_2$CH$_3$ |
| 11-124 | F | Cl | H | N(CH$_2$C=CH)SO$_2$CH$_3$ |
| 11-125 | Cl | F | H | N(CH$_2$C=CH)SO$_2$CH$_3$ |

TABLE 130

|  | X | Y | R¹ | B |
|---|---|---|---|---|
| 11-126 | Cl | Cl | H | N(CH$_2$C=CH)SO$_2$CH$_3$ |
| 11-127 | H | F | H | NHCOOCH$_3$ |
| 11-128 | H | Cl | H | NHCOOCH$_3$ |
| 11-129 | F | F | H | NHCOOCH$_3$ |
| 11-130 | F | Cl | H | NHCOOCH$_3$ |
| 11-131 | Cl | F | H | NHCOOCH$_3$ |
| 11-132 | Cl | Cl | H | NHCOOCH$_3$ |
| 11-133 | H | F | H | NHCOOC$_2$H$_5$ |
| 11-134 | H | Cl | H | NHCOOC$_2$H$_5$ |
| 11-135 | F | F | H | NHCOOC$_2$H$_5$ |
| 11-136 | F | Cl | H | NHCOOC$_2$H$_5$ |
| 11-137 | Cl | F | H | NHCOOC$_2$H$_5$ |
| 11-138 | Cl | Cl | H | NHCOOC$_2$H$_5$ |
| 11-139 | H | F | H | NHCOOnC$_3$H$_7$ |
| 11-140 | H | Cl | H | NHCOOnC$_3$H$_7$ |
| 11-141 | F | F | H | NHCOOnC$_3$H$_7$ |
| 11-142 | F | Cl | H | NHCOOnC$_3$H$_7$ |
| 11-143 | Cl | F | H | NHCOOnC$_3$H$_7$ |
| 11-144 | Cl | Cl | H | NHCOOnC$_3$H$_7$ |
| 11-145 | H | F | H | NHCOOiC$_3$H$_7$ |
| 11-146 | H | Cl | H | NHCOOiC$_3$H$_7$ |
| 11-147 | F | F | H | NHCOOiC$_3$H$_7$ |
| 11-148 | F | Cl | H | NHCOOiC$_3$H$_7$ |
| 11-149 | Cl | F | H | NHCOOiC$_3$H$_7$ |
| 11-150 | Cl | Cl | H | NHCOOiC$_3$H$_7$ |

TABLE 131

|  | X | Y | R$^1$ | B |
|---|---|---|---|---|
| 11-151 | H | F | H | NHCOOnC$_4$H$_9$ |
| 11-152 | H | Cl | H | NHCOOnC$_4$H$_9$ |
| 11-153 | F | F | H | NHCOOnC$_4$H$_9$ |
| 11-154 | F | Cl | H | NHCOOnC$_4$H$_9$ |
| 11-155 | Cl | F | H | NHCOOnC$_4$H$_9$ |
| 11-156 | Cl | Cl | H | NHCOOnC$_4$H$_9$ |
| 11-157 | H | F | H | NHCOOnC$_5$H$_{11}$ |
| 11-158 | H | Cl | H | NHCOOnC$_5$H$_{11}$ |
| 11-159 | F | F | H | NHCOOnC$_5$H$_{11}$ |
| 11-160 | F | Cl | H | NHCOOnC$_5$H$_{11}$ |
| 11-161 | Cl | F | H | NHCOOnC$_5$H$_{11}$ |
| 11-162 | Cl | Cl | H | NHCOOnC$_5$H$_{11}$ |
| 11-163 | H | F | H | NHCH$_2$COOCH$_3$ |
| 11-164 | H | Cl | H | NHCH$_2$COOCH$_3$ |
| 11-165 | F | F | H | NHCH$_2$COOCH$_3$ |
| 11-166 | F | Cl | H | NHCH$_2$COOCH$_3$ |
| 11-167 | Cl | F | H | NHCH$_2$COOCH$_3$ |
| 11-168 | Cl | Cl | H | NHCH$_2$COOCH$_3$ |
| 11-169 | H | F | H | NHCH$_2$COOC$_2$H$_5$ |
| 11-170 | H | Cl | H | NHCH$_2$COOC$_2$H$_5$ |
| 11-171 | F | F | H | NHCH$_2$COOC$_2$H$_5$ |
| 11-172 | F | Cl | H | NHCH$_2$COOC$_2$H$_5$ |
| 11-173 | Cl | F | H | NHCH$_2$COOC$_2$H$_5$ |
| 11-174 | Cl | Cl | H | NHCH$_2$COOC$_2$H$_5$ |
| 11-175 | H | F | H | NHCH$_2$COOnC$_3$H$_7$ |

TABLE 132

|  | X | Y | R$^1$ | B |
|---|---|---|---|---|
| 11-176 | H | Cl | H | NHCH$_2$COOnC$_3$H$_7$ |
| 11-177 | F | F | H | NHCH$_2$COOnC$_3$H$_7$ |
| 11-178 | F | Cl | H | NHCH$_2$COOnC$_3$H$_7$ |
| 11-179 | Cl | F | H | NHCH$_2$COOnC$_3$H$_7$ |
| 11-180 | Cl | Cl | H | NHCH$_2$COOnC$_3$H$_7$ |
| 11-181 | H | F | H | NHCH$_2$COOnC$_4$H$_9$ |
| 11-182 | H | Cl | H | NHCH$_2$COOnC$_4$H$_9$ |
| 11-183 | F | F | H | NHCH$_2$COOnC$_4$H$_9$ |
| 11-184 | F | Cl | H | NHCH$_2$COOnC$_4$H$_9$ |
| 11-185 | Cl | F | H | NHCH$_2$COOnC$_4$H$_9$ |
| 11-186 | Cl | Cl | H | NHCH$_2$COOnC$_4$H$_9$ |
| 11-187 | H | F | H | NHCH$_2$COOnC$_5$H$_{11}$ |
| 11-188 | H | Cl | H | NHCH$_2$COOnC$_5$H$_{11}$ |
| 11-189 | F | F | H | NHCH$_2$COOnC$_5$H$_{11}$ |
| 11-190 | F | Cl | H | NHCH$_2$COOnC$_5$H$_{11}$ |
| 11-191 | Cl | F | H | NHCH$_2$COOnC$_5$H$_{11}$ |
| 11-192 | Cl | Cl | H | NHCH$_2$COOnC$_5$H$_{11}$ |
| 11-193 | H | F | H | NHCH$_2$COOiC$_3$H$_7$ |
| 11-194 | H | Cl | H | NHCH$_2$COOiC$_3$H$_7$ |
| 11-195 | F | F | H | NHCH$_2$COOiC$_3$H$_7$ |
| 11-196 | F | Cl | H | NHCH$_2$COOiC$_3$H$_7$ |
| 11-197 | Cl | F | H | NHCH$_2$COOiC$_3$H$_7$ |
| 11-198 | Cl | Cl | H | NHCH$_2$COOiC$_3$H$_7$ |
| 11-199 | H | F | H | NHCH$_2$COOcC$_5$H$_9$ |
| 11-200 | H | Cl | H | NHCH$_2$COOcC$_5$H$_9$ |

TABLE 133

|  | X | Y | R$^1$ | B |
|---|---|---|---|---|
| 11-201 | F | F | H | NHCH$_2$COOcC$_5$H$_9$ |
| 11-202 | F | Cl | H | NHCH$_2$COOcC$_5$H$_9$ |
| 11-203 | Cl | F | H | NHCH$_2$COOcC$_5$H$_9$ |
| 11-204 | Cl | Cl | H | NHCH$_2$COOcC$_5$H$_9$ |
| 11-205 | H | F | H | NHCH$_2$COOcC$_6$H$_{11}$ |
| 11-206 | H | Cl | H | NHCH$_2$COOcC$_6$H$_{11}$ |
| 11-207 | F | F | H | NHCH$_2$COOcC$_6$H$_{11}$ |
| 11-208 | F | Cl | H | NHCH$_2$COOcC$_6$H$_{11}$ |
| 11-209 | Cl | F | H | NHCH$_2$COOcC$_6$H$_{11}$ |
| 11-210 | Cl | Cl | H | NHCH$_2$COOcC$_6$H$_{11}$ |
| 11-211 | H | F | H | NHCH(CH$_3$)COOCH$_3$ |
| 11-212 | H | Cl | H | NHCH(CH$_3$)COOCH$_3$ |
| 11-213 | F | F | H | NHCH(CH$_3$)COOCH$_3$ |
| 11-214 | F | Cl | H | NHCH(CH$_3$)COOCH$_3$ |
| 11-215 | Cl | F | H | NHCH(CH$_3$)COOCH$_3$ |
| 11-216 | Cl | Cl | H | NHCH(CH$_3$)COOCH$_3$ |
| 11-217 | H | F | H | NHCH(CH$_3$)COOC$_2$H$_5$ |
| 11-218 | H | Cl | H | NHCH(CH$_3$)COOC$_2$H$_5$ |
| 11-219 | F | F | H | NHCH(CH$_3$)COOC$_2$H$_5$ |
| 11-220 | F | Cl | H | NHCH(CH$_3$)COOC$_2$H$_5$ |
| 11-221 | Cl | F | H | NHCH(CH$_3$)COOC$_2$H$_5$ |
| 11-222 | Cl | Cl | H | NHCH(CH$_3$)COOC$_2$H$_5$ |
| 11-223 | H | F | H | NHCH(CH$_3$)COOnC$_3$H$_7$ |
| 11-224 | H | Cl | H | NHCH(CH$_3$)COOnC$_3$H$_7$ |
| 11-225 | F | F | H | NHCH(CH$_3$)COOnC$_3$H$_7$ |

TABLE 134

|  | X | Y | R$^1$ | B |
|---|---|---|---|---|
| 11-226 | F | Cl | H | NHCH(CH$_3$)COOnC$_3$H$_7$ |
| 11-227 | Cl | F | H | NHCH(CH$_3$)COOnC$_3$H$_7$ |
| 11-228 | Cl | Cl | H | NHCH(CH$_3$)COOnC$_3$H$_7$ |
| 11-229 | H | F | H | NHCH(CH$_3$)COOnC$_4$H$_9$ |
| 11-230 | H | Cl | H | NHCH(CH$_3$)COOnC$_4$H$_9$ |
| 11-231 | F | F | H | NHCH(CH$_3$)COOnC$_4$H$_9$ |
| 11-232 | F | Cl | H | NHCH(CH$_3$)COOnC$_4$H$_9$ |
| 11-233 | Cl | F | H | NHCH(CH$_3$)COOnC$_4$H$_9$ |
| 11-234 | Cl | Cl | H | NHCH(CH$_3$)COOnC$_4$H$_9$ |
| 11-235 | H | F | H | NHCH(CH$_3$)COOnC$_5$H$_{11}$ |
| 11-236 | H | Cl | H | NHCH(CH$_3$)COOnC$_5$H$_{11}$ |
| 11-237 | F | F | H | NHCH(CH$_3$)COOnC$_5$H$_{11}$ |
| 11-238 | F | Cl | H | NHCH(CH$_3$)COOnC$_5$H$_{11}$ |
| 11-239 | Cl | F | H | NHCH(CH$_3$)COOnC$_5$H$_{11}$ |
| 11-240 | Cl | Cl | H | NHCH(CH$_3$)COOnC$_5$H$_{11}$ |
| 11-241 | H | F | H | NHCH(CH$_3$)COOiC$_3$H$_7$ |
| 11-242 | H | Cl | H | NHCH(CH$_3$)COOiC$_3$H$_7$ |
| 11-243 | F | F | H | NHCH(CH$_3$)COOiC$_3$H$_7$ |
| 11-244 | F | Cl | H | NHCH(CH$_3$)COOiC$_3$H$_7$ |
| 11-245 | Cl | F | H | NHCH(CH$_3$)COOiC$_3$H$_7$ |
| 11-246 | Cl | Cl | H | NHCH(CH$_3$)COOiC$_3$H$_7$ |
| 11-247 | H | F | H | NHCH(CH$_3$)COOcC$_5$H$_9$ |
| 11-248 | H | Cl | H | NHCH(CH$_3$)COOcC$_5$H$_9$ |
| 11-249 | F | F | H | NHCH(CH$_3$)COOcC$_5$H$_9$ |
| 11-250 | F | Cl | H | NHCH(CH$_3$)COOcC$_5$H$_9$ |

TABLE 135

|  | X | Y | R$^1$ | B |
|---|---|---|---|---|
| 11-251 | Cl | F | H | NHCH(CH$_3$)COOcC$_5$H$_9$ |
| 11-252 | Cl | Cl | H | NHCH(CH$_3$)COOcC$_5$H$_9$ |
| 11-253 | H | F | H | NHCH(CH$_3$)COOcC$_6$H$_{11}$ |
| 11-254 | H | Cl | H | NHCH(CH$_3$)COOcC$_6$H$_{11}$ |
| 11-255 | F | F | H | NHCH(CH$_3$)COOcC$_6$H$_{11}$ |
| 11-256 | F | Cl | H | NHCH(CH$_3$)COOcC$_6$H$_{11}$ |
| 11-257 | Cl | F | H | NHCH(CH$_3$)COOcC$_6$H$_{11}$ |
| 11-258 | Cl | Cl | H | NHCH(CH$_3$)COOcC$_6$H$_{11}$ |
| 11-259 | H | F | H | OCH$_3$ |
| 11-260 | H | Cl | H | OCH$_3$ |
| 11-261 | F | F | H | OCH$_3$ |
| 11-262 | F | Cl | H | OCH$_3$ |
| 11-263 | Cl | F | H | OCH$_3$ |
| 11-264 | Cl | Cl | H | OCH$_3$ |
| 11-265 | H | F | H | OC$_2$H$_5$ |
| 11-266 | H | Cl | H | OC$_2$H$_5$ |
| 11-267 | F | F | H | OC$_2$H$_5$ |
| 11-268 | F | Cl | H | OC$_2$H$_5$ |
| 11-269 | Cl | F | H | OC$_2$H$_5$ |
| 11-270 | Cl | Cl | H | OC$_2$H$_5$ |
| 11-271 | H | F | H | OiC$_3$H$_7$ |
| 11-272 | H | Cl | H | OiC$_3$H$_7$ |
| 11-273 | F | F | H | OiC$_3$H$_7$ |

TABLE 135-continued

|  | X | Y | R¹ | B |
|---|---|---|---|---|
| 11-274 | F | Cl | H | OiC₃H₇ |
| 11-275 | Cl | F | H | OiC₃H₇ |

TABLE 136

|  | X | Y | R¹ | B |
|---|---|---|---|---|
| 11-276 | Cl | Cl | H | OiC₃H₇ |
| 11-277 | H | F | H | OnC₃H₇ |
| 11-278 | H | Cl | H | OnC₃H₇ |
| 11-279 | F | F | H | OnC₃H₇ |
| 11-280 | F | Cl | H | OnC₃H₇ |
| 11-281 | Cl | F | H | OnC₃H₇ |
| 11-282 | Cl | Cl | H | OnC₃H₇ |
| 11-283 | H | F | H | OCH₂CH₂Cl |
| 11-284 | H | Cl | H | OCH₂CH₂Cl |
| 11-285 | F | F | H | OCH₂CH₂Cl |
| 11-286 | F | Cl | H | OCH₂CH₂Cl |
| 11-287 | Cl | F | H | OCH₂CH₂Cl |
| 11-288 | Cl | Cl | H | OCH₂CH₂Cl |
| 11-289 | H | F | H | OCF₂CF₂H |
| 11-290 | H | Cl | H | OCF₂CF₂H |
| 11-291 | F | F | H | OCF₂CF₂H |
| 11-292 | F | Cl | H | OCF₂CF₂H |
| 11-293 | Cl | F | H | OCF₂CF₂H |
| 11-294 | Cl | Cl | H | OCF₂CF₂H |
| 11-295 | H | F | H | OcC₅H₉ |
| 11-296 | H | Cl | H | OcC₅H₉ |
| 11-297 | F | F | H | OcC₅H₉ |
| 11-298 | F | Cl | H | OcC₅H₉ |
| 11-299 | Cl | F | H | OcC₅H₉ |
| 11-300 | Cl | Cl | H | OcC₅H₉ |

TABLE 137

|  | X | Y | R¹ | B |
|---|---|---|---|---|
| 11-301 | H | F | H | OcC₆H₁₁ |
| 11-302 | H | Cl | H | OcC₆H₁₁ |
| 11-303 | F | F | H | OcC₆H₁₁ |
| 11-304 | F | Cl | H | OcC₆H₁₁ |
| 11-305 | Cl | F | H | OcC₆H₁₁ |
| 11-306 | Cl | Cl | H | OcC₆H₁₁ |
| 11-307 | H | F | H | OCH₂CH=CH₂ |
| 11-308 | H | Cl | H | OCH₂CH=CH₂ |
| 11-309 | F | F | H | OCH₂CH=CH₂ |
| 11-310 | F | Cl | H | OCH₂CH=CH₂ |
| 11-311 | Cl | F | H | OCH₂CH=CH₂ |
| 11-312 | Cl | Cl | H | OCH₂CH=CH₂ |
| 11-313 | H | F | H | OCH₂CCl=CH₂ |
| 11-314 | H | Cl | H | OCH₂CCl=CH₂ |
| 11-315 | F | F | H | OCH₂CCl=CH₂ |
| 11-316 | F | Cl | H | OCH₂CCl=CH₂ |
| 11-317 | Cl | F | H | OCH₂CCl=CH₂ |
| 11-318 | Cl | Cl | H | OCH₂CCl=CH₂ |
| 11-319 | H | F | H | OCH₂CCl=CHCl |
| 11-320 | H | Cl | H | OCH₂CCl=CHCl |
| 11-321 | F | F | H | OCH₂CCl=CHCl |
| 11-322 | F | Cl | H | OCH₂CCl=CHCl |
| 11-323 | Cl | F | H | OCH₂CCl=CHCl |
| 11-324 | Cl | Cl | H | OCH₂CCl=CHCl |
| 11-325 | H | F | H | OCH(CH₃)CH=CH₂ |

TABLE 138

|  | X | Y | R¹ | B |
|---|---|---|---|---|
| 11-326 | H | Cl | H | OCH(CH₃)CH=CH₂ |
| 11-327 | F | F | H | OCH(CH₃)CH=CH₂ |
| 11-328 | F | Cl | H | OCH(CH₃)CH=CH₂ |
| 11-329 | Cl | F | H | OCH(CH₃)CH=CH₂ |
| 11-330 | Cl | Cl | H | OCH(CH₃)CH=CH₂ |
| 11-331 | H | F | H | OCH₂C(CH₃)=CH₂ |
| 11-332 | H | Cl | H | OCH₂C(CH₃)=CH₂ |
| 11-333 | F | F | H | OCH₂C(CH₃)=CH₂ |
| 11-334 | F | Cl | H | OCH₂C(CH₃)=CH₂ |
| 11-335 | Cl | F | H | OCH₂C(CH₃)=CH₂ |
| 11-336 | Cl | Cl | H | OCH₂C(CH₃)=CH₂ |
| 11-337 | H | F | H | OCH₂C≡CH |
| 11-338 | H | Cl | H | OCH₂C≡CH |
| 11-339 | F | F | H | OCH₂C≡CH |
| 11-340 | F | Cl | H | OCH₂C≡CH |
| 11-341 | Cl | F | H | OCH₂C≡CH |
| 11-342 | Cl | Cl | H | OCH₂C≡CH |
| 11-343 | H | F | H | OCH(CH₃)C≡CH |
| 11-344 | H | Cl | H | OCH(CH₃)C≡CH |
| 11-345 | F | F | H | OCH(CH₃)C≡CH |
| 11-346 | F | Cl | H | OCH(CH₃)C≡CH |
| 11-347 | Cl | F | H | OCH(CH₃)C≡CH |
| 11-348 | Cl | Cl | H | OCH(CH₃)C≡CH |
| 11-349 | H | F | H | OCH₂C≡CBr |
| 11-350 | H | Cl | H | OCH₂C≡CBr |

TABLE 139

|  | X | Y | R¹ | B |
|---|---|---|---|---|
| 11-351 | F | F | H | OCH₂C≡CBr |
| 11-352 | F | Cl | H | OCH₂C≡CBr |
| 11-353 | Cl | F | H | OCH₂C≡CBr |
| 11-354 | Cl | Cl | H | OCH₂C≡CBr |
| 11-355 | H | F | H | OCH₂C≡CCl |
| 11-356 | H | Cl | H | OCH₂C≡CCl |
| 11-357 | F | F | H | OCH₂C≡CCl |
| 11-358 | F | Cl | H | OCH₂C≡CCl |
| 11-359 | Cl | F | H | OCH₂C≡CCl |
| 11-360 | Cl | Cl | H | OCH₂C≡CCl |
| 11-361 | H | F | H | OCH₂C≡CCH₂Cl |
| 11-362 | H | Cl | H | OCH₂C≡CCH₂Cl |
| 11-363 | F | F | H | OCH₂C≡CCH₂Cl |
| 11-364 | F | Cl | H | OCH₂C≡CCH₂Cl |
| 11-365 | Cl | F | H | OCH₂C≡CCH₂Cl |
| 11-366 | Cl | Cl | H | OCH₂C≡CCH₂Cl |
| 11-367 | H | F | H | OCH₂CN |
| 11-368 | H | Cl | H | OCH₂CN |
| 11-369 | F | F | H | OCH₂CN |
| 11-370 | F | Cl | H | OCH₂CN |
| 1I-371 | Cl | F | H | OCH₂CN |
| 11-372 | Cl | Cl | H | OCH₂CN |
| 11-373 | H | F | H | OCH₂OCH₃ |
| 11-374 | H | Cl | H | OCH₂OCH₃ |
| 11-375 | F | F | H | OCH₂OCH₃ |

TABLE 140

|  | X | Y | R¹ | B |
|---|---|---|---|---|
| 11-376 | F | Cl | H | OCH₂OCH₃ |
| 11-377 | Cl | F | H | OCH₂OCH₃ |
| 11-378 | Cl | Cl | H | OCH₂OCH₃ |
| 11-379 | H | F | H | OCH₂OC₂H₅ |
| 11-380 | H | Cl | H | OCH₂OC₂H₅ |
| 11-381 | F | F | H | OCH₂OC₂H₅ |
| 11-382 | F | Cl | H | OCH₂OC₂H₅ |
| 11-383 | Cl | F | H | OCH₂OC₂H₅ |
| 11-384 | Cl | Cl | H | OCH₂OC₂H₅ |
| 11-385 | H | F | H | OCH₂SCH₃ |
| 11-386 | H | Cl | H | OCH₂SCH₃ |
| 11-387 | F | F | H | OCH₂SCH₃ |
| 11-388 | F | Cl | H | OCH₂SCH₃ |
| 11-389 | Cl | F | H | OCH₂SCH₃ |
| 11-390 | Cl | Cl | H | OCH₂SCH₃ |

TABLE 140-continued

| | X | Y | R$^1$ | B |
|---|---|---|---|---|
| 11-391 | H | F | H | OCH$_2$COOH |
| 11-392 | H | Cl | H | OCH$_2$COOH |
| 11-393 | F | F | H | OCH$_2$COOH |
| 11-394 | F | Cl | H | OCH$_2$COOH |
| 11-395 | Cl | F | H | OCH$_2$COOH |
| 11-396 | Cl | Cl | H | OCH$_2$COOH |
| 11-397 | H | F | H | OCH$_2$COOCH$_3$ |
| 11-398 | H | Cl | H | OCH$_2$COOCH$_3$ |
| 11-399 | F | F | H | OCH$_2$COOCH$_3$ |
| 11-400 | F | Cl | H | OCH$_2$COOCH$_3$ |

TABLE 141

| | X | Y | R$^1$ | B |
|---|---|---|---|---|
| 11-401 | Cl | F | H | OCH$_2$COOCH$_3$ |
| 11-402 | Cl | Cl | H | OCH$_2$COOCH$_3$ |
| 11-403 | H | F | H | OCH$_2$COOC$_2$H$_5$ |
| 11-404 | H | Cl | H | OCH$_2$COOC$_2$H$_5$ |
| 11-405 | F | F | H | OCH$_2$COOC$_2$H$_5$ |
| 11-406 | F | Cl | H | OCH$_2$COOC$_2$H$_5$ |
| 11-407 | Cl | F | H | OCH$_2$COOC$_2$H$_5$ |
| 11-408 | Cl | Cl | H | OCH$_2$COOC$_2$H$_5$ |
| 11-409 | H | F | H | OCH$_2$COOnC$_3$H$_7$ |
| 11-410 | H | Cl | H | OCH$_2$COOnC$_3$H$_7$ |
| 11-411 | F | F | H | OCH$_2$COOnC$_3$H$_7$ |
| 11-412 | F | Cl | H | OCH$_2$COOnC$_3$H$_7$ |
| 11-413 | Cl | F | H | OCH$_2$COOnC$_3$H$_7$ |
| 11-414 | Cl | Cl | H | OCH$_2$COOnC$_3$H$_7$ |
| 11-415 | H | F | H | OCH$_2$COOnC$_4$H$_9$ |
| 11-416 | H | Cl | H | OCH$_2$COOnC$_4$H$_9$ |
| 11-417 | F | F | H | OCH$_2$COOnC$_4$H$_9$ |
| 11-418 | F | Cl | H | OCH$_2$COOnC$_4$H$_9$ |
| 11-419 | Cl | F | H | OCH$_2$COOnC$_4$H$_9$ |
| 11-420 | Cl | Cl | H | OCH$_2$COOnC$_4$H$_9$ |
| 11-421 | H | F | H | OCH$_2$COOnC$_5$H$_{11}$ |
| 11-422 | H | Cl | H | OCH$_2$COOnC$_5$H$_{11}$ |
| 11-423 | F | F | H | OCH$_2$COOnC$_5$H$_{11}$ |
| 11-424 | F | Cl | H | OCH$_2$COOnC$_5$H$_{11}$ |
| 11-425 | Cl | F | H | OCH$_2$COOnC$_5$H$_{11}$ |

TABLE 142

| | X | Y | R$^1$ | B |
|---|---|---|---|---|
| 11-426 | Cl | Cl | H | OCH$_2$COOnC$_5$H$_{11}$ |
| 11-427 | H | F | H | OCH$_2$COOiC$_3$H$_7$ |
| 11-428 | H | Cl | H | OCH$_2$COOiC$_3$H$_7$ |
| 11-429 | F | F | H | OCH$_2$COOiC$_3$H$_7$ |
| 11-430 | F | Cl | H | OCH$_2$COOiC$_3$H$_7$ |
| 11-431 | Cl | F | H | OCH$_2$COOiC$_3$H$_7$ |
| 11-432 | Cl | Cl | H | OCH$_2$COOiC$_3$H$_7$ |
| 11-433 | H | F | H | OCH$_2$COOcC$_5$H$_9$ |
| 11-434 | H | Cl | H | OCH$_2$COOcC$_5$H$_9$ |
| 11-435 | F | F | H | OCH$_2$COOcC$_5$H$_9$ |
| 11-436 | F | Cl | H | OCH$_2$COOcC$_5$H$_9$ |
| 11-437 | Cl | F | H | OCH$_2$COOcC$_5$H$_9$ |
| 11-438 | Cl | Cl | H | OCH$_2$COOcC$_5$H$_9$ |
| 11-439 | H | F | H | OCH$_2$COOcC$_6$H$_{11}$ |
| 11-440 | H | Cl | H | OCH$_2$COOcC$_6$H$_{11}$ |
| 11-441 | F | F | H | OCH$_2$COOcC$_6$H$_{11}$ |
| 11-442 | F | Cl | H | OCH$_2$COOcC$_6$H$_{11}$ |
| 11-443 | Cl | F | H | OCH$_2$COOcC$_6$H$_{11}$ |
| 11-444 | Cl | Cl | H | OCH$_2$COOcC$_6$H$_{11}$ |
| 11-445 | H | F | H | OCH(CH$_3$)COOH |
| 11-446 | H | Cl | H | OCH(CH$_3$)COOH |
| 11-447 | F | F | H | OCH(CH$_3$)COOH |
| 11-448 | F | Cl | H | OCH(CH$_3$)COOH |
| 11-449 | Cl | F | H | OCH(CH$_3$)COOH |
| 11-450 | Cl | Cl | H | OCH(CH$_3$)COOH |

TABLE 143

| | X | Y | R$^1$ | B |
|---|---|---|---|---|
| 11-451 | H | F | H | OCH(CH$_3$)COOCH$_3$ |
| 11-452 | H | Cl | H | OCH(CH$_3$)COOCH$_3$ |
| 11-453 | F | F | H | OCH(CH$_3$)COOCH$_3$ |
| 11-454 | F | Cl | H | OCH(CH$_3$)COOCH$_3$ |
| 11-455 | Cl | F | H | OCH(CH$_3$)COOCH$_3$ |
| 11-456 | Cl | Cl | H | OCH(CH$_3$)COOCH$_3$ |
| 11-457 | H | F | H | OCH(CH$_3$)COOC$_2$H$_5$ |
| 11-458 | H | Cl | H | OCH(CH$_3$)COOC$_2$H$_5$ |
| 11-459 | F | F | H | OCH(CH$_3$)COOC$_2$H$_5$ |
| 11-460 | F | Cl | H | OCH(CH$_3$)COOC$_2$H$_5$ |
| 11-461 | Cl | F | H | OCH(CH$_3$)COOC$_2$H$_5$ |
| 11-462 | Cl | Cl | H | OCH(CH$_3$)COOC$_2$H$_5$ |
| 11-463 | H | F | H | OCH(CH$_3$)COOnC$_3$H$_7$ |
| 11-464 | H | Cl | H | OCH(CH$_3$)COOnC$_3$H$_7$ |
| 11-465 | F | F | H | OCH(CH$_3$)COOnC$_3$H$_7$ |
| 11-466 | F | Cl | H | OCH(CH$_3$)COOnC$_3$H$_7$ |
| 11-467 | Cl | F | H | OCH(CH$_3$)COOnC$_3$H$_7$ |
| 11-468 | Cl | Cl | H | OCH(CH$_3$)COOnC$_3$H$_7$ |
| 11-469 | H | F | H | OCH(CH$_3$)COOnC$_4$H$_9$ |
| 11-470 | H | Cl | H | OCH(CH$_3$)COOnC$_4$H$_9$ |
| 11-471 | F | F | H | OCH(CH$_3$)COOnC$_4$H$_9$ |
| 11-472 | F | Cl | H | OCH(CH$_3$)COOnC$_4$H$_9$ |
| 11-473 | Cl | F | H | OCH(CH$_3$)COOnC$_4$H$_9$ |
| 11-474 | Cl | Cl | H | OCH(CH$_3$)COOnC$_4$H$_9$ |
| 11-475 | H | F | H | OCH(CH$_3$)COOnC$_5$H$_{11}$ |

TABLE 144

| | X | Y | R$^1$ | B |
|---|---|---|---|---|
| 11-476 | H | Cl | H | OCH(CH$_3$)COOnC$_5$H$_{11}$ |
| 11-477 | F | F | H | OCH(CH$_3$)COOnC$_5$H$_{11}$ |
| 11-478 | F | Cl | H | OCH(CH$_3$)COOnC$_5$H$_{11}$ |
| 11-479 | Cl | F | H | OCH(CH$_3$)COOnC$_5$H$_{11}$ |
| 11-480 | Cl | Cl | H | OCH(CH$_3$)COOnC$_5$H$_{11}$ |
| 11-481 | H | F | H | OCH(CH$_3$)COOiC$_3$H$_7$ |
| 11-482 | H | Cl | H | OCH(CH$_3$)COOiC$_3$H$_7$ |
| 11-483 | F | F | H | OCH(CH$_3$)COOiC$_3$H$_7$ |
| 11-484 | F | Cl | H | OCH(9H$_3$)COOiC$_3$H$_7$ |
| 11-485 | Cl | F | H | OCH(CH$_3$)COOiC$_3$H$_7$ |
| 11-486 | Cl | Cl | H | OCH(CH$_3$)COOiC$_3$H$_7$ |
| 11-487 | H | F | H | OCH(CH$_3$)COOcC$_5$H$_9$ |
| 11-488 | H | Cl | H | OCH(CH$_3$)COOcC$_5$H$_9$ |
| 11-489 | F | F | H | OCH(CH$_3$)COOcC$_5$H$_9$ |
| 11-490 | F | Cl | H | OCH(CH$_3$)COOcC$_5$H$_9$ |
| 11-491 | Cl | F | H | OCH(CH$_3$)COOcC$_5$H$_9$ |
| 11-492 | Cl | Cl | H | OCH(CH$_3$)CGOcC$_5$H$_9$ |
| 11-493 | H | F | H | OCH(CH$_3$)COOcC$_6$H$_{11}$ |
| 11-494 | H | Cl | H | OCH(CH$_3$)COOcC$_6$H$_{11}$ |
| 11-495 | F | F | H | OCH(CH$_3$)COOcC$_6$H$_{11}$ |
| 11-496 | F | Cl | H | OCH(CH$_3$)COOcC$_6$H$_{11}$ |
| 11-497 | Cl | F | H | OCH(CH$_3$)COOcC$_6$H$_{11}$ |
| 11-498 | Cl | Cl | H | OCH(CH$_3$)COOcC$_6$H$_{11}$ |
| 11-499 | H | F | H | OCH$_2$CONH$_2$ |
| 11-500 | H | Cl | H | OCH$_2$CONH$_2$ |

TABLE 145

| | X | Y | R$^1$ | B |
|---|---|---|---|---|
| 11-501 | F | F | H | OCH$_2$CONH$_2$ |
| 11-502 | F | Cl | H | OCH$_2$CONH$_2$ |
| 11-503 | Cl | F | H | OCH$_2$CONH$_2$ |
| 11-504 | Cl | Cl | H | OCH$_2$CONH$_2$ |
| 11-505 | H | F | H | OCH$_2$CONHCH$_3$ |
| 11-506 | H | Cl | H | OCH$_2$CONHCH$_3$ |
| 11-507 | F | F | H | OCH$_2$CONHCH$_3$ |
| 11-508 | F | Cl | H | OCH$_2$CONHCH$_3$ |
| 11-509 | Cl | F | H | OCH$_2$CONHCH$_3$ |
| 11-510 | Cl | Cl | H | OCH$_2$CONHCH$_3$ |
| 11-511 | H | F | H | OCH$_2$CON(CH$_3$)$_2$ |
| 11-512 | H | Cl | H | OCH$_2$CON(CH$_3$)$_2$ |

TABLE 145-continued

|  | X | Y | R¹ | B |
|---|---|---|---|---|
| 11-513 | F | F | H | OCH₂CON(CH₃)₂ |
| 11-514 | F | Cl | H | OCH₂CON(CH₃)₂ |
| 11-515 | Cl | F | H | OCH₂CON(CH₃)₂ |
| 11-516 | Cl | Cl | H | OCH₂CON(CH₃)₂ |
| 11-517 | H | F | H | OCH₂CON(C₂H₅)₂ |
| 11-518 | H | Cl | H | OCH₂CON(C₂H₅)₂ |
| 11-519 | F | F | H | OCH₂CON(C₂H₅)₂ |
| 11-520 | F | Cl | H | OCH₂CON(C₂H₅)₂ |
| 11-521 | Cl | F | H | OCH₂CON(C₂H₅)₂ |
| 11-522 | Cl | Cl | H | OCH₂CON(C₂H₅)₂ |
| 11-523 | H | F | H | OCH₂CON(CH₃)C₂H₅ |
| 11-524 | H | Cl | H | OCH₂CON(CH₃)C₂H₅ |
| 11-525 | F | F | H | OCH₂CON(CH₃)C₂H₅ |

TABLE 146

|  | X | Y | R¹ | B |
|---|---|---|---|---|
| 11-526 | F | Cl | H | OCH₂CON(CH₃)C₂H₅ |
| 11-527 | Cl | F | H | OCH₂CON(CH₃)C₂H₅ |
| 11-528 | Cl | Cl | H | OCH₂CON(CH₃)C₂H₅ |
| 11-529 | H | F | H | OCH₂CON(tetramethylene) |
| 11-530 | H | Cl | H | OCH₂CON(tetramethylene) |
| 11-531 | F | F | H | OCH₂CON(tetramethylene) |
| 11-532 | F | Cl | H | OCH₂CON(tetramethylene) |
| 11-533 | Cl | F | H | OCH₂CON(tetramethylene) |
| 11-534 | Cl | Cl | H | OCH₂CON(tetramethylene) |
| 11-535 | H | F | H | OCH₂CON(pentamethylene) |
| 11-536 | H | Cl | H | OCH₂CON(pentamethylene) |
| 11-537 | F | F | H | OCH₂CON(pentamethylene) |
| 11-538 | F | Cl | H | OCH₂CON(pentamethylene) |
| 11-539 | Cl | F | H | OCH₂CON(pentamethylene) |
| 11-540 | Cl | Cl | H | OCH₂CON(pentamethylene) |
| 11-541 | H | F | H | OCH₂CON(ethyleneoxyethylene) |
| 11-542 | H | Cl | H | OCH₂CON(ethyleneoxyethylene) |
| 11-543 | F | F | H | OCH₂CON(ethyleneoxyethylene) |
| 11-544 | F | Cl | H | OCH₂CON(ethyleneoxyethylene) |
| 11-545 | Cl | F | H | OCH₂CON(ethyleneoxyethylene) |
| 11-546 | Cl | Cl | H | OCH₂CON(ethyleneoxyethylene) |
| 11-547 | H | F | H | OCH(CH₃)CONH₂ |
| 11-548 | H | Cl | H | OCH(CH₃)CONH₂ |
| 11-549 | F | F | H | OCH(CH₃)CONH₂ |
| 11-550 | F | Cl | H | OCH(CH₃)CONH₂ |

TABLE 147

|  | X | Y | R¹ | B |
|---|---|---|---|---|
| 11-551 | Cl | F | H | OCH(CH₃)CONH₂ |
| 11-552 | Cl | Cl | H | OCH(CH₃)CONH₂ |
| 11-553 | H | F | H | OCH(CH₃)CONHCH₃ |
| 11-554 | H | Cl | H | OCH(CH₃)CONHCH₃ |
| 11-555 | F | F | H | OCH(CH₃)CONHCH₃ |
| 11-556 | F | Cl | H | OCH(CH₃)CONHCH₃ |
| 11-557 | Cl | F | H | OCH(CH₃)CONHCH₃ |
| 11-558 | Cl | Cl | H | OCH(CH₃)CONHCH₃ |
| 11-559 | H | F | H | OCH(CH₃)CON(CH₃)₂ |
| 11-560 | H | Cl | H | OCH(CH₃)CON(CH₃)₂ |
| 11-561 | F | F | H | OCH(CH₃)CON(CH₃)₂ |
| 11-562 | F | Cl | H | OCH(CH₃)CON(CH₃)₂ |
| 11-563 | Cl | F | H | OCH(CH₃)CON(CH₃)₂ |
| 11-564 | Cl | Cl | H | OCH(CH₃)CON(CH₃)₂ |
| 11-565 | H | F | H | OCH(CH₃)CON(C₂H₅)₂ |
| 11-566 | H | Cl | H | OCH(CH₃)CON(C₂H₅)₂ |
| 11-567 | F | F | H | OCH(CH₃)CON(C₂H₅)₂ |
| 11-568 | F | Cl | H | OCH(CH₃)CON(C₂H₅)₂ |
| 11-569 | Cl | F | H | OCH(CH₃)CON(C₂H₅)₂ |
| 11-570 | Cl | Cl | H | OCH(CH₃)CON(C₂H₅)₂ |
| 11-571 | H | F | H | OCH(CH₃)CON(CH₃)C₂H₅ |
| 11-572 | H | Cl | H | OCH(CH₃)CON(CH₃)C₂H₅ |
| 11-573 | F | F | H | OCH(CH₃)CON(CH₃)C₂H₅ |

TABLE 147-continued

|  | X | Y | R¹ | B |
|---|---|---|---|---|
| 11-574 | F | Cl | H | OCH(CH₃)CON(CH₃)C₂H₅ |
| 11-575 | Cl | F | H | OCH(CH₃)CON(CH₃)C₂H₅ |

TABLE 148

|  | X | Y | R¹ | B |
|---|---|---|---|---|
| 11-576 | Cl | Cl | H | OCH(CH₃)CON(CH₃)C₂H₅ |
| 11-577 | H | F | H | OCH(CH₃)CON(tetramethylene) |
| 11-578 | H | Cl | H | OCH(CH₃)CON(tetramethylene) |
| 11-579 | F | F | H | OCH(CH₃)CON(tetramethylene) |
| 11-580 | F | Cl | H | OCH(CH₃)CON(tetramethylene) |
| 11-581 | Cl | F | H | OCH(CH₃)CON(tetramethylene) |
| 11-582 | Cl | Cl | H | OCH(CH₃)CON(tetramethylene) |
| 11-583 | H | F | H | OCH(CH₃)CON(pentamethylene) |
| 11-584 | H | Cl | H | OCH(CH₃)CON(pentamethylene) |
| 11-585 | F | F | H | OCH(CH₃)CON(pentamethylene) |
| 11-586 | F | Cl | H | OCH(CH₃)CON(pentamethylene) |
| 11-587 | Cl | F | H | OCH(CH₃)CON(pentamethylene) |
| 11-588 | Cl | Cl | H | OCH(CH₃)CON(pentamethylene) |
| 11-589 | H | F | H | OCH(CH₃)CON(ethyleneoxyethylene) |
| 11-590 | H | Cl | H | OCH(CH₃)CON(ethyleneoxyethylene) |
| 11-591 | F | F | H | OCH(CH₃)CON(ethyleneoxyethylene) |
| 11-592 | F | Cl | H | OCH(CH₃)CON(ethyleneoxyethylene) |
| 11-593 | Cl | F | H | OCH(CH₃)CON(ethyleneoxyethylene) |
| 11-594 | Cl | Cl | H | OCH(CH₃)CON(ethyleneoxyethylene) |
| 11-595 | H | F | H | OCH₂COON(CH₃)₂ |
| 11-596 | H | Cl | H | OCH₂COON(CH₃)₂ |
| 11-597 | F | F | H | OCH₂COON(CH₃)₂ |
| 11-598 | F | Cl | H | OCH₂COON(CH₃)₂ |
| 11-599 | Cl | F | H | OCH₂COON(CH₃)₂ |
| 11-600 | Cl | Cl | H | OCH₂COON(CH₃)₂ |

TABLE 149

|  | X | Y | R¹ | B |
|---|---|---|---|---|
| 11-601 | H | F | H | OCH₂COON(C₂H₅)₂ |
| 11-602 | H | Cl | H | OCH₂COON(C₂H₅)₂ |
| 11-603 | F | F | H | OCH₂COON(C₂H₅)₂ |
| 11-604 | F | Cl | H | OCH₂COON(C₂H₅)₂ |
| 11-605 | Cl | F | H | OCH₂COON(C₂H₅)₂ |
| 11-606 | Cl | Cl | H | OCH₂COON(C₂H₅)₂ |
| 11-607 | H | F | H | OCH(CH₃)COON(CH₃)₂ |
| 11-608 | H | Cl | H | OCH(CH₃)COON(CH₃)₂ |
| 11-609 | F | F | H | OCH(CH₃)COON(CH₃)₂ |
| 11-610 | F | Cl | H | OCH(CH₃)COON(CH₃)₂ |
| 11-611 | Cl | F | H | OCH(CH₃)COON(CH₃)₂ |
| 11-612 | Cl | Cl | H | OCH(CH₃)COON(CH₃)₂ |
| 11-613 | H | F | H | OCH(CH₃)COON(C₂H₅)₂ |
| 11-614 | H | Cl | H | OCH(CH₃)COON(C₂H₅)₂ |
| 11-615 | F | F | H | OCH(CH₃)COON(C₂H₅)₂ |
| 11-616 | F | Cl | H | OCH(CH₃)COON(C₂H₅)₂ |
| 11-617 | Cl | F | H | OCH(CH₃)COON(C₂H₅)₂ |
| 11-618 | Cl | Cl | H | OCH(CH₃)COON(C₂H₅)₂ |
| 11-619 | H | F | H | SCH₃ |
| 11-620 | H | Cl | H | SCH₃ |
| 11-621 | F | F | H | SCH₃ |
| 11-622 | F | Cl | H | SCH₃ |
| 11-623 | Cl | F | H | SCH₃ |
| 11-624 | Cl | Cl | H | SCH₃ |
| 11-625 | H | F | H | SC₂H₅ |

TABLE 150

|  | X | Y | R¹ | B |
|---|---|---|---|---|
| 11-626 | H | Cl | H | SC₂H₅ |
| 11-627 | F | F | H | SC₂H₅ |
| 11-628 | F | Cl | H | SC₂H₅ |

TABLE 150-continued

| | X | Y | R¹ | B |
|---|---|---|---|---|
| 11-629 | Cl | F | H | SC$_2$H$_5$ |
| 11-630 | Cl | Cl | H | SC$_2$H$_5$ |
| 11-631 | H | F | H | SiC$_3$H$_7$ |
| 11-632 | H | Cl | H | SiC$_3$H$_7$ |
| 11-633 | F | F | H | SiC$_3$H$_7$ |
| 11-634 | F | Cl | H | SiC$_3$H$_7$ |
| 11-635 | Cl | F | H | SiC$_3$H$_7$ |
| 11-636 | Cl | Cl | H | SiC$_3$H$_7$ |
| 11-637 | H | F | H | SnC$_3$H$_7$ |
| 11-638 | H | Cl | H | SnC$_3$H$_7$ |
| 11-639 | F | F | H | SnC$_3$H$_7$ |
| 11-640 | F | Cl | H | SnC$_3$H$_7$ |
| 11-641 | Cl | F | H | SnC$_3$H$_7$ |
| 11-642 | Cl | Cl | H | SnC$_3$H$_7$ |
| 11-643 | H | F | H | SCH$_2$CH$_2$Cl |
| 11-644 | H | Cl | H | SCH$_2$CH$_2$Cl |
| 11-645 | F | F | H | SCH$_2$CH$_2$Cl |
| 11-646 | F | Cl | H | SCH$_2$CH$_2$Cl |
| 11-647 | Cl | F | H | SCH$_2$CH$_2$Cl |
| 11-648 | Cl | Cl | H | SCH$_2$CH$_2$Cl |
| 11-649 | H | F | H | ScC$_5$H$_9$ |
| 11-650 | H | Cl | H | ScC$_5$H$_9$ |

TABLE 151

| | X | Y | R¹ | B |
|---|---|---|---|---|
| 11-651 | F | F | H | ScC$_5$H$_9$ |
| 11-652 | F | Cl | H | ScC$_5$H$_9$ |
| 11-653 | Cl | F | H | ScC$_5$H$_9$ |
| 11-654 | Cl | Cl | H | ScC$_5$H$_9$ |
| 11-655 | H | F | H | ScC$_6$H$_{11}$ |
| 11-656 | H | Cl | H | ScC$_6$H$_{11}$ |
| 11-657 | F | F | H | ScC$_6$H$_{11}$ |
| 11-658 | F | Cl | H | ScC$_6$H$_{11}$ |
| 11-659 | Cl | F | H | ScC$_6$H$_{11}$ |
| 11-660 | Cl | Cl | H | ScC$_6$H$_{11}$ |
| 11-661 | H | F | H | SCH$_2$CH=CH$_2$ |
| 11-662 | H | Cl | H | SCH$_2$CH=CH$_2$ |
| 11-663 | F | F | H | SCH$_2$CH=CH$_2$ |
| 11-664 | F | Cl | H | SCH$_2$CH=CH$_2$ |
| 11-665 | Cl | F | H | SCH$_2$CH=CH$_2$ |
| 11-666 | Cl | Cl | H | SCH$_2$CH=CH$_2$ |
| 11-667 | H | F | H | SCH$_2$CCl=CH$_2$ |
| 11-668 | H | Cl | H | SCH$_2$CCl=CH$_2$ |
| 11-669 | F | F | H | SCH$_2$CCl=CH$_2$ |
| 11-670 | F | Cl | H | SCH$_2$CCl=CH$_2$ |
| 11-671 | Cl | F | H | SCH$_2$CCl=CH$_2$ |
| 11-672 | Cl | Cl | H | SCH$_2$CCl=CH$_2$ |
| 11-673 | H | F | H | SCH$_2$CCl=CHCl |
| 11-674 | H | Cl | H | SCH$_2$CCl=CHCl |
| 11-675 | F | F | H | SCH$_2$CCl=CHCl |

TABLE 152

| | X | Y | R¹ | B |
|---|---|---|---|---|
| 11-676 | F | Cl | H | SCH$_2$CCl=CHCl |
| 11-677 | Cl | F | H | SCH$_2$CCl=CHCl |
| 11-678 | Cl | Cl | H | SCH$_2$CCl=CHCl |
| 11-679 | H | F | H | SCH(CH$_3$)CH=CH$_2$ |
| 11-680 | H | Cl | H | SCH(CH$_3$)CH=CH$_2$ |
| 11-681 | F | F | H | SCH(CH$_3$)CH=CH$_2$ |
| 11-682 | F | Cl | H | SCH(CH$_3$)CH=CH$_2$ |
| 11-683 | Cl | F | H | SCH(CH$_3$)CH=CH$_2$ |
| 11-684 | Cl | Cl | H | SCH(CH$_3$)CH=CH$_2$ |
| 11-685 | H | F | H | SCH$_2$C≡CH |
| 11-686 | H | Cl | H | SCH$_2$C≡CH |
| 11-687 | F | F | H | SCH$_2$C≡CH |
| 11-688 | F | Cl | H | SCH$_2$C≡CH |
| 11-689 | Cl | F | H | SCH$_2$C≡CH |
| 11-690 | Cl | Cl | H | SCH$_2$C≡CH |

TABLE 152-continued

| | X | Y | R¹ | B |
|---|---|---|---|---|
| 11-691 | H | F | H | SCH(CH$_3$)C≡CH |
| 11-692 | H | Cl | H | SCH(CH$_3$)C≡CH |
| 11-693 | F | F | H | SCH(CH$_3$)C≡CH |
| 11-694 | F | Cl | H | SCH(CH$_3$)C≡CH |
| 11-695 | Cl | F | H | SCH(CH$_3$)C≡CH |
| 11-696 | Cl | Cl | H | SCH(CH$_3$)C≡CH |
| 11-697 | H | F | H | SCH$_2$COOH |
| 11-698 | H | Cl | H | SCH$_2$COOH |
| 11-699 | F | F | H | SCH$_2$COOH |
| 11-700 | F | Cl | H | SCH$_2$COOH |

TABLE 153

| | X | Y | R¹ | B |
|---|---|---|---|---|
| 11-701 | Cl | F | H | SCH$_2$COOH |
| 11-702 | Cl | Cl | H | SCH$_2$COOH |
| 11-703 | H | F | H | SCH$_2$COOCH$_3$ |
| 11-704 | H | Cl | H | SCH$_2$COOCH$_3$ |
| 11-705 | F | F | H | SCH$_2$COOCH$_3$ |
| 11-706 | F | Cl | H | SCH$_2$COOCH$_3$ |
| 11-707 | Cl | F | H | SCH$_2$COOCH$_3$ |
| 11-708 | Cl | Cl | H | SCH$_2$COOCH$_3$ |
| 11-709 | H | F | H | SCH$_2$COOC$_2$H$_5$ |
| 11-710 | H | Cl | H | SCH$_2$COOC$_2$H$_5$ |
| 11-711 | F | F | H | SCH$_2$COOC$_2$H$_5$ |
| 11-712 | F | Cl | H | SCH$_2$COOC$_2$H$_5$ |
| 11-713 | Cl | F | H | SCH$_2$COOC$_2$H$_5$ |
| 11-714 | Cl | Cl | H | SCH$_2$COOC$_2$H$_5$ |
| 11-715 | H | F | H | SCH$_2$COOnC$_3$H$_7$ |
| 11-716 | H | Cl | H | SCH$_2$COOnC$_3$H$_7$ |
| 11-717 | F | F | H | SCH$_2$COOnC$_3$H$_7$ |
| 11-718 | F | Cl | H | SCH$_2$COOnC$_3$H$_7$ |
| 11-719 | Cl | F | H | SCH$_2$COOnC$_3$H$_7$ |
| 11-720 | Cl | Cl | H | SCH$_2$COOnC$_3$H$_7$ |
| 11-721 | H | F | H | SCH$_2$COOnC$_4$H$_9$ |
| 11-722 | H | Cl | H | SCH$_2$COOnC$_4$H$_9$ |
| 11-723 | F | F | H | SCH$_2$COOnC$_4$H$_9$ |
| 11-724 | F | Cl | H | SCH$_2$COOnC$_4$H$_9$ |
| 11-725 | Cl | F | H | SCH$_2$COOnC$_4$H$_9$ |

TABLE 154

| | X | Y | R¹ | B |
|---|---|---|---|---|
| 11-726 | Cl | Cl | H | SCH$_2$COOnC$_4$H$_9$ |
| 11-727 | H | F | H | SCH$_2$COOnC$_5$H$_{11}$ |
| 11-728 | H | Cl | H | SCH$_2$COOnC$_5$H$_{11}$ |
| 11-729 | F | F | H | SCH$_2$COOnC$_5$H$_{11}$ |
| 11-730 | F | Cl | H | SCH$_2$COOnC$_5$H$_{11}$ |
| 11-731 | Cl | F | H | SCH$_2$COOnC$_5$H$_{11}$ |
| 11-732 | Cl | Cl | H | SCH$_2$COOnC$_5$H$_{11}$ |
| 11-733 | H | F | H | SCH$_2$COOiC$_3$H$_7$ |
| 11-734 | H | Cl | H | SCH$_2$COOiC$_3$H$_7$ |
| 11-735 | F | F | H | SCH$_2$COOiC$_3$H$_7$ |
| 11-736 | F | Cl | H | SCH$_2$COOiC$_3$H$_7$ |
| 11-737 | Cl | F | H | SCH$_2$COOiC$_3$H$_7$ |
| 11-738 | Cl | Cl | H | SCH$_2$COOiC$_3$H$_7$ |
| 11-739 | H | F | H | SCH$_2$COOCC$_5$H$_9$ |
| 11-740 | H | Cl | H | SCH$_2$COOCC$_5$H$_9$ |
| 11-741 | F | F | H | SCH$_2$COOCC$_5$H$_9$ |
| 11-742 | F | Cl | H | SCH$_2$CQOcC$_5$H$_9$ |
| 11-743 | Cl | F | H | SCH$_2$COOcC$_5$H$_9$ |
| 11-744 | Cl | Cl | H | SCH$_2$COOCC$_5$H$_9$ |
| 11-745 | H | F | H | SCH$_2$COOCC$_6$H$_{11}$ |
| 11-746 | H | Cl | H | SCH$_2$COOCC$_6$H$_{11}$ |
| 11-747 | F | F | H | SCH$_2$COOCC$_6$H$_{11}$ |
| 11-748 | F | Cl | H | SCH$_2$COOcC$_6$H$_{11}$ |
| 11-749 | Cl | F | H | SCH$_2$COOeC$_6$H$_{11}$ |
| 11-750 | Cl | Cl | H | SCH$_2$COOcC$_6$H$_{11}$ |

TABLE 155

| | X | Y | R$^1$ | B |
|---|---|---|---|---|
| 11-751 | H | F | H | SCH(CH$_3$)COOH |
| 11-752 | H | Cl | H | SCH(CH$_3$)COOH |
| 11-753 | F | F | H | SCH(CH$_3$)COOH |
| 11-754 | F | Cl | H | SCH(CH$_3$)COOH |
| 11-755 | Cl | F | H | SCH(CH$_3$)COOH |
| 11-756 | Cl | Cl | H | SCH(CH$_3$)COOH |
| 11-757 | H | F | H | SCH(CH$_3$)COOCH$_3$ |
| 11-758 | H | Cl | H | SCH(CH$_3$)COOCH$_3$ |
| 11-759 | F | F | H | SCH(CH$_3$)COOCH$_3$ |
| 11-760 | F | Cl | H | SCH(CH$_3$)COOCH$_3$ |
| 11-761 | Cl | F | H | SCH(CH$_3$)COOCH$_3$ |
| 11-762 | Cl | Cl | H | SCH(CH$_3$)COOCH$_3$ |
| 11-763 | H | F | H | SCH(CH$_3$)COOC$_2$H$_5$ |
| 11-764 | H | Cl | H | SCH(CH$_3$)COOC$_2$H$_5$ |
| 11-765 | F | F | H | SCH(CH$_3$)COOC$_2$H$_5$ |
| 11-766 | F | Cl | H | SCH(CH$_3$)COOC$_2$H$_5$ |
| 11-767 | Cl | F | H | SCH(CH$_3$)COOC$_2$H$_5$ |
| 11-768 | Cl | Cl | H | SCH(CH$_3$)COOC$_2$H$_5$ |
| 11-769 | H | F | H | SCH(CH$_3$)COOnC$_3$H$_7$ |
| 11-770 | H | Cl | H | SCH(CH$_3$)COOnC$_3$H$_7$ |
| 11-771 | F | F | H | SCH(CH$_3$)COOnC$_3$H$_7$ |
| 11-772 | F | Cl | H | SCH(CH$_3$)COOnC$_3$H$_7$ |
| 11-773 | Cl | F | H | SCH(CH$_3$)COOnC$_3$H$_7$ |
| 11-774 | Cl | Cl | H | SCH(CH$_3$)COOnC$_3$H$_7$ |
| 11-775 | H | F | H | SCH(CH$_3$)COOnC$_4$H$_9$ |

TABLE 156

| | X | Y | R$^1$ | B |
|---|---|---|---|---|
| 11-776 | H | Cl | H | SCH(CH$_3$)COOnC$_4$H$_9$ |
| 11-777 | F | F | H | SCH(CH$_3$)COOnC$_4$H$_9$ |
| 11-778 | F | Cl | H | SCH(CH$_3$)COOnC$_4$H$_9$ |
| 11-779 | Cl | F | H | SCH(CH$_3$)COOnC$_4$H$_9$ |
| 11-780 | Cl | Cl | H | SCH(CH$_3$)COOnC$_4$H$_9$ |
| 11-781 | H | F | H | SCH(CH$_3$)COOnC$_5$H$_{11}$ |
| 11-782 | H | Cl | H | SCH(CH$_3$)COOnC$_5$H$_{11}$ |
| 11-783 | F | F | H | SCH(CH$_3$)COOnC$_5$H$_{11}$ |
| 11-784 | F | Cl | H | SCH(CH$_3$)COOnC$_5$H$_{11}$ |
| 11-785 | Cl | F | H | SCH(CH$_3$)COOnC$_5$H$_{11}$ |
| 11-786 | Cl | Cl | H | SCH(CH$_3$)COOnC$_5$H$_{11}$ |
| 11-787 | H | F | H | SCH(CH$_3$)COOiC$_3$H$_7$ |
| 11-788 | H | Cl | H | SCH(CH$_3$)COOiC$_3$H$_7$ |
| 11-789 | F | F | H | SCH(CH$_3$)COOiC$_3$H$_7$ |
| 11-790 | F | Cl | H | SCH(CH$_3$)COOiC$_3$H$_7$ |
| 11-791 | Cl | F | H | SCH(CH$_3$)COOiC$_3$H$_7$ |
| 11-792 | Cl | Cl | H | SCH(CH$_3$)COOiC$_3$H$_7$ |
| 11-793 | H | F | H | SCH(CH$_3$)COOcC$_5$H$_9$ |
| 11-794 | H | Cl | H | SCH(CH$_3$)COOcC$_5$H$_9$ |
| 11-795 | F | F | H | SCH(CH$_3$)COOcC$_5$H$_9$ |
| 11-796 | F | Cl | H | SCH(CH$_3$)COOcC$_5$H$_9$ |
| 11-797 | Cl | F | H | SCH(CH$_3$)COOcC$_5$H$_9$ |
| 11-798 | Cl | Cl | H | SCH(CH$_3$)COOcC$_5$H$_9$ |
| 11-799 | H | F | H | SCH(CH$_3$)COOcC$_6$H$_{11}$ |
| 11-800 | H | Cl | H | SCH(CH$_3$)COOcC$_6$H$_{11}$ |

TABLE 157

| | X | Y | R$^1$ | B |
|---|---|---|---|---|
| 11-801 | F | F | H | SCH(CH$_3$)COOcC$_6$H$_{11}$ |
| 11-802 | F | Cl | H | SCH(CH$_3$)COOcC$_6$H$_{11}$ |
| 11-803 | Cl | F | H | SCH(CH$_3$)COOcC$_6$H$_{11}$ |
| 11-804 | Cl | Cl | H | SCH(CH$_3$)COOcC$_6$H$_{11}$ |
| 11-805 | H | F | H | SCH$_2$CONH$_2$ |
| 11-806 | H | Cl | H | SCH$_2$CONH$_2$ |
| 11-807 | F | F | H | SCH$_2$CONH$_2$ |
| 11-808 | F | Cl | H | SCH$_2$CONH$_2$ |
| 11-809 | Cl | F | H | SCH$_2$CONH$_2$ |
| 11-810 | Cl | Cl | H | SCH$_2$CONH$_2$ |
| 11-811 | H | F | H | SCH$_2$CONHCH$_3$ |
| 11-812 | H | Cl | H | SCH$_2$CONHCH$_3$ |
| 11-813 | F | F | H | SCH$_2$CONHCH$_3$ |
| 11-814 | F | Cl | H | SCH$_2$CONHCH$_3$ |
| 11-815 | Cl | F | H | SCH$_2$CONHCH$_3$ |
| 11-816 | Cl | Cl | H | SCH$_2$CONHCH$_3$ |
| 11-817 | H | F | H | SCH$_2$CON(CH$_3$)$_2$ |
| 11-818 | H | Cl | H | SCH$_2$CON(CH$_3$)$_2$ |
| 11-819 | F | F | H | SCH$_2$CON(CH$_3$)$_2$ |
| 11-820 | F | Cl | H | SCH$_2$CON(CH$_3$)$_2$ |
| 11-821 | Cl | F | H | SCH$_2$CON(CH$_3$)$_2$ |
| 11-822 | Cl | Cl | H | SCH$_2$CON(CH$_3$)$_2$ |
| 11-823 | H | F | H | SCH$_2$CON(C$_2$H$_5$)$_2$ |
| 11-824 | H | Cl | H | SCH$_2$CON(C$_2$H$_5$)$_2$ |
| 11-825 | F | F | H | SCH$_2$CON(C$_2$H$_5$)$_2$ |

TABLE 158

| | X | Y | R$^1$ | B |
|---|---|---|---|---|
| 11-826 | F | Cl | H | SCH$_2$CON(C$_2$H$_5$)$_2$ |
| 11-827 | Cl | F | H | SCH$_2$CON(C$_2$H$_5$)$_2$ |
| 11-828 | Cl | Cl | H | SCH$_2$CON(C$_2$H$_5$)$_2$ |
| 11-829 | H | F | H | SCH$_2$CON(CH$_3$)C$_2$H$_5$ |
| 11-830 | H | Cl | H | SCH$_2$CON(CH$_3$)C$_2$H$_5$ |
| 11-831 | F | F | H | SCH$_2$CON(CH$_3$)C$_2$H$_5$ |
| 11-832 | F | Cl | H | SCH$_2$CON(CH$_3$)C$_2$H$_5$ |
| 11-833 | Cl | F | H | SCH$_2$CON(CH$_3$)C$_2$H$_5$ |
| 11-834 | Cl | Cl | H | SCH$_2$CON(CH$_3$)C$_2$H$_5$ |
| 11-835 | H | F | H | SCH$_2$CON(tetramethylene) |
| 11-836 | H | Cl | H | SCH$_2$CON(tetramethylene) |
| 11-837 | F | F | H | SCH$_2$CON(tetramethylene) |
| 11-838 | F | Cl | H | SCH$_2$CON(tetramethylene) |
| 11-839 | Cl | F | H | SCH$_2$CON(tetramethylene) |
| 11-840 | Cl | Cl | H | SCH$_2$CON(tetramethylene) |
| 11-841 | H | F | H | SCH$_2$CON(pentamethylene) |
| 11-842 | H | Cl | H | SCH$_2$CON(pentamethylene) |
| 11-843 | F | F | H | SCH$_2$CON(pentamethylene) |
| 11-844 | F | Cl | H | SCH$_2$CON(pentamethylene) |
| 11-845 | Cl | F | H | SCH$_2$CON(pentamethylene) |
| 11-846 | Cl | Cl | H | SCH$_2$CON(pentamethylene) |
| 11-847 | H | F | H | SCH$_2$CON(ethyleneoxyethylene) |
| 11-848 | H | Cl | H | SCH$_2$CON(ethyleneoxyethylene) |
| 11-849 | F | F | H | SCH$_2$CON(ethyleneoxyethylene) |
| 11-850 | F | Cl | H | SCH$_2$CON(ethyleneoxyethylene) |

TABLE 159

| | X | Y | R$^1$ | B |
|---|---|---|---|---|
| 11-851 | Cl | F | H | SCH$_2$CON(ethyleneoxyethylene) |
| 11-852 | Cl | Cl | H | SCH$_2$CON(ethyleneoxyethylene) |
| 11-853 | H | F | H | SCH(CH$_3$)CONH$_2$ |
| 11-854 | H | Cl | H | SCH(CH$_3$)CONH$_2$ |
| 11-855 | F | F | H | SCH(CH$_3$)CONH$_2$ |
| 11-856 | F | Cl | H | SCH(CH$_3$)CONH$_2$ |
| 11-857 | Cl | F | H | SCH(CH$_3$)CONH$_2$ |
| 11-858 | Cl | Cl | H | SCH(CH$_3$)CONH$_2$ |
| 11-859 | H | F | H | SCH(CH$_3$)CONHCH$_3$ |
| 11-860 | H | Cl | H | SCH(CH$_3$)CONHCH$_3$ |
| 11-861 | F | F | H | SCH(CH$_3$)CONHCH$_3$ |
| 11-862 | F | Cl | H | SCH(CH$_3$)CONHCH$_3$ |
| 11-863 | Cl | F | H | SCH(CH$_3$)CONHCH$_3$ |
| 11-864 | Cl | Cl | H | SCH(CH$_3$)CONHCH$_3$ |
| 11-865 | H | F | H | SCH(CH$_3$)CON(CH$_3$)$_2$ |
| 11-866 | H | Cl | H | SCH(CH$_3$)CON(CH$_3$)$_2$ |
| 11-867 | F | F | H | SCH(CH$_3$)CON(CH$_3$)$_2$ |
| 11-868 | F | Cl | H | SCH(CH$_3$)CON(CH$_3$)$_2$ |
| 11-869 | Cl | F | H | SCH(CH$_3$)CON(CH$_3$)$_2$ |
| 11-870 | Cl | Cl | H | SCH(CH$_3$)CON(CH$_3$)$_2$ |
| 11-871 | H | F | H | SCH(CH$_3$)CON(C$_2$H$_5$)$_2$ |
| 11-872 | H | Cl | H | SCH(CH$_3$)CON(C$_2$H$_5$)$_2$ |
| 11-873 | F | F | H | SCH(CH$_3$)CON(C$_2$H$_5$)$_2$ |

TABLE 159-continued

| | X | Y | R$^1$ | B |
|---|---|---|---|---|
| 11-874 | F | Cl | H | SCH(CH$_3$)CON(C$_2$H$_5$)$_2$ |
| 11-875 | Cl | F | H | SCH(CH$_3$)CON(C$_2$H$_5$)$_2$ |

TABLE 160

| | X | Y | R$^1$ | B |
|---|---|---|---|---|
| 11-876 | Cl | Cl | H | SCH(CH$_3$)CON(C$_2$H$_5$)$_2$ |
| 11-877 | H | F | H | SCH(CH$_3$)CON(CH$_3$)C$_2$H$_5$ |
| 11-878 | H | Cl | H | SCH(CH$_3$)CON(CH$_3$)C$_2$H$_5$ |
| 11-879 | F | F | H | SCH(CH$_3$)CON(CH$_3$)C$_2$H$_5$ |
| 11-880 | F | Cl | H | SCH(CH$_3$)CON(CH$_3$)C$_2$H$_5$ |
| 11-881 | Cl | F | H | SCH(CH$_3$)CON(CH$_3$)C$_2$H$_5$ |
| 11-882 | Cl | Cl | H | SCH(CH$_3$)CON(CH$_3$)C$_2$H$_5$ |
| 11-883 | H | F | H | SCH(CH$_3$)CON(CH$_3$)C$_2$H$_5$ |
| 11-884 | H | Cl | H | SCH(CH$_3$)CON(CH$_3$)C$_2$H$_5$ |
| 11-885 | F | F | H | SCH(CH$_3$)CON(CH$_3$)C$_2$H$_5$ |
| 11-886 | F | Cl | H | SCH(CH$_3$)CON(CH$_3$)C$_2$H$_5$ |
| 11-887 | Cl | F | H | SCH(CH$_3$)CON(CH$_3$)C$_2$H$_5$ |
| 11-888 | Cl | Cl | H | SCH(CH$_3$)CON(CH$_3$)C$_2$H$_5$ |
| 11-889 | H | F | H | SCH(CH$_3$)CON(tetramethylene) |
| 11-890 | H | Cl | H | SCH(CH$_3$)CON(tetramethylene) |
| 11-891 | F | F | H | SCH(CH$_3$)CON(tetramethylene) |
| 11-892 | F | Cl | H | SCH(CH$_3$)CON(tetramethylene) |
| 11-893 | Cl | F | H | SCH(CH$_3$)CON(tetramethylene) |
| 11-894 | Cl | Cl | H | SCH(CH$_3$)CON(tetramethylene) |
| 11-895 | H | F | H | SCH(CH$_3$)CON(pentamethylene) |
| 11-896 | H | Cl | H | SCH(CH$_3$)CON(pentamethylene) |
| 11-897 | F | F | H | SCH(CH$_3$)CON(pentamethylene) |
| 11-898 | F | Cl | H | SCH(CH$_3$)CON(pentamethylene) |
| 11-899 | Cl | F | H | SCH(CH$_3$)CON(pentamethylene) |
| 11-900 | Cl | Cl | H | SCH(CH$_3$)CON(pentamethylene) |

TABLE 161

| | X | Y | R$^1$ | B |
|---|---|---|---|---|
| 11-901 | H | F | H | SCH(CH$_3$)CON(ethyleneoxyethylene) |
| 11-902 | H | Cl | H | SCH(CH$_3$)CON(ethyleneoxyethylene) |
| 11-903 | F | F | H | SCH(CH$_3$)CON(ethyleneoxyethylene) |
| 11-904 | F | Cl | H | SCH(CH$_3$)CON(ethyleneoxyethylene) |
| 11-905 | Cl | F | H | SCH(CH$_3$)CON(ethyleneoxyethylene) |
| 11-906 | Cl | Cl | H | SCH(CH$_3$)CON(ethyleneoxyethylene) |
| 11-907 | H | F | H | SO$_2$OCH$_3$ |
| 11-908 | H | Cl | H | SO$_2$OCH$_3$ |
| 11-909 | F | F | H | SO$_2$OCH$_3$ |
| 11-910 | F | Cl | H | SO$_2$OCH$_3$ |
| 11-911 | Cl | F | H | SO$_2$OCH$_3$ |
| 11-912 | Cl | Cl | H | SO$_2$OCH$_3$ |
| 11-913 | H | F | H | SO$_2$OC$_2$H$_5$ |
| 11-914 | H | Cl | H | SO$_2$OC$_2$H$_5$ |
| 11-915 | F | F | H | SO$_2$OC$_2$H$_5$ |
| 11-916 | F | Cl | H | SO$_2$OC$_2$H$_5$ |
| 11-917 | Cl | F | H | SO$_2$OC$_2$H$_5$ |
| 11-918 | Cl | Cl | H | SO$_2$OC$_2$H$_5$ |
| 11-919 | H | F | H | SO$_2$OiC$_3$H$_7$ |
| 11-920 | H | Cl | H | SO$_2$OiC$_3$H$_7$ |
| 11-921 | F | F | H | SO$_2$OiC$_3$H$_7$ |
| 11-922 | F | Cl | H | SO$_2$OiC$_3$H$_7$ |
| 11-923 | Cl | F | H | SO$_2$OiC$_3$H$_7$ |
| 11-924 | Cl | Cl | H | SO$_2$OiC$_3$H$_7$ |
| 11-925 | H | F | H | SO$_2$OCH$_2$CH=CH$_2$ |

TABLE 162

| | X | Y | R$^1$ | B |
|---|---|---|---|---|
| 11-926 | H | Cl | H | SO$_2$OCH$_2$CH=CH$_2$ |
| 11-927 | F | F | H | SO$_2$OCH$_2$CH=CH$_2$ |
| 11-928 | F | Cl | H | SO$_2$OCH$_2$CH=CH$_2$ |

TABLE 162-continued

| | X | Y | R$^1$ | B |
|---|---|---|---|---|
| 11-929 | Cl | F | H | SO$_2$OCH$_2$CH=CH$_2$ |
| 11-930 | Cl | Cl | H | SO$_2$OCH$_2$CH=CH$_2$ |
| 11-931 | H | F | H | SO$_2$N(CH$_3$)$_2$ |
| 11-932 | H | Cl | H | SO$_2$N(CH$_3$)$_2$ |
| 11-933 | F | F | H | SO$_2$N(CH$_3$)$_2$ |
| 11-934 | F | Cl | H | SO$_2$N(CH$_3$)$_2$ |
| 11-935 | Cl | F | H | SO$_2$N(CH$_3$)$_2$ |
| 11-936 | Cl | Cl | H | SO$_2$N(CH$_3$)$_2$ |
| 11-937 | H | F | H | SO$_2$N(C$_2$H$_5$)$_2$ |
| 11-938 | H | Cl | H | SO$_2$N(C$_2$H$_5$)$_2$ |
| 11-939 | F | F | H | SO$_2$N(C$_2$H$_5$)$_2$ |
| 11-940 | F | Cl | H | SO$_2$N(C$_2$H$_5$)$_2$ |
| 11-941 | Cl | F | H | SO$_2$N(C$_2$H$_5$)$_2$ |
| 11-942 | Cl | Cl | H | SO$_2$N(C$_2$H$_5$)$_2$ |
| 11-943 | H | F | H | COOH |
| 11-944 | H | Cl | H | COOH |
| 11-945 | F | F | H | COOH |
| 11-946 | F | Cl | H | COOH |
| 11-947 | Cl | F | H | COOH |
| 11-948 | Cl | Cl | H | COOH |
| 11-949 | H | F | H | COOCH$_3$ |
| 11-950 | H | Cl | H | COOCH$_3$ |

TABLE 163

| | X | Y | R$^1$ | B |
|---|---|---|---|---|
| 11-951 | F | F | H | COOCH$_3$ |
| 11-952 | F | Cl | H | COOCH$_3$ |
| 11-953 | Cl | F | H | COOCH$_3$ |
| 11-954 | Cl | Cl | H | COOCH$_3$ |
| 11-955 | H | F | H | COOC$_2$H$_5$ |
| 11-956 | H | Cl | H | COOC$_2$H$_5$ |
| 11-957 | F | F | H | COOC$_2$H$_5$ |
| 11-958 | F | Cl | H | COOC$_2$H$_5$ |
| 11-959 | Cl | F | H | COOC$_2$H$_5$ |
| 11-960 | Cl | Cl | H | COOC$_2$H$_5$ |
| 11-961 | H | F | H | COOnC$_3$H$_7$ |
| 11-962 | H | Cl | H | COOnC$_3$H$_7$ |
| 11-963 | F | F | H | COOnC$_3$H$_7$ |
| 11-964 | F | Cl | H | COOnC$_3$H$_7$ |
| 11-965 | Cl | F | H | COOnC$_3$H$_7$ |
| 11-966 | Cl | Cl | H | COOnC$_3$H$_7$ |
| 11-967 | H | F | H | COOnC$_4$H$_9$ |
| 11-968 | H | Cl | H | COOnC$_4$H$_9$ |
| 11-969 | F | F | H | COOnC$_4$H$_9$ |
| 11-970 | F | Cl | H | COOnC$_4$H$_9$ |
| 11-971 | Cl | F | H | COOnC$_4$H$_9$ |
| 11-972 | Cl | Cl | H | COOnC$_4$H$_9$ |
| 11-973 | H | F | H | COOnC$_5$H$_{11}$ |
| 11-974 | H | Cl | H | COOnC$_5$H$_{11}$ |
| 11-975 | F | F | H | COOnC$_5$H$_{11}$ |

TABLE 164

| | X | Y | R$^1$ | B |
|---|---|---|---|---|
| 11-976 | F | Cl | H | COOnC$_5$H$_{11}$ |
| 11-977 | Cl | F | H | COOnC$_5$H$_{11}$ |
| 11-978 | Cl | Cl | H | COOnC$_5$H$_{11}$ |
| 11-979 | H | F | H | COOiC$_3$H$_7$ |
| 11-980 | H | Cl | H | COOiC$_3$H$_7$ |
| 11-981 | F | F | H | COOiC$_3$H$_7$ |
| 11-982 | F | Cl | H | COOiC$_3$H$_7$ |
| 11-983 | Cl | F | H | COOiC$_3$H$_7$ |
| 11-984 | Cl | Cl | H | COOiC$_3$H$_7$ |
| 11-985 | H | F | H | COOcC$_5$H$_9$ |
| 11-986 | H | Cl | H | COOcC$_5$H$_9$ |
| 11-987 | F | F | H | COOcC$_5$H$_9$ |
| 11-988 | F | Cl | H | COOcC$_5$H$_9$ |
| 11-989 | Cl | F | H | COOcC$_5$H$_9$ |
| 11-990 | Cl | Cl | H | COOcC$_5$H$_9$ |

TABLE 164-continued

| | X | Y | R$^1$ | B |
|---|---|---|---|---|
| 11-991 | H | F | H | COOcC$_6$H$_{11}$ |
| 11-992 | H | Cl | H | COOcC$_6$H$_{11}$ |
| 11-993 | F | F | H | COOcC$_6$H$_{11}$ |
| 11-994 | F | Cl | H | COOcC$_6$H$_{11}$ |
| 11-995 | Cl | F | H | COOcC$_6$H$_{11}$ |
| 11-996 | Cl | Cl | H | COOcC$_6$H$_{11}$ |
| 11-997 | H | F | H | COOCH$_2$C$_6$H$_5$ |
| 11-998 | H | Cl | H | COOCH$_2$C$_6$H$_5$ |
| 11-999 | F | F | H | COOCH$_2$C$_6$H$_5$ |
| 11-1000 | F | Cl | H | COOCH$_2$C$_6$H$_5$ |

TABLE 165

| | X | Y | R$^1$ | B |
|---|---|---|---|---|
| 11-1001 | Cl | F | H | COOCH$_2$C$_6$H$_5$ |
| 11-1002 | Cl | Cl | H | COOCH$_2$C$_6$H$_5$ |
| 11-1003 | H | F | H | COOCH$_2$CH$_2$Cl |
| 11-1004 | H | Cl | H | COOCH$_2$CH$_2$Cl |
| 11-1005 | F | F | H | COOCH$_2$CH$_2$Cl |
| 11-1006 | F | Cl | H | COOCH$_2$CH$_2$Cl |
| 11-1007 | Cl | F | H | COOCH$_2$CH$_2$Cl |
| 11-1008 | Cl | Cl | H | COOCH$_2$CH$_2$Cl |
| 11-1009 | H | F | H | COOCH$_2$CH$_2$Br |
| 11-1010 | H | Cl | H | COOCH$_2$CH$_2$Br |
| 11-1011 | F | F | H | COOCH$_2$CH$_2$Br |
| 11-1012 | F | Cl | H | COOCH$_2$CH$_2$Br |
| 11-1013 | Cl | F | H | COOCH$_2$CH$_2$Br |
| 11-1014 | Cl | Cl | H | COOCH$_2$CH$_2$Br |
| 11-1015 | H | F | H | CONH$_2$ |
| 11-1016 | H | Cl | H | CONH$_2$ |
| 11-1017 | F | F | H | CONH$_2$ |
| 11-1018 | F | Cl | H | CONH$_2$ |
| 11-1019 | Cl | F | H | CONH$_2$ |
| 11-1020 | Cl | Cl | H | CONH$_2$ |
| 11-1021 | H | F | H | CONHCH$_3$ |
| 11-1022 | H | Cl | H | CONHCH$_3$ |
| 11-1023 | F | F | H | CONHCH$_3$ |
| 11-1024 | F | Cl | H | CONHCH$_3$ |
| 11-1025 | Cl | F | H | CONHCH$_3$ |

TABLE 166

| | X | Y | R$^1$ | B |
|---|---|---|---|---|
| 11-1026 | Cl | Cl | H | CONHCH$_3$ |
| 11-1027 | H | F | H | CONHC$_2$H$_5$ |
| 11-1028 | H | Cl | H | CONHC$_2$H$_5$ |
| 11-1029 | F | F | H | CONHC$_2$H$_5$ |
| 11-1030 | F | Cl | H | CONHC$_2$H$_5$ |
| 11-1031 | Cl | F | H | CONHC$_2$H$_5$ |
| 11-1032 | Cl | Cl | H | CONHC$_2$H$_5$ |
| 11-1033 | H | F | H | CON(CH$_3$)$_2$ |
| 11-1034 | H | Cl | H | CON(CH$_3$)$_2$ |
| 11-1035 | F | F | H | CON(CH$_3$)$_2$ |
| 11-1036 | F | Cl | H | CON(CH$_3$)$_2$ |
| 11-1037 | Cl | F | H | CON(CH$_3$)$_2$ |
| 11-1038 | Cl | Cl | H | CON(CH$_3$)$_2$ |
| 11-1039 | H | F | H | CON(C$_2$H$_5$)$_2$ |
| 11-1040 | H | Cl | H | CON(C$_2$H$_5$)$_2$ |
| 11-1041 | F | F | H | CON(C$_2$H$_5$)$_2$ |
| 11-1042 | F | Cl | H | CON(C$_2$H$_5$)$_2$ |
| 11-1043 | Cl | F | H | CON(C$_2$H$_5$)$_2$ |
| 11-1044 | Cl | Cl | H | CON(C$_2$H$_5$)$_2$ |
| 11-1045 | H | F | H | CON(CH$_3$)(C$_2$H$_5$) |
| 11-1046 | H | Cl | H | CON(CH$_3$)(C$_2$H$_5$) |
| 11-1047 | F | F | H | CON(CH$_3$)(C$_2$H$_5$) |
| 11-1048 | F | Cl | H | CON(CH$_3$)(C$_2$H$_5$) |
| 11-1049 | Cl | F | H | CON(CH$_3$)(C$_2$H$_5$) |
| 11-1050 | Cl | Cl | H | CON(CH$_3$)(C$_2$H$_5$) |

TABLE 167

| | X | Y | R$^1$ | B |
|---|---|---|---|---|
| 11-1051 | H | F | H | COCH$_3$ |
| 11-1052 | H | Cl | H | COCH$_3$ |
| 11-1053 | F | F | H | COCH$_3$ |
| 11-1054 | F | Cl | H | COCH$_3$ |
| 11-1055 | Cl | F | H | COCH$_3$ |
| 11-1056 | Cl | Cl | H | COCH$_3$ |
| 11-1057 | H | F | H | COC$_2$H$_5$ |
| 11-1058 | H | Cl | H | COC$_2$H$_5$ |
| 11-1059 | F | F | H | COC$_2$H$_5$ |
| 11-1060 | F | Cl | H | COC$_2$H$_5$ |
| 11-1061 | Cl | F | H | COC$_2$H$_5$ |
| 11-1062 | Cl | Cl | H | COC$_2$H$_5$ |
| 11-1063 | H | F | H | COCH$_2$Cl |
| 11-1064 | H | Cl | H | COCH$_2$Cl |
| 11-1065 | F | F | H | COCH$_2$Cl |
| 11-1066 | F | Cl | H | COCH$_2$Cl |
| 11-1067 | Cl | F | H | COCH$_2$Cl |
| 11-1068 | Cl | Cl | H | COCH$_2$Cl |
| 11-1069 | H | F | H | CHO |
| 11-1070 | H | Cl | H | CHO |
| 11-1071 | F | F | H | CHO |
| 11-1072 | F | Cl | H | CHO |
| 11-1073 | Cl | F | H | CHO |
| 11-1074 | Cl | Cl | H | CHO |
| 11-1075 | H | F | H | CH$_2$CH$_2$COOH |

TABLE 168

| | X | Y | R$^1$ | B |
|---|---|---|---|---|
| 11-1076 | H | Cl | H | CH$_2$CH$_2$COOH |
| 11-1077 | F | F | H | CH$_2$CH$_2$COOH |
| 11-1078 | F | Cl | H | CH$_2$CH$_2$COOH |
| 11-1079 | Cl | F | H | CH$_2$CH$_2$COOH |
| 11-1080 | Cl | Cl | H | CH$_2$CH$_2$COOH |
| 11-1081 | H | F | H | CH$_2$CH$_2$COOCH$_3$ |
| 11-1082 | H | Cl | H | CH$_2$CH$_2$COOCH$_3$ |
| 11-1083 | F | F | H | CH$_2$CH$_2$COOCH$_3$ |
| 11-1084 | F | Cl | H | CH$_2$CH$_2$COOCH$_3$ |
| 11-1085 | Cl | F | H | CH$_2$CH$_2$COOCH$_3$ |
| 11-1086 | Cl | Cl | H | CH$_2$CH$_2$COOCH$_3$ |
| 11-1087 | H | F | H | CH$_2$CH$_2$COOC$_2$H$_5$ |
| 11-1088 | H | Cl | H | CH$_2$CH$_2$COOC$_2$H$_5$ |
| 11-1089 | F | F | H | CH$_2$CH$_2$COOC$_2$H$_5$ |
| 11-1090 | F | Cl | H | CH$_2$CH$_2$COOC$_2$H$_5$ |
| 11-1091 | Cl | F | H | CH$_2$CH$_2$COOC$_2$H$_5$ |
| 11-1092 | Cl | Cl | H | CH$_2$CH$_2$COOC$_2$H$_5$ |
| 11-1093 | H | F | H | CH$_2$CHClCOOCH$_3$ |
| 11-1094 | H | Cl | H | CH$_2$CHClCOOCH$_3$ |
| 11-1095 | F | F | H | CH$_2$CHClCOOCH$_3$ |
| 11-1096 | F | Cl | H | CH$_2$CHClCOOCH$_3$ |
| 11-1097 | Cl | F | H | CH$_2$CHClCOOCH$_3$ |
| 11-1098 | Cl | Cl | H | CH$_2$CHClCOOCH$_3$ |
| 11-1099 | H | F | H | CH$_2$CHClCOOC$_2$H$_5$ |
| 11-1100 | H | Cl | H | CH$_2$CHClCOOC$_2$H$_5$ |

TABLE 169

| | X | Y | R$^1$ | B |
|---|---|---|---|---|
| 11-1101 | F | F | H | CH$_2$CHClCOOC$_2$H$_5$ |
| 11-1102 | F | Cl | H | CH$_2$CHClCOOC$_2$H$_5$ |
| 11-1103 | Cl | F | H | CH$_2$CHClCOOC$_2$H$_5$ |
| 11-1104 | Cl | Cl | H | CH$_2$CHClCOOC$_2$H$_5$ |
| 11-1105 | H | F | H | CH=CHCOOCH$_3$ |
| 11-1106 | H | Cl | H | CH=CHCOOCH$_3$ |
| 11-1107 | F | F | H | CH=CHCOOCH$_3$ |
| 11-1108 | F | Cl | H | CH=CHCOOCH$_3$ |
| 11-1109 | Cl | F | H | CH=CHCOOCH$_3$ |
| 11-1110 | Cl | Cl | H | CH=CHCOOCH$_3$ |
| 11-1111 | H | F | H | CH=CHCOOC$_2$H$_5$ |
| 11-1112 | H | Cl | H | CH=CHCOOC$_2$H$_5$ |

TABLE 169-continued

|  | X | Y | R$^1$ | B |
|---|---|---|---|---|
| 11-1113 | F | F | H | CH=CHCOOC$_2$H$_5$ |
| 11-1114 | F | Cl | H | CH=CHCOOC$_2$H$_5$ |
| 11-1115 | Cl | F | H | CH=CHCOOC$_2$H$_5$ |
| 11-1116 | Cl | Cl | H | CH=CHCOOC$_2$H$_5$ |
| 11-1117 | H | F | H | C(CH$_3$)=NOH |
| 11-1118 | H | Cl | H | C(CH$_3$)=NOH |
| 11-1119 | F | F | H | C(CH$_3$)=NOH |
| 11-1120 | F | Cl | H | C(CH$_3$)=NOH |
| 11-1121 | Cl | F | H | C(CH$_3$)=NOH |
| 11-1122 | Cl | Cl | H | C(CH$_3$)=NOH |
| 11-1123 | H | F | H | C(CH$_3$)=NOCH$_3$ |
| 11-1124 | H | Cl | H | C(CH$_3$)=NOCH$_3$ |
| 11-1125 | F | F | H | C(CH$_3$)=NOCH$_3$ |

TABLE 170

|  | X | Y | R$^1$ | B |
|---|---|---|---|---|
| 11-1126 | F | Cl | H | C(CH$_3$)=NOCH$_3$ |
| 11-1127 | Cl | F | H | C(CH$_3$)=NOCH$_3$ |
| 11-1128 | Cl | Cl | H | C(CH$_3$)=NOCH$_3$ |
| 11-1129 | H | F | H | C(CH$_3$)=NOC$_2$H$_5$ |
| 11-1130 | H | Cl | H | C(CH$_3$)=NOC$_2$H$_5$ |
| 11-1131 | F | F | H | C(CH$_3$)=NOC$_2$H$_5$ |
| 11-1132 | F | Cl | H | C(CH$_3$)=NOC$_2$H$_5$ |
| 11-1133 | Cl | F | H | C(CH$_3$)=NOC$_2$H$_5$ |
| 11-1134 | Cl | Cl | H | C(CH$_3$)=NOC$_2$H$_5$ |
| 11-1135 | H | F | H | C(CH$_3$)=NOiC$_3$H$_7$ |
| 11-1136 | H | Cl | H | C(CH$_3$)=NOiC$_3$H$_7$ |
| 11-1137 | F | F | H | C(CH$_3$)=NOiC$_3$H$_7$ |
| 11-1138 | F | Cl | H | C(CH$_3$)=NOiC$_3$H$_7$ |
| 11-1139 | Cl | F | H | C(CH$_3$)=NOiC$_3$H$_7$ |
| 11-1140 | Cl | Cl | H | C(CH$_3$)=NOiC$_3$H$_7$ |
| 11-1141 | H | F | H | C(CH$_3$)=NNH$_2$ |
| 11-1142 | H | Cl | H | C(CH$_3$)=NNH$_2$ |
| 11-1143 | F | F | H | C(CH$_3$)=NNH$_2$ |
| 11-1144 | F | Cl | H | C(CH$_3$)=NNH$_2$ |
| 11-1145 | Cl | F | H | C(CH$_3$)=NNH$_2$ |
| 11-1146 | Cl | Cl | H | C(CH$_3$)=NNH$_2$ |
| 11-1147 | H | F | H | C(CH$_3$)=NNHCH$_3$ |
| 11-1148 | H | Cl | H | C(CH$_3$)=NNHCH$_3$ |
| 11-1149 | F | F | H | C(CH$_3$)=NNHCH$_3$ |
| 11-1150 | F | Cl | H | C(CH$_3$)=NNHCH$_3$ |

TABLE 171

|  | X | Y | R$^1$ | B |
|---|---|---|---|---|
| 11-1151 | Cl | F | H | C(CH$_3$)=NNHCH$_3$ |
| 11-1152 | Cl | Cl | H | C(CH$_3$)=NNHCH$_3$ |
| 11-1153 | H | F | H | C(CH$_3$)=NN(CH$_3$)$_2$ |
| 11-1154 | H | Cl | H | C(CH$_3$)=NN(CH$_3$)$_2$ |
| 11-1155 | F | F | H | C(CH$_3$)=NN(CH$_3$)$_2$ |
| 11-1156 | F | Cl | H | C(CH$_3$)=NN(CH$_3$)$_2$ |
| 11-1157 | Cl | F | H | C(CH$_3$)=NN(CH$_3$)$_2$ |
| 11-1158 | Cl | Cl | H | C(CH$_3$)=NN(CH$_3$)$_2$ |
| 11-1159 | H | F | H | C(CH$_3$)=NNHC$_2$H$_5$ |
| 11-1160 | H | Cl | H | C(CH$_3$)=NNHC$_2$H$_5$ |
| 11-1161 | F | F | H | C(CH$_3$)=NNHC$_2$H$_5$ |
| 11-1162 | F | Cl | H | C(CH$_3$)=NNHC$_2$H$_5$ |
| 11-1163 | Cl | F | H | C(CH$_3$)=NNHC$_2$H$_5$ |
| 11-1164 | Cl | Cl | H | C(CH$_3$)=NNHC$_2$H$_5$ |
| 11-1165 | H | F | H | C(CH$_3$)=NN(C$_2$H$_5$)$_2$ |
| 11-1166 | H | Cl | H | C(CH$_3$)=NN(C$_2$H$_5$)$_2$ |
| 11-1167 | F | F | H | C(CH$_3$)=NN(C$_2$H$_5$)$_2$ |
| 11-1168 | F | Cl | H | C(CH$_3$)=NN(C$_2$H$_5$)$_2$ |
| 11-1169 | Cl | F | H | C(CH$_3$)=NN(C$_2$H$_5$)$_2$ |
| 11-1170 | Cl | Cl | H | C(CH$_3$)=NN(C$_2$H$_5$)$_2$ |
| 11-1171 | H | F | H | C(C$_2$H$_5$)=NNH$_2$ |
| 11-1172 | H | Cl | H | C(C$_2$H$_5$)=NNH$_2$ |
| 11-1173 | F | F | H | C(C$_2$H$_5$)=NNH$_2$ |

TABLE 171-continued

|  | X | Y | R$^1$ | B |
|---|---|---|---|---|
| 11-1174 | F | Cl | H | C(C$_2$H$_5$)=NNH$_2$ |
| 11-1175 | Cl | F | H | C(C$_2$H$_5$)=NNH$_2$ |

TABLE 172

|  | X | Y | R$^1$ | B |
|---|---|---|---|---|
| 11-1176 | Cl | Cl | H | C(C$_2$H$_5$)=NNH$_2$ |
| 11-1177 | H | F | H | C(C$_2$H$_5$)=NNHCH$_3$ |
| 11-1178 | H | Cl | H | C(C$_2$H$_5$)=NNHCH$_3$ |
| 11-1179 | F | F | H | C(C$_2$H$_5$)=NNHCH$_3$ |
| 11-1180 | F | Cl | H | C(C$_2$H$_5$)=NNHCH$_3$ |
| 11-1181 | Cl | F | H | C(C$_2$H$_5$)=NNHCH$_3$ |
| 11-1182 | Cl | Cl | H | C(C$_2$H$_5$)=NNHCH$_3$ |
| 11-1183 | H | F | H | C(C$_2$H$_5$)=NN(CH$_3$)$_2$ |
| 11-1184 | H | Cl | H | C(C$_2$H$_5$)=NN(CH$_3$)$_2$ |
| 11-1185 | F | F | H | C(C$_2$H$_5$)=NN(CH$_3$)$_2$ |
| 11-1186 | F | Cl | H | C(C$_2$H$_5$)=NN(CH$_3$)$_2$ |
| 11-1187 | Cl | F | H | C(C$_2$H$_5$)=NN(CH$_3$)$_2$ |
| 11-1188 | Cl | Cl | H | C(C$_2$H$_5$)=NN(CH$_3$)$_2$ |
| 11-1189 | H | F | H | C(C$_2$H$_5$)=NNHC$_2$H$_5$ |
| 11-1190 | H | Cl | H | C(C$_2$H$_5$)=NNHC$_2$H$_5$ |
| 11-1191 | F | F | H | C(C$_2$H$_5$)=NNHC$_2$H$_5$ |
| 11-1192 | F | Cl | H | C(C$_2$H$_5$)=NNHC$_2$H$_5$ |
| 11-1193 | Cl | F | H | C(C$_2$H$_5$)=NNHC$_2$H$_5$ |
| 11-1194 | Cl | Cl | H | C(C$_2$H$_5$)=NNHC$_2$H$_5$ |
| 11-1195 | H | F | H | C(C$_2$H$_5$)=NN(C$_2$H$_5$)$_2$ |
| 11-1196 | H | Cl | H | C(C$_2$H$_5$)=NN(C$_2$H$_5$)$_2$ |
| 11-1197 | F | F | H | C(C$_2$H$_5$)=NN(C$_2$H$_5$)$_2$ |
| 11-1198 | F | Cl | H | C(C$_2$H$_5$)=NN(C$_2$H$_5$)$_2$ |
| 11-1199 | Cl | F | H | C(C$_2$H$_5$)=NN(C$_2$H$_5$)$_2$ |
| 11-1200 | Cl | Cl | H | C(C$_2$H$_5$)=NN(C$_2$H$_5$)$_2$ |

TABLE 173

|  | X | Y | R$^1$ | B |
|---|---|---|---|---|
| 11-1201 | H | F | H | C(CH$_3$)(OCH$_3$)$_2$ |
| 11-1202 | H | Cl | H | C(CH$_3$)(OCH$_3$)$_2$ |
| 11-1203 | F | F | H | C(CH$_3$)(OCH$_3$)$_2$ |
| 11-1204 | F | Cl | H | C(CH$_3$)(OCH$_3$)$_2$ |
| 11-1205 | Cl | F | H | C(CH$_3$)(OCH$_3$)$_2$ |
| 11-1206 | Cl | Cl | H | C(CH$_3$)(OCH$_3$)$_2$ |
| 11-1207 | H | F | H | C(CH$_3$)(OC$_2$H$_5$)$_2$ |
| 11-1208 | H | Cl | H | C(CH$_3$)(OC$_2$H$_5$)$_2$ |
| 11-1209 | F | F | H | C(CH$_3$)(OC$_2$H$_5$)$_2$ |
| 11-1210 | F | Cl | H | C(CH$_3$)(OC$_2$H$_5$)$_2$ |
| 11-1211 | Cl | F | H | C(CH$_3$)(OC$_2$H$_5$)$_2$ |
| 11-1212 | Cl | Cl | H | C(CH$_3$)(OC$_2$H$_5$)$_2$ |
| 11-1213 | H | F | H | C(CH$_3$)(OiC$_3$H$_7$)$_2$ |
| 11-1214 | H | Cl | H | C(CH$_3$)(OiC$_3$H$_7$)$_2$ |
| 11-1215 | F | F | H | C(CH$_3$)(OiC$_3$H$_7$)$_2$ |
| 11-1216 | F | Cl | H | C(CH$_3$)(OiC$_3$H$_7$)$_2$ |
| 11-1217 | Cl | F | H | C(CH$_3$)(OiC$_3$H$_7$)$_2$ |
| 11-1218 | Cl | Cl | H | C(CH$_3$)(OiC$_3$H$_7$)$_2$ |
| 11-1219 | H | F | H | C(CH$_3$)(OCH$_2$CH$_2$O) |
| 11-1220 | H | Cl | H | C(CH$_3$)(OCH$_2$CH$_2$O) |
| 11-1221 | F | F | H | C(CH$_3$)(OCH$_2$CH$_2$O) |
| 11-1222 | F | Cl | H | C(CH$_3$)(OCH$_2$CH$_2$O) |
| 11-1223 | Cl | F | H | C(CH$_3$)(OCH$_2$CH$_2$O) |
| 11-1224 | Cl | Cl | H | C(CH$_3$)(OCH$_2$CH$_2$O) |
| 11-1225 | H | F | H | C(CH$_3$)(OCH$_2$CH$_2$CH$_2$O) |

TABLE 174

|  | X | Y | R$^1$ | B |
|---|---|---|---|---|
| 11-1226 | H | Cl | H | C(CH$_3$)(OCH$_2$CH$_2$CH$_2$O) |
| 11-1227 | F | F | H | C(CH$_3$)(OCH$_2$CH$_2$CH$_2$O) |
| 11-1228 | F | Cl | H | C(CH$_3$)(OCH$_2$CH$_2$CH$_2$O) |

TABLE 174-continued

| | X | Y | R$^1$ | B |
|---|---|---|---|---|
| 11-1229 | Cl | F | H | C(CH$_3$)(OCH$_2$CH$_2$CH$_2$O) |
| 11-1230 | Cl | Cl | H | C(CH$_3$)(OCH$_2$CH$_2$CH$_2$O) |
| 11-1231 | H | F | H | C(C$_2$H$_5$)(OCH$_2$CH$_2$O) |
| 11-1232 | H | Cl | H | C(C$_2$H$_5$)(OCH$_2$CH$_2$O) |
| 11-1233 | F | F | H | C(C$_2$H$_5$)(OCH$_2$CH$_2$O) |
| 11-1234 | F | Cl | H | C(C$_2$H$_5$)(OCH$_2$CH$_2$O) |
| 11-1235 | Cl | F | H | C(C$_2$H$_5$)(OCH$_2$CH$_2$O) |
| 11-1236 | Cl | Cl | H | C(C$_2$H$_5$)(OCH$_2$CH$_2$O) |
| 11-1237 | H | F | H | C(C$_2$H$_5$)(OCH$_2$CH$_2$CH$_2$O) |
| 11-1238 | H | Cl | H | C(C$_2$H$_5$)(OCH$_2$CH$_2$CH$_2$O) |
| 11-1239 | F | F | H | C(C$_2$H$_5$)(OCH$_2$CH$_2$CH$_2$O) |
| 11-1240 | F | Cl | H | C(C$_2$H$_5$)(OCH$_2$CH$_2$CH$_2$O) |
| 11-1241 | Cl | F | H | C(C$_2$H$_5$)(OCH$_2$CH$_2$CH$_2$O) |
| 11-1242 | Cl | Cl | H | C(C$_2$H$_5$)(OCH$_2$CH$_2$CH$_2$O) |
| 11-1243 | H | F | H | OCH$_2$CH(CH$_3$)$_2$ |
| 11-1244 | H | Cl | H | OCH$_2$CH(CH$_3$)$_2$ |
| 11-1245 | F | F | H | OCH$_2$CH(CH$_3$)$_2$ |
| 11-1246 | F | Cl | H | OCH$_2$CH(CH$_3$)$_2$ |
| 11-1247 | Cl | F | H | OCH$_2$CH(CH$_3$)$_2$ |
| 11-1248 | Cl | Cl | H | OCH$_2$CH(CH$_3$)$_2$ |
| 11-1249 | H | F | H | OCH$_2$CH$_2$F |
| 11-1250 | H | Cl | H | OCH$_2$CH$_2$F |

TABLE 175

| | X | Y | R$^1$ | B |
|---|---|---|---|---|
| 11-1251 | F | F | H | OCH$_2$CH$_2$F |
| 11-1252 | F | Cl | H | OCH$_2$CH$_2$F |
| 11-1253 | Cl | F | H | OCH$_2$CH$_2$F |
| 11-1254 | Cl | Cl | H | OCH$_2$CH$_2$F |
| 11-1255 | H | Cl | H | CH$_2$OH |
| 11-1256 | F | Cl | H | CH$_2$OH |
| 11-1257 | H | Cl | H | CH$_2$OCOCH$_3$ |
| 11-1258 | F | Cl | H | CH$_2$OCOCH$_3$ |

Compounds of the general formula:

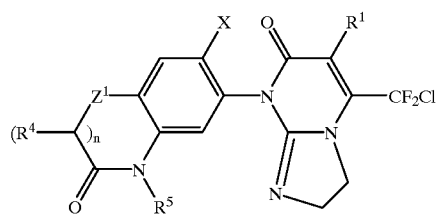

TABLE 176

| | X | Z$^1$ | n | R$^1$ | R$^4$ | R$^5$ |
|---|---|---|---|---|---|---|
| 12-1 | H | O | 1 | H | H | H |
| 12-2 | F | O | 1 | H | H | H |
| 12-3 | H | O | 1 | H | H | CH$_3$ |
| 12-4 | F | O | 1 | H | H | CH$_3$ |
| 12-5 | H | O | 1 | H | H | C$_2$H$_5$ |
| 12-6 | F | O | 1 | H | H | C$_2$H$_5$ |
| 12-7 | H | O | 1 | H | H | nC$_3$H$_7$ |
| 12-8 | F | O | 1 | H | H | nC$_3$H$_7$ |
| 12-9 | H | O | 1 | H | H | nC$_4$H$_9$ |
| 12-10 | F | O | 1 | H | H | nC$_4$H$_9$ |
| 12-11 | H | O | 1 | H | H | nC$_5$H$_{11}$ |
| 12-12 | F | O | 1 | H | H | nC$_5$H$_{11}$ |
| 12-13 | H | O | 1 | H | H | iC$_3$H$_7$ |
| 12-14 | F | O | 1 | H | H | iC$_3$H$_7$ |
| 12-15 | H | O | 1 | H | H | CH$_2$CH$_2$Cl |
| 12-16 | F | O | 1 | H | H | CH$_2$CH$_2$Cl |
| 12-17 | H | O | 1 | H | H | CH$_2$CH$_2$Br |

TABLE 176-continued

| | X | Z$^1$ | n | R$^1$ | R$^4$ | R$^5$ |
|---|---|---|---|---|---|---|
| 12-18 | F | O | 1 | H | H | CH$_2$CH$_2$Br |
| 12-19 | H | O | 1 | H | H | CH$_2$CH=CH$_2$ |
| 12-20 | F | O | 1 | H | H | CH$_2$CH=CH$_2$ |
| 12-21 | H | O | 1 | H | H | CH(CH$_3$)CH=CH$_2$ |
| 12-22 | F | O | 1 | H | H | CH(CH$_3$)CH=CH$_2$ |
| 12-23 | H | O | 1 | H | H | CH$_2$CCl=CH$_2$ |
| 12-24 | F | O | 1 | H | H | CH$_2$CCl=CH$_2$ |
| 12-25 | H | O | 1 | H | H | CH$_2$C≡CH |

TABLE 177

| | X | Z$^1$ | n | R$^1$ | R$^4$ | R$^5$ |
|---|---|---|---|---|---|---|
| 12-26 | F | O | 1 | H | H | CH$_2$C≡CH |
| 12-27 | H | O | 1 | H | H | CH(CH$_3$)C≡CH |
| 12-28 | F | O | 1 | H | H | CH(CH$_3$)C≡CH |
| 12-29 | H | O | 1 | H | H | CH$_2$CN |
| 12-30 | F | O | 1 | H | H | CH$_2$CN |
| 12-31 | H | O | 1 | H | H | CH$_2$OCH$_3$ |
| 12-32 | F | O | 1 | H | H | CH$_2$OCH$_3$ |
| 12-33 | H | O | 1 | H | H | CH$_2$OC$_2$H$_5$ |
| 12-34 | F | O | 1 | H | H | CH$_2$OC$_2$H$_5$ |
| 12-35 | H | O | 1 | H | H | CH$_2$COOH |
| 12-36 | F | O | 1 | H | H | CH$_2$COOH |
| 12-37 | H | O | 1 | H | H | CH$_2$COOCH$_3$ |
| 12-38 | F | O | 1 | H | H | CH$_2$COOCH$_3$ |
| 12-39 | H | O | 1 | H | H | CH$_2$COOC$_2$H$_5$ |
| 12-40 | F | O | 1 | H | H | CH$_2$COOC$_2$H$_5$ |
| 12-41 | H | O | 1 | H | H | CH$_2$COOnC$_3$H$_7$ |
| 12-42 | F | O | 1 | H | H | CH$_2$COOnC$_3$H$_7$ |
| 12-43 | H | O | 1 | H | H | CH$_2$COOnC$_4$H$_9$ |
| 12-44 | F | O | 1 | H | H | CH$_2$COOnC$_4$H$_9$ |
| 12-45 | H | O | 1 | H | H | CH$_2$COOnC$_5$H$_{11}$ |
| 12-46 | F | O | 1 | H | H | CH$_2$COOnC$_5$H$_{11}$ |
| 12-47 | H | O | 1 | H | H | CH$_2$COOiC$_3$H$_7$ |
| 12-48 | F | O | 1 | H | H | CH$_2$COOiC$_3$H$_7$ |
| 12-49 | H | O | 1 | H | H | CH$_2$COOcC$_5$H$_9$ |
| 12-50 | F | O | 1 | H | H | CH$_2$COOcC$_5$H$_9$ |

TABLE 178

| | X | Z$^1$ | n | R$^1$ | R$^4$ | R$^5$ |
|---|---|---|---|---|---|---|
| 12-51 | H | O | 1 | H | H | CH$_2$COOcC$_6$H$_{11}$ |
| 12-52 | F | O | 1 | H | H | CH$_2$COOcC$_6$H$_{11}$ |
| 12-53 | H | O | 1 | H | H | CH(CH$_3$)COOH |
| 12-54 | F | O | 1 | H | H | CH(CH$_3$)COOH |
| 12-55 | H | O | 1 | H | H | CH(CH$_3$)COOCH$_3$ |
| 12-56 | F | O | 1 | H | H | CH(CH$_3$)COOCH$_3$ |
| 12-57 | H | O | 1 | H | H | CH(CH$_3$)COOC$_2$H$_5$ |
| 12-58 | F | O | 1 | H | H | CH(CH$_3$)COOC$_2$H$_5$ |
| 12-59 | H | O | 1 | H | H | CH(CH$_3$)COOnC$_3$H$_7$ |
| 12-60 | F | O | 1 | H | H | CH(CH$_3$)COOnC$_3$H$_7$ |
| 12-61 | H | O | 1 | H | H | CH(CH$_3$)COOnC$_4$H$_9$ |
| 12-62 | F | O | 1 | H | H | CH(CH$_3$)COOnC$_4$H$_9$ |
| 12-63 | H | O | 1 | H | H | CH(CH$_3$)COOnC$_5$H$_{11}$ |
| 12-64 | F | O | 1 | H | H | CH(CH$_3$)COOnC$_5$H$_{11}$ |
| 12-65 | H | O | 1 | H | H | CH(CH$_3$)COOiC$_3$H$_7$ |
| 12-66 | F | O | 1 | H | H | CH(CH$_3$)COOiC$_3$H$_7$ |
| 12-67 | H | O | 1 | H | H | CH(CH$_3$)COOcC$_5$H$_9$ |
| 12-68 | F | O | 1 | H | H | CH(CH$_3$)COOcC$_5$H$_9$ |
| 12-69 | H | O | 1 | H | H | CH(CH$_3$)COOcC$_6$H$_{11}$ |
| 12-70 | F | O | 1 | H | H | CH(CH$_3$)COOcC$_6$H$_{11}$ |
| 12-71 | H | O | 1 | H | CH$_3$ | H |
| 12-72 | F | O | 1 | H | CH$_3$ | H |
| 12-73 | H | O | 1 | H | CH$_3$ | CH$_3$ |
| 12-74 | F | O | 1 | H | CH$_3$ | CH$_3$ |
| 12-75 | H | O | 1 | H | CH$_3$ | C$_2$H$_5$ |

TABLE 179

|  | X | Z¹ | n | R¹ | R⁴ | R⁵ |
|---|---|---|---|---|---|---|
| 12-76 | F | O | 1 | H | CH₃ | C₂H₅ |
| 12-77 | H | O | 1 | H | CH₃ | nC₃H₇ |
| 12-78 | F | O | 1 | H | CH₃ | nC₃H₇ |
| 12-79 | H | O | 1 | H | CH₃ | nC₄H₉ |
| 12-80 | F | O | 1 | H | CH₃ | nC₄H₉ |
| 12-81 | H | O | 1 | H | CH₃ | nC₅H₁₁ |
| 12-82 | F | O | 1 | H | CH₃ | nC₅H₁₁ |
| 12-83 | H | O | 1 | H | CH₃ | iC₃H₇ |
| 12-84 | F | O | 1 | H | CH₃ | iC₃H₇ |
| 12-85 | H | O | 1 | H | CH₃ | CH₂CH₂Cl |
| 12-86 | F | O | 1 | H | CH₃ | CH₂CH₂Cl |
| 12-87 | H | O | 1 | H | CH₃ | CH₂CH₂Br |
| 12-88 | F | O | 1 | H | CH₃ | CH₂CH₂Br |
| 12-89 | H | O | 1 | H | CH₃ | CH₂CH=CH₂ |
| 12-90 | F | O | 1 | H | CH₃ | CH₂CH=CH₂ |
| 12-91 | H | O | 1 | H | CH₃ | CH(CH₃)CH=CH₂ |
| 12-92 | F | O | 1 | H | CH₃ | CH(CH₃)CH=CH₂ |
| 12-93 | H | O | 1 | H | CH₃ | CH₂CCl=CH₂ |
| 12-94 | F | O | 1 | H | CH₃ | CH₂CCl=CH₂ |
| 12-95 | H | O | 1 | H | CH₃ | CH₂C≡CH |
| 12-96 | F | O | 1 | H | CH₃ | CH₂C≡CH |
| 12-97 | H | O | 1 | H | CH₃ | CH(CH₃)C≡CH |
| 12-98 | F | O | 1 | H | CH₃ | CH(CH₃)C≡CH |
| 12-99 | H | O | 1 | H | CH₃ | CH₂CN |
| 12-100 | F | O | 1 | H | CH₃ | CH₂CN |

TABLE 180

|  | X | Z¹ | n | R¹ | R⁴ | R⁵ |
|---|---|---|---|---|---|---|
| 12-101 | H | O | 1 | H | CH₃ | CH₂OCH₃ |
| 12-102 | F | O | 1 | H | CH₃ | CH₂OCH₃ |
| 12-103 | H | O | 1 | H | CH₃ | CH₂OC₂H₅ |
| 12-104 | F | O | 1 | H | CH₃ | CH₂OC₂H₅ |
| 12-105 | H | O | 0 | H | — | H |
| 12-106 | F | O | 0 | H | — | H |
| 12-107 | H | O | 0 | H | — | CH₃ |
| 12-108 | F | O | 0 | H | — | CH₃ |
| 12-109 | H | O | 0 | H | — | C₂H₅ |
| 12-110 | F | O | 0 | H | — | C₂H₅ |
| 12-111 | H | O | 0 | H | — | nC₃H₇ |
| 12-112 | F | O | 0 | H | — | nC₃H₇ |
| 12-113 | H | O | 0 | H | — | nC₄H₉ |
| 12-114 | F | O | 0 | H | — | nC₄H₉ |
| 12-115 | H | O | 0 | H | — | nC₅H₁₁ |
| 12-116 | F | O | 0 | H | — | nC₅H₁₁ |
| 12-117 | H | O | 0 | H | — | iC₃H₇ |
| 12-118 | F | O | 0 | H | — | iC₃H₇ |
| 12-119 | H | O | 0 | H | — | CH₂CH₂Cl |
| 12-120 | F | O | 0 | H | — | CH₂CH₂Cl |
| 12-121 | H | O | 0 | H | — | CH₂CH₂Br |
| 12-122 | F | O | 0 | H | — | CH₂CH₂Br |
| 12-123 | H | O | 0 | H | — | CH₂CH=CH₂ |
| 12-124 | F | O | 0 | H | — | CH₂CH=CH₂ |
| 12-125 | H | O | 0 | H | — | CH(CH₃)CH=CH₂ |

TABLE 181

|  | X | Z¹ | n | R¹ | R⁴ | R⁵ |
|---|---|---|---|---|---|---|
| 12-126 | F | O | 0 | H | — | CH(CH₃)CH=CH₂ |
| 12-127 | H | O | 0 | H | — | CH₂CCl=CH₂ |
| 12-128 | F | O | 0 | H | — | CH₂CCl=CH₂ |
| 12-129 | H | O | 0 | H | — | CH₂C≡CH |
| 12-130 | F | O | 0 | H | — | CH₂C≡CH |
| 12-131 | H | O | 0 | H | — | CH(CH₃)C≡CH |
| 12-132 | F | O | 0 | H | — | CH(CH₃)C≡CH |
| 12-133 | H | O | 0 | H | — | CH₂CN |
| 12-134 | F | O | 0 | H | — | CH₂CN |
| 12-135 | H | O | 0 | H | — | CH₂OCH₃ |
| 12-136 | F | O | 0 | H | — | CH₂OCH₃ |
| 12-137 | H | O | 0 | H | — | CH₂OC₂H₅ |

TABLE 181-continued

|  | X | Z¹ | n | R¹ | R⁴ | R⁵ |
|---|---|---|---|---|---|---|
| 12-138 | F | O | 0 | H | — | CH₂OC₂H₅ |
| 12-139 | H | S | 0 | H | — | H |
| 12-140 | F | S | 0 | H | — | H |
| 12-141 | H | S | 0 | H | — | CH₃ |
| 12-142 | F | S | 0 | H | — | CH₃ |
| 12-143 | H | S | 0 | H | — | C₂H₅ |
| 12-144 | F | S | 0 | H | — | C₂H₅ |
| 12-145 | H | S | 0 | H | — | nC₃H₇ |
| 12-146 | F | S | 0 | H | — | nC₃H₇ |
| 12-147 | H | S | 0 | H | — | nC₄H₉ |
| 12-148 | F | S | 0 | H | — | nC₄H₉ |
| 12-149 | H | S | 0 | H | — | nC₅H₁₁ |
| 12-150 | F | S | 0 | H | — | nC₅H₁₁ |

TABLE 182

|  | X | Z¹ | n | R¹ | R⁴ | R⁵ |
|---|---|---|---|---|---|---|
| 12-151 | H | S | 0 | H | — | iC₃H₇ |
| 12-152 | F | S | 0 | H | — | iC₃H₇ |
| 12-153 | H | S | 0 | H | — | CH₂CH₂Cl |
| 12-154 | F | S | 0 | H | — | CH₂CH₂Cl |
| 12-155 | H | S | 0 | H | — | CH₂CH₂Br |
| 12-156 | F | S | 0 | H | — | CH₂CH₂Br |
| 12-157 | H | S | 0 | H | — | CH₂CH=CH₂ |
| 12-158 | F | S | 0 | H | — | CH₂CH=CH₂ |
| 12-159 | H | S | 0 | H | — | CH(CH₃)CH=CH₂ |
| 12-160 | F | S | 0 | H | — | CH(CH₃)CH=CH₂ |
| 12-161 | H | S | 0 | H | — | CH₂CCl=CH₂ |
| 12-162 | F | S | 0 | H | — | CH₂CCl=CH₂ |
| 12-163 | H | S | 0 | H | — | CH₂C≡CH |
| 12-164 | F | S | 0 | H | — | CH₂C≡CH |
| 12-165 | H | S | 0 | H | — | CH(CH₃)C≡CH |
| 12-166 | F | S | 0 | H | — | CH(CH₃)C≡CH |
| 12-167 | H | S | 0 | H | — | CH₂CN |
| 12-168 | F | S | 0 | H | — | CH₂CN |
| 12-169 | H | S | 0 | H | — | CH₂OCH₃ |
| 12-170 | F | S | 0 | H | — | CH₂OCH₃ |
| 12-171 | H | S | 0 | H | — | CH₂OC₂H₅ |
| 12-172 | F | S | 0 | H | — | CH₂OC₂H₅ |
| 12-173 | H | S | 0 | H | — | CH₂COOH |
| 12-174 | F | S | 0 | H | — | CH₂COOH |
| 12-175 | H | S | 0 | H | — | CH₂COOCH₃ |

TABLE 183

|  | X | Z¹ | n | R¹ | R⁴ | R⁵ |
|---|---|---|---|---|---|---|
| 12-176 | F | S | 0 | H | — | CH₂COOCH₃ |
| 12-177 | H | S | 0 | H | — | CH₂COOC₂H₅ |
| 12-178 | F | S | 0 | H | — | CH₂COOC₂H₅ |
| 12-179 | H | S | 0 | H | — | CH₂COOnC₃H₇ |
| 12-180 | F | S | 0 | H | — | CH₂COOnC₃H₇ |
| 12-181 | H | S | 0 | H | — | CH₂COOnC₄H₉ |
| 12-182 | F | S | 0 | H | — | CH₂COOnC₄H₉ |
| 12-183 | H | S | 0 | H | — | CH₂COOnC₅H₁₁ |
| 12-184 | F | S | 0 | H | — | CH₂COOnC₅H₁₁ |
| 12-185 | H | S | 0 | H | — | CH₂COOiC₃H₇ |
| 12-186 | F | S | 0 | H | — | CH₂COOiC₃H₇ |
| 12-187 | H | S | 0 | H | — | CH₂COOcC₅H₉ |
| 12-188 | F | S | 0 | H | — | CH₂COOcC₅H₉ |
| 12-189 | H | S | 0 | H | — | CH₂COOcC₆H₁₁ |
| 12-190 | F | S | 0 | H | — | CH₂COOcC₆H₁₁ |
| 12-191 | H | S | 0 | H | — | CH(CH₃)COOH |
| 12-192 | F | S | 0 | H | — | CH(CH₃)COOH |
| 12-193 | H | S | 0 | H | — | CH(CH₃)COOCH₃ |
| 12-194 | F | S | 0 | H | — | CH(CH₃)COOCH₃ |
| 12-195 | H | S | 0 | H | — | CH(CH₃)COOC₂H₅ |
| 12-196 | F | S | 0 | H | — | CH(CH₃)COOC₂H₅ |
| 12-197 | H | S | 0 | H | — | CH(CH₃)COOnC₃H₇ |
| 12-198 | F | S | 0 | H | — | CH(CH₃)COOnC₃H₇ |
| 12-199 | H | S | 0 | H | — | CH(CH₃)COOnC₄H₉ |

TABLE 183-continued

|  | X | $Z^1$ | n | $R^1$ | $R^4$ | $R^5$ |
|---|---|---|---|---|---|---|
| 12-200 | F | S | 0 | H | — | $CH(CH_3)COOnC_4H_9$ |

TABLE 184

|  | X | $Z^1$ | n | $R^1$ | $R^4$ | $R^5$ |
|---|---|---|---|---|---|---|
| 12-201 | H | S | 0 | H | — | $CH(CH_3)COOnC_5H_{11}$ |
| 12-202 | F | S | 0 | H | — | $CH(CH_3)COOnC_5H_{11}$ |
| 12-203 | H | S | 0 | H | — | $CH(CH_3)COOiC_3H_7$ |
| 12-204 | F | S | 0 | H | — | $CH(CH_3)COOiC_3H_7$ |
| 12-205 | H | S | 0 | H | — | $CH(CH_3)COOcC_5H_9$ |
| 12-206 | F | S | 0 | H | — | $CH(CH_3)COOcC_5H_9$ |
| 12-207 | H | S | 0 | H | — | $CH(CH_3)COOcC_6H_{11}$ |
| 12-208 | F | S | 0 | H | — | $CH(CH_3)COOcC_6H_{11}$ |

Compounds of the general formula:

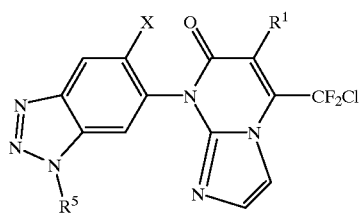

TABLE 185

|  | X | $R^1$ | $R^5$ |
|---|---|---|---|
| 15-1 | H | H | $CH_3$ |
| 15-2 | F | H | $CH_3$ |
| 15-3 | Cl | H | $CH_3$ |
| 15-4 | H | H | $C_2H_5$ |
| 15-5 | F | H | $C_2H_5$ |
| 15-6 | Cl | H | $C_2H_5$ |
| 15-7 | H | H | $nC_3H_7$ |
| 15-8 | F | H | $nC_3H_7$ |
| 15-9 | Cl | H | $nC_3H_7$ |
| 15-10 | H | H | $nC_4H_9$ |
| 15-11 | F | H | $nC_4H_9$ |
| 15-12 | Cl | H | $nC_4H_9$ |
| 15-13 | H | H | $iC_4H_9$ |
| 15-14 | F | H | $iC_4H_9$ |
| 15-15 | Cl | H | $iC_4H_9$ |
| 15-16 | H | H | $CH_2CH=CH_2$ |
| 15-17 | F | H | $CH_2CH=CH_2$ |
| 15-18 | Cl | H | $CH_2CH=CH_2$ |
| 15-19 | H | H | $CH(CH_3)CH=CH_2$ |
| 15-20 | F | H | $CH(CH_3)CH=CH_2$ |
| 15-21 | Cl | H | $CH(CH_3)CH=CH_2$ |
| 15-22 | H | H | $CH_2C\equiv CH$ |
| 15-23 | F | H | $CH_2C\equiv CH$ |
| 15-24 | Cl | H | $CH_2C\equiv CH$ |
| 15-25 | H | H | $CH(CH_3)C\equiv CH$ |

TABLE 186

|  | X | $R^1$ | $R^5$ |
|---|---|---|---|
| 15-26 | F | H | $CH(CH_3)CH=CH$ |
| 15-27 | Cl | H | $CH(CH_3)CH=CH$ |

Compounds of the general formula:

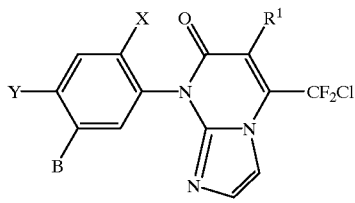

TABLE 187

|  | X | Y | $R^1$ | B |
|---|---|---|---|---|
| 16-1 | H | F | H | H |
| 16-2 | H | Cl | H | H |
| 16-3 | H | Br | H | H |
| 16-4 | F | F | H | H |
| 16-5 | F | Cl | H | H |
| 16-6 | F | Br | H | H |
| 16-7 | Cl | F | H | H |
| 16-8 | Cl | Cl | H | H |
| 16-9 | Cl | Br | H | H |
| 16-10 | H | F | H | $NO_2$ |
| 16-11 | H | Cl | H | $NO_2$ |
| 16-12 | H | Br | H | $NO_2$ |
| 16-13 | F | F | H | $NO_2$ |
| 16-14 | F | Cl | H | $NO_2$ |
| 16-15 | F | Br | H | $NO_2$ |
| 16-16 | Cl | F | H | $NO_2$ |
| 16-17 | Cl | Cl | H | $NO_2$ |
| 16-18 | Cl | Br | H | $NO_2$ |
| 16-19 | H | F | H | $NH_2$ |
| 16-20 | H | Cl | H | $NH_2$ |
| 16-21 | H | Br | H | $NH_2$ |
| 16-22 | F | F | H | $NH_2$ |
| 16-23 | F | Cl | H | $NH_2$ |
| 16-24 | F | Br | H | $NH_2$ |
| 16-25 | Cl | F | H | $NH_2$ |

TABLE 188

|  | X | Y | $R^1$ | B |
|---|---|---|---|---|
| 16-26 | Cl | Cl | H | $NH_2$ |
| 16-27 | Cl | Br | H | $NH_2$ |
| 16-28 | H | F | H | OH |
| 16-29 | H | Cl | H | OH |
| 16-30 | H | Br | H | OH |
| 16-31 | F | F | H | OH |
| 16-32 | F | Cl | H | OH |
| 16-33 | F | Br | H | OH |
| 16-34 | Cl | F | H | OH |
| 16-35 | Cl | Cl | H | OH |
| 16-36 | Cl | Br | H | OH |
| 16-37 | H | F | H | SH |
| 16-38 | H | Cl | H | SH |
| 16-39 | H | Br | H | SH |
| 16-40 | F | F | H | SH |
| 16-41 | F | Cl | H | SH |
| 16-42 | F | Br | H | SH |
| 16-43 | Cl | F | H | SH |
| 16-44 | Cl | Cl | H | SH |
| 16-45 | Cl | Br | H | SH |
| 16-46 | H | F | H | $SO_2Cl$ |
| 16-47 | H | Cl | H | $SO_2Cl$ |
| 16-48 | H | Br | H | $SO_2Cl$ |
| 16-49 | F | F | H | $SO_2Cl$ |
| 16-50 | F | Cl | H | $SO_2Cl$ |

TABLE 189

| | X | Y | R¹ | B |
|---|---|---|---|---|
| 16-51 | F | Br | H | SO$_2$Cl |
| 16-52 | Cl | F | H | SO$_2$Cl |
| 16-53 | Cl | Cl | H | SO$_2$Cl |
| 16-54 | Cl | Br | H | SO$_2$Cl |
| 16-55 | H | F | H | NHCH$_3$ |
| 16-56 | H | Cl | H | NHCH$_3$ |
| 16-57 | F | F | H | NHCH$_3$ |
| 16-58 | F | Cl | H | NHCH$_3$ |
| 16-59 | Cl | F | H | NHCH$_3$ |
| 16-60 | Cl | Cl | H | NHCH$_3$ |
| 16-61 | H | F | H | NHC$_2$H$_5$ |
| 16-62 | H | Cl | H | NHC$_2$H$_5$ |
| 16-63 | F | F | H | NHC$_2$H$_5$ |
| 16-64 | F | Cl | H | NHC$_2$H$_5$ |
| 16-65 | Cl | F | H | NHC$_2$H$_5$ |
| 16-66 | Cl | Cl | H | NHC$_2$H$_5$ |
| 16-67 | H | F | H | NHCH$_2$CH=CH$_2$ |
| 16-68 | H | Cl | H | NHCH$_2$CH=CH$_2$ |
| 16-69 | F | F | H | NHCH$_2$CH=CH$_2$ |
| 16-70 | F | Cl | H | NHCH$_2$CH=CH$_2$ |
| 16-71 | Cl | F | H | NHCH$_2$CH=CH$_2$ |
| 16-72 | Cl | Cl | H | NHCH$_2$CH=CH$_2$ |
| 16-73 | H | F | H | NHCH$_2$C≡CH |
| 16-74 | H | Cl | H | NHCH$_2$C≡CH |
| 16-75 | F | F | H | NHCH$_2$C≡CH |

TABLE 190

| | X | Y | R¹ | B |
|---|---|---|---|---|
| 16-76 | F | Cl | H | NHCH$_2$C≡CH |
| 16-77 | Cl | F | H | NHCH$_2$C≡CH |
| 16-78 | Cl | Cl | H | NHCH$_2$C≡CH |
| 16-79 | H | F | H | NHCH(CH$_3$)C≡CH |
| 16-80 | H | Cl | H | NHCH(CH$_3$)C≡CH |
| 16-81 | F | F | H | NHCH(CH$_3$)C≡CH |
| 16-82 | F | Cl | H | NHCH(CH$_3$)C≡CH |
| 16-83 | Cl | F | H | NHCH(CH$_3$)C≡CH |
| 16-84 | Cl | Cl | H | NHCH(CH$_3$)C≡CH |
| 16-85 | H | F | H | NHSO$_2$CH$_3$ |
| 16-86 | H | Cl | H | NHSO$_2$CH$_3$ |
| 16-87 | F | F | H | NHSO$_2$CH$_3$ |
| 16-88 | F | Cl | H | NHSO$_2$CH$_3$ |
| 16-89 | Cl | F | H | NHSO$_2$CH$_3$ |
| 16-90 | Cl | CL | H | NHSO$_2$CH$_3$ |
| 16-91 | H | F | H | NHSO$_2$C$_2$H$_5$ |
| 16-92 | H | Cl | H | NHSO$_2$C$_2$H$_5$ |
| 16-93 | F | F | H | NHSO$_2$C$_2$H$_5$ |
| 16-94 | F | Cl | H | NHSO$_2$C$_2$H$_5$ |
| 16-95 | Cl | F | H | NHSO$_2$C$_2$H$_5$ |
| 16-96 | Cl | Cl | H | NHSO$_2$C$_2$H$_5$ |
| 16-97 | H | F | H | NHSO$_2$CH$_2$Cl |
| 16-98 | H | Cl | H | NHSO$_2$CH$_2$Cl |
| 16-99 | F | F | H | NHSO$_2$CH$_2$Cl |
| 16-100 | F | Cl | H | NHSO$_2$CH$_2$Cl |

TABLE 191

| | X | Y | R¹ | B |
|---|---|---|---|---|
| 16-101 | Cl | F | H | NHSO$_2$CH$_2$Cl |
| 16-102 | Cl | Cl | H | NHSO$_2$CH$_2$Cl |
| 16-103 | H | F | H | NHSO$_2$CF$_3$ |
| 16-104 | H | Cl | H | NHSO$_2$CF$_3$ |
| 16-105 | F | F | H | NHSO$_2$CF$_3$ |
| 16-106 | F | Cl | H | NHSO$_2$CF$_3$ |
| 16-107 | Cl | F | H | NHSO$_2$CF$_3$ |
| 16-108 | Cl | Cl | H | NHSO$_2$CF$_3$ |
| 16-109 | H | F | H | N(SO$_2$CH$_3$)$_2$ |
| 16-110 | H | Cl | H | N(SO$_2$CH$_3$)$_2$ |
| 16-111 | F | F | H | N(SO$_2$CH$_3$)$_2$ |
| 16-112 | F | Cl | H | N(SO$_2$CH$_3$)$_2$ |

TABLE 191-continued

| | X | Y | R¹ | B |
|---|---|---|---|---|
| 16-113 | Cl | F | H | N(SO$_2$CH$_3$)$_2$ |
| 16-114 | Cl | Cl | H | N(SO$_2$CH$_3$)$_2$ |
| 16-115 | H | F | H | N(CH$_3$)SO$_2$CH$_3$ |
| 16-116 | H | Cl | H | N(CH$_3$)SO$_2$CH$_3$ |
| 16-117 | F | F | H | N(CH$_3$)SO$_2$CH$_3$ |
| 16-118 | F | Cl | H | N(CH$_3$)SO$_2$CH$_3$ |
| 16-119 | Cl | F | H | N(CH$_3$)SO$_2$CH$_3$ |
| 16-120 | Cl | Cl | H | N(CH$_3$)SO$_2$CH$_3$ |
| 16-121 | H | F | H | N(CH$_2$C≡CH)SO$_2$CH$_3$ |
| 16-122 | H | Cl | H | N(CH$_2$C≡CH)SO$_2$CH$_3$ |
| 16-123 | F | F | H | N(CH$_2$C≡CH)SO$_2$CH$_3$ |
| 16-124 | F | Cl | H | N(CH$_2$C≡CH)SO$_2$CH$_3$ |
| 16-125 | Cl | F | H | N(CH$_2$C≡CH)SO$_2$CH$_3$ |

TABLE 192

| | X | Y | R¹ | B |
|---|---|---|---|---|
| 16-126 | Cl | Cl | H | N(CH$_2$C≡CH)SO$_2$CH$_3$ |
| 16-127 | H | F | H | NHCOOCH$_3$ |
| 16-128 | H | Cl | H | NHCOOCH$_3$ |
| 16-129 | F | F | H | NHCOOCH$_3$ |
| 16-130 | F | Cl | H | NHCOOCH$_3$ |
| 16-131 | Cl | F | H | NHCOOCH$_3$ |
| 16-132 | Cl | Cl | H | NHCOOCH$_3$ |
| 16-133 | H | F | H | NHCOOC$_2$H$_5$ |
| 16-134 | H | Cl | H | NHCOOC$_2$H$_5$ |
| 16-135 | F | F | H | NHCOOC$_2$H$_5$ |
| 16-136 | F | Cl | H | NHCOOC$_2$H$_5$ |
| 16-137 | Cl | F | H | NHCOOC$_2$H$_5$ |
| 16-138 | Cl | Cl | H | NHCOOC$_2$H$_5$ |
| 16-139 | H | F | H | NHCOOnC$_3$H$_7$ |
| 16-140 | H | Cl | H | NHCOOnC$_3$H$_7$ |
| 16-141 | F | F | H | NHCOOnC$_3$H$_7$ |
| 16-142 | F | Cl | H | NHCOOnC$_3$H$_7$ |
| 16-143 | Cl | F | H | NHCOOnC$_3$H$_7$ |
| 16-144 | Cl | Cl | H | NHCOOnC$_3$H$_7$ |
| 16-145 | H | F | H | NHCOOiC$_3$H$_7$ |
| 16-146 | H | Cl | H | NHCOOiC$_3$H$_7$ |
| 16-147 | F | F | H | NHCOOiC$_3$H$_7$ |
| 16-148 | F | Cl | H | NHCOOiC$_3$H$_7$ |
| 16-149 | Cl | F | H | NHCOOiC$_3$H$_7$ |
| 16-150 | Cl | Cl | H | NHCOOiC$_3$H$_7$ |

TABLE 193

| | X | Y | R¹ | B |
|---|---|---|---|---|
| 16-151 | H | F | H | NHCOOnC$_4$H$_9$ |
| 16-152 | H | Cl | H | NHCOOnC$_4$H$_9$ |
| 16-153 | F | F | H | NHCOOnC$_4$H$_9$ |
| 16-154 | F | Cl | H | NHCOOnC$_4$H$_9$ |
| 16-155 | Cl | F | H | NHCOOnC$_4$H$_9$ |
| 16-156 | Cl | Cl | H | NHCOOnC$_4$H$_9$ |
| 16-157 | H | F | H | NHCOOnC$_5$H$_{11}$ |
| 16-158 | H | Cl | H | NHCOOnC$_5$H$_{11}$ |
| 16-159 | F | F | H | NHCOOnC$_5$H$_{11}$ |
| 16-160 | F | Cl | H | NHCOOnC$_5$H$_{11}$ |
| 16-161 | Cl | F | H | NHCOOnC$_5$H$_{11}$ |
| 16-162 | Cl | Cl | H | NHCOOnC$_5$H$_{11}$ |
| 16-163 | H | F | H | NHCH$_2$COOCH$_3$ |
| 16-164 | H | Cl | H | NHCH$_2$COOCH$_3$ |
| 16-165 | F | F | H | NHCH$_2$COOCH$_3$ |
| 16-166 | F | Cl | H | NHCH$_2$COOCH$_3$ |
| 16-167 | Cl | F | H | NHCH$_2$COOCH$_3$ |
| 16-168 | Cl | Cl | H | NHCH$_2$COOCH$_3$ |
| 16-169 | H | F | H | NHCH$_2$COOC$_2$H$_5$ |
| 16-170 | H | Cl | H | NHCH$_2$COOC$_2$H$_5$ |
| 16-171 | F | F | H | NHCH$_2$COOC$_2$H$_5$ |
| 16-172 | F | Cl | H | NHCH$_2$COOC$_2$H$_5$ |
| 16-173 | Cl | F | H | NHCH$_2$COOC$_2$H$_5$ |

TABLE 193-continued

| | X | Y | R¹ | B |
|---|---|---|---|---|
| 16-174 | Cl | Cl | H | NHCH$_2$COOC$_2$H$_5$ |
| 16-175 | H | F | H | NHCH$_2$COOnC$_3$H$_7$ |

TABLE 194

| | X | Y | R¹ | B |
|---|---|---|---|---|
| 16-176 | H | Cl | H | NHCH$_2$COOnC$_3$H$_7$ |
| 16-177 | F | F | H | NHCH$_2$COOnC$_3$H$_7$ |
| 16-178 | F | Cl | H | NHCH$_2$COOnC$_3$H$_7$ |
| 16-179 | Cl | F | H | NHCH$_2$COOnC$_3$H$_7$ |
| 16-180 | Cl | Cl | H | NHCH$_2$COOnC$_3$H$_7$ |
| 16-181 | H | F | H | NHCH$_2$COOnC$_4$H$_9$ |
| 16-182 | H | Cl | H | NHCH$_2$COOnC$_4$H$_9$ |
| 16-183 | F | F | H | NHCH$_2$COOnC$_4$H$_9$ |
| 16-184 | F | Cl | H | NHCH$_2$COOnC$_4$H$_9$ |
| 16-185 | Cl | F | H | NHCH$_2$COOnC$_4$H$_9$ |
| 16-186 | Cl | Cl | H | NHCH$_2$COOnC$_4$H$_9$ |
| 16-187 | H | F | H | NHCH$_2$COOnC$_5$H$_{11}$ |
| 16-188 | H | Cl | H | NHCH$_2$COOnC$_5$H$_{11}$ |
| 16-189 | F | F | H | NHCH$_2$COOnC$_5$H$_{11}$ |
| 16-190 | F | Cl | H | NHCH$_2$COOnC$_5$H$_{11}$ |
| 16-191 | Cl | F | H | NHCH$_2$COOnC$_5$H$_{11}$ |
| 16-192 | Cl | Cl | H | NHCH$_2$COOnC$_5$H$_{11}$ |
| 16-193 | H | F | H | NHCH$_2$COOiC$_3$H$_7$ |
| 16-194 | H | Cl | H | NHCH$_2$COOiC$_3$H$_7$ |
| 16-195 | F | F | H | NHCH$_2$COOiC$_3$H$_7$ |
| 16-196 | F | Cl | H | NHCH$_2$COOiC$_3$H$_7$ |
| 16-197 | Cl | F | H | NHCH$_2$COOiC$_3$H$_7$ |
| 16-198 | Cl | Cl | H | NHCH$_2$COOiC$_3$H$_7$ |
| 16-199 | H | F | H | NHCH$_2$COOcC$_5$H$_9$ |
| 16-200 | H | Cl | H | NHCH$_2$COOcC$_5$H$_9$ |

TABLE 195

| | X | Y | R¹ | B |
|---|---|---|---|---|
| 16-201 | F | F | H | NHCH$_2$COOcC$_5$H$_9$ |
| 16-202 | F | Cl | H | NHCH$_2$COOcC$_5$H$_9$ |
| 16-203 | Cl | F | H | NHCH$_2$COOcC$_5$H$_9$ |
| 16-204 | Cl | Cl | H | NHCH$_2$COOcC$_5$H$_9$ |
| 16-205 | H | F | H | NHCH$_2$COOcC$_6$H$_{11}$ |
| 16-206 | H | Cl | H | NHCH$_2$COOcC$_6$H$_{11}$ |
| 16-207 | F | F | H | NHCH$_2$COOcC$_6$H$_{11}$ |
| 16-208 | F | Cl | H | NHCH$_2$COOcC$_6$H$_{11}$ |
| 16-209 | Cl | F | H | NHCH$_2$COOcC$_6$H$_{11}$ |
| 16-210 | Cl | Cl | H | NHCH$_2$COOcC$_6$H$_{11}$ |
| 16-211 | H | F | H | NHCH(CH$_3$)COOCH$_3$ |
| 16-212 | H | Cl | H | NHCH(CH$_3$)COOCH$_3$ |
| 16-213 | F | F | H | NHCH(CH$_3$)COOCH$_3$ |
| 16-214 | F | Cl | H | NHCH(CH$_3$)COOCH$_3$ |
| 16-215 | Cl | F | H | NHCH(CH$_3$)COOCH$_3$ |
| 16-216 | Cl | Cl | H | NHCH(CH$_3$)COOCH$_3$ |
| 16-217 | H | F | H | NHCH(CH$_3$)COOC$_2$H$_5$ |
| 16-218 | H | Cl | H | NHCH(CH$_3$)COOC$_2$H$_5$ |
| 16-219 | F | F | H | NHCH(CH$_3$)COOC$_2$H$_5$ |
| 16-220 | F | Cl | H | NHCH(CH$_3$)COOC$_2$H$_5$ |
| 16-221 | Cl | F | H | NHCH(CH$_3$)COOC$_2$H$_5$ |
| 16-222 | Cl | Cl | H | NHCH(CH$_3$)COOC$_2$H$_5$ |
| 16-223 | H | F | H | NHCH(CH$_3$)COOnC$_3$H$_7$ |
| 16-224 | H | Cl | H | NHCH(CH$_3$)COOnC$_3$H$_7$ |
| 16-225 | F | F | H | NHCH(CH$_3$)COOnC$_3$H$_7$ |

TABLE 196

| | X | Y | R¹ | B |
|---|---|---|---|---|
| 16-226 | F | Cl | H | NHCH(CH$_3$)COOnC$_3$H$_7$ |
| 16-227 | Cl | F | H | NHCH(CH$_3$)COOnC$_3$H$_7$ |
| 16-228 | Cl | Cl | H | NHCH(CH$_3$)COOnC$_3$H$_7$ |

TABLE 196-continued

| | X | Y | R¹ | B |
|---|---|---|---|---|
| 16-229 | H | F | H | NHCH(CH$_3$)COOnC$_4$H$_9$ |
| 16-230 | H | Cl | H | NHCH(CH$_3$)COOnC$_4$H$_9$ |
| 16-231 | F | F | H | NHCH(CH$_3$)COOnC$_4$H$_9$ |
| 16-232 | F | Cl | H | NHCH(CH$_3$)COOnC$_4$H$_9$ |
| 16-233 | Cl | F | H | NHCH(CH$_3$)COOnC$_4$H$_9$ |
| 16-234 | Cl | Cl | H | NHCH(CH$_3$)COOnC$_4$H$_9$ |
| 16-235 | H | F | H | NHCH(CH$_3$)COOnC$_5$H$_{11}$ |
| 16-236 | H | Cl | H | NHCH(CH$_3$)COOnC$_5$H$_{11}$ |
| 16-237 | F | F | H | NHCH(CH$_3$)COOnC$_5$H$_{11}$ |
| 16-238 | F | Cl | H | NHCH(CH$_3$)COOnC$_5$H$_{11}$ |
| 16-239 | Cl | F | H | NHCH(CH$_3$)COOnC$_5$H$_{11}$ |
| 16-240 | Cl | Cl | H | NHCH(CH$_3$)COOnC$_5$H$_{11}$ |
| 16-241 | H | F | H | NHCH(CH$_3$)COOiC$_3$H$_7$ |
| 16-242 | H | Cl | H | NHCH(CH$_3$)COOiC$_3$H$_7$ |
| 16-243 | F | F | H | NHCH(CH$_3$)COOiC$_3$H$_7$ |
| 16-244 | F | Cl | H | NHCH(CH$_3$)COOiC$_3$H$_7$ |
| 16-245 | Cl | F | H | NHCH(CH$_3$)COOiC$_3$H$_7$ |
| 16-246 | Cl | Cl | H | NHCH(CH$_3$)COOiC$_3$H$_7$ |
| 16-247 | H | F | H | NHCH(CH$_3$)COOcC$_5$H$_9$ |
| 16-248 | H | Cl | H | NHCH(CH$_3$)COOcC$_5$H$_9$ |
| 16-249 | F | F | H | NHCH(CH$_3$)COOcC$_5$H$_9$ |
| 16-250 | F | Cl | H | NHCH(CH$_3$)COOcC$_5$H$_9$ |

TABLE 197

| | X | Y | R¹ | B |
|---|---|---|---|---|
| 16-251 | Cl | F | H | NHCH(CH$_3$)COOcC$_5$H$_9$ |
| 16-252 | Cl | Cl | H | NHCH(CH$_3$)COOcC$_5$H$_9$ |
| 16-253 | H | F | H | NHCH(CH$_3$)COOcC$_6$H$_{11}$ |
| 16-254 | H | Cl | H | NHCH(CH$_3$)COOcC$_6$H$_{11}$ |
| 16-255 | F | F | H | NHCH(CH$_3$)COOcC$_6$H$_{11}$ |
| 16-256 | F | Cl | H | NHCH(CH$_3$)COOcC$_6$H$_{11}$ |
| 16-257 | Cl | F | H | NHCH(CH$_3$)COOcC$_6$H$_{11}$ |
| 16-258 | Cl | Cl | H | NHCH(CH$_3$)COOcC$_6$H$_{11}$ |
| 16-259 | H | F | H | OCH$_3$ |
| 16-260 | H | Cl | H | OCH$_3$ |
| 16-261 | F | F | H | OCH$_3$ |
| 16-262 | F | Cl | H | OCH$_3$ |
| 16-263 | Cl | F | H | OCH$_3$ |
| 16-264 | Cl | Cl | H | OCH$_3$ |
| 16-265 | H | F | H | OC$_2$H$_5$ |
| 16-266 | H | Cl | H | OC$_2$H$_5$ |
| 16-267 | F | F | H | OC$_2$H$_5$ |
| 16-268 | F | Cl | H | OC$_2$H$_5$ |
| 16-269 | Cl | F | H | OC$_2$H$_5$ |
| 16-270 | Cl | Cl | H | OC$_2$H$_5$ |
| 16-271 | H | F | H | OiC$_3$H$_7$ |
| 16-272 | H | Cl | H | OiC$_3$H$_7$ |
| 16-273 | F | F | H | OiC$_3$H$_7$ |
| 16-274 | F | Cl | H | OiC$_3$H$_7$ |
| 16-275 | Cl | F | H | OiC$_3$H$_7$ |

TABLE 198

| | X | Y | R¹ | B |
|---|---|---|---|---|
| 16-276 | Cl | Cl | H | OiC$_3$H$_7$ |
| 16-277 | H | F | H | OnC$_3$H$_7$ |
| 16-278 | H | Cl | H | OnC$_3$H$_7$ |
| 16-279 | F | F | H | OnC$_3$H$_7$ |
| 16-280 | F | Cl | H | OnC$_3$H$_7$ |
| 16-281 | Cl | F | H | OnC$_3$H$_7$ |
| 16-282 | Cl | Cl | H | OnC$_3$H$_7$ |
| 16-283 | H | F | H | OCH$_2$CH$_2$Cl |
| 16-284 | H | Cl | H | OCH$_2$CH$_2$Cl |
| 16-285 | F | F | H | OCH$_2$CH$_2$Cl |
| 16-286 | F | Cl | H | OCH$_2$CH$_2$Cl |
| 16-287 | Cl | F | H | OCH$_2$CH$_2$Cl |
| 16-288 | Cl | Cl | H | OCH$_2$CH$_2$Cl |
| 16-289 | H | F | H | OCF$_2$CF$_2$H |
| 16-290 | H | Cl | H | OCF$_2$CF$_2$H |

TABLE 198-continued

|  | X | Y | R¹ | B |
|---|---|---|---|---|
| 16-291 | F | F | H | OCF₂CF₂H |
| 16-292 | F | Cl | H | OCF₂CF₂H |
| 16-293 | Cl | F | H | OCF₂CF₂H |
| 16-294 | Cl | Cl | H | OCF₂CF₂H |
| 16-295 | H | F | H | OcC₅H₉ |
| 16-296 | H | Cl | H | OcC₅H₉ |
| 16-297 | F | F | H | OcC₅H₉ |
| 16-298 | F | Cl | H | OcC₅H₉ |
| 16-299 | Cl | F | H | OcC₅H₉ |
| 16-300 | Cl | Cl | H | OcC₅H₉ |

TABLE 199

|  | X | Y | R¹ | B |
|---|---|---|---|---|
| 16-301 | H | F | H | OcC₆H₁₁ |
| 16-302 | H | Cl | H | OcC₆H₁₁ |
| 16-303 | F | F | H | OcC₆H₁₁ |
| 16-304 | F | Cl | H | OcC₆H₁₁ |
| 16-305 | Cl | F | H | OcC₆H₁₁ |
| 16-306 | Cl | Cl | H | OcC₆H₁₁ |
| 16-307 | H | F | H | OCH₂CH=CH₂ |
| 16-308 | H | Cl | H | OCH₂CH=CH₂ |
| 16-309 | F | F | H | OCH₂CH=CH₂ |
| 16-310 | F | Cl | H | OCH₂CH=CH₂ |
| 16-311 | Cl | F | H | OCH₂CH=CH₂ |
| 16-312 | Cl | Cl | H | OCH₂CH=CH₂ |
| 16-313 | H | F | H | OCH₂CCl=CH₂ |
| 16-314 | H | Cl | H | OCH₂CCl=CH₂ |
| 16-315 | F | F | H | OCH₂CCl=CH₂ |
| 16-316 | F | Cl | H | OCH₂CCl=CH₂ |
| 16-317 | Cl | F | H | OCH₂CCl=CH₂ |
| 16-318 | Cl | Cl | H | OCH₂CCl=CH₂ |
| 16-319 | H | F | H | OCH₂CCl=CHCl |
| 16-320 | H | Cl | H | OCH₂CCl=CHCl |
| 16-321 | F | F | H | OCH₂CCl=CHCl |
| 16-322 | F | Cl | H | OCH₂CCl=CHCl |
| 16-323 | Cl | F | H | OCH₂CCl=CHCl |
| 16-324 | Cl | Cl | H | OCH₂CCl=CHCl |
| 16-325 | H | F | H | OCH(CH₃)CH=CH₂ |

TABLE 200

|  | X | Y | R¹ | B |
|---|---|---|---|---|
| 16-326 | H | Cl | H | OCH(CH₃)CH=CH₂ |
| 16-327 | F | F | H | OCH(CH₃)CH=CH₂ |
| 16-328 | F | Cl | H | OCH(CH₃)CH=CH₂ |
| 16-329 | Cl | F | H | OCH(CH₃)CH=CH₂ |
| 16-330 | Cl | Cl | H | OCH(CH₃)CH=CH₂ |
| 16-331 | H | F | H | OCH₂C(CH₃)=CH₂ |
| 16-332 | H | Cl | H | OCH₂C(CH₃)=CH₂ |
| 16-333 | F | F | H | OCH₂C(CH₃)=CH₂ |
| 16-334 | F | Cl | H | OCH₂C(CH₃)=CH₂ |
| 16-335 | Cl | F | H | OCH₂C(CH₃)=CH₂ |
| 16-336 | Cl | Cl | H | OCH₂C(CH₃)=CH₂ |
| 16-337 | H | F | H | OCH₂C≡CH |
| 16-338 | H | Cl | H | OCH₂C≡CH |
| 16-339 | F | F | H | OCH₂C≡CH |
| 16-340 | F | Cl | H | OCH₂C≡CH |
| 16-341 | Cl | F | H | OCH₂C≡CH |
| 16-342 | Cl | Cl | H | OCH₂C≡CH |
| 16-343 | H | F | H | OCH(CH₃)C≡CH |
| 16-344 | H | Cl | H | OCH(CH₃)C≡CH |
| 16-345 | F | F | H | OCH(CH₃)C≡CH |
| 16-346 | F | Cl | H | OCH(CH₃)C≡CH |
| 16-347 | Cl | F | H | OCH(CH₃)C≡CH |
| 16-348 | Cl | Cl | H | OCH(CH₃)C≡CH |
| 16-349 | H | F | H | OCH₂C≡CBr |
| 16-350 | H | Cl | H | OCH₂C≡CBr |

TABLE 201

|  | X | Y | R¹ | B |
|---|---|---|---|---|
| 16-351 | F | F | H | OCH₂C≡CBr |
| 16-352 | F | Cl | H | OCH₂C≡CBr |
| 16-353 | Cl | F | H | OCH₂C≡CBr |
| 16-354 | Cl | Cl | H | OCH₂C≡CBr |
| 16-355 | H | F | H | OCH₂C≡CCl |
| 16-356 | H | Cl | H | OCH₂C≡CCl |
| 16-357 | F | F | H | OCH₂C≡CCl |
| 16-358 | F | Cl | H | OCH₂C≡CCl |
| 16-359 | Cl | F | H | OCH₂C≡CCl |
| 16-360 | Cl | Cl | H | OCH₂C≡CCl |
| 16-361 | H | F | H | OCH₂C≡CCH₂Cl |
| 16-362 | H | Cl | H | OCH₂C≡CCH₂Cl |
| 16-363 | F | F | H | OCH₂C≡CCH₂Cl |
| 16-364 | F | Cl | H | OCH₂C≡CCH₂Cl |
| 16-365 | Cl | F | H | OCH₂C≡CCH₂Cl |
| 16-366 | Cl | Cl | H | OCH₂C≡CCH₂Cl |
| 16-367 | H | F | H | OCH₂CN |
| 16-368 | H | Cl | H | OCH₂CN |
| 16-369 | F | F | H | OCH₂CN |
| 16-370 | F | Cl | H | OCH₂CN |
| 16-371 | Cl | F | H | OCH₂CN |
| 16-372 | Cl | Cl | H | OCH₂CN |
| 16-373 | H | F | H | OCH₂OCH₃ |
| 16-374 | H | Cl | H | OCH₂OCH₃ |
| 16-375 | F | F | H | OCH₂OCH₃ |

TABLE 202

|  | X | Y | R¹ | B |
|---|---|---|---|---|
| 16-376 | F | Cl | H | OCH₂OCH₃ |
| 16-377 | Cl | F | H | OCH₂OCH₃ |
| 16-378 | Cl | Cl | H | OCH₂OCH₃ |
| 16-379 | H | F | H | OCH₂OC₂H₅ |
| 16-380 | H | Cl | H | OCH₂OC₂H₅ |
| 16-381 | F | F | H | OCH₂OC₂H₅ |
| 16-382 | F | Cl | H | OCH₂OC₂H₅ |
| 16-383 | Cl | F | H | OCH₂OC₂H₅ |
| 16-384 | Cl | Cl | H | OCH₂OC₂H₅ |
| 16-385 | H | F | H | OCH₂SCH₃ |
| 16-386 | H | Cl | H | OCH₂SCH₃ |
| 16-387 | F | F | H | OCH₂SCH₃ |
| 16-388 | F | Cl | H | OCH₂SCH₃ |
| 16-389 | Cl | F | H | OCH₂SCH₃ |
| 16-390 | Cl | Cl | H | OCH₂SCH₃ |
| 16-391 | H | F | H | OCH₂COOH |
| 16-392 | H | Cl | H | OCH₂COOH |
| 16-393 | F | F | H | OCH₂COOH |
| 16-394 | F | Cl | H | OCH₂COOH |
| 16-395 | Cl | F | H | OCH₂COOH |
| 16-396 | Cl | Cl | H | OCH₂COOH |
| 16-397 | H | F | H | OCH₂COOCH₃ |
| 16-398 | H | Cl | H | OCH₂COOCH₃ |
| 16-399 | F | F | H | OCH₂COOCH₃ |
| 16-400 | F | Cl | H | OCH₂COOCH₃ |

TABLE 203

|  | X | Y | R¹ | B |
|---|---|---|---|---|
| 16-401 | Cl | F | H | OCH₂COOCH₃ |
| 16-402 | Cl | Cl | H | OCH₂COOCH₃ |
| 16-403 | H | F | H | OCH₂COOC₂H₅ |
| 16-404 | H | Cl | H | OCH₂COOC₂H₅ |
| 16-405 | F | F | H | OCH₂COOC₂H₅ |
| 16-406 | F | Cl | H | OCH₂COOC₂H₅ |
| 16-407 | Cl | F | H | OCH₂COOC₂H₅ |
| 16-408 | Cl | Cl | H | OCH₂COOC₂H₅ |
| 16-409 | H | F | H | OCH₂COOnC₃H₇ |
| 16-410 | H | Cl | H | OCH₂COOnC₃H₇ |
| 16-411 | F | F | H | OCH₂COOnC₃H₇ |
| 16-412 | F | Cl | H | OCH₂COOnC₃H₇ |

TABLE 203-continued

| | X | Y | R¹ | B |
|---|---|---|---|---|
| 16-413 | Cl | F | H | OCH$_2$COOnC$_3$H$_7$ |
| 16-414 | Cl | Cl | H | OCH$_2$COOnC$_3$H$_7$ |
| 16-415 | H | F | H | OCH$_2$COOnC$_4$H$_9$ |
| 16-416 | H | Cl | H | OCH$_2$COOnC$_4$H$_9$ |
| 16-417 | F | F | H | OCH$_2$COOnC$_4$H$_9$ |
| 16-418 | F | Cl | H | OCH$_2$COOnC$_4$H$_9$ |
| 16-419 | Cl | F | H | OCH$_2$COOnC$_4$H$_9$ |
| 16-420 | Cl | Cl | H | OCH$_2$COOnC$_4$H$_9$ |
| 16-421 | H | F | H | OCH$_2$COOnC$_5$H$_{11}$ |
| 16-422 | H | Cl | H | OCH$_2$COOnC$_5$H$_{11}$ |
| 16-423 | F | F | H | OCH$_2$COOnC$_5$H$_{11}$ |
| 16-424 | F | Cl | H | OCH$_2$COOnC$_5$H$_{11}$ |
| 16-425 | Cl | F | H | OCH$_2$COOnC$_5$H$_{11}$ |

TABLE 204

| | X | Y | R¹ | B |
|---|---|---|---|---|
| 16-426 | Cl | Cl | H | OCH$_2$COOnC$_5$H$_{11}$ |
| 16-427 | H | F | H | OCH$_2$COOiC$_3$H$_7$ |
| 16-428 | H | Cl | H | OCH$_2$COOiC$_3$H$_7$ |
| 16-429 | F | F | H | OCH$_2$COOiC$_3$H$_7$ |
| 16-430 | F | Cl | H | OCH$_2$COOiC$_3$H$_7$ |
| 16-431 | Cl | F | H | OCH$_2$COOiC$_3$H$_7$ |
| 16-432 | Cl | Cl | H | OCH$_2$COOiC$_3$H$_7$ |
| 16-433 | H | F | H | OCH$_2$COOcC$_5$H$_9$ |
| 16-434 | H | Cl | H | OCH$_2$COOcC$_5$H$_9$ |
| 16-435 | F | F | H | OCH$_2$COOcC$_5$H$_9$ |
| 16-436 | F | Cl | H | OCH$_2$COOcC$_5$H$_9$ |
| 16-437 | Cl | F | H | OCH$_2$COOcC$_5$H$_9$ |
| 16-438 | Cl | Cl | H | OCH$_2$COOcC$_5$H$_9$ |
| 16-439 | H | F | H | OCH$_2$COOcC$_6$H$_{11}$ |
| 16-440 | H | Cl | H | OCH$_2$COOcC$_6$H$_{11}$ |
| 16-441 | F | F | H | OCH$_2$COOcC$_6$H$_{11}$ |
| 16-442 | F | Cl | H | OCH$_2$COOcC$_6$H$_{11}$ |
| 16-443 | Cl | F | H | OCH$_2$COOcC$_6$H$_{11}$ |
| 16-444 | Cl | Cl | H | OCH$_2$COOcC$_6$H$_{11}$ |
| 16-445 | H | F | H | OCH(CH$_3$)COOH |
| 16-446 | H | Cl | H | OCH(CH$_3$)COOH |
| 16-447 | F | F | H | OCH(CH$_3$)COOH |
| 16-448 | F | Cl | H | OCH(CH$_3$)COOH |
| 16-449 | Cl | F | H | OCH(CH$_3$)COOH |
| 16-450 | Cl | Cl | H | OCH(CH$_3$)COOH |

TABLE 205

| | X | Y | R¹ | B |
|---|---|---|---|---|
| 16-451 | H | F | H | OCH(CH$_3$)COOCH$_3$ |
| 16-452 | H | Cl | H | OCH(CH$_3$)COOCH$_3$ |
| 16-453 | F | F | H | OCH(CH$_3$)COOCH$_3$ |
| 16-454 | F | Cl | H | OCH(CH$_3$)COOCH$_3$ |
| 16-455 | Cl | F | H | OCH(CH$_3$)COOCH$_3$ |
| 16-456 | Cl | Cl | H | OCH(CH$_3$)COOCH$_3$ |
| 16-457 | H | F | H | OCH(CH$_3$)COOC$_2$H$_5$ |
| 16-458 | H | Cl | H | OCH(CH$_3$)COOC$_2$H$_5$ |
| 16-459 | F | F | H | OCH(CH$_3$)COOC$_2$H$_5$ |
| 16-460 | F | Cl | H | OCH(CH$_3$)COOC$_2$H$_5$ |
| 16-461 | Cl | F | H | OCH(CH$_3$)COOC$_2$H$_5$ |
| 16-462 | Cl | Cl | H | OCH(CH$_3$)COOC$_2$H$_5$ |
| 16-463 | H | F | H | OCH(CH$_3$)COOnC$_3$H$_7$ |
| 16-464 | H | CL | H | OCH(CH$_3$)COOnC$_3$H$_7$ |
| 16-465 | F | F | H | OCH(CH$_3$)COOnC$_3$H$_7$ |
| 16-466 | F | Cl | H | OCH(CH$_3$)COOnC$_3$H$_7$ |
| 16-467 | Cl | F | H | OCH(CH$_3$)COOnC$_3$H$_7$ |
| 16-468 | Cl | Cl | H | OCH(CH$_3$)COOnC$_3$H$_7$ |
| 16-469 | H | F | H | OCH(CH$_3$)COOnC$_4$H$_9$ |
| 16-470 | H | Cl | H | OCH(CH$_3$)COOnC$_4$H$_9$ |
| 16-471 | F | F | H | OCH(CH$_3$)COOnC$_4$H$_9$ |
| 16-472 | F | Cl | H | OCH(CH$_3$)COOnC$_4$H$_9$ |
| 16-473 | Cl | F | H | OCH(CH$_3$)COOnC$_4$H$_9$ |

TABLE 205-continued

| | X | Y | R¹ | B |
|---|---|---|---|---|
| 16-474 | Cl | Cl | H | OCH(CH$_3$)COOnC$_4$H$_9$ |
| 16-475 | H | F | H | OCH(CH$_3$)COOnC$_5$H$_{11}$ |

TABLE 206

| | X | Y | R¹ | B |
|---|---|---|---|---|
| 16-476 | H | Cl | H | OCH(CH$_3$)COOnC$_5$H$_{11}$ |
| 16-477 | F | F | H | OCH(CH$_3$)COOnC$_5$H$_{11}$ |
| 16-478 | F | Cl | H | OCH(CH$_3$)COOnC$_5$H$_{11}$ |
| 16-479 | Cl | F | H | OCH(CH$_3$)COOnC$_5$H$_{11}$ |
| 16-480 | Cl | Cl | H | OCH(CH$_3$)COOnC$_5$H$_{11}$ |
| 16-481 | H | F | H | OCH(CH$_3$)COOiC$_3$H$_7$ |
| 16-482 | H | Cl | H | OCH(CH$_3$)COOiC$_3$H$_7$ |
| 16-483 | F | F | H | OCH(CH$_3$)COOiC$_3$H$_7$ |
| 16-484 | F | Cl | H | OCH(CH$_3$)COOiC$_3$H$_7$ |
| 16-485 | Cl | F | H | OCH(CH$_3$)COOiC$_3$H$_7$ |
| 16-486 | Cl | Cl | H | OCH(CH$_3$)COOiC$_3$H$_7$ |
| 16-487 | H | F | H | OCH(CH$_3$)COOcC$_5$H$_9$ |
| 16-488 | H | CL | H | OCH(CH$_3$)COOcC$_5$H$_9$ |
| 16-489 | F | F | H | OCH(CH$_3$)COOcC$_5$H$_9$ |
| 16-490 | F | Cl | H | OCH(CH$_3$)COOcC$_5$H$_9$ |
| 16-491 | Cl | F | H | OCH(CH$_3$)COOcC$_5$H$_9$ |
| 16-492 | Cl | Cl | H | OCH(CH$_3$)COOcC$_5$H$_9$ |
| 16-493 | H | F | H | OCH(CH$_3$)COOcC$_6$H$_{11}$ |
| 16-494 | H | Cl | H | OCH(CH$_3$)COOcC$_6$H$_{11}$ |
| 16-495 | F | F | H | OCH(CH$_3$)COOcC$_6$H$_{11}$ |
| 16-496 | F | Cl | H | OCH(CH$_3$)COOcC$_6$H$_{11}$ |
| 16-497 | Cl | F | H | OCH(CH$_3$)COOcC$_6$H$_{11}$ |
| 16-498 | Cl | Cl | H | OCH(CH$_3$)COOcC$_6$H$_{11}$ |
| 16-499 | H | F | H | OCH$_2$CONH$_2$ |
| 16-500 | H | Cl | H | OCH$_2$CONH$_2$ |

TABLE 207

| | X | Y | R¹ | B |
|---|---|---|---|---|
| 16-501 | F | F | H | OCH$_2$CONH$_2$ |
| 16-502 | F | Cl | H | OCH$_2$CONH$_2$ |
| 16-503 | Cl | F | H | OCH$_2$CONH$_2$ |
| 16-504 | Cl | Cl | H | OCH$_2$CONH$_2$ |
| 16-505 | H | F | H | OCH$_2$CONHCH$_3$ |
| 16-506 | H | Cl | H | OCH$_2$CONHCH$_3$ |
| 16-507 | F | F | H | OCH$_2$CONHCH$_3$ |
| 16-508 | F | Cl | H | OCH$_2$CONHCH$_3$ |
| 16-509 | Cl | F | H | OCH$_2$CONHCH$_3$ |
| 16-510 | Cl | Cl | H | OCH$_2$CONHCH$_3$ |
| 16-511 | H | F | H | OCH$_2$CON(CH$_3$)$_2$ |
| 16-512 | H | Cl | H | OCH$_2$CON(CH$_3$)$_2$ |
| 16-513 | F | F | H | OCH$_2$CON(CH$_3$)$_2$ |
| 16-514 | F | Cl | H | OCH$_2$CON(CH$_3$)$_2$ |
| 16-515 | Cl | F | H | OCH$_2$CON(CH$_3$)$_2$ |
| 16-516 | Cl | Cl | H | OCH$_2$CON(CH$_3$)$_2$ |
| 16-517 | H | F | H | OCH$_2$CON(C$_2$H$_5$)$_2$ |
| 16-518 | H | Cl | H | OCH$_2$CON(C$_2$H$_5$)$_2$ |
| 16-519 | F | F | H | OCH$_2$CON(C$_2$H$_5$)$_2$ |
| 16-520 | F | Cl | H | OCH$_2$CON(C$_2$H$_5$)$_2$ |
| 16-521 | Cl | F | H | OCH$_2$CON(C$_2$H$_5$)$_2$ |
| 16-522 | Cl | Cl | H | OCH$_2$CON(C$_2$H$_5$)$_2$ |
| 16-523 | H | F | H | OCH$_2$CON(CH$_3$)C$_2$H$_5$ |
| 16-524 | H | Cl | H | OCH$_2$CON(CH$_3$)C$_2$H$_5$ |
| 16-525 | F | F | H | OCH$_2$CON(CH$_3$)C$_2$H$_5$ |

TABLE 208

| | X | Y | R¹ | B |
|---|---|---|---|---|
| 16-526 | F | Cl | H | OCH$_2$CON(CH$_3$)C$_2$H$_5$ |
| 16-527 | Cl | F | H | OCH$_2$CON(CH$_3$)C$_2$H$_5$ |
| 16-528 | Cl | Cl | H | OCH$_2$CON(CH$_3$)C$_2$H$_5$ |

TABLE 208-continued

| | X | Y | R$^1$ | B |
|---|---|---|---|---|
| 16-529 | H | F | H | OCH$_2$CON(tetramethylene) |
| 16-530 | H | Cl | H | OCH$_2$CON(tetramethylene) |
| 16-531 | F | F | H | OCH$_2$CON(tetramethylene) |
| 16-532 | F | Cl | H | OCH$_2$CON(tetramethylene) |
| 16-533 | Cl | F | H | OCH$_2$CON(tetramethylene) |
| 16-534 | Cl | Cl | H | OCH$_2$CON(tetramethylene) |
| 16-535 | H | F | H | OCH$_2$CON(pentamethylene) |
| 16-536 | H | Cl | H | OCH$_2$CON(pentamethylene) |
| 16-537 | F | F | H | OCH$_2$CON(pentamethylene) |
| 16-538 | F | Cl | H | OCH$_2$CON(pentamethylene) |
| 16-539 | Cl | F | H | OCH$_2$CON(pentamethylene) |
| 16-540 | Cl | Cl | H | OCH$_2$CON(pentamethylene) |
| 16-541 | H | F | H | OCH$_2$CON(ethyleneoxyethylene) |
| 16-542 | H | Cl | H | OCH$_2$CON(ethyleneoxyethylene) |
| 16-543 | F | F | H | OCH$_2$CON(ethyleneoxyethylene) |
| 16-544 | F | Cl | H | OCH$_2$CON(ethyleneoxyethylene) |
| 16-545 | Cl | F | H | OCH$_2$CON(ethyleneoxyethylene) |
| 16-546 | Cl | Cl | H | OCH$_2$CON(ethyleneoxyethylene) |
| 16-547 | H | F | H | OCH(CH$_3$)CONH$_2$ |
| 16-548 | H | Cl | H | OCH(CH$_3$)CONH$_2$ |
| 16-549 | F | F | H | OCH(CH$_3$)CONH$_2$ |
| 16-550 | F | Cl | H | OCH(CH$_3$)CONH$_2$ |

TABLE 209

| | X | Y | R$^1$ | B |
|---|---|---|---|---|
| 16-551 | Cl | F | H | OCH(CH$_3$)CONH$_2$ |
| 16-552 | Cl | Cl | H | OCH(CH$_3$)CONH$_2$ |
| 16-553 | H | F | H | OCH(CH$_3$)CONHCH$_3$ |
| 16-554 | H | Cl | H | OCH(CH$_3$)CONHCH$_3$ |
| 16-555 | F | F | H | OCH(CH$_3$)CONHCH$_3$ |
| 16-556 | F | Cl | H | OCH(CH$_3$)CONHCH$_3$ |
| 16-557 | Cl | F | H | OCH(CH$_3$)CONHCH$_3$ |
| 16-558 | Cl | Cl | H | OCH(CH$_3$)CONHCH$_3$ |
| 16-559 | H | F | H | OCH(CH$_3$)CON(CH$_3$)$_2$ |
| 16-560 | H | Cl | H | OCH(CH$_3$)CON(CH$_3$)$_2$ |
| 16-561 | F | F | H | OCH(CH$_3$)CON(CH$_3$)$_2$ |
| 16-562 | F | Cl | H | OCH(CH$_3$)CON(CH$_3$)$_2$ |
| 16-563 | Cl | F | H | OCH(CH$_3$)CON(CH$_3$)$_2$ |
| 16-564 | Cl | Cl | H | OCH(CH$_3$)CON(CH$_3$)$_2$ |
| 16-565 | H | F | H | OCH(CH$_3$)CON(C$_2$H$_5$)$_2$ |
| 16-566 | H | Cl | H | OCH(CH$_3$)CON(C$_2$H$_5$)$_2$ |
| 16-567 | F | F | H | OCH(CH$_3$)CON(C$_2$H$_5$)$_2$ |
| 16-568 | F | Cl | H | OCH(CH$_3$)CON(C$_2$H$_5$)$_2$ |
| 16-569 | Cl | F | H | OCH(CH$_3$)CON(C$_2$H$_5$)$_2$ |
| 16-570 | Cl | Cl | H | OCH(CH$_3$)CON(C$_2$H$_5$)$_2$ |
| 16-571 | H | F | H | OCH(CH$_3$)CON(CH$_3$)C$_2$H$_5$ |
| 16-572 | H | Cl | H | OCH(CH$_3$)CON(CH$_3$)C$_2$H$_5$ |
| 16-573 | F | F | H | OCH(CH$_3$)CON(CH$_3$)C$_2$H$_5$ |
| 16-574 | F | Cl | H | OCH(CH$_3$)CON(CH$_3$)C$_2$H$_5$ |
| 16-575 | Cl | F | H | OCH(CH$_3$)CON(CH$_3$)C$_2$H$_5$ |

TABLE 210

| | X | Y | R$^1$ | B |
|---|---|---|---|---|
| 16-576 | Cl | Cl | H | OCH(CH$_3$)CON(CH$_3$)C$_2$H$_5$ |
| 16-577 | H | F | H | OCH(CH$_3$)CON(tetramethylene) |
| 16-578 | H | Cl | H | OCH(CH$_3$)CON(tetramethylene) |
| 16-579 | F | F | H | OCH(CH$_3$)CON(tetramethylene) |
| 16-580 | F | Cl | H | OCH(CH$_3$)CON(tetramethylene) |
| 16-581 | Cl | F | H | OCH(CH$_3$)CON(tetramethylene) |
| 16-582 | Cl | Cl | H | OCH(CH$_3$)CON(tetramethylene) |
| 16-583 | H | F | H | OCH(CH$_3$)CON(pentamethylene) |
| 16-584 | H | Cl | H | OCH(CH$_3$)CON(pentamethylene) |
| 16-585 | F | F | H | OCH(CH$_3$)CON(pentamethylene) |
| 16-586 | F | Cl | H | OCH(CH$_3$)CON(pentamethylene) |
| 16-587 | Cl | F | H | OCH(CH$_3$)CON(pentamethylene) |
| 16-588 | Cl | Cl | H | OCH(CH$_3$)CON(pentamethylene) |
| 16-589 | H | F | H | OCH(CH$_3$)CON(ethyleneoxyethylene) |
| 16-590 | H | Cl | H | OCH(CH$_3$)CON(ethyleneoxyethylene) |

TABLE 210-continued

| | X | Y | R$^1$ | B |
|---|---|---|---|---|
| 16-591 | F | F | H | OCH(CH$_3$)CON(ethyleneoxyethylene) |
| 16-592 | F | Cl | H | OCH(CH$_3$)CON(ethyleneoxyethylene) |
| 16-593 | Cl | F | H | OCH(CH$_3$)CON(ethyleneoxyethylene) |
| 16-594 | Cl | Cl | H | OCH(CH$_3$)CON(ethyleneoxyethylene) |
| 16-595 | H | F | H | OCH$_2$COON(CH$_3$)$_2$ |
| 16-596 | H | Cl | H | OCH$_2$COON(CH$_3$)$_2$ |
| 16-597 | F | F | H | OCH$_2$COON(CH$_3$)$_2$ |
| 16-598 | F | Cl | H | OCH$_2$COON(CH$_3$)$_2$ |
| 16-599 | Cl | F | H | OCH$_2$COON(CH$_3$)$_2$ |
| 16-600 | Cl | Cl | H | OCH$_2$COON(CH$_3$)$_2$ |

TABLE 211

| | X | Y | R$^1$ | B |
|---|---|---|---|---|
| 16-601 | H | F | H | OCH$_2$COON(C$_2$H$_5$)$_2$ |
| 16-602 | H | Cl | H | OCH$_2$COON(C$_2$H$_5$)$_2$ |
| 16-603 | F | F | H | OCH$_2$COON(C$_2$H$_5$)$_2$ |
| 16-604 | F | Cl | H | OCH$_2$COON(C$_2$H$_5$)$_2$ |
| 16-605 | Cl | F | H | OCH$_2$COON(C$_2$H$_5$)$_2$ |
| 16-606 | Cl | Cl | H | OCH$_2$COON(C$_2$H$_5$)$_2$ |
| 16-607 | H | F | H | OCH(CH$_3$)COON(CH$_3$)$_2$ |
| 16-608 | H | Cl | H | OCH(CH$_3$)COON(CH$_3$)$_2$ |
| 16-609 | F | F | H | OCH(CH$_3$)COON(CH$_3$)$_2$ |
| 16-610 | F | Cl | H | OCH(CH$_3$)COON(CH$_3$)$_2$ |
| 16-611 | Cl | F | H | OCH(CH$_3$)COON(CH$_3$)$_2$ |
| 16-612 | Cl | Cl | H | OCH(CH$_3$)COON(CH$_3$)$_2$ |
| 16-613 | H | F | H | OCH(CH$_3$)COON(C$_2$H$_5$)$_2$ |
| 16-614 | H | Cl | H | OCH(CH$_3$)COON(C$_2$H$_5$)$_2$ |
| 16-615 | F | F | H | OCH(CH$_3$)COON(C$_2$H$_5$)$_2$ |
| 16-616 | F | Cl | H | OCH(CH$_3$)COON(C$_2$H$_5$)$_2$ |
| 16-617 | Cl | F | H | OCH(CH$_3$)COON(C$_2$H$_5$)$_2$ |
| 16-618 | Cl | Cl | H | OCH(CH$_3$)COON(C$_2$H$_5$)$_2$ |
| 16-619 | H | F | H | SCH$_3$ |
| 16-620 | H | Cl | H | SCH$_3$ |
| 16-621 | F | F | H | SCH$_3$ |
| 16-622 | F | Cl | H | SCH$_3$ |
| 16-623 | Cl | F | H | SCH$_3$ |
| 16-624 | Cl | Cl | H | SCH$_3$ |
| 16-625 | H | F | H | SC$_2$H$_5$ |

TABLE 212

| | X | Y | R$^1$ | B |
|---|---|---|---|---|
| 16-626 | H | Cl | H | SC$_2$H$_5$ |
| 16-627 | F | F | H | SC$_2$H$_5$ |
| 16-628 | F | Cl | H | SC$_2$H$_5$ |
| 16-629 | Cl | F | H | SC$_2$H$_5$ |
| 16-630 | Cl | Cl | H | SC$_2$H$_5$ |
| 16-631 | H | F | H | SiC$_3$H$_7$ |
| 16-632 | H | Cl | H | SiC$_3$H$_7$ |
| 16-633 | F | F | H | SiC$_3$H$_7$ |
| 16-634 | F | Cl | H | SiC$_3$H$_7$ |
| 16-635 | Cl | F | H | SiC$_3$H$_7$ |
| 16-636 | Cl | Cl | H | SiC$_3$H$_7$ |
| 16-637 | H | F | H | SnC$_3$H$_7$ |
| 16-638 | H | Cl | H | SnC$_3$H$_7$ |
| 16-639 | F | F | H | SnC$_3$H$_7$ |
| 16-640 | F | Cl | H | SnC$_3$H$_7$ |
| 16-641 | Cl | F | H | SnC$_3$H$_7$ |
| 16-642 | Cl | Cl | H | SnC$_3$H$_7$ |
| 16-643 | H | F | H | SCH$_2$CH$_2$Cl |
| 16-644 | H | Cl | H | SCH$_2$CH$_2$Cl |
| 16-645 | F | F | H | SCH$_2$CH$_2$Cl |
| 16-646 | F | Cl | H | SCH$_2$CH$_2$Cl |
| 16-647 | Cl | F | H | SCH$_2$CH$_2$Cl |
| 16-648 | Cl | Cl | H | SCH$_2$CH$_2$Cl |
| 16-649 | H | F | H | ScC$_5$H$_9$ |
| 16-650 | H | Cl | H | ScC$_5$H$_9$ |

TABLE 213

|  | X | Y | R$^1$ | B |
|---|---|---|---|---|
| 16-651 | F | F | H | ScC$_5$H$_9$ |
| 16-652 | F | Cl | H | ScC$_5$H$_9$ |
| 16-653 | Cl | F | H | ScC$_5$H$_9$ |
| 16-654 | Cl | Cl | H | ScC$_5$H$_9$ |
| 16-655 | H | F | H | ScC$_6$H$_{11}$ |
| 16-656 | H | Cl | H | ScC$_6$H$_{11}$ |
| 16-657 | F | F | H | ScC$_6$H$_{11}$ |
| 16-658 | F | Cl | H | ScC$_6$H$_{11}$ |
| 16-659 | Cl | F | H | ScC$_6$H$_{11}$ |
| 16-660 | Cl | Cl | H | ScC$_6$H$_{11}$ |
| 16-661 | H | F | H | SCH$_2$CH=CH$_2$ |
| 16-662 | H | CL | H | SCH$_2$CH=CH$_2$ |
| 16-663 | F | F | H | SCH$_2$CH=CH$_2$ |
| 16-664 | F | Cl | H | SCH$_2$CH=CH$_2$ |
| 16-665 | Cl | F | H | SCH$_2$CH=CH$_2$ |
| 16-666 | Cl | Cl | H | SCH$_2$CH=CH$_2$ |
| 16-667 | H | F | H | SCH$_2$CCl=CH$_2$ |
| 16-668 | H | Cl | H | SCH$_2$CCl=CH$_2$ |
| 16-669 | F | F | H | SCH$_2$CCl=CH$_2$ |
| 16-670 | F | Cl | H | SCH$_2$CCl=CH$_2$ |
| 16-671 | Cl | F | H | SCH$_2$CCl=CH$_2$ |
| 16-672 | Cl | Cl | H | SCH$_2$CCl=CH$_2$ |
| 16-673 | H | F | H | SCH$_2$CCl=CHCl |
| 16-674 | H | Cl | H | SCH$_2$CCl=CHCl |
| 16-675 | F | F | H | SCH$_2$CCl=CHCl |

TABLE 214

|  | X | Y | R$^1$ | B |
|---|---|---|---|---|
| 16-676 | F | Cl | H | SCH$_2$CCl=CHCl |
| 16-677 | Cl | F | H | SCH$_2$CCl=CHCl |
| 16-678 | Cl | Cl | H | SCH$_2$CCl=CHCl |
| 16-679 | H | F | H | SCH(CH$_3$)CH=CH$_2$ |
| 16-680 | H | Cl | H | SCH(CH$_3$)CH=CH$_2$ |
| 16-681 | F | F | H | SCH(CH$_3$)CH=CH$_2$ |
| 16-682 | F | Cl | H | SCH(CH$_3$)CH=CH$_2$ |
| 16-683 | Cl | F | H | SCH(CH$_3$)CH=CH$_2$ |
| 16-684 | Cl | Cl | H | SCH(CH$_3$)CH=CH$_2$ |
| 16-685 | H | F | H | SCH$_2$C≡CH |
| 16-686 | H | Cl | H | SCH$_2$C≡CH |
| 16-687 | F | F | H | SCH$_2$C≡CH |
| 16-688 | F | Cl | H | SCH$_2$C≡CH |
| 16-689 | Cl | F | H | SCH$_2$C≡CH |
| 16-690 | Cl | Cl | H | SCH$_2$C≡CH |
| 16-691 | H | F | H | SCH(CH$_3$)C≡CH |
| 16-692 | H | Cl | H | SCH(CH$_3$)C≡CH |
| 16-693 | F | F | H | SCH(CH$_3$)C≡CH |
| 16-694 | F | Cl | H | SCH(CH$_3$)C≡CH |
| 16-695 | Cl | F | H | SCH(CH$_3$)C≡CH |
| 16-696 | Cl | Cl | H | SCH(CH$_3$)C≡CH |
| 16-697 | H | F | H | SCH$_2$COOH |
| 16-698 | H | Cl | H | SCH$_2$COOH |
| 16-699 | F | F | H | SCH$_2$COOH |
| 16-700 | F | Cl | H | SCH$_2$COOH |

TABLE 215

|  | X | Y | R$^1$ | B |
|---|---|---|---|---|
| 16-701 | Cl | F | H | SCH$_2$COOH |
| 16-702 | Cl | Cl | H | SCH$_2$COOH |
| 16-703 | H | F | H | SCH$_2$COOCH$_3$ |
| 16-704 | H | Cl | H | SCH$_2$COOCH$_3$ |
| 16-705 | F | F | H | SCH$_2$COOCH$_3$ |
| 16-706 | F | Cl | H | SCH$_2$COOCH$_3$ |
| 16-707 | Cl | F | H | SCH$_2$COOCH$_3$ |
| 16-708 | Cl | Cl | H | SCH$_2$COOCH$_3$ |
| 16-709 | H | F | H | SCH$_2$COOC$_2$H$_5$ |
| 16-710 | H | Cl | H | SCH$_2$COOC$_2$H$_5$ |
| 16-711 | F | F | H | SCH$_2$COOC$_2$H$_5$ |
| 16-712 | F | Cl | H | SCH$_2$COOC$_2$H$_5$ |

TABLE 215-continued

|  | X | Y | R$^1$ | B |
|---|---|---|---|---|
| 16-713 | Cl | F | H | SCH$_2$COOC$_2$H$_5$ |
| 16-714 | Cl | Cl | H | SCH$_2$COOC$_2$H$_5$ |
| 16-715 | H | F | H | SCH$_2$COOnC$_3$H$_7$ |
| 16-716 | H | Cl | H | SCH$_2$COOnC$_3$H$_7$ |
| 16-717 | F | F | H | SCH$_2$COOnC$_3$H$_7$ |
| 16-718 | F | Cl | H | SCH$_2$COOnC$_3$H$_7$ |
| 16-719 | Cl | F | H | SCH$_2$COOnC$_3$H$_7$ |
| 16-720 | Cl | Cl | H | SCH$_2$COOnC$_3$H$_7$ |
| 16-721 | H | F | H | SCH$_2$COOnC$_4$H$_9$ |
| 16-722 | H | Cl | H | SCH$_2$COOnC$_4$H$_9$ |
| 16-723 | F | F | H | SCH$_2$COOnC$_4$H$_9$ |
| 16-724 | F | Cl | H | SCH$_2$COOnC$_4$H$_9$ |
| 16-725 | Cl | F | H | SCH$_2$COOnC$_4$H$_9$ |

TABLE 216

|  | X | Y | R$^1$ | B |
|---|---|---|---|---|
| 16-726 | Cl | Cl | H | SCH$_2$COOnC$_4$H$_9$ |
| 16-727 | H | F | H | SCH$_2$COOnC$_5$H$_{11}$ |
| 16-728 | H | Cl | H | SCH$_2$COOnC$_5$H$_{11}$ |
| 16-729 | F | F | H | SCH$_2$COOnC$_5$H$_{11}$ |
| 16-730 | F | Cl | H | SCH$_2$COOnC$_5$H$_{11}$ |
| 16-731 | Cl | F | H | SCH$_2$COOnC$_5$H$_{11}$ |
| 16-732 | Cl | Cl | H | SCH$_2$COOnC$_5$H$_{11}$ |
| 16-733 | H | F | H | SCH$_2$COOiC$_3$H$_7$ |
| 16-734 | H | Cl | H | SCH$_2$COOiC$_3$H$_7$ |
| 16-735 | F | F | H | SCH$_2$COOiC$_3$H$_7$ |
| 16-736 | F | Cl | H | SCH$_2$COOiC$_3$H$_7$ |
| 16-737 | Cl | F | H | SCH$_2$COOiC$_3$H$_7$ |
| 16-738 | Cl | Cl | H | SCH$_2$COOiC$_3$H$_7$ |
| 16-739 | H | F | H | SCH$_2$COOcC$_5$H$_9$ |
| 16-740 | H | Cl | H | SCH$_2$COOcC$_5$H$_9$ |
| 16-741 | F | F | H | SCH$_2$COOcC$_5$H$_9$ |
| 16-742 | F | Cl | H | SCH$_2$COOcC$_5$H$_9$ |
| 16-743 | Cl | F | H | SCH$_2$COOcC$_5$H$_9$ |
| 16-744 | Cl | Cl | H | SCH$_2$COOcC$_5$H$_9$ |
| 16-745 | H | F | H | SCH$_2$COOcC$_6$H$_{11}$ |
| 16-746 | H | Cl | H | SCH$_2$COOcC$_6$H$_{11}$ |
| 16-747 | F | F | H | SCH$_2$COOcC$_6$H$_{11}$ |
| 16-748 | F | Cl | H | SCH$_2$COOcC$_6$H$_{11}$ |
| 16-749 | Cl | F | H | SCH$_2$COOcC$_6$H$_{11}$ |
| 16-750 | Cl | Cl | H | SCH$_2$COOcC$_6$H$_{11}$ |

TABLE 217

|  | X | Y | R$^1$ | B |
|---|---|---|---|---|
| 16-751 | H | F | H | SCH(CH$_3$)COOH |
| 16-752 | H | Cl | H | SCH(CH$_3$)COOH |
| 16-753 | F | F | H | SCH(CH$_3$)COOH |
| 16-754 | F | Cl | H | SCH(CH$_3$)COOH |
| 16-755 | Cl | F | H | SCH(CH$_3$)COOH |
| 16-756 | Cl | Cl | H | SCH(CH$_3$)COOH |
| 16-757 | H | F | H | SCH(CH$_3$)COOCH$_3$ |
| 16-758 | H | Cl | H | SCH(CH$_3$)COOCH$_3$ |
| 16-759 | F | F | H | SCH(CH$_3$)COOCH$_3$ |
| 16-760 | F | Cl | H | SCH(CH$_3$)COOCH$_3$ |
| 16-761 | Cl | F | H | SCH(CH$_3$)COOCH$_3$ |
| 16-762 | Cl | Cl | H | SCH(CH$_3$)COOCH$_3$ |
| 16-763 | H | F | H | SCH(CH$_3$)COOC$_2$H$_5$ |
| 16-764 | H | Cl | H | SCH(CH$_3$)COOC$_2$H$_5$ |
| 16-765 | F | F | H | SCH(CH$_3$)COOC$_2$H$_5$ |
| 16-766 | F | Cl | H | SCH(CH$_3$)COOC$_2$H$_5$ |
| 16-767 | Cl | F | H | SCH(CH$_3$)COOC$_2$H$_5$ |
| 16-768 | Cl | Cl | H | SCH(CH$_3$)COOC$_2$H$_5$ |
| 16-769 | H | F | H | SCH(CH$_3$)COOnC$_3$H$_7$ |
| 16-770 | H | Cl | H | SCH(CH$_3$)COOnC$_3$H$_7$ |
| 16-771 | F | F | H | SCH(CH$_3$)COOnC$_3$H$_7$ |
| 16-772 | F | Cl | H | SCH(CH$_3$)COOnC$_3$H$_7$ |
| 16-773 | Cl | F | H | SCH(CH$_3$)COOnC$_3$H$_7$ |

TABLE 217-continued

|  | X | Y | R¹ | B |
|---|---|---|---|---|
| 16-774 | Cl | Cl | H | SCH(CH₃)COOnC₃H₇ |
| 16-775 | H | F | H | SCH(CH₃)COOnC₄H₉ |

TABLE 218

|  | X | Y | R¹ | B |
|---|---|---|---|---|
| 16-776 | H | Cl | H | SCH(CH₃)COOnC₄H₉ |
| 16-777 | F | F | H | SCH(CH₃)COOnC₄H₉ |
| 16-778 | F | Cl | H | SCH(CH₃)COOnC₄H₉ |
| 16-779 | Cl | F | H | SCH(CH₃)COOnC₄H₉ |
| 16-780 | Cl | Cl | H | SCH(CH₃)COOnC₄H₉ |
| 16-781 | H | F | H | SCH(CH₃)COOnC₅H₁₁ |
| 16-782 | H | Cl | H | SCH(CH₃)COOnC₅H₁₁ |
| 16-783 | F | F | H | SCH(CH₃)COOnC₅H₁₁ |
| 16-784 | F | Cl | H | SCH(CH₃)COOnC₅H₁₁ |
| 16-785 | Cl | F | H | SCH(CH₃)COOnC₅H₁₁ |
| 16-786 | Cl | Cl | H | SCH(CH₃)COOnC₅H₁₁ |
| 16-787 | H | F | H | SCH(CH₃)COOiC₃H₇ |
| 16-788 | H | Cl | H | SCH(CH₃)COOiC₃H₇ |
| 16-789 | F | F | H | SCH(CH₃)COOiC₃H₇ |
| 16-790 | F | Cl | H | SCH(CH₃)COOiC₃H₇ |
| 16-791 | Cl | F | H | SCH(CH₃)COOiC₃H₇ |
| 16-792 | Cl | Cl | H | SCH(CH₃)COOiC₃H₇ |
| 16-793 | H | F | H | SCH(CH₃)COOcC₅H₉ |
| 16-794 | H | Cl | H | SCH(CH₃)COOcC₅H₉ |
| 16-795 | F | F | H | SCH(CH₃)COOcC₅H₉ |
| 16-796 | F | Cl | H | SCH(CH₃)COOcC₅H₉ |
| 16-797 | Cl | F | H | SCH(CH₃)COOcC₅H₉ |
| 16-798 | Cl | Cl | H | SCH(CH₃)COOcC₅H₉ |
| 16-799 | H | F | H | SCH(CH₃)COOcC₆H₁₁ |
| 16-800 | H | Cl | H | SCH(CH₃)COOcC₆H₁₁ |

TABLE 219

|  | X | Y | R¹ | B |
|---|---|---|---|---|
| 16-801 | F | F | H | SCH(CH₃)COOcC₆H₁₁ |
| 16-802 | F | Cl | H | SCH(CH₃)COOcC₆H₁₁ |
| 16-803 | Cl | F | H | SCH(CH₃)COOcC₆H₁₁ |
| 16-804 | Cl | Cl | H | SCH(CH₃)COOcC₆H₁₁ |
| 16-805 | H | F | H | SCH₂CONH₂ |
| 16-806 | H | Cl | H | SCH₂CONH₂ |
| 16-807 | F | F | H | SCH₂CONH₂ |
| 16-808 | F | Cl | H | SCH₂CONH₂ |
| 16-809 | Cl | F | H | SCH₂CONH₂ |
| 16-810 | Cl | Cl | H | SCH₂CONH₂ |
| 16-811 | H | F | H | SCH₂CONHCH₃ |
| 16-812 | H | Cl | H | SCH₂CONHCH₃ |
| 16-813 | F | F | H | SCH₂CONHCH₃ |
| 16-814 | F | Cl | H | SCH₂CONHCH₃ |
| 16-815 | Cl | F | H | SCH₂CONHCH₃ |
| 16-816 | Cl | Cl | H | SCH₂CONHCH₃ |
| 16-817 | H | F | H | SCH₂CON(CH₃)₂ |
| 16-818 | H | Cl | H | SCH₂CON(CH₃)₂ |
| 16-819 | F | F | H | SCH₂CON(CH₃)₂ |
| 16-820 | F | Cl | H | SCH₂CON(CH₃)₂ |
| 16-821 | Cl | F | H | SCH₂CON(CH₃)₂ |
| 16-822 | Cl | Cl | H | SCH₂CON(CH₃)₂ |
| 16-823 | H | F | H | SCH₂CON(C₂H₅)₂ |
| 16-824 | H | Cl | H | SCH₂CON(C₂H₅)₂ |
| 16-825 | F | F | H | SCH₂CON(C₂H₅)₂ |

TABLE 220

|  | X | Y | R¹ | B |
|---|---|---|---|---|
| 16-826 | F | Cl | H | SCH₂CON(C₂H₅)₂ |
| 16-827 | Cl | F | H | SCH₂CON(C₂H₅)₂ |
| 16-828 | Cl | Cl | H | SCH₂CON(C₂H₅)₂ |

TABLE 220-continued

|  | X | Y | R¹ | B |
|---|---|---|---|---|
| 16-829 | H | F | H | SCH₂CON(CH₃)C₂H₅ |
| 16-830 | H | Cl | H | SCH₂CON(CH₃)C₂H₅ |
| 16-831 | F | F | H | SCH₂CON(CH₃)C₂H₅ |
| 16-832 | F | Cl | H | SCH₂CON(CH₃)C₂H₅ |
| 16-833 | Cl | F | H | SCH₂CON(CH₃)C₂H₅ |
| 16-834 | Cl | Cl | H | SCH₂CON(CH₃)C₂H₅ |
| 16-835 | H | F | H | SCH₂CON(tetramethylene) |
| 16-836 | H | Cl | H | SCH₂CON(tetramethylene) |
| 16-837 | F | F | H | SCH₂CON(tetramethylene) |
| 16-838 | F | Cl | H | SCH₂CON(tetramethylene) |
| 16-839 | Cl | F | H | SCH₂CON(tetramethylene) |
| 16-840 | Cl | Cl | H | SCH₂CON(tetramethylene) |
| 16-841 | H | F | H | SCH₂CON(pentamethylene) |
| 16-842 | H | Cl | H | SCH₂CON(pentamethylene) |
| 16-843 | F | F | H | SCH₂CON(pentamethylene) |
| 16-844 | F | Cl | H | SCH₂CON(pentamethylene) |
| 16-845 | Cl | F | H | SCH₂CON(pentamethylene) |
| 16-846 | Cl | Cl | H | SCH₂CON(pentamethylene) |
| 16-847 | H | F | H | SCH₂CON(ethyleneoxyethylene) |
| 16-848 | H | Cl | H | SCH₂CON(ethyleneoxyethylene) |
| 16-849 | F | F | H | SCH₂CON(ethyleneoxyethylene) |
| 16-850 | F | Cl | H | SCH₂CON(ethyleneoxyethylene) |

TABLE 221

|  | X | Y | R¹ | B |
|---|---|---|---|---|
| 16-851 | Cl | F | H | SCH₂CON(ethyleneoxyethylene) |
| 16-852 | Cl | Cl | H | SCH₂CON(ethyleneoxyethylene) |
| 16-853 | H | F | H | SCH(CH₃)CONH₂ |
| 16-854 | H | Cl | H | SCH(CH₃)CONH₂ |
| 16-855 | F | F | H | SCH(CH₃)CONH₂ |
| 16-856 | F | Cl | H | SCH(CH₃)CONH₂ |
| 16-857 | Cl | F | H | SCH(CH₃)CONH₂ |
| 16-858 | Cl | Cl | H | SCH(CH₃)CONH₂ |
| 16-859 | H | F | H | SCH(CH₃)CONHCH₃ |
| 16-860 | H | Cl | H | SCH(CH₃)CONHCH₃ |
| 16-861 | F | F | H | SCH(CH₃)CONHCH₃ |
| 16-862 | F | Cl | H | SCH(CH₃)CONHCH₃ |
| 16-863 | Cl | F | H | SCH(CH₃)CONHCH₃ |
| 16-864 | Cl | Cl | H | SCH(CH₃)CONHCH₃ |
| 16-865 | H | F | H | SCH(CH₃)CON(CH₃)₂ |
| 16-866 | H | Cl | H | SCH(CH₃)CON(CH₃)₂ |
| 16-867 | F | F | H | SCH(CH₃)CON(CH₃)₂ |
| 16-868 | F | Cl | H | SCH(CH₃)CON(CH₃)₂ |
| 16-869 | Cl | F | H | SCH(CH₃)CON(CH₃)₂ |
| 16-870 | Cl | Cl | H | SCH(CH₃)CON(CH₃)₂ |
| 16-871 | H | F | H | SCH(CH₃)CON(C₂H₅)₂ |
| 16-872 | H | Cl | H | SCH(CH₃)CON(C₂H₅)₂ |
| 16-873 | F | F | H | SCH(CH₃)CON(C₂H₅)₂ |
| 16-874 | F | Cl | H | SCH(CH₃)CON(C₂H₅)₂ |
| 16-875 | Cl | F | H | SCH(CH₃)CON(C₂H₅)₂ |

TABLE 222

|  | X | Y | R¹ | B |
|---|---|---|---|---|
| 16-876 | Cl | Cl | H | SCH(CH₃)CON(C₂H₅)₂ |
| 16-877 | H | F | H | SCH(CH₃)CON(CH₃)C₂H₅ |
| 16-878 | H | Cl | H | SCH(CH₃)CON(CH₃)C₂H₅ |
| 16-879 | F | F | H | SCH(CH₃)CON(CH₃)C₂H₅ |
| 16-880 | F | Cl | H | SCH(CH₃)CON(CH₃)C₂H₅ |
| 16-881 | Cl | F | H | SCH(CH₃)CON(CH₃)C₂H₅ |
| 16-882 | Cl | Cl | H | SCH(CH₃)CON(CH₃)C₂H₅ |
| 16-883 | H | F | H | SCH(CH₃)CON(CH₃)C₂H₅ |
| 16-884 | H | Cl | H | SCH(CH₃)CON(CH₃)C₂H₅ |
| 16-885 | F | F | H | SCH(CH₃)CON(CH₃)C₂H₅ |
| 16-886 | F | Cl | H | SCH(CH₃)CON(CH₃)C₂H₅ |
| 16-887 | Cl | F | H | SCH(CH₃)CON(CH₃)C₂H₅ |
| 16-888 | Cl | Cl | H | SCH(CH₃)CON(CH₃)C₂H₅ |
| 16-889 | H | F | H | SCH(CH₃)CON(tetramethylene) |
| 16-890 | H | Cl | H | SCH(CH₃)CON(tetramethylene) |

TABLE 222-continued

| | X | Y | R$^1$ | B |
|---|---|---|---|---|
| 16-891 | F | F | H | SCH(CH$_3$)CON(tetramethylene) |
| 16-892 | F | Cl | H | SCH(CH$_3$)CON(tetramethylene) |
| 16-893 | Cl | F | H | SCH(CH$_3$)CON(tetramethylene) |
| 16-894 | Cl | Cl | H | SCH(CH$_3$)CON(tetramethylene) |
| 16-895 | H | F | H | SCH(CH$_3$)CON(pentamethylene) |
| 16-896 | H | Cl | H | SCH(CH$_3$)CON(pentamethylene) |
| 16-897 | F | F | H | SCH(CH$_3$)CON(pentamethylene) |
| 16-898 | F | Cl | H | SCH(CH$_3$)CON(pentamethylene) |
| 16-899 | Cl | F | H | SCH(CH$_3$)CON(pentamethylene) |
| 16-900 | Cl | Cl | H | SCH(CH$_3$)CON(pentamethylene) |

TABLE 223

| | X | Y | R$^1$ | B |
|---|---|---|---|---|
| 16-901 | H | F | H | SCH(CH$_3$)CON(ethyleneoxyethylene) |
| 16-902 | H | Cl | H | SCH(CH$_3$)CON(ethyleneoxyethylene) |
| 16-903 | F | F | H | SCH(CH$_3$)CON(ethyleneoxyethylene) |
| 16-904 | F | Cl | H | SCH(CH$_3$)CON(ethyleneoxyethylene) |
| 16-905 | Cl | F | H | SCH(CH$_3$)CON(ethyleneoxyethylene) |
| 16-906 | Cl | Cl | H | SCH(CH$_3$)CON(ethyleneoxyethylene) |
| 16-907 | H | F | H | SO$_2$OCH$_3$ |
| 16-908 | H | Cl | H | SO$_2$OCH$_3$ |
| 16-909 | F | F | H | SO$_2$OCH$_3$ |
| 16-910 | F | Cl | H | SO$_2$OCH$_3$ |
| 16-911 | Cl | F | H | SO$_2$OCH$_3$ |
| 16-912 | Cl | Cl | H | SO$_2$OCH$_3$ |
| 16-913 | H | F | H | SO$_2$OC$_2$H$_5$ |
| 16-914 | H | Cl | H | SO$_2$OC$_2$H$_5$ |
| 16-915 | F | F | H | SO$_2$OC$_2$H$_5$ |
| 16-916 | F | Cl | H | SO$_2$OC$_2$H$_5$ |
| 16-917 | Cl | F | H | SO$_2$OC$_2$H$_5$ |
| 16-918 | Cl | Cl | H | SO$_2$OC$_2$H$_5$ |
| 16-919 | H | F | H | SO$_2$OiC$_3$H$_7$ |
| 16-920 | H | Cl | H | SO$_2$OiC$_3$H$_7$ |
| 16-921 | F | F | H | SO$_2$OiC$_3$H$_7$ |
| 16-922 | F | Cl | H | SO$_2$OiC$_3$H$_7$ |
| 16-923 | Cl | F | H | SO$_2$OiC$_3$H$_7$ |
| 16-924 | Cl | Cl | H | SO$_2$OiC$_3$H$_7$ |
| 16-925 | H | F | H | SO$_2$OCH$_2$CH=CH$_2$ |

TABLE 224

| | X | Y | R$^1$ | B |
|---|---|---|---|---|
| 16-926 | H | Cl | H | SO$_2$OCH$_2$CH=CH$_2$ |
| 16-927 | F | F | H | SO$_2$OCH$_2$CH=CH$_2$ |
| 16-928 | F | Cl | H | SO$_2$OCH$_2$CH=CH$_2$ |
| 16-929 | Cl | F | H | SO$_2$OCH$_2$CH=CH$_2$ |
| 16-930 | Cl | Cl | H | SO$_2$OCH$_2$CH=CH$_2$ |
| 16-931 | H | F | H | SO$_2$N(CH$_3$)$_2$ |
| 16-932 | H | Cl | H | SO$_2$N(CH$_3$)$_2$ |
| 16-933 | F | F | H | SO$_2$N(CH$_3$)$_2$ |
| 16-934 | F | Cl | H | SO$_2$N(CH$_3$)$_2$ |
| 16-935 | Cl | F | H | SO$_2$N(CH$_3$)$_2$ |
| 16-936 | Cl | Cl | H | SO$_2$N(CH$_3$)$_2$ |
| 16-937 | H | F | H | SO$_2$N(C$_2$H$_5$)$_2$ |
| 16-938 | H | Cl | H | SO$_2$N(C$_2$H$_5$)$_2$ |
| 16-939 | F | F | H | SO$_2$N(C$_2$H$_5$)$_2$ |
| 16-940 | F | Cl | H | SO$_2$N(C$_2$H$_5$)$_2$ |
| 16-941 | Cl | F | H | SO$_2$N(C$_2$H$_5$)$_2$ |
| 16-942 | Cl | Cl | H | SO$_2$N(C$_2$H$_5$)$_2$ |
| 16-943 | H | F | H | COOH |
| 16-944 | H | Cl | H | COOH |
| 16-945 | F | F | H | COOH |
| 16-946 | F | Cl | H | COOH |
| 16-947 | Cl | F | H | COOH |
| 16-948 | Cl | Cl | H | COOH |
| 16-949 | H | F | H | COOCH$_3$ |
| 16-950 | H | Cl | H | COOCH$_3$ |

TABLE 225

| | X | Y | R$^1$ | B |
|---|---|---|---|---|
| 16-951 | F | F | H | COOCH$_3$ |
| 16-952 | F | Cl | H | COOCH$_3$ |
| 16-953 | Cl | F | H | COOCH$_3$ |
| 16-954 | Cl | Cl | H | COOCH$_3$ |
| 16-955 | H | F | H | COOC$_2$H$_5$ |
| 16-956 | H | Cl | H | COOC$_2$H$_5$ |
| 16-957 | F | F | H | COOC$_2$H$_5$ |
| 16-958 | F | Cl | H | COOC$_2$H$_5$ |
| 16-959 | Cl | F | H | COOC$_2$H$_5$ |
| 16-960 | Cl | Cl | H | COOC$_2$H$_5$ |
| 16-961 | H | F | H | COOnC$_3$H$_7$ |
| 16-962 | H | Cl | H | COOnC$_3$H$_7$ |
| 16-963 | F | F | H | COOnC$_3$H$_7$ |
| 16-964 | F | Cl | H | COOnC$_3$H$_7$ |
| 16-965 | Cl | F | H | COOnC$_3$H$_7$ |
| 16-966 | Cl | Cl | H | COOnC$_3$H$_7$ |
| 16-967 | H | F | H | COOnC$_4$H$_9$ |
| 16-968 | H | Cl | H | COOnC$_4$H$_9$ |
| 16-969 | F | F | H | COOnC$_4$H$_9$ |
| 16-970 | F | Cl | H | COOnC$_4$H$_9$ |
| 16-971 | Cl | F | H | COOnC$_4$H$_9$ |
| 16-972 | Cl | Cl | H | COOnC$_4$H$_9$ |
| 16-973 | H | F | H | COOnC$_5$H$_{11}$ |
| 16-974 | H | Cl | H | COOnC$_5$H$_{11}$ |
| 16-975 | F | F | H | COOnC$_5$H$_{11}$ |

TABLE 226

| | X | Y | R$^1$ | B |
|---|---|---|---|---|
| 16-976 | F | Cl | H | COOnC$_5$H$_{11}$ |
| 16-977 | Cl | F | H | COOnC$_5$H$_{11}$ |
| 16-978 | Cl | Cl | H | COOnC$_5$H$_{11}$ |
| 16-979 | H | F | H | COOiC$_3$H$_7$ |
| 16-980 | H | Cl | H | COOiC$_3$H$_7$ |
| 16-981 | F | F | H | COOiC$_3$H$_7$ |
| 16-982 | F | Cl | H | COOiC$_3$H$_7$ |
| 16-983 | Cl | F | H | COOiC$_3$H$_7$ |
| 16-984 | Cl | Cl | H | COOiC$_3$H$_7$ |
| 16-985 | H | F | H | COOcC$_5$H$_9$ |
| 16-986 | H | Cl | H | COOcC$_5$H$_9$ |
| 16-987 | F | F | H | COOcC$_5$H$_9$ |
| 16-988 | F | Cl | H | COOcC$_5$H$_9$ |
| 16-989 | Cl | F | H | COOcC$_5$H$_9$ |
| 16-990 | Cl | Cl | H | COOcC$_5$H$_9$ |
| 16-991 | H | F | H | COOcC$_6$H$_{11}$ |
| 16-992 | H | Cl | H | COOcC$_6$H$_{11}$ |
| 16-993 | F | F | H | COOcC$_6$H$_{11}$ |
| 16-994 | F | Cl | H | COOcC$_6$H$_{11}$ |
| 16-995 | Cl | F | H | COOcC$_6$H$_{11}$ |
| 16-996 | Cl | Cl | H | COOcC$_6$H$_{11}$ |
| 16-997 | H | F | H | COOCH$_2$C$_6$H$_5$ |
| 16-998 | H | Cl | H | COOCH$_2$C$_6$H$_5$ |
| 16-999 | F | F | H | COOCH$_2$C$_6$H$_5$ |
| 16-1000 | F | Cl | H | COOCH$_2$C$_6$H$_5$ |

TABLE 227

| | X | Y | R$^1$ | B |
|---|---|---|---|---|
| 16-1001 | Cl | F | H | COOCH$_2$C$_6$H$_5$ |
| 16-1002 | Cl | Cl | H | COOCH$_2$C$_6$H$_5$ |
| 16-1003 | H | F | H | COOCH$_2$CH$_2$Cl |
| 16-1004 | H | Cl | H | COOCH$_2$CH$_2$Cl |
| 16-1005 | F | F | H | COOCH$_2$CH$_2$Cl |
| 16-1006 | F | Cl | H | COOCH$_2$CH$_2$Cl |
| 16-1007 | Cl | F | H | COOCH$_2$CH$_2$Cl |
| 16-1008 | Cl | Cl | H | COOCH$_2$CH$_2$Cl |
| 16-1009 | H | F | H | COOCH$_2$CH$_2$Br |
| 16-1010 | H | Cl | H | COOCH$_2$CH$_2$Br |
| 16-1011 | F | F | H | COOCH$_2$CH$_2$Br |
| 16-1012 | F | Cl | H | COOCH$_2$CH$_2$Br |

TABLE 227-continued

|         | X  | Y  | R¹ | B                                    |
|---------|----|----|----|--------------------------------------|
| 16-1013 | Cl | F  | H  | COOCH$_2$CH$_2$Br                    |
| 16-1014 | Cl | Cl | H  | COOCH$_2$CH$_2$Br                    |
| 16-1015 | H  | F  | H  | CONH$_2$                             |
| 16-1016 | H  | Cl | H  | CONH$_2$                             |
| 16-1017 | F  | F  | H  | CONH$_2$                             |
| 16-1018 | F  | Cl | H  | CONH$_2$                             |
| 16-1019 | Cl | F  | H  | CONH$_2$                             |
| 16-1020 | Cl | Cl | H  | CONH$_2$                             |
| 16-1021 | H  | F  | H  | CONHCH$_3$                           |
| 16-1022 | H  | Cl | H  | CONHCH$_3$                           |
| 16-1023 | F  | F  | H  | CONHCH$_3$                           |
| 16-1024 | F  | Cl | H  | CONHCH$_3$                           |
| 16-1025 | Cl | F  | H  | CONHCH$_3$                           |

TABLE 228

|         | X  | Y  | R¹ | B                                    |
|---------|----|----|----|--------------------------------------|
| 16-1026 | Cl | Cl | H  | CONHCH$_3$                           |
| 16-1027 | H  | F  | H  | CONHC$_2$H$_5$                       |
| 16-1028 | H  | Cl | H  | CONHC$_2$H$_5$                       |
| 16-1029 | F  | F  | H  | CONHC$_2$H$_5$                       |
| 16-1030 | F  | Cl | H  | CONHC$_2$H$_5$                       |
| 16-1031 | Cl | F  | H  | CONHC$_2$H$_5$                       |
| 16-1032 | Cl | Cl | H  | CONHC$_2$H$_5$                       |
| 16-1033 | H  | F  | H  | CON(CH$_3$)$_2$                      |
| 16-1034 | H  | Cl | H  | CON(CH$_3$)$_2$                      |
| 16-1035 | F  | F  | H  | CON(CH$_3$)$_2$                      |
| 16-1036 | F  | Cl | H  | CON(CH$_3$)$_2$                      |
| 16-1037 | Cl | F  | H  | CON(CH$_3$)$_2$                      |
| 16-1038 | Cl | Cl | H  | CON(CH$_3$)$_2$                      |
| 16-1039 | H  | F  | H  | CON(C$_2$H$_5$)$_2$                  |
| 16-1040 | H  | Cl | H  | CON(C$_2$H$_5$)$_2$                  |
| 16-1041 | F  | F  | H  | CON(C$_2$H$_5$)$_2$                  |
| 16-1042 | F  | Cl | H  | CON(C$_2$H$_5$)$_2$                  |
| 16-1043 | Cl | F  | H  | CON(C$_2$H$_5$)$_2$                  |
| 16-1044 | Cl | Cl | H  | CON(C$_2$H$_5$)$_2$                  |
| 16-1045 | H  | F  | H  | CON(CH$_3$)(C$_2$H$_5$)              |
| 16-1046 | H  | Cl | H  | CON(CH$_3$)(C$_2$H$_5$)              |
| 16-1047 | F  | F  | H  | CON(CH$_3$)(C$_2$H$_5$)              |
| 16-1048 | F  | Cl | H  | CON(CH$_3$)(C$_2$H$_5$)              |
| 16-1049 | Cl | F  | H  | CON(CH$_3$)(C$_2$H$_5$)              |
| 16-1050 | Cl | Cl | H  | CON(CH$_3$)(C$_2$H$_5$)              |

TABLE 229

|         | X  | Y  | R¹ | B                                    |
|---------|----|----|----|--------------------------------------|
| 16-1051 | H  | F  | H  | COCH$_3$                             |
| 16-1052 | H  | Cl | H  | COCH$_3$                             |
| 16-1053 | F  | F  | H  | COCH$_3$                             |
| 16-1054 | F  | Cl | H  | COCH$_3$                             |
| 16-1055 | Cl | F  | H  | COCH$_3$                             |
| 16-1056 | Cl | Cl | H  | COCH$_3$                             |
| 16-1057 | H  | F  | H  | COC$_2$H$_5$                         |
| 16-1058 | H  | Cl | H  | COC$_2$H$_5$                         |
| 16-1059 | F  | F  | H  | COC$_2$H$_5$                         |
| 16-1060 | F  | Cl | H  | COC$_2$H$_5$                         |
| 16-1061 | Cl | F  | H  | COC$_2$H$_5$                         |
| 16-1062 | Cl | Cl | H  | COC$_2$H$_5$                         |
| 16-1063 | H  | F  | H  | COCH$_2$Cl                           |
| 16-1064 | H  | Cl | H  | COCH$_2$Cl                           |
| 16-1065 | F  | F  | H  | COCH$_2$Cl                           |
| 16-1066 | F  | Cl | H  | COCH$_2$Cl                           |
| 16-1067 | Cl | F  | H  | COCH$_2$Cl                           |
| 16-1068 | Cl | Cl | H  | COCH$_2$Cl                           |
| 16-1069 | H  | F  | H  | CHO                                  |
| 16-1070 | H  | Cl | H  | CHO                                  |
| 16-1071 | F  | F  | H  | CHO                                  |
| 16-1072 | F  | Cl | H  | CHO                                  |
| 16-1073 | Cl | F  | H  | CHO                                  |

TABLE 229-continued

|         | X  | Y  | R¹ | B                                    |
|---------|----|----|----|--------------------------------------|
| 16-1074 | Cl | Cl | H  | CHO                                  |
| 16-1075 | H  | F  | H  | CH$_2$CH$_2$COOH                     |

TABLE 230

|         | X  | Y  | R¹ | B                                    |
|---------|----|----|----|--------------------------------------|
| 16-1076 | H  | Cl | H  | CH$_2$CH$_2$COOH                     |
| 16-1077 | F  | F  | H  | CH$_2$CH$_2$COOH                     |
| 16-1078 | F  | Cl | H  | CH$_2$CH$_2$COOH                     |
| 16-1079 | Cl | F  | H  | CH$_2$CH$_2$COOH                     |
| 16-1080 | Cl | Cl | H  | CH$_2$CH$_2$COOH                     |
| 16-1081 | H  | F  | H  | CH$_2$CH$_2$COOCH$_3$                |
| 16-1082 | H  | Cl | H  | CH$_2$CH$_2$COOCH$_3$                |
| 16-1083 | F  | F  | H  | CH$_2$CH$_2$COOCH$_3$                |
| 16-1084 | F  | Cl | H  | CH$_2$CH$_2$COOCH$_3$                |
| 16-1085 | Cl | F  | H  | CH$_2$CH$_2$COOCH$_3$                |
| 16-1086 | Cl | Cl | H  | CH$_2$CH$_2$COOCH$_3$                |
| 16-1087 | H  | F  | H  | CH$_2$CH$_2$COOC$_2$H$_5$            |
| 16-1088 | H  | Cl | H  | CH$_2$CH$_2$COOC$_2$H$_5$            |
| 16-1089 | F  | F  | H  | CH$_2$CH$_2$COOC$_2$H$_5$            |
| 16-1090 | F  | Cl | H  | CH$_2$CH$_2$COOC$_2$H$_5$            |
| 16-1091 | Cl | F  | H  | CH$_2$CH$_2$COOC$_2$H$_5$            |
| 16-1092 | Cl | Cl | H  | CH$_2$CH$_2$COOC$_2$H$_5$            |
| 16-1093 | H  | F  | H  | CH$_2$CHClCOOCH$_3$                  |
| 16-1094 | H  | Cl | H  | CH$_2$CHClCOOCH$_3$                  |
| 16-1095 | F  | F  | H  | CH$_2$CHClCOOCH$_3$                  |
| 16-1096 | F  | Cl | H  | CH$_2$CHClCOOCH$_3$                  |
| 16-1097 | Cl | F  | H  | CH$_2$CHClCOOCH$_3$                  |
| 16-1098 | Cl | Cl | H  | CH$_2$CHClCOOCH$_3$                  |
| 16-1099 | H  | F  | H  | CH$_2$CHClCOOC$_2$H$_5$              |
| 16-1100 | H  | Cl | H  | CH$_2$CHClCOOC$_2$H$_5$              |

TABLE 231

|         | X  | Y  | R¹ | B                                    |
|---------|----|----|----|--------------------------------------|
| 16-1101 | F  | F  | H  | CH$_2$CHClCOOC$_2$H$_5$              |
| 16-1102 | F  | Cl | H  | CH$_2$CHClCOOC$_2$H$_5$              |
| 16-1103 | Cl | F  | H  | CH$_2$CHClCOOC$_2$H$_5$              |
| 16-1104 | Cl | Cl | H  | CH$_2$CHClCOOC$_2$H$_5$              |
| 16-1105 | H  | F  | H  | CH=CHCOOCH$_3$                       |
| 16-1106 | H  | Cl | H  | CH=CHCOOCH$_3$                       |
| 16-1107 | F  | F  | H  | CH=CHCOOCH$_3$                       |
| 16-1108 | F  | Cl | H  | CH=CHCOOCH$_3$                       |
| 16-1109 | Cl | F  | H  | CH=CHCOOCH$_3$                       |
| 16-1110 | Cl | Cl | H  | CH=CHCOOCH$_3$                       |
| 16-1111 | H  | F  | H  | CH=CHCOOC$_2$H$_5$                   |
| 16-1112 | H  | Cl | H  | CH=CHCOOC$_2$H$_5$                   |
| 16-1113 | F  | F  | H  | CH=CHCOOC$_2$H$_5$                   |
| 16-1114 | F  | Cl | H  | CH=CHCOOC$_2$H$_5$                   |
| 16-1115 | Cl | F  | H  | CH=CHCOOC$_2$H$_5$                   |
| 16-1116 | Cl | Cl | H  | CH=CHCOOC$_2$H$_5$                   |
| 16-1117 | H  | F  | H  | C(CH$_3$)=NOH                        |
| 16-1118 | H  | Cl | H  | C(CH$_3$)=NOH                        |
| 16-1119 | F  | F  | H  | C(CH$_3$)=NOH                        |
| 16-1120 | F  | Cl | H  | C(CH$_3$)=NOH                        |
| 16-1121 | Cl | F  | H  | C(CH$_3$)=NOH                        |
| 16-1122 | Cl | Cl | H  | C(CH$_3$)=NOH                        |
| 16-1123 | H  | F  | H  | C(CH$_3$)=NOCH$_3$                   |
| 16-1124 | H  | Cl | H  | C(CH$_3$)=NOCH$_3$                   |
| 16-1125 | F  | F  | H  | C(CH$_3$)=NOCH$_3$                   |

TABLE 232

|         | X  | Y  | R¹ | B                                    |
|---------|----|----|----|--------------------------------------|
| 16-1126 | F  | Cl | H  | C(CH$_3$)=NOCH$_3$                   |
| 16-1127 | Cl | F  | H  | C(CH$_3$)=NOCH$_3$                   |
| 16-1128 | Cl | Cl | H  | C(CH$_3$)=NOCH$_3$                   |

TABLE 232-continued

| | X | Y | R¹ | B |
|---|---|---|---|---|
| 16-1129 | H | F | H | C(CH₃)=NOC₂H₅ |
| 16-1130 | H | Cl | H | C(CH₃)=NOC₂H₅ |
| 16-1131 | F | F | H | C(CH₃)=NOC₂H₅ |
| 16-1132 | F | Cl | H | C(CH₃)=NOC₂H₅ |
| 16-1133 | Cl | F | H | C(CH₃)=NOC₂H₅ |
| 16-1134 | Cl | Cl | H | C(CH₃)=NOC₂H₅ |
| 16-1135 | H | F | H | C(CH₃)=NOiC₃H₇ |
| 16-1136 | H | Cl | H | C(CH₃)=NOiC₃H₇ |
| 16-1137 | F | F | H | C(CH₃)=NOiC₃H₇ |
| 16-1138 | F | Cl | H | C(CH₃)=NOiC₃H₇ |
| 16-1139 | Cl | F | H | C(CH₃)=NOiC₃H₇ |
| 16-1140 | Cl | Cl | H | C(CH₃)=NOiC₃H₇ |
| 16-1141 | H | F | H | C(CH₃)=NNH₂ |
| 16-1142 | H | Cl | H | C(CH₃)=NNH₂ |
| 16-1143 | F | F | H | C(CH₃)=NNH₂ |
| 16-1144 | F | Cl | H | C(CH₃)=NNH₂ |
| 16-1145 | Cl | F | H | C(CH₃)=NNH₂ |
| 16-1146 | Cl | Cl | H | C(CH₃)=NNH₂ |
| 16-1147 | H | F | H | C(CH₃)=NNHCH₃ |
| 16-1148 | H | Cl | H | C(CH₃)=NNHCH₃ |
| 16-1149 | F | F | H | C(CH₃)=NNHCH₃ |
| 16-1150 | F | Cl | H | C(CH₃)=NNHCH₃ |

TABLE 233

| | X | Y | R¹ | B |
|---|---|---|---|---|
| 16-1151 | Cl | F | H | C(CH₃)=NNHCH₃ |
| 16-1152 | Cl | Cl | H | C(CH₃)=NNHCH₃ |
| 16-1153 | H | F | H | C(CH₃)=NN(CH₃)₂ |
| 16-1154 | H | Cl | H | C(CH₃)=NN(CH₃)₂ |
| 16-1155 | F | F | H | C(CH₃)=NN(CH₃)₂ |
| 16-1156 | F | Cl | H | C(CH₃)=NN(CH₃)₂ |
| 16-1157 | Cl | F | H | C(CH₃)=NN(CH₃)₂ |
| 16-1158 | Cl | Cl | H | C(CH₃)=NN(CH₃)₂ |
| 16-1159 | H | F | H | C(CH₃)=NNHC₂H₅ |
| 16-1160 | H | Cl | H | C(CH₃)=NNHC₂H₅ |
| 16-1161 | F | F | H | C(CH₃)=NNHC₂H₅ |
| 16-1162 | F | Cl | H | C(CH₃)=NNHC₂H₅ |
| 16-1163 | Cl | F | H | C(CH₃)=NNHC₂H₅ |
| 16-1164 | Cl | Cl | H | C(CH₃)=NNHC₂H₅ |
| 16-1165 | H | F | H | C(CH₃)=NN(C₂H₅)₂ |
| 16-1166 | H | Cl | H | C(CH₃)=NN(C₂H₅)₂ |
| 16-1167 | F | F | H | C(CH₃)=NN(C₂H₅)₂ |
| 16-1168 | F | Cl | H | C(CH₃)=NN(C₂H₅)₂ |
| 16-1169 | Cl | F | H | C(CH₃)=NN(C₂H₅)₂ |
| 16-1170 | Cl | Cl | H | C(CH₃)=NN(C₂H₅)₂ |
| 16-1171 | H | F | H | C(C₂H₅)=NNH₂ |
| 16-1172 | H | Cl | H | C(C₂H₅)=NNH₂ |
| 16-1173 | F | F | H | C(C₂H₅)=NNH₂ |
| 16-1174 | F | Cl | H | C(C₂H₅)=NNH₂ |
| 16-1175 | Cl | F | H | C(C₂H₅)=NNH₂ |

TABLE 234

| | X | Y | R¹ | B |
|---|---|---|---|---|
| 16-1176 | Cl | Cl | H | C(C₂H₅)=NNH₂ |
| 16-1177 | H | F | H | C(C₂H₅)=NNHCH₃ |
| 16-1178 | H | Cl | H | C(C₂H₅)=NNHCH₃ |
| 16-1179 | F | F | H | C(C₂H₅)=NNHCH₃ |
| 16-1180 | F | Cl | H | C(C₂H₅)=NNHCH₃ |
| 16-1181 | Cl | F | H | C(C₂H₅)=NNHCH₃ |
| 16-1182 | Cl | Cl | H | C(C₂H₅)=NNHCH₃ |
| 16-1183 | H | F | H | C(C₂H₅)=NN(CH₃)₂ |
| 16-1184 | H | Cl | H | C(C₂H₅)=NN(CH₃)₂ |
| 16-1185 | F | F | H | C(C₂H₅)=NN(CH₃)₂ |
| 16-1186 | F | Cl | H | C(C₂H₅)=NN(CH₃)₂ |
| 16-1187 | Cl | F | H | C(C₂H₅)=NN(CH₃)₂ |
| 16-1188 | Cl | Cl | H | C(C₂H₅)=NN(CH₃)₂ |
| 16-1189 | H | F | H | C(C₂H₅)=NNHC₂H₅ |
| 16-1190 | H | Cl | H | C(C₂H₅)=NNHC₂H₅ |

TABLE 234-continued

| | X | Y | R¹ | B |
|---|---|---|---|---|
| 16-1191 | F | F | H | C(C₂H₅)=NNHC₂H₅ |
| 16-1192 | F | Cl | H | C(C₂H₅)=NNHC₂H₅ |
| 16-1193 | Cl | F | H | C(C₂H₅)=NNHC₂H₅ |
| 16-1194 | Cl | Cl | H | C(C₂H₅)=NNHC₂H₅ |
| 16-1195 | H | F | H | C(C₂H₅)=NN(C₂H₅)₂ |
| 16-1196 | H | Cl | H | C(C₂H₅)=NN(C₂H₅)₂ |
| 16-1197 | F | F | H | C(C₂H₅)=NN(C₂H₅)₂ |
| 16-1198 | F | Cl | H | C(C₂H₅)=NN(C₂H₅)₂ |
| 16-1199 | Cl | F | H | C(C₂H₅)=NN(C₂H₅)₂ |
| 16-1200 | Cl | Cl | H | C(C₂H₅)=NN(C₂H₅)₂ |

TABLE 235

| | X | Y | R¹ | B |
|---|---|---|---|---|
| 16-1201 | H | F | H | C(CH₃)(OCH₃)₂ |
| 16-1202 | H | Cl | H | C(CH₃)(OCH₃)₂ |
| 16-1203 | F | F | H | C(CH₃)(OCH₃)₂ |
| 16-1204 | F | Cl | H | C(CH₃)(OCH₃)₂ |
| 16-1205 | Cl | F | H | C(CH₃)(OCH₃)₂ |
| 16-1206 | Cl | Cl | H | C(CH₃)(OCH₃)₂ |
| 16-1207 | H | F | H | C(CH₃)(OC₂H₅)₂ |
| 16-1208 | H | Cl | H | C(CH₃)(OC₂H₅)₂ |
| 16-1209 | F | F | H | C(CH₃)(OC₂H₅)₂ |
| 16-1210 | F | Cl | H | C(CH₃)(OC₂H₅)₂ |
| 16-1211 | Cl | F | H | C(CH₃)(OC₂H₅)₂ |
| 16-1212 | Cl | Cl | H | C(CH₃)(OC₂H₅)₂ |
| 16-1213 | H | F | H | C(CH₃)(OiC₃H₇)₂ |
| 16-1214 | H | Cl | H | C(CH₃)(OiC₃H₇)₂ |
| 16-1215 | F | F | H | C(CH₃)(OiC₃H₇)₂ |
| 16-1216 | F | Cl | H | C(CH₃)(OiC₃H₇)₂ |
| 16-1217 | Cl | F | H | C(CH₃)(OiC₃H₇)₂ |
| 16-1218 | Cl | Cl | H | C(CH₃)(OiC₃H₇)₂ |
| 16-1219 | H | F | H | C(CH₃)(OCH₂CH₂O) |
| 16-1220 | H | Cl | H | C(CH₃)(OCH₂CH₂O) |
| 16-1221 | F | F | H | C(CH₃)(OCH₂CH₂O) |
| 16-1222 | F | Cl | H | C(CH₃)(OCH₂CH₂O) |
| 16-1223 | Cl | F | H | C(CH₃)(OCH₂CH₂O) |
| 16-1224 | Cl | Cl | H | C(CH₃)(OCH₂CH₂O) |
| 16-1225 | H | F | H | C(CH₃)(OCH₂CH₂CH₂O) |

TABLE 236

| | X | Y | R¹ | B |
|---|---|---|---|---|
| 16-1226 | H | Cl | H | C(CH₃)(OCH₂CH₂CH₂O) |
| 16-1227 | F | F | H | C(CH₃)(OCH₂CH₂CH₂O) |
| 16-1228 | F | Cl | H | C(CH₃)(OCH₂CH₂CH₂O) |
| 16-1229 | Cl | F | H | C(CH₃)(OCH₂CH₂CH₂O) |
| 16-1230 | Cl | Cl | H | C(CH₃)(OCH₂CH₂CH₂O) |
| 16-1231 | H | F | H | C(C₂H₅)(OCH₂CH₂O) |
| 16-1232 | H | Cl | H | C(C₂H₅)(OCH₂CH₂O) |
| 16-1233 | F | F | H | C(C₂H₅)(OCH₂CH₂O) |
| 16-1234 | F | Cl | H | C(C₂H₅)(OCH₂CH₂O) |
| 16-1235 | Cl | F | H | C(C₂H₅)(OCH₂CH₂O) |
| 16-1236 | Cl | Cl | H | C(C₂H₅)(OCH₂CH₂O) |
| 16-1237 | H | F | H | C(C₂H₅)(OCH₂CH₂CH₂O) |
| 16-1238 | H | Cl | H | C(C₂H₅)(OCH₂CH₂CH₂O) |
| 16-1239 | F | F | H | C(C₂H₅)(OCH₂CH₂CH₂O) |
| 16-1240 | F | Cl | H | C(C₂H₅)(OCH₂CH₂CH₂O) |
| 16-1241 | Cl | F | H | C(C₂H₅)(OCH₂CH₂CH₂O) |
| 16-1242 | Cl | Cl | H | C(C₂H₅)(OCH₂CH₂CH₂O) |
| 16-1243 | H | F | H | OCH₂CH(CH₃)₂ |
| 16-1244 | H | Cl | H | OCH₂CH(CH₃)₂ |
| 16-1245 | F | F | H | OCH₂CH(CH₃)₂ |
| 16-1246 | F | Cl | H | OCH₂CH(CH₃)₂ |
| 16-1247 | Cl | F | H | OCH₂CH(CH₃)₂ |
| 16-1248 | Cl | Cl | H | OCH₂CH(CH₃)₂ |
| 16-1249 | H | F | H | OCH₂CH₂F |
| 16-1250 | H | Cl | H | OCH₂CH₂F |

TABLE 237

|  | X | Y | R¹ | B |
|---|---|---|---|---|
| 16-1251 | F | F | H | OCH₂CH₂F |
| 16-1252 | F | Cl | H | OCH₂CH₂F |
| 16-1253 | Cl | F | H | OCH₂CH₂F |
| 16-1254 | Cl | Cl | H | OCH₂CH₂F |
| 16-1255 | H | Cl | H | CH₂OH |
| 16-1256 | F | Cl | H | CH₂OH |
| 16-1257 | H | Cl | H | CH₂OCOCH₃ |
| 16-1258 | F | Cl | H | CH₂OCOCH₃ |

Compounds of the general formula:

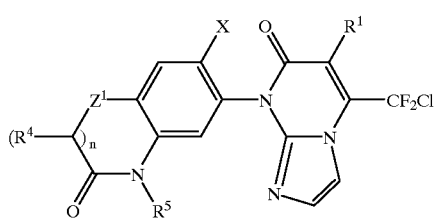

TABLE 238

|  | X | Z¹ | n | R¹ | R⁴ | R⁵ |
|---|---|---|---|---|---|---|
| 17-1 | H | O | 1 | H | H | H |
| 17-2 | F | O | 1 | H | H | H |
| 17-3 | H | O | 1 | H | H | CH₃ |
| 17-4 | F | O | 1 | H | H | CH₃ |
| 17-5 | H | O | 1 | H | H | C₂H₅ |
| 17-6 | F | O | 1 | H | H | C₂H₅ |
| 17-7 | H | O | 1 | H | H | nC₃H₇ |
| 17-8 | F | O | 1 | H | H | nC₃H₇ |
| 17-9 | H | O | 1 | H | H | nC₄H₉ |
| 17-10 | F | O | 1 | H | H | nC₄H₉ |
| 17-11 | H | O | 1 | H | H | nC₅H₁₁ |
| 17-12 | F | O | 1 | H | H | nC₅H₁₁ |
| 17-13 | H | O | 1 | H | H | iC₃H₇ |
| 17-14 | F | O | 1 | H | H | iC₃H₇ |
| 17-15 | H | O | 1 | H | H | CH₂CH₂Cl |
| 17-16 | F | O | 1 | H | H | CH₂CH₂Cl |
| 17-17 | H | O | 1 | H | H | CH₂CH₂Br |
| 17-18 | F | O | 1 | H | H | CH₂CH₂Br |
| 17-19 | H | O | 1 | H | H | CH₂CH=CH₂ |
| 17-20 | F | O | 1 | H | H | CH₂CH=CH₂ |
| 17-21 | H | O | 1 | H | H | CH(CH₃)CH=CH₂ |
| 17-22 | F | O | 1 | H | H | CH(CH₃)CH=CH₂ |
| 17-23 | H | O | 1 | H | H | CH₂CCl=CH₂ |
| 17-24 | F | O | 1 | H | H | CH₂CCl=CH₂ |
| 17-25 | H | O | 1 | H | H | CH₂C≡CH |

TABLE 239

|  | X | Z¹ | n | R¹ | R⁴ | R⁵ |
|---|---|---|---|---|---|---|
| 17-26 | F | O | 1 | H | H | CH₂C≡CH |
| 17-27 | H | O | 1 | H | H | CH(CH₃)C≡CH |
| 17-28 | F | O | 1 | H | H | CH(CH₃)C≡CH |
| 17-29 | H | O | 1 | H | H | CH₂CN |
| 17-30 | F | O | 1 | H | H | CH₂CN |
| 17-31 | H | O | 1 | H | H | CH₂OCH₃ |
| 17-32 | F | O | 1 | H | H | CH₂OCH₃ |
| 17-33 | H | O | 1 | H | H | CH₂OC₂H₅ |
| 17-34 | F | O | 1 | H | H | CH₂OC₂H₅ |
| 17-35 | H | O | 1 | H | H | CH₂COOH |
| 17-36 | F | O | 1 | H | H | CH₂COOH |
| 17-37 | H | O | 1 | H | H | CH₂COOCH₃ |
| 17-38 | F | O | 1 | H | H | CH₂COOCH₃ |
| 17-39 | H | O | 1 | H | H | CH₂COOC₂H₅ |

TABLE 239-continued

|  | X | Z¹ | n | R¹ | R⁴ | R⁵ |
|---|---|---|---|---|---|---|
| 17-40 | F | O | 1 | H | H | CH₂COOC₂H₅ |
| 17-41 | H | O | 1 | H | H | CH₂COOnC₃H₇ |
| 17-42 | F | O | 1 | H | H | CH₂COOnC₃H₇ |
| 17-43 | H | O | 1 | H | H | CH₂COOnC₄H₉ |
| 17-44 | F | O | 1 | H | H | CH₂COOnC₄H₉ |
| 17-45 | H | O | 1 | H | H | CH₂COOnC₅H₁₁ |
| 17-46 | F | O | 1 | H | H | CH₂COOnC₅H₁₁ |
| 17-47 | H | O | 1 | H | H | CH₂COOiC₃H₇ |
| 17-48 | F | O | 1 | H | H | CH₂COOiC₃H₇ |
| 17-49 | H | O | 1 | H | H | CH₂COOcC₅H₉ |
| 17-50 | F | O | 1 | H | H | CH₂COOcC₅H₉ |

TABLE 240

|  | X | Z¹ | n | R¹ | R⁴ | R⁵ |
|---|---|---|---|---|---|---|
| 17-51 | H | O | 1 | H | H | CH₂COOcC₆H₁₁ |
| 17-52 | F | O | 1 | H | H | CH₂COOcC₆H₁₁ |
| 17-53 | H | O | 1 | H | H | CH(CH₃)COOH |
| 17-54 | F | O | 1 | H | H | CH(CH₃)COOH |
| 17-55 | H | O | 1 | H | H | CH(CH₃)COOCH₃ |
| 17-56 | F | O | 1 | H | H | CH(CH₃)COOCH₃ |
| 17-57 | H | O | 1 | H | H | CH(CH₃)COOC₂H₅ |
| 17-58 | F | O | 1 | H | H | CH(CH₃)COOC₂H₅ |
| 17-59 | H | O | 1 | H | H | CH(CH₃)COOnC₃H₇ |
| 17-60 | F | O | 1 | H | H | CH(CH₃)COOnC₃H₇ |
| 17-61 | H | O | 1 | H | H | CH(CH₃)COOnC₄H₉ |
| 17-62 | F | O | 1 | H | H | CH(CH₃)COOnC₄H₉ |
| 17-63 | H | O | 1 | H | H | CH(CH₃)COOnC₅H₁₁ |
| 17-64 | F | O | 1 | H | H | CH(CH₃)COOnC₅H₁₁ |
| 17-65 | H | O | 1 | H | H | CH(CH₃)COOiC₃H₇ |
| 17-66 | F | O | 1 | H | H | CH(CH₃)COOiC₃H₇ |
| 17-67 | H | O | 1 | H | H | CH(CH₃)COOcC₅H₉ |
| 17-68 | F | O | 1 | H | H | CH(CH₃)COOcC₅H₉ |
| 17-69 | H | O | 1 | H | H | CH(CH₃)COOcC₆H₁₁ |
| 17-70 | F | O | 1 | H | H | CH(CH₃)COOcC₆H₁₁ |
| 17-71 | H | O | 1 | H | CH₃ | H |
| 17-72 | F | O | 1 | H | CH₃ | H |
| 17-73 | H | O | 1 | H | CH₃ | CH₃ |
| 17-74 | F | O | 1 | H | CH₃ | CH₃ |
| 17-75 | H | O | 1 | H | CH₃ | C₂H₅ |

TABLE 241

|  | X | Z¹ | n | R¹ | R⁴ | R⁵ |
|---|---|---|---|---|---|---|
| 17-76 | F | O | 1 | H | CH₃ | C₂H₅ |
| 17-77 | H | O | 1 | H | CH₃ | nC₃H₇ |
| 17-78 | F | O | 1 | H | CH₃ | nC₃H₇ |
| 17-79 | H | O | 1 | H | CH₃ | nC₄H₉ |
| 17-80 | F | O | 1 | H | CH₃ | nC₄H₉ |
| 17-81 | H | O | 1 | H | CH₃ | nC₅H₁₁ |
| 17-82 | F | O | 1 | H | CH₃ | nC₅H₁₁ |
| 17-83 | H | O | 1 | H | CH₃ | iC₃H₇ |
| 17-84 | F | O | 1 | H | CH₃ | iC₃H₇ |
| 17-85 | H | O | 1 | H | CH₃ | CH₂CH₂Cl |
| 17-86 | F | O | 1 | H | CH₃ | CH₂CH₂Cl |
| 17-87 | H | O | 1 | H | CH₃ | CH₂CH₂Br |
| 17-88 | F | O | 1 | H | CH₃ | CH₂CH₂Br |
| 17-89 | H | O | 1 | H | CH₃ | CH₂CH=CH₂ |
| 17-90 | F | O | 1 | H | CH₃ | CH₂CH=CH₂ |
| 17-91 | H | O | 1 | H | CH₃ | CH(CH₃)CH=CH₂ |
| 17-92 | F | O | 1 | H | CH₃ | CH(CH₃)CH=CH₂ |
| 17-93 | H | O | 1 | H | CH₃ | CH₂CCl=CH₂ |
| 17-94 | F | O | 1 | H | CH₃ | CH₂CCl=CH₂ |
| 17-95 | H | O | 1 | H | CH₃ | CH₂C≡CH |
| 17-96 | F | O | 1 | H | CH₃ | CH₂C≡CH |
| 17-97 | H | O | 1 | H | CH₃ | CH(CH₃)C≡CH |
| 17-98 | F | O | 1 | H | CH₃ | CH(CH₃)C≡CH |
| 17-99 | H | O | 1 | H | CH₃ | CH₂CN |
| 17-100 | F | O | 1 | H | CH₃ | CH₂CN |

TABLE 242

| | X | $Z^1$ | n | $R^1$ | $R^4$ | $R^5$ |
|---|---|---|---|---|---|---|
| 17-101 | H | O | 1 | H | $CH_3$ | $CH_2OCH_3$ |
| 17-102 | F | O | 1 | H | $CH_3$ | $CH_2OCH_3$ |
| 17-103 | H | O | 1 | H | $CH_3$ | $CH_2OC_2H_5$ |
| 17-104 | F | O | 1 | H | $CH_3$ | $CH_2OC_2H_5$ |
| 17-105 | H | O | 0 | H | — | H |
| 17-106 | F | O | 0 | H | — | H |
| 17-107 | H | O | 0 | H | — | $CH_3$ |
| 17-108 | F | O | 0 | H | — | $CH_3$ |
| 17-109 | H | O | 0 | H | — | $C_2H_5$ |
| 17-110 | F | O | 0 | H | — | $C_2H_5$ |
| 17-111 | H | O | 0 | H | — | $nC_3H_7$ |
| 17-112 | F | O | 0 | H | — | $nC_3H_7$ |
| 17-113 | H | O | 0 | H | — | $nC_4H_9$ |
| 17-114 | F | O | 0 | H | — | $nC_4H_9$ |
| 17-115 | H | O | 0 | H | — | $nC_5H_{11}$ |
| 17-116 | F | O | 0 | H | — | $nC_5H_{11}$ |
| 17-117 | H | O | 0 | H | — | $iC_3H_7$ |
| 17-118 | F | O | 0 | H | — | $iC_3H_7$ |
| 17-119 | H | O | 0 | H | — | $CH_2CH_2Cl$ |
| 17-120 | F | O | 0 | H | — | $CH_2CH_2Cl$ |
| 17-121 | H | O | 0 | H | — | $CH_2CH_2Br$ |
| 17-122 | F | O | 0 | H | — | $CH_2CH_2Br$ |
| 17-123 | H | O | 0 | H | — | $CH_2CH=CH_2$ |
| 17-124 | F | O | 0 | H | — | $CH_2CH=CH_2$ |
| 17-125 | H | O | 0 | H | — | $CH(CH_3)CH=CH_2$ |

TABLE 243

| | X | $Z^1$ | n | $R^1$ | $R^4$ | $R^5$ |
|---|---|---|---|---|---|---|
| 17-126 | F | O | 0 | H | — | $CH(CH_3)CH=CH_2$ |
| 17-127 | H | O | 0 | H | — | $CH_2CCl=CH_2$ |
| 17-128 | F | O | 0 | H | — | $CH_2CCl=CH_2$ |
| 17-129 | H | O | 0 | H | — | $CH_2C\equiv CH$ |
| 17-130 | F | O | 0 | H | — | $CH_2C\equiv CH$ |
| 17-131 | H | O | 0 | H | — | $CH(CH_3)C\equiv CH$ |
| 17-132 | F | O | 0 | H | — | $CH(CH_3)C\equiv CH$ |
| 17-133 | H | O | 0 | H | — | $CH_2CN$ |
| 17-134 | F | O | 0 | H | — | $CH_2CN$ |
| 17-135 | H | O | 0 | H | — | $CH_2OCH_3$ |
| 17-136 | F | O | 0 | H | — | $CH_2OCH_3$ |
| 17-137 | H | O | 0 | H | — | $CH_2OC_2H_5$ |
| 17-138 | F | O | 0 | H | — | $CH_2OC_2H_5$ |
| 17-139 | H | S | 0 | H | — | H |
| 17-140 | F | S | 0 | H | — | H |
| 17-141 | H | S | 0 | H | — | $CH_3$ |
| 17-142 | F | S | 0 | H | — | $CH_3$ |
| 17-143 | H | S | 0 | H | — | $C_2H_5$ |
| 17-144 | F | S | 0 | H | — | $C_2H_5$ |
| 17-145 | H | S | 0 | H | — | $nC_3H_7$ |
| 17-146 | F | S | 0 | H | — | $nC_3H_7$ |
| 17-147 | H | S | 0 | H | — | $nC_4H_9$ |
| 17-148 | F | S | 0 | H | — | $nC_4H_9$ |
| 17-149 | H | S | 0 | H | — | $nC_5H_{11}$ |
| 17-150 | F | S | 0 | H | — | $nC_5H_{11}$ |

TABLE 244

| | X | $Z^1$ | n | $R^1$ | $R^4$ | $R^5$ |
|---|---|---|---|---|---|---|
| 17-151 | H | S | 0 | H | — | $iC_3H_7$ |
| 17-152 | F | S | 0 | H | — | $iC_3H_7$ |
| 17-153 | H | S | 0 | H | — | $CH_2CH_2Cl$ |
| 17-154 | F | S | 0 | H | — | $CH_2CH_2Cl$ |
| 17-155 | H | S | 0 | H | — | $CH_2CH_2Br$ |
| 17-156 | F | S | 0 | H | — | $CH_2CH_2Br$ |
| 17-157 | H | S | 0 | H | — | $CH_2CH=CH_2$ |
| 17-158 | F | S | 0 | H | — | $CH_2CH=CH_2$ |
| 17-159 | H | S | 0 | H | — | $CH(CH_3)CH=CH_2$ |
| 17-160 | F | S | 0 | H | — | $CH(CH_3)CH=CH_2$ |
| 17-161 | H | S | 0 | H | — | $CH_2CCl=CH_2$ |
| 17-162 | F | S | 0 | H | — | $CH_2CCl=CH_2$ |

TABLE 244-continued

| | X | $Z^1$ | n | $R^1$ | $R^4$ | $R^5$ |
|---|---|---|---|---|---|---|
| 17-163 | H | S | 0 | H | — | $CH_2C\equiv CH$ |
| 17-164 | F | S | 0 | H | — | $CH_2C\equiv CH$ |
| 17-165 | H | S | 0 | H | — | $CH(CH_3)C\equiv CH$ |
| 17-166 | F | S | 0 | H | — | $CH(CH_3)C\equiv CH$ |
| 17-167 | H | S | 0 | H | — | $CH_2CN$ |
| 17-168 | F | S | 0 | H | — | $CH_2CN$ |
| 17-169 | H | S | 0 | H | — | $CH_2OCH_3$ |
| 17-170 | F | S | 0 | H | — | $CH_2OCH_3$ |
| 17-171 | H | S | 0 | H | — | $CH_2OC_2H_5$ |
| 17-172 | F | S | 0 | H | — | $CH_2OC_2H_5$ |
| 17-173 | H | S | 0 | H | — | $CH_2COOH$ |
| 17-174 | F | S | 0 | H | — | $CH_2COOH$ |
| 17-175 | H | S | 0 | H | — | $CH_2COOCH_3$ |

TABLE 245

| | X | $Z^1$ | n | $R^1$ | $R^4$ | $R^5$ |
|---|---|---|---|---|---|---|
| 17-176 | F | S | 0 | H | — | $CH_2COOCH_3$ |
| 17-177 | H | S | 0 | H | — | $CH_2COOC_2H_5$ |
| 17-178 | F | S | 0 | H | — | $CH_2COOC_2H_5$ |
| 17-179 | H | S | 0 | H | — | $CH_2COOnC_3H_7$ |
| 17-180 | F | S | 0 | H | — | $CH_2COOnC_3H_7$ |
| 17-181 | H | S | 0 | H | — | $CH_2COOnC_4H_9$ |
| 17-182 | F | S | 0 | H | — | $CH_2COOnC_4H_9$ |
| 17-183 | H | S | 0 | H | — | $CH_2COOnC_5H_{11}$ |
| 17-184 | F | S | 0 | H | — | $CH_2COOnC_5H_{11}$ |
| 17-185 | H | S | 0 | H | — | $CH_2COOiC_3H_7$ |
| 17-186 | F | S | 0 | H | — | $CH_2COOiC_3H_7$ |
| 17-187 | H | S | 0 | H | — | $CH_2COOcC_5H_9$ |
| 17-188 | F | S | 0 | H | — | $CH_2COOcC_5H_9$ |
| 17-189 | H | S | 0 | H | — | $CH_2COOcC_6H_{11}$ |
| 17-190 | F | S | 0 | H | — | $CH_2COOcC_6H_{11}$ |
| 17-191 | H | s | 0 | H | — | $CH(CH_3)COOH$ |
| 17-192 | F | S | 0 | H | — | $CH(CH_3)COOH$ |
| 17-193 | H | S | 0 | H | — | $CH(CH_3)COOCH_3$ |
| 17-194 | F | S | 0 | H | — | $CH(CH_3)COOCH_3$ |
| 17-195 | H | S | 0 | H | — | $CH(CH_3)COOC_2H_5$ |
| 17-196 | F | S | 0 | H | — | $CH(CH_3)COOC_2H_5$ |
| 17-197 | H | S | 0 | H | — | $CH(CH_3)COOnC_3H_7$ |
| 17-198 | F | S | 0 | H | — | $CH(CH_3)COOnC_3H_7$ |
| 17-199 | H | S | 0 | H | — | $CH(CH_3)COOnC_4H_9$ |
| 17-200 | F | S | 0 | H | — | $CH(CH_3)COOnC_4H_9$ |

TABLE 246

| | X | $Z^1$ | n | $R^1$ | $R^4$ | $R^5$ |
|---|---|---|---|---|---|---|
| 17-201 | H | S | 0 | H | — | $CH(CH_3)COOnC_5H_{11}$ |
| 17-202 | F | S | 0 | H | — | $CH(CH_3)COOnC_5H_{11}$ |
| 17-203 | H | S | 0 | H | — | $CH(CH_3)COOiC_3H_7$ |
| 17-204 | F | S | 0 | H | — | $CH(CH_3)COOiC_3H_7$ |
| 17-205 | H | S | 0 | H | — | $CH(CH_3)COOcC_5H_9$ |
| 17-206 | F | S | 0 | H | — | $CH(CH_3)COOcC_5H_9$ |
| 17-207 | H | S | 0 | H | — | $CH(CH_3)COOcC_6H_{11}$ |
| 17-208 | F | S | 0 | H | — | $CH(CH_3)COOcC_6H_{11}$ |

Compounds of the general formula:

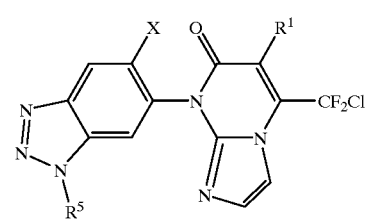

TABLE 247

| | X | R¹ | R⁵ |
|---|---|---|---|
| 20-1 | H | H | CH₃ |
| 20-2 | F | H | CH₃ |
| 20-3 | Cl | H | CH₃ |
| 20-4 | H | H | C₂H₅ |
| 20-5 | F | H | C₂H₅ |
| 20-6 | Cl | H | C₂H₅ |
| 20-7 | H | H | nC₃H₇ |
| 20-8 | F | H | nC₃H₇ |
| 20-9 | Cl | H | nC₃H₇ |
| 20-10 | H | H | nC₄H₉ |
| 20-11 | F | H | nC₄H₉ |
| 20-12 | Cl | H | nC₄H₉ |
| 20-13 | H | H | iC₄H₉ |
| 20-14 | F | H | iC₄H₉ |
| 20-15 | Cl | H | iC₄H₉ |
| 20-16 | H | H | CH₂CH=CH₂ |
| 20-17 | F | H | CH₂CH=CH₂ |
| 20-18 | Cl | H | CH₂CH=CH₂ |
| 20-19 | H | H | CH(CH₃)CH=CH₂ |
| 20-20 | F | H | CH(CH₃)CH=CH₂ |
| 20-21 | Cl | H | CH(CH₃)CH=CH₂ |
| 20-22 | H | H | CH₂C≡CH |
| 20-23 | F | H | CH₂C≡CH |
| 20-24 | Cl | H | CH₂C≡CH |
| 20-25 | H | H | CH(CH₃)C≡CH |

TABLE 248

| | X | R¹ | R⁵ |
|---|---|---|---|
| 20-26 | F | H | CH(CH₃)C≡CH |
| 20-27 | Cl | H | CH(CH₃)C≡CH |

For some of the present compounds, their physical properties, i.e., melting points or data of ¹H-NMR (250 or 300 MHz, CDCl₃, TMS) in $\delta$ (ppm), are shown as follows:

1–11 3.90–3.99 (2H, m), 4.10–4.18 (2H, m), 5.91 (1H, s), 7.50 (1H, dd, J=2.4, 8.7 Hz), 7.67 (H, d, J=8.7 Hz), 7.95 (1H, d, J=2.4 Hz)

1–218 m.p., 84.2° C.

1–376 m.p., 81.8° C.

1–382 m.p., 131.8° C.

1–388 m.p., 131.3° C.

1–424 m.p., 88.0° C.

1–430 1.22–1.29 (6H, m), 3.87–3.96 (2H, m), 4.07–4.17 (2H, m), 4.62 (2H, s), 5.11 (1H, m), 5.86 (1H, s), 6.87 (1H, d, J=6.2 Hz), 7.31 (1H, d,J=8.9 Hz)

1–634 m.p., 144.2° C.

1–688 m.p., 145.2° C.

1–760 3.65 (2H, s), 3.70 (3H, s), 3.94 (2H, t, J=8.9 Hz), 4.14 (2H, t, J=8.9 Hz), 5.87 (1H, s), 7.34 (1H, d, J=9.0 Hz), 7.47 (1H, d, J=7.3 Hz)

1–956 m.p., 135.8° C.

1–958 1.38 (3H, t, J=7.1 Hz), 3.91–3.98 (2H, m), 4.08–4.18 (2H, m), 4.37 (2H, q, J=7.1 Hz), 5.89 (1H, s), 7.37 (1H, d, J=9.3 Hz), 7.96 (1H, d, 7.7 Hz)

1–1094 3.31 (1H, dd, J=7.5, 14.0 Hz), 3.50 (1H, dd, J=7.5, 14.0 Hz), 3.74 (3H, s), 3.84–3.96 (2H, m), 4.06–4.16 (2H, m), 4.58 (1H, dd, J=7.5, 7.5 Hz), 5.87 (1H, s), 7.13–7.26 (2H, s), 7.44–7.53 (1H, m)

1–1252 m.p., 125.2° C.

6–5 m.p., 171.4° C.; decomposition

6–14 m.p., 177.0° C.; decomposition

6–23 m.p., 187.7° C.; decomposition

6–88 m.p., 230.5° C.; decomposition

6–100 m.p., 244.7° C.; decomposition

6–220 1.20–1.28 (3H, m), 1.50 (3H, d, J=6.9 Hz), 4.07 (1H, q, J=7.0 Hz), 4.15–4.24 (2H, m), 4.83–4.92 (1H, m), 6.56 (0.5H, s), 6.58 (0.5H, s), 6.68 (1H, d, J=3.2 Hz), 7.12–7.15 (1H, m), 7.23–7.25 (1H, m), 7.31 (1H, d, J=9.0 Hz)

6–310 3.19 (1H, ddt, J=15.4, 6.8, 1.3 Hz), 3.44 (1H, ddt, J=15.4, 6.2, 1.3 Hz), 4.77 (1H, ddd, J=17.0, 3.1, 1.3 Hz), 4.84 (1H, ddd, J=10.1, 3.1, 1.3 Hz), 5.69 (1H, dddd, J=17.0, 10.1, 6.8, 6.2 Hz), 6.68 (1H, s), 7.2–7.3 (2H, m)

6–340 m.p., 158.7° C.

6–346 1.71 (3H, d, J=7.5 Hz), 2.5–2.6 (1H, m), 4.7–4.9 (1H, m), 6.69 (1H, s), 7.1–7.2 (1H, m), 7.2–7.3 (2H, m), 7.38 (1H, d, J=10.8 Hz)

6–406 m.p., 108.3° C.

6–956 m.p., 134.2° C.

6–958 1.37 (3H, t, J=7.1 Hz), 4.38 (2H, q, J=7.1 Hz), 6.70 (1H, s), 7.15 (1H, d, J=2.0 Hz), 7.27 (1H, d, J=2.0 Hz), 7.45 (1H, d, J=9.3 Hz), 8.08 (1H, d, J=7.7 Hz)

6–980 m.p., 138.7° C.

6–1102 1.22–1.30 (3H, m), 3.28–3.60 (2H, m), 4.13–4.24 (2H, m), 4.54 (1H, t, J=7.5 Hz), 6.68 (0.5H, s), 6.69 (0.5H, s), 7.10–7.13 (1H, m), 7.25 (1H, d, J=2.0 Hz), 7.38–7.43 (2H, m)

7–26 m.p., 241.3° C.; decomposition

7–152 m.p., 210.9° C.

11–274 1.33–1.39 (6H, m), 3.89–3.97 (2H, m), 4.16–4.24 (2 H, m), 4.40–4.49 (1H, m), 5.83 (1H, s), 6.87 (1H, d, J=6.5 Hz), 7.28 (1H, d, J=8.9 Hz)

11–340 m.p., 131.7° C.

11–406 m.p., 97.5° C. 16–2 m.p., 189.6° C. 16–340 m.p., 162.9° C.

The following are formulation examples for the present compounds. In these example, the present compounds are designated by their compound numbers shown in Tables 1 to 248 and parts are by weight.

Formulation Example 1

Fifty parts of each of the present compounds 1-2, 1-32, 1-220, 1-262, 1-268, 1-274, 1-280, 1-340, 1-346, 1-376, 1-382, 1-388, 1-406, 1-424, 1-430, 1-460, 1-562, 1-634, 1-688, 1-712, 1-760, 1-956, 1-958, 1-1096, 2-26, 6-5, 6-23, 6-88, 6-100, 6-220, 6-274, 6-310, 6-316, 6-334, 6-340, 6-346, 6-406, 6-956, 6-958, 6-980, 6-1102, 7-26, 7-152,11-340, 11-406, 16-2, 16-274, and 16-340, 3 parts of calcium lignin sulfonate, 2 parts of sodium laurylsulfate, and 45 parts of synthetic hydrated silicon oxide are well pulverized and mixed to give a wettable powder for each compound.

Formulation Example 2

Ten parts of each of the present compounds 1-2, 1-32, 1-220, 1-262, 1-268, 1-274, 1-280, 1-340, 1-346, 1-376, 1-382, 1-388, 1-406, 1-424, 1-430, 1-460, 1-562, 1-634, 1-688, 1-712, 1-760, 1-956, 1-958, 1-1096, 2-26, 6-5, 6-23, 6-88, 6-100, 6-220, 6-274, 6-310, 6-316, 6-334, 6-340, 6-346, 6-406, 6-956, 6-958, 6-980, 6-1102, 7-26, 7-152,11-340, 11-406, 16-2, 16-274, and 16-340, 14 parts of polyoxyethylene styryl phenyl ether, 6 parts of calcium dodecylbenzenesulfonate, 35 parts of xylene, and 35 parts of cyclohexanone are well mixed to give an emulsifiable concentrate for each compound.

Formulation Example 3

Two parts of the present compounds 1-2, 1-32, 1-220, 1-262, 1-268, 1-274, 1-280, 1-340, 1-346, 1-376, 1-382, 1-388, 1-406, 1-424, 1-430, 1-460, 1-562, 1-634, 1-688, 1-712, 1-760, 1-956, 1-958, 1-1096, 2-26, 6-5, 6-23, 6-88, 6-100, 6-220, 6-274, 6-310, 6-316, 6-334, 6-340, 6-346, 6-406, 6-956, 6-958, 6-980, 6-1102, 7-26, 7-152, 11-340, 11-406, 16-2, 16-274, and 16-340, 2 parts of synthetic hydrated silicon oxide, 2 parts of calcium lignin sulfonate, 30 parts of bentonite, and 64 parts of kaolin clay are well pulverized and mixed. The mixture is well kneaded with the addition of water, and then granulated and dried to give a granule for each compound.

Formulation Example 4

Twenty-five parts of the present compounds 1-2, 1-32, 1-220, 1-262, 1-268, 1-274, 1-280, 1-340, 1-346, 1-376, 1-382, 1-388, 1-406, 1-424, 1-430, 1-460, 1-562, 1-634, 1-688, 1-712, 1-760, 1-956, 1-958, 1-1096, 2-26, 6-5, 6-23, 6-88, 6-100, 6-220, 6-274, 6-310, 6-316, 6-334, 6-340, 6-346, 6-406, 6-956, 6-958, 6-980, 6-1102, 7-26, 7-152, 11-340, 11-406, 16-2, 16-274, and 16-340, 50 parts of 10% aqueous polyvinyl alcohol solution, and 25 parts of water are mixed and then wet pulverized until the mean particle size comes to 5 µm or smaller to give a flowable for each compound.

Formulation Example 5

Five parts of the present compounds 1-2, 1-32, 1-220, 1-262, 1-268, 1-274, 1-280, 1-340, 1-346, 1-376, 1-382, 1-388, 1-406, 1-424, 1-430, 1-460, 1-562, 1-634, 1-688, 1-712, 1-760, 1-956, 1-958, 1-1096, 2-26, 6-5, 6-23, 6-88, 6-100, 6-220, 6-274, 6-310, 6-316, 6-334, 6-340, 6-346, 6-406, 6-956, 6-958, 6-980, 6-1102, 7-26, 7-152, 11-340, 11-406, 16-2, 16-274, and 16-340 is added to 40 parts of 10% aqueous polyvinyl alcohol solution and dispersed therein by emulsification with a homogenizer until the mean particle size comes to 10 µm or smaller, and 55 parts of water is added to give a thick emulsion for each compound.

The following test example will demonstrate that the present compounds are useful as the active ingredients of herbicides. In this example, the present compounds are designated by their compound numbers shown in Tables 1 to 248.

Test Example Foliar treatment on upland fields Cylindrical plastic pots each having a diameter of 10 cm and a depth of 10 cm were filled with soil and then seeded with ivyleaf morningglory (*Ipomoea hederacea*) and velvetleaf (*Abutilon theophrasti*). These test plants were grown in a greenhouse for 19 days. Each of the test compounds listed below was formulated into an emulsifiable concentrate according to Formulation Example 2 and then diluted in its prescribed amount with water containing a spreading agent. The dilution was uniformly sprayed over the foliage of the test plants with a sprayer at a rate of 1000 liters per hectare After the application, the test plants were grown in the greenhouse for 7 days, and the herbicidal activity was examined. As a result, it was found that present compounds 1-2, 1-5, 1-14, 1-32, 1-88, 1-218, 1-220, 1-262, 1-268, 1-274, 1-280, 1-310, 1-340, 1-346, 1-370, 1-376, 1-382, 1-388, 1-406, 1-424, 1-430, 1-448, 1-454, 1-460, 1-514, 1-562, 1-634, 1-688, 1-706, 1-712, 1-760, 1-956, 1-958, 1-1094, 1-1096, 1-1246, 1-1252, 1-1255, 2-26, 6-5, 6-23, 6-88, 6-100, 6-220, 6-274, 6-310, 6-316, 6-334, 6-340, 6-346, 6-406, 6-956, 6-958, 6-980, 6-1102, 7-26, 7-152, 11-2, 11-274, 11-340, 11-406, 16-2, 16-274, and 16-340 made both test plants completely dead in a dosage of 500 g/ha.

What is claimed is:

1. A pyrimidinone derivative of the general formula:

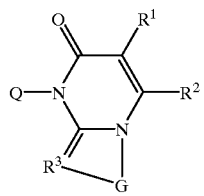

wherein:
$R^1$ is hydrogen or $C_1$–$C_3$ alkyl;
$R^2$ is $C_1$–$C_3$ haloalkyl;
$R^3$ is nitrogen or CH;
G is any group of the general formula:

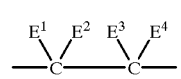

G-1

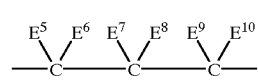

G-2

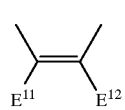

G-3 wherein:
$E^1$, $E^2$, $E^3$, $E^4$, $E^5$, $E^6$, $E^7$, $E^8$, $E^9$, $E^{10}$, $E^{11}$, and $E^{12}$ are independently hydrogen or $C_1$–$C_3$ alkyl; and
Q is any group of the general formula:

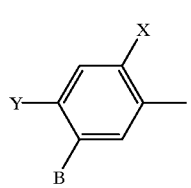

Q-1

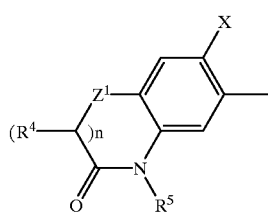

Q-2

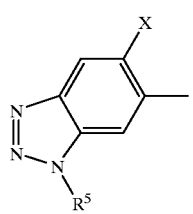

Q-5 wherein:
X is hydrogen or halogen;

Y is halogen, nitro, cyano, or trifluoromethyl;
$Z^1$ is oxygen, sulfur, NH, or $CH_2$;
n is 0 or 1;
$R^4$ is hydrogen or $C_1-C_3$ alkyl;
$R^3$ is hydrogen, $C_1-C_6$ alkyl, $C_1-C_6$ haloalkyl, $(C_3-C_8$ cycloalkyl) $C_1-C_6$ alkyl, $C_3-C_6$ alkenyl, $C_3-C_6$ haloalkenyl, $C_3-C_6$ alkynyl, $C_3-C_6$ haloalkynyl, cyano $C_1-C_6$ alkyl, $C_1-C_4$ alkoxy $C_1-C_4$ alkyl, $C_1-C_3$ alkoxy $C_1-C_3$ alkoxy $C_1-C_3$ alkyl, carboxy $C_1-C_6$ alkyl, $(C_1-C_6$ alkoxy)carbonyl $C_1-C_6$ alkyl, $\{(C_1-C_4$ alkoxy) $C_1-C_4$ alkoxy$\}$carbonyl $C_1-C_6$ alkyl, $(C_3-C_8$ cycloalkoxy)carbonyl $C_1-C_6$ alkyl, $C_1-C_4$ alkylthio $C_1-C_4$ alkyl, hydroxy $C_1-C_6$ alkyl, $-CH_2CON(R^{12})R^{13}$, $-CH_2COON(R^{12})R^{13}$, $-CH(C_1-C_4$ alkyl)$CON(R^{12})R^{13}$, or $-CH(C_1-C_4$ alkyl)$COON(R^{12})R^{13}$,
wherein:
$R^{12}$ and $R^{13}$ are independently hydrogen, $C_1-C_6$ alkyl, $C_3-C_8$ cycloalkyl, $C_1-C_6$ haloalkyl, $C_3-C_6$ alkenyl, $C_3-C_6$ alkynyl, cyano $C_1-C_6$ alkyl, $C_1-C_4$ alkoxy $C_1-C_4$ alkyl, $C_1-C_4$ alkylthio $C_1-C_4$ alkyl, carboxy $C_1-C_6$ alkyl, $(C_1-C_6$ alkoxy) carbonyl $C_1-C_6$ alkyl, $(C_3-C_8$ cycloalkoxy)carbonyl $C_1-C_6$ alkyl, $(C_1-C_6$ alkyl) carbonyloxy $C_2-C_6$ alkyl, $(C_1-C_6$ alkyl) carbonylamino $C_2-C_6$ alkyl, hydroxy $C_2-C_6$ alkyl, optionally substituted benzyl, optionally substituted phenyl, or $\{(C_1-C_4$ alkoxy) $C_1-C_4$ alkyl$\}$carbonyl $C_1-C_6$ alkyl, or $R^{12}$ and $R^{13}$ are taken together to form trimethylene, tetramethylene, pentamethylene, ethyleneoxyethylene, or ethylenethioethylene; and
B is hydrogen, halogen, nitro, cyano, chlorosulfonyl, $OR^{10}$, $SR^{10}$, $SO_2OR^{21}$, $N(R^{12})R^{13}$, $SO_2N(R^{12})R^{13}$, $NR^{12}(COR^9)$, $NR^{12}(SO_2R^{28})$, $N(SO_2R^{28})(SO_2R^{29})$, $N(SO_2R^{28})(COR^9)$, $NHCOOR^{11}$, $CONR^{12}R^{13}$, $CSNR^{12}R^{13}$, $COR^{30}$, $CR^{23}=CR^{24}COR^{30}$, $CR^{23}=CR^{24}CON(R^{12})R^{13}$, $CH_2CHWCON(R^{12})R^{13}$, $CR^{30}=NOR^{31}$, $CR^{30}=NN(R^{12})R^{13}$, $CR^{30}(Z^2R^{32})_2$, $OCO_2R^{32}$, $OCOR^{32}$, $COOR^{22}$, $CH_2OR^{10}$, $CR^{23}=CR^{24}COOR^{25}$, or $CH_2CHWCOOR_{25}$,
wherein:
$R^{12}$ and $R^{13}$ are as defined above;
W is hydrogen, chlorine, or bromine;
$Z^2$ is oxygen or sulfur;
$R^9$ is hydrogen, $C_1-C_6$ alkyl, $C_1-C_6$ haloalkyl, $C_3-C_8$ cycloalkyl, or $C_3-C_6$ alkenyl;
$R^{11}$ is hydrogen, $C_1-C_6$ alkyl, $C_3-C_8$ cycloalkyl, or $C_3-C_6$ alkenyl;
$R^{28}$ and $R^{29}$ are independently $C_1-C_6$ alkyl, $C_1-C_6$ haloalkyl, or phenyl;
$R^{30}$ is hydrogen, $C_1-C_6$ alkyl, $C_3-C_6$ alkenyl, or $C_3-C_6$ alkynyl;
$R^{31}$ is hydrogen, $C_1-C_6$ alkyl, $C_1-C_6$ haloalkyl, $C_3-C_6$ alkenyl, $C_3-C_6$ haloalkenyl, $C_3-C_6$ alkynyl, cyano $C_1-C_6$ alkyl, $C_2-C_8$ alkoxyalkyl, $C_2-C_8$ alkylthioalkyl, carboxy $C_1-C_6$ alkyl, $(C_1-C_6$ alkoxy)carbonyl $C_1-C_6$ alkyl, $(C_3-C_8$ cycloalkoxy)-carbonyl $C_1-C_6$ alkyl, or $\{(C_1-C_4$ alkoxy) $C_1-C_4$ alkoxy$\}$carbonyl $C_1-C_6$ alkyl;
$R^{32}$ is hydrogen, $C_1-C_6$ alkyl, $C_3-C_8$ cycloalkyl, or $C_3-C_6$ alkenyl;
$R^{10}$ is hydrogen, $C_1-C_6$ alkyl, $C_1-C_6$ haloalkyl, $C_3-C_8$ cycloalkyl, benzyl, $C_3-C_6$ alkenyl, $C_3-C_6$ haloalkenyl, $C_3-C_6$ alkynyl, $C_3-C_6$ haloalkynyl, cyano $C_1-C_6$ alkyl, $C_1-C_4$ alkoxy $C_1-C_4$ alkyl, $C_1-C_4$ alkylthio $C_1-C_4$ alkyl, carboxy $C_1-C_6$ alkyl, $(C_1-C_8$ alkoxy)carbonyl $C_1-C_6$ alkyl, $(C_1-C_6$ haloalkoxy)-carbonyl $C_1-C_6$ alkyl, $\{(C_1-C_4$ alkoxy) $C_1-C_4$ alkoxy$\}$carbonyl $C_1-C_6$ alkyl, $(C_3-C_8$ cycloalkoxy)carbonyl $C_1-C_6$ alkyl, $(C_3-C_8$ cycloalkyl) $C_1-C_6$ alkoxycarbonyl $C_1-C_6$ alkyl, $-CH_2COON-(R^{12})R^{13}$, $-CH(C_1-C_4$ alkyl)$COON(R^{12})R^{13}$, $-CH_2CON(R^{12})R^{13}$, $-CH(C_1-C_4$ alkyl)$CON(R^{12})R^{13}$ (wherein $R^{12}$ and $R^{13}$ are as defined above), $C_2-C_6$ alkenyloxycarbonyl $C_1-C_6$ alkyl, $C_3-C_6$ haloalkenyloxycarbonyl $C_1-C_6$ alkyl, $C_3-C_6$ alkynyloxycarbonyl $C_1-C_6$ alkyl, $C_3-C_6$ haloalkynyloxycarbonyl $C_1-C_6$ alkyl, $(C_1-C_6$ alkylthio)carbonyl $C_1-C_6$ alkyl, $(C_1-C_6$ haloalkylthio)-carbonyl $C_1-C_6$ alkyl, $(C_3-C_6$ alkenylthio)carbonyl $C_1-C_6$ alkyl, $(C_3-C_6$ haloalkenylthio)carbonyl $C_1-C_6$ alkyl, $(C_3-C_6$ alkynylthio)carbonyl $C_1-C_6$ alkyl, $(C_3-C_6$ haloalkynylthio)carbonyl $C_1-C_6$ alkyl, $(C_3-C_8$ cycloalkylthio)carbonyl $C_1-C_6$ alkyl, $(C_3-C_8$ cyclohaloalkylthio)carbonyl $C_1-C_6$ alkyl, $((C_3-C_8$ cycloalkyl) $C_1-C_6$ alkylthio)carbonyl $C_1-C_6$ alkyl, di$(C_1-C_6$ alkyl)C=NO carbonyl $C_1-C_6$ alkyl, (optionally substituted benzylthio)-carbonyl $C_1-C_6$ alkyl, (optionally substituted phenylthio)-carbonyl $C_1-C_6$ alkyl, hydroxy $C_2-C_6$ alkoxycarbonyl $C_1-C_6$ alkyl, $(C_1-C_6$ alkyl) carbonyloxy $C_2-C_6$ alkoxycarbonyl $C_1-C_6$ alkyl, $(C_1-C_6$ alkyl)carbonylamino $C_2-C_6$ alkoxycarbonyl $C_1-C_6$ alkyl, $\{(C_1-C_6$ alkoxy)carbonyl $C_1-C_6$ alkyl$\}$oxycarbonyl $C_1-C_6$ alkyl, hydroxy $C_1-C_6$ alkyl, $C_1-C_6$ alkoxycarbonyl, $C_1-C_6$ haloalkoxycarbonyl, $C_3-C_8$ cycloalkoxycarbonyl, $C_3-C_6$ alkenyloxycarbonyl, optionally substituted benzyloxycarbonyl, $C_1-C_6$ alkylcarbonyl, optionally substituted benzyloxycarbonyl $C_1-C_6$ alkyl, optionally substituted phenoxycarbonyl $C_1-C_6$ alkyl, optionally substituted furyloxycarbonyl $C_1-C_6$ alkyl, optionally substituted furyl $C_1-C_6$ alkyloxycarbonyl $C_1-C_6$ alkyl, optionally substituted thienyloxycarbonyl $C_1-C_6$ alkyl, optionally substituted thienyl $C_1-C_6$ alkyloxycarbonyl $C_1-C_6$ alkyl, optionally substituted pyrrolyloxycarbonyl $C_1-C_6$ alkyl, optionally substituted pyrrolyloxy $C_1-C_6$ alkyloxycarbonyl $C_1-C_6$ alkyl, optionally substituted imidazoyloxycarbonyl $C_1-C_6$ alkyl, optionally substituted imidazoyl $C_1-C_6$ alkyloxycarbonyl $C_1-C_6$ alkyl, optionally substituted pyrazoyloxycarbonyl $C_1-C_6$ alkyl, optionally substituted pyrazoyl $C_1-C_6$ alkyloxycarbonyl $C_1-C_6$ alkyl, optionally substituted thiazoyloxycarbonyl $C_1-C_6$ alkyl, optionally substituted thiazoyl $C_1-C_6$ alkyloxycarbonyl $C_1-C_6$ alkyl, optionally substituted oxazoyloxycarbonyl $C_1-C_6$ alkyl, optionally substituted oxazoyl $C_1-C_6$ alkyloxycarbonyl $C_1-C_6$ alkyl, optionally substituted isothiazoyloxycarbonyl $C_1-C_6$ alkyl, optionally substituted isothiazoyl $C_1-C_6$ alkyloxycarbonyl $C_1-C_6$ alkyl, optionally substituted isoxazoyloxycarbonyl $C_1-C_6$ alkyl, optionally substituted isoxazoyl $C_1-C_6$ alkyloxycarbonyl $C_1-C_6$ alkyl, optionally substituted pyridyloxycarbonyl $C_1-C_6$ alkyl, optionally substituted pyridyl $C_1-C_6$ alkyloxycarbonyl $C_1-C_6$ alkyl, optionally substituted pyradinyloxycarbonyl $C_1-C_6$ alkyl, optionally substituted pyradinyl $C_1-C_6$ alkyloxycarbonyl $C_1-C_6$ alkyl, optionally substituted pyriaidinyloxy carbonyl $C_1$–$C_6$ alkyl, optionally substituted pyrimidinyl $C_1$–$C_6$ alkyloxycarbonyl $C_1$–$C_6$ alkyl, optionally substituted pyridazinyloxycarbonyl $C_1$–$C_6$ alkyl, optionally substituted pyridazinyl $C_1$–$C_6$ alkyloxycarbonyl $C_1$–$C_6$ alkyl, optionally substituted indolidinyloxycarbonyl $C_1$–$C_6$ alkyl, optionally substituted indolidinyl $C_1$–$C_6$ alkyloxycarbonyl $C_1$–$C_6$ alkyl, optionally substituted indolyloxycarbonyl $C_1$–$C_6$ alkyl, optionally substituted indolyl $C_1$–$C_6$ alkyloxycarbonyl $C_1$–$C_6$ alkyl, optionally substituted indazolyloxycarbonyl $C_1$–$C_6$ alkyl, optionally substituted indazolyl $C_1$–$C_6$ alkyloxycarbonyl $C_1$–$C_6$ alkyl, optionally substituted quinolyloxycarbonyl $C_1$–$C_6$ alkyl, optionally substituted quinolyl $C_1$–$C_6$ alkyloxycarbonyl $C_1$–$C_6$ alkyl, optionally substituted isoquinolyloxycarbonyl $C_1$–$C_6$ alkyl, or optionally substituted isoquinolyl $C_1$–$C_6$ alkyloxycarbonyl $C_1$–$C_6$ alkyl, or a group of the general formula:

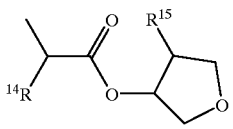

wherein:
$R^{14}$ is hydrogen or $C_1$–$C_5$ alkyl; and
$R^{15}$ is hydrogen, hydroxyl, or a group of —O—$COR^{16}$,
wherein:
$R^{16}$ is $C_1$–$C_6$ alkyl, $C_1$–$C_6$ haloalkyl, $C_3$–$C_6$ alkenyl, $C_3$–$C_8$ cycloalkyl, optionally substituted phenyl, optionally substituted benzyl, or $C_1$–$C_6$ alkoxy;
or a group of the general formula:

wherein:
$R^{17}$ is hydrogen, halogen, or $C_1$–$C_6$ alkyl; and
$R^{18}$ is $C_3$–$C_8$ cycloalkyl, benzyl, $C_2$–$C_{10}$ alkyl with an epoxy group, $C_3$–$C_8$ cycloalkyl $C_1$–$C_6$ alkyl, $C_3$–$C_8$ cycloalkyl $C_2$–$C_6$ alkenyl, carboxy $C_2$–$C_6$ alkenyl, ($C_1$–$C_8$ alkoxy)carbonyl $C_2$–$C_6$ alkenyl, ($C_1$–$C_8$ haloalkoxy)carbonyl $C_2$–$C_6$ alkenyl, {($C_1$–$C_4$ alkoxy) $C_1$–$C_4$ alkoxy}carbonyl $C_2$–$C_6$ alkenyl, ($C_3$–$C_8$ cycloalkoxy)-carbonyl $C_2$–$C_6$ alkenyl, $C_1$–$C_6$ alkyl substituted with $OR^{19}$ and $OR^{20}$ on the same carbon atom, $C_2$–$C_6$ alkenyl substituted with $OR^{19}$ and $OR^{20}$ on the same carbon atom, $C_1$–$C_6$ alkyl substituted with $SR^{19}$ and $SR^{20}$ on the same carbon atom, or $C_2$–$C_6$ alkenyl substituted with $SR^{19}$ and $SR^{20}$ on the same carbon atom,
wherein:
$R^{19}$ and $R^{20}$ are independently $C_1$–$C_6$ alkyl, $C_1$–$C_6$ haloalkyl, or $R^{19}$ and $R^{20}$ are taken together to form ethylene optionally substituted with halogen, trimethylene optionally substituted with halogen, tetramethylene optionally substituted with halogen, pentamethylene optionally substituted with halogen, or ethyleneoxyethylene optionally substituted with halogen;

$R^{21}$ is $C_1$–$C_6$ alkyl, $C_1$–$C_6$ haloalkyl, $C_3$–$C_8$ cycloalkyl, $C_3$–$C_6$ alkenyl, $C_3$–$C_6$ haloalkenyl, $C_3$–$C_6$ alkynyl, $C_3$–$C_6$ haloalkynyl, or benzyl;
$R^{22}$ is hydrogen, $C_1$–$C_6$ alkyl, $C_1$–$C_6$ haloalkyl, $C_3$–$C_8$ cycloalkyl, benzyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_8$ alkoxy)carbonyl $C_1$–$C_6$ alkyl, ($C_1$–$C_6$ haloalkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, ($C_1$–$C_6$ alkyl)-carbonyl $C_1$–$C_6$ alkyl, ($C_1$–$C_6$ haloalkyl)carbonyl $C_1$–$C_6$ alkyl, {($C_1$–$C_4$ alkoxy) $C_1$–$C_4$ alkyl}carbonyl $C_1$–$C_6$ alkyl, ($C_3$–$C_8$ cycloalkyl)carbonyl $C_1$–$C_6$ alkyl, {($C_1$–$C_6$ alkoxy)carbonyl $C_1$–$C_6$ alkyl}oxycarbonyl $C_1$–$C_6$ alkyl, hydroxy $C_1$–$C_6$ alkyl, —$CH_2$-COON($R^{26}$)$R^{27}$, —CH($C_1$–$C_4$ alkyl) COON($R^{26}$)$R^{27}$, —$CH_2$CON—($R^{26}$)$R^{27}$, or —CH($C_1$–$C_4$ alkyl) CON($R^{26}$)$R^{27}$,
wherein:
$R^{26}$ and $R^{27}$ are independently hydrogen, $C_1$–$C_6$ alkyl, $C_1$–$C_6$ haloalkyl, $C_3$–$C_6$ alkenyl, $C_3$–$C_6$ alkynyl, cyano $C_1$–$C_6$ alkyl, $C_1$–$C_4$ alkoxy $C_1$–$C_4$ alkyl, $C_1$–$C_4$ alkylthio $C_1$–$C_4$ alkyl, carboxy $C_1$–$C_6$ alkyl, ($C_1$–$C_6$ alkoxy)carbonyl $C_1$–$C_6$ alkyl, ($C_3$–$C_8$ cycloalkoxy)-carbonyl $C_1$–$C_6$ alkyl, or {($C_1$–$C_4$ alkoxy) $C_1$–$C_4$ alkyl}-carbonyl $C_1$–$C_6$ alkyl, or $R^{26}$ and $R^{27}$ are taken together to form tetramethylene, pentamethylene, or ethyleneoxyethylene;
$R^{23}$ and $R^{24}$ are independently hydrogen or $C_1$–$C_6$ alkyl; and
$R^{25}$ is hydrogen, $C_1$–$C_6$ alkyl, $C_1$–$C_6$ haloalkyl, $C_3$–$C_8$ cycloalkyl, or $C_3$–$C_6$ alkenyl.

2. The pyrimidinone derivative according to claim 1, wherein Q is Q-1.

3. The pyrimidinone derivative according to claim 1, wherein Q is Q-2.

4. The pyrimidinone derivative according to claim 1, wherein Q is Q-5.

5. The pyrimidinone derivative according to claims 1 to 4, wherein $R^3$ is nitrogen.

6. The pyrimidinone derivative according to claims 1 to 4, wherein $R^3$ is CH.

7. The pyrimidinone derivative according to claims 1 to 6, wherein G is G-1.

8. The pyrimidinone derivative according to claims 1 to 6, wherein G is G-3.

9. The pyrimidinone derivative according to claims 1 to 8, wherein $R^2$ is trifluoromethyl.

10. The pyrimidinone derivative according to claims 1 to 8, wherein $R^2$ is chlorodifluoromethyl.

11. A herbicide comprising a pyrimidinone derivative according to claim 1, and an inert carrier or diluent.

12. A method for controlling weeds, which comprises applying a pyrimidinone derivative according to claim 1 to an area where the weeds grow or will grow.

13. A compound selected from the group consisting of
7-Fluoro-6-[7-oxo-5-trifluoromethyl-2,3,7,8-tetrahydroimidazo[1,2-a]-pyrimidin-8-yl]-4-propargyl-3,4-dihydro-2H-1,4-benzo[]xadin-3-one
6-[7-Oxo-5-trifluoromethyl-2,3,7,8-tetrahydroimidazo[1,2-a]pyrimidin-8-yl]-4-propargyl-3,4-dihydro-2H-1,4-benzoxadin-3-one
6-Fluoro-5-[7-oxo-5-trifluoromethyl-2,3,7,8-tetrahydrbimidazo[1,2-a]-pyrimidin-8-yl]-3-propargyl-2,3-dihydro-1,3-benzothiazol-2-one 6-[7-Oxo-5-trifluoromethyl-2,3,7,8-tetrahydroimidazo[1,2-a]pyrimidin-8-yl]-3-propargyl-2,3-dihydro-1,3-benzothiazol-2-one 8-(4-Chloro-2-fluoro-5-methoxyphenyl)-5-trifluoromethyl-2, 3,7,8-tetrahydroimidazo[1,2-a]pyrimidin-7-one 8-(4-Chloro-2-fluoro-5-ethoxyphenyl)-5-trifluoromethyl-2,3,7,8-tetrahydroimidazo[1,2-a]pyrimidin-7-one 8-(4-Chloro-2-fluoro-5-isopropoxyphenyl)-5-trifluoromethyl-2,3,7,8-tetrahydroimidazo[1,2-a]pyrimidin-7-one 8-(4-Chloro -2-fluoro-5-prop argyloxyphenyl)-5-trifluoromethyl-2,3,7,8-tetrahydroimidazo[1,2-a]pyrimidin-7-one 8-(4-Chloro-2-fluoro-5-(1-methylpropargyloxy)phenyl)-5-trifluoromethyl-2,3,7,8-tetrahydroimidazo[1,2-a]pyrimidin-7-one {2-Chloro-4-fluoro-5-(7-oxo-5-trifluoromethyl-2, 3,7, 8-tetrahydroimidazo[1,2-a]pyrimidin-8-yl)phenoxy}acetic acid methyl ester {2-Chloro-4-fluoro-5-(7-oxo-5-trifluoromethyl-2, 3,7, 8-tetrahydroimidazo[1,2-a]pyrimidin-8-yl)phenoxy}acetic acid ethyl ester {2-Chloro-4-fluoro-5-(7-oxo-5-trifluoromethyl-2,3,7,8-tetrahydroimidazo[1,2-a]pyrimidin-8-yl)phenoxy}acetic acid isopropyl ester 2-{2-Chloro-4-fluoro-5-(7-oxo.5-trifluoromethyl-2,3,7,8-tetrahydroimidazo[1,2-a]pyrimidin-8-yl)phenoxy}propionic acid methyl ester 2-(2-Chloro-4-fluoro-5-(7-oxo-5-trifluoromethyl-2,3,7,8-tetrahydroimidazo[1,2-a]pyrimidin-8-yl)phenoxy[]propionic acid ethyl ester 2-{2-Chloro-4-fluoro-5-(7-oxo-5-trifluoromethyl-2,3,7,8-tetrahydroimidazo[1,2-a]pyrimidin-8-yl)phenoxy}propionic acid isopropyl ester {2-Chloro-4-fluoro-5-(7-oxo-5-trifluoromethyl-2,3,7,8-tetrahydroimidazo[1,2-a]pyrimidin-8-yl)phenylthio}acetic acid methyl ester {2-Chloro-4-fluoro-5-(7-oxo-5-trifluoromethyl-2, 3,7,8-tetrahydroimidazo[1,2-a]pyrimidin-8-yl)phenylthio}acetic acid ethyl ester 2-{2-Chloro-4-fluoro-5-(7-oxo-5-trifluoromethyl-2,3,7,8-tetrahydroimidazo[1,2-a]pyrimidin-8-yl)phenylthio}propionic acid methyl ester 2-{2-Chloro-4-fluoro-5-(7-oxo-5-trifluoromethyl-2,3,7,8-tetrahydroimidazo[1,2-a]pyrimidin-8-yl)phenylthio}propionic acid ethyl ester {2-Chloro-4-fluoro-5-(7-oxo-5-trifluoromethyl-2,3,7,8-tetrahydroimidazo[1,2-a]pyrimidin-8-yl)phenylamino}acetic acid methyl ester {2-Chloro-4-fluoro-5-(7-oxo-5-trifluoromethyl-2, 3, 7,8-tetrahydroimidazo[1,2-a]pyrimidin-8-yl)phenylamino}acetic acid ethyl ester 2-{2-Chloro-4-fluoro-5-(7-oxo-5-trifluoromethyl-2, 3, 7,8-tetrahydroimidazo[1,2-a]pyrimidin-8-yl)phenylamino}propionic acid methyl ester 2-{2-Chloro-4-fluoro-5-(7-oxo-5-trifluoromethyl-2, 3,7, 8-tetrahydroimidazo[1,2-a]pyrimidin-8-yl)phenylamino}propionic acid ethyl ester N-{2-Chloro-4-fluoro-5-(7-oxo-5-trifluoromethyl-2,3,7,8-tetrahydroimidazo[1,2-a]pyrimidin-8-yl)phenyl}methanesulfonamide N-{2-Chloro-4-fluoro-5-(7-oxo-5-trifluoromethyl-2,3,7, 8-tetrahydroimidazo[1,2-a]pyrimidin-8-yl)phenyl}chloromethanesulfonamide, N-{2-Chloro-5-(7-oxo-5-trifluoromethyl-2,3,7,8-tetrahydroimidazo-[1,2-a]pyrimidin-8-yl)phenyl}methanesulfonamide 2-Chloro-4-fluoro-5-(7-oxo-5-trifluoromethyl-2, 3,7,8-tetrahydroimidazo[1,2-a]pyrimidin-8-yl)benzoic acid methyl ester 2-Chloro-4-fluoro-5-(7-oxo-5-trifluoromethyl-2, 3,7, 8-tetrahydroimidazo[1,2-a]pyrimidin-8-yl)benzoic acid ethyl ester 2-Chloro-5-(7-oxo-5-trifluoromethyl-2,3,7,8-tetrahydroimidazo[1,2-a]-pyrimidin-8-yl)benzoic acid methyl ester 2-Chloro-5-(7-oxo-5-trifluoromethyl-2,3,7,8-tetrahydroimidazo[1,2-a]-pyrimidin-8-yl)benzoic acid ethyl ester 7-Fluoro-6-[7-oxo-5-trifluoromethyl-7,8-dihydroimidazo[1,2-a]pyrimidin-8-yl]-4-propargyl-3,4-dihydro-2H-1, 4-benzoxadin-3-one 6-[7-Oxo-5-trifluoromethyl-7,8-dihydroimidazo[1,2-a]pyrimidin-8-yl]-4-propargyl-3,4-dihydro-2H-1,4-benzoxadin-3-one 6-Fluoro-5-[7-oxo-5-trifluoromethyl-7,8-dihydroimidazo[1,2-a]pyrimidin-8-yl]-3-propargyl-2,3-dihydro-1,3-benzothiazol-2-one 5-[7-Oxo-5-trifluoromethyl-7,8-dihydroimidazo[1,2-a]pyrimidin-8-yl]-3-propargyl-2,3-dihydro-1,3-benzothiazol-2-one 8-(4-Chloro-2-fluoro-5-isopropoxyphenyl)-5-trifluoromethyl-7,8-dihydroimidazo[1,2-a]pyrimidin-7-one 8-(4-Chloro-2-fluoro-5-propargyloxyphenyl)-5-trifluoromethyl-7,8-dihydroimidazo[1,2-a]pyrimidin-7-one 8-(4-Chloro-2-fluoro-5-(1-methylpropargyloxy)phenyl)-5-trifluoromethyl-7,8-dihydroimidazo[1,2-a]pyrimidin-7-one {2-Chloro-4-fluoro-5-(7-oxo-5-trifluoromethyl-7,8-dihydroimidazo-[1,2-a]pyrimidin-8-yl)phenoxy}acetic acid methyl ester {2-Chloro-4-fluoro-5-(7-oxo-5-trifluoromethyl-7,8-dihydroimidazo-[1,2-a]pyrimidin-8-yl)phenoxy}acetic acid ethyl ester {2-Chloro-4-fluoro-5-(7-oxo-5-trifluoromethyl-7,8-dihydroimidazo-[1,2-a]pyrimidin-8-yl)phenoxy}acetic acid isopropyl ester 2-{2-Chloro-4-fluoro-5-(7-oxo-5-trifluoromethyl-7,8-dihydroimidazo-[1,2-a]pyrimidin-8-yl)phenoxy}propionic acid methyl ester 2-{2-Chloro-4-fluoro-5-(7-oxo-5-trifluoromethyl-7,8-dihydroimidazo-[1,2-a]pyrimidin-8-yl)phenoxy}propionic acid ethyl ester 2-{2-Chloro-4-fluoro-5-(7-oxo-5-trifluoromethyl-7,8-dihydroimidazo-[1,2-a]pyrimidin-8-yl)phenoxy}propionic acid isopropyl ester {2-Chloro-4-fluoro-5-(7-oxo-5-trifluoromethyl-7,8-dihydroimidazo-[1,2-a]pyrimidin-8-yl)phenylthio}acetic acid methyl ester {2-Chloro-4-fluoro-5-(7-oxo-5-trifluoromethyl-7,8-dihydroimidazo-[1,2-a]pyrimidin-8-yl)phenylthio}acetic acid ethyl ester 2-{2-Chloro-4-fluoro-5-(7-oxo-5-trifluoromethyl-7,8-dihydroimidazo-[1,2-a]pyrimidin-8-yl)phenylthio}propionic acid methyl ester 2-{2-Chloro-4-fluoro-5-(7-oxo-5-trifluoromethyl-7,8-dihydroimidazo-[1,2-a]pyrimidin-8-yl)phenylthio}propionic acid ethyl ester {2-Chloro-4-fluoro-5-(7-oxo-5-trifluoromethyl-7,8-dihydroimidazo-[1,2-a]pyrimidin-8-yl)phenylamino}acetic acid methyl ester {2-Chloro-4-fluoro-5-(7-oxo-5-trifluoromethyl-7,8-dihydroimidazo-[1,2-a]pyrimidin-8-yl)phenylamino}acetic acid ethyl ester 2-{2-Chloro-4-fluoro-5-(7-oxo-5-trifluoromethyl-7,8-dihydroimidazo-[1,2-a]pyrimidin-8-yl)phenylamino}propionic acid methyl ester 2-{2-Chloro-4-fluoro-5-(7-oxo-5-trifluoromethyl-7,8-dihydroimidazo-[1,2-a]pyrimidin-8-yl)phenylamino}propionic acid ethyl ester N-{2-Chloro-4-fluoro-5-(7-oxo-5-trifluoromethyl-7,8-dihydroimidazo-[1,2-a]pyrimidin-8-yl)phenyl}methanesulfonamide N-{2-Chloro-4-fluoro-5-(7-oxo-5-trifluoromethyl-7,8-dihydroimidazo-[1,2-a]pyrimidin-8-yl)phenyl}chloromethanesulfonamide N-{2-Chloro-5-(7-oxo-5-trifluoromethyl-7,8-dihydroimidazo[1,2-a]-pyrimidin-8-yl)phenyl}methanesulfonamide 2-Chloro-4-fluoro-5-(7-oxo-5-trifluoromethyl-7,8-dihydroimidazo-[1,2-a]pyrimidin-8-yl)benzoic acid methyl ester 2-Chloro-4-fluoro-5-(7-oxo-5-trifluoromethyl-7,8-dihydroimidazo-[1,2-a]pyrimidin-8-yl)benzoic acid ethyl ester 2-Chloro-5-(7-oxo-5-trifluoromethyl-7,8-dihydroimidazo[1,2-a]-pyrimidin-8-yl)benzoic acid methyl ester 2-Chloro-5-(7-oxo-5-trifluoromethyl-7,8-dihydroimidazo[1,2-a]-pyrimidin-8-yl)benzoic acid ethyl ester.

* * * * *